United States Patent
Ganesan et al.

(10) Patent No.: US 12,134,658 B2
(45) Date of Patent: Nov. 5, 2024

(54) MATERIALS AND METHODS FOR MULTIDIRECTIONAL BIOTRANSPORTATION IN VIROTHERAPEUTICS

(71) Applicant: JANSSEN BIOTECH, INC., Horsham, PA (US)

(72) Inventors: Rajkumar Ganesan, Blue Bell, PA (US); Adam Zwolak, Bala Cynwyd, PA (US); Ian White, Conshohocken, PA (US); Ninkka Tamot, Colmar, PA (US); Paul B. Harvilla, Nazareth, PA (US); Rajitha Doddareddy, Fort Washington, PA (US); Sanjaya Singh, Blue Bell, PA (US); Martin Jack Borrok, III, Chalfont, PA (US)

(73) Assignee: JANSSEN BIOTECH, INC., Horsham, PA (US)

(*) Notice: Subject to any disclaimer, the term of this patent is extended or adjusted under 35 U.S.C. 154(b) by 54 days.

(21) Appl. No.: 17/391,744

(22) Filed: Aug. 2, 2021

(65) Prior Publication Data
US 2022/0033522 A1    Feb. 3, 2022

Related U.S. Application Data

(60) Provisional application No. 63/222,332, filed on Jul. 15, 2021, provisional application No. 63/145,883, (Continued)

(51) Int. Cl.
C07K 16/40    (2006.01)
A61K 39/00    (2006.01)
(Continued)

(52) U.S. Cl.
CPC .............. *C07K 16/40* (2013.01); *C07K 16/10* (2013.01); *C07K 16/283* (2013.01);
(Continued)

(58) Field of Classification Search
CPC ...... C07K 16/40; C07K 16/10; C07K 16/283; C07K 2317/565; C07K 2317/569;
(Continued)

(56) References Cited

U.S. PATENT DOCUMENTS 3,832,253 A    8/1974    Di et al.
3,854,480 A    12/1974    Zaffaroni
(Continued)

FOREIGN PATENT DOCUMENTS

CN    111560076 A    *    8/2020    ............. A61K 39/12
EP    0239400 A2        9/1987
(Continued)

OTHER PUBLICATIONS

Wu et al., Identification of Human Single-Domain Antibodies against SARS-CoV-2, Jun. 10, 2020, Cell Host & Microbe; vol. 27, Issue 6; pp. 891-898. (Year: 2020).*
(Continued)

*Primary Examiner* — Aurora M Fontainhas
*Assistant Examiner* — Selam Berhane
(74) *Attorney, Agent, or Firm* — Riverside Law LLP

(57) ABSTRACT

Provided herein are multispecific molecules comprising a first binding domain that specifically binds to polymeric immunoglobulin receptor (pIgR) and a second binding domain that specifically binds to severe acute respiratory syndrome coronavirus 2 (SARS-CoV-2) and related methods for the treatment of patients infected with SARS-CoV-2.

18 Claims, 15 Drawing Sheets

Specification includes a Sequence Listing.

Related U.S. Application Data filed on Feb. 4, 2021, provisional application No. 63/145,896, filed on Feb. 4, 2021, provisional application No. 63/145,877, filed on Feb. 4, 2021, provisional application No. 63/145,893, filed on Feb. 4, 2021, provisional application No. 63/145,875, filed on Feb. 4, 2021, provisional application No. 63/145,888, filed on Feb. 4, 2021, provisional application No. 63/145,887, filed on Feb. 4, 2021, provisional application No. 63/145,876, filed on Feb. 4, 2021, provisional application No. 63/145,880, filed on Feb. 4, 2021, provisional application No. 63/145,873, filed on Feb. 4, 2021, provisional application No. 63/145,890, filed on Feb. 4, 2021, provisional application No. 63/075,687, filed on Sep. 8, 2020, provisional application No. 63/075,673, filed on Sep. 8, 2020, provisional application No. 63/075,647, filed on Sep. 8, 2020, provisional application No. 63/075,664, filed on Sep. 8, 2020, provisional application No. 63/075,677, filed on Sep. 8, 2020, provisional application No. 63/075,580, filed on Sep. 8, 2020, provisional application No. 63/075,606, filed on Sep. 8, 2020, provisional application No. 63/075,539, filed on Sep. 8, 2020, provisional application No. 63/075,628, filed on Sep. 8, 2020, provisional application No. 63/075,568, filed on Sep. 8, 2020, provisional application No. 63/075,504, filed on Sep. 8, 2020, provisional application No. 63/060,552, filed on Aug. 3, 2020, provisional application No. 63/060,372, filed on Aug. 3, 2020, provisional application No. 63/060,385, filed on Aug. 3, 2020, provisional application No. 63/060,307, filed on Aug. 3, 2020, provisional application No. 63/060,409, filed on Aug. 3, 2020, provisional application No. 63/060,354, filed on Aug. 3, 2020, provisional application No. 63/060,435, filed on Aug. 3, 2020, provisional application No. 63/060,293, filed on Aug. 3, 2020, provisional application No. 63/060,421, filed on Aug. 3, 2020, provisional application No. 63/060,359, filed on Aug. 3, 2020, provisional application No. 63/060,444, filed on Aug. 3, 2020.

(51) Int. Cl.
   *C07K 16/10*      (2006.01)
   *C07K 16/28*      (2006.01)

(52) U.S. Cl.
   CPC .. *A61K 2039/505* (2013.01); *C07K 2317/565* (2013.01); *C07K 2317/569* (2013.01); *C07K 2317/73* (2013.01); *C07K 2317/732* (2013.01); *C07K 2317/92* (2013.01)

(58) Field of Classification Search
   CPC .......... C07K 2317/73; C07K 2317/732; C07K 2317/92; A61K 2039/505
   See application file for complete search history.

(56) References Cited

U.S. PATENT DOCUMENTS

| | | |
|---|---|---|
| 4,179,337 A | 12/1979 | Davis et al. |
| 4,301,144 A | 11/1981 | Iwashita et al. |
| 4,452,775 A | 6/1984 | Kent |
| 4,496,689 A | 1/1985 | Mitra |
| 4,526,938 A | 7/1985 | Churchill |
| 4,640,835 A | 2/1987 | Shimizu et al. |
| 4,667,014 A | 5/1987 | Nestor et al. |
| 4,670,417 A | 6/1987 | Iwasaki et al. |
| 4,676,980 A | 6/1987 | Segal et al. |
| 4,748,034 A | 5/1988 | Rham |
| 4,791,192 A | 12/1988 | Nakagawa et al. |
| 4,816,567 A | 3/1989 | Cabilly et al. |
| 4,946,778 A | 8/1990 | Ladner et al. |
| 5,075,109 A | 12/1991 | Tice et al. |
| 5,112,946 A | 5/1992 | Maione |
| 5,128,326 A | 7/1992 | Balazs et al. |
| 5,208,020 A | 5/1993 | Chari et al. |
| 5,225,539 A | 7/1993 | Winter |
| 5,260,203 A | 11/1993 | Ladner et al. |
| 5,336,603 A | 8/1994 | Capon et al. |
| 5,349,053 A | 9/1994 | Landolfi |
| 5,359,046 A | 10/1994 | Capon et al. |
| 5,447,851 A | 9/1995 | Beutler et al. |
| 5,476,786 A | 12/1995 | Huston |
| 5,482,858 A | 1/1996 | Huston et al. |
| 5,530,101 A | 6/1996 | Queen et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,569,825 A | 10/1996 | Lonberg et al. |
| 5,585,089 A | 12/1996 | Queen et al. |
| 5,605,793 A | 2/1997 | Stemmer |
| 5,622,929 A | 4/1997 | Willner et al. |
| 5,639,641 A | 6/1997 | Pedersen et al. |
| 5,679,377 A | 10/1997 | Bernstein et al. |
| 5,693,761 A | 12/1997 | Queen et al. |
| 5,714,352 A | 2/1998 | Jakobovits |
| 5,723,125 A | 3/1998 | Chang et al. |
| 5,766,886 A | 6/1998 | Studnicka et al. |
| 5,770,196 A | 6/1998 | Studnicka |
| 5,783,181 A | 7/1998 | Browne et al. |
| 5,807,715 A | 9/1998 | Morrison et al. |
| 5,811,238 A | 9/1998 | Morrison et al. |
| 5,821,123 A | 10/1998 | Studnicka |
| 5,827,690 A | 10/1998 | Meade et al. |
| 5,830,721 A | 11/1998 | Stemmer et al. |
| 5,834,252 A | 11/1998 | Stemmer et al. |
| 5,837,242 A | 11/1998 | Holliger et al. |
| 5,837,458 A | 11/1998 | Minshull et al. |
| 5,844,095 A | 12/1998 | Linsley et al. |
| 5,869,619 A | 2/1999 | Studnicka |
| 5,908,626 A | 6/1999 | Chang et al. |
| 5,912,015 A | 6/1999 | Bernstein et al. |
| 5,916,597 A | 6/1999 | Lee et al. |
| 5,989,463 A | 11/1999 | Tracy et al. |
| 6,054,297 A | 4/2000 | Carter et al. |
| 6,075,181 A | 6/2000 | Kucherlapati et al. |
| 6,150,584 A | 11/2000 | Kucherlapati et al. |
| 6,194,556 B1 * | 2/2001 | Acton ...................... C12N 9/48 536/23.4 |
| 6,265,150 B1 | 7/2001 | Terstappen et al. |
| 6,340,743 B1 | 1/2002 | Mostov et al. |
| 6,387,397 B1 | 5/2002 | Chen et al. |
| 6,407,213 B1 | 6/2002 | Carter et al. |
| 6,492,123 B1 | 12/2002 | Holliger et al. |
| 6,639,055 B1 | 10/2003 | Carter et al. |
| 6,719,971 B1 | 4/2004 | Carter et al. |
| 6,800,738 B1 | 10/2004 | Carter et al. |
| 6,989,250 B2 | 1/2006 | Soderlind et al. |
| 7,404,954 B2 | 7/2008 | Mostov et al. |
| 7,612,181 B2 | 11/2009 | Wu et al. |
| 7,985,840 B2 | 7/2011 | Fuh et al. |
| 8,685,897 B2 | 4/2014 | Bowers et al. |
| 9,409,989 B2 | 8/2016 | Arathoon et al. |
| 9,718,872 B2 | 8/2017 | Kyratsous et al. |
| 2002/0102657 A1 | 8/2002 | Mostov et al. |
| 2002/0197266 A1 | 12/2002 | Debinski |
| 2003/0161809 A1 | 8/2003 | Houston et al. |
| 2003/0166160 A1 | 9/2003 | Hawley et al. |
| 2003/0186374 A1 | 10/2003 | Hufton et al. |
| 2004/0005709 A1 | 1/2004 | Hoogenboom et al. |
| 2004/0157330 A1 | 8/2004 | Sheridan et al. |
| 2005/0042664 A1 | 2/2005 | Wu et al. |
| 2005/0201932 A1 | 9/2005 | Mostov |
| 2007/0004909 A1 | 1/2007 | Johnson et al. |
| 2009/0060910 A1 | 3/2009 | Johnson et al. |
| 2009/0075378 A1 | 3/2009 | Horlick et al. |
| 2009/0182127 A1 | 7/2009 | Kjaergaard et al. |

(56) References Cited

U.S. PATENT DOCUMENTS

| | | |
|---|---|---|
| 2010/0015133 A1 | 1/2010 | Igawa et al. |
| 2010/0136018 A1 | 6/2010 | Dolk et al. |
| 2011/0123532 A1 | 5/2011 | Gurney et al. |
| 2011/0183855 A1 | 7/2011 | Horlick et al. |
| 2012/0028301 A1 | 2/2012 | Horlick et al. |
| 2014/0094392 A1 | 4/2014 | Bowers et al. |
| 2014/0170705 A1 | 6/2014 | Bowers et al. |
| 2014/0377779 A1 | 12/2014 | Yong et al. |
| 2015/0330993 A1 | 11/2015 | Anderson et al. |
| 2017/0334983 A1 | 11/2017 | Kolkman et al. |
| 2017/0349648 A1 | 12/2017 | Simard |
| 2017/0355756 A1* | 12/2017 | Julien ............... A61P 25/00 |
| 2022/0112276 A1 | 4/2022 | Harvilla et al. |
| 2022/0324970 A1 | 10/2022 | Ganesan et al. |
| 2023/0019640 A1 | 1/2023 | Ganesan |

FOREIGN PATENT DOCUMENTS

| | | | |
|---|---|---|---|
| EP | 0239400 A3 | 9/1987 | |
| EP | 0367166 A1 | 5/1990 | |
| EP | 0394827 A1 | 10/1990 | |
| EP | 0519596 A1 | 12/1992 | |
| EP | 0307434 B1 | 9/1993 | |
| EP | 0592106 A1 | 4/1994 | |
| EP | 0239400 B1 | 8/1994 | |
| EP | 0307434 B2 | 7/1998 | |
| EP | 0592106 B1 | 11/2004 | |
| EP | 0519596 B1 | 2/2005 | |
| GB | 2188638 A | 10/1987 | |
| GB | 2188638 B | 5/1990 | |
| WO | WO 1991005548 A1 | 5/1991 | |
| WO | WO 1991006570 A1 | 7/1991 | |
| WO | WO 1991009967 A1 | 6/1993 | |
| WO | WO 1993011161 A1 | 6/1993 | |
| WO | WO 1993011794 A1 | 6/1993 | |
| WO | WO 1993017105 A1 | 9/1993 | |
| WO | WO 1996004388 A1 | 2/1996 | |
| WO | WO 1996020698 A2 | 7/1996 | |
| WO | WO 1996020698 A3 | 7/1996 | |
| WO | WO 1996022024 A1 | 7/1996 | |
| WO | WO 1997034631 A1 | 9/1997 | |
| WO | WO 1999004813 A1 | 2/1999 | |
| WO | WO 1999015154 A1 | 4/1999 | |
| WO | WO 1999020253 A1 | 4/1999 | |
| WO | WO 2000047611 A2 | 8/2000 | |
| WO | WO 2000047611 A3 | 8/2000 | |
| WO | WO 2002083840 A2 | 10/2002 | |
| WO | WO 2002083840 A3 | 10/2002 | |
| WO | 02098448 | 12/2002 | |
| WO | WO 2006028936 A2 | 3/2006 | |
| WO | WO 2006028936 A3 | 3/2006 | |
| WO | 2008046125 | 4/2008 | |
| WO | 2008074867 | 6/2008 | |
| WO | 2008074868 | 6/2008 | |
| WO | WO-2008068048 A2 * | 6/2008 | ............ A61P 31/10 |
| WO | 2009080764 | 7/2009 | |
| WO | WO 2011131746 A2 | 10/2011 | |
| WO | WO 2011131746 A3 | 10/2011 | |
| WO | 2013036130 | 3/2013 | |
| WO | 2013119870 | 8/2013 | |
| WO | WO 2015057873 A1 | 4/2015 | |
| WO | WO 2018183712 A1 | 10/2018 | |
| WO | WO 2020205477 A1 | 10/2020 | |
| WO | WO 2021025997 A1 | 2/2021 | |
| WO | WO 2021026000 A1 | 2/2021 | |
| WO | WO 2022031576 A1 | 2/2022 | |
| WO | WO 2022081460 A1 | 4/2022 | |

OTHER PUBLICATIONS

Zhang et al., New understanding of the damage of SARS-COV-2 infection outside the respiratory system, Jul. 2020, Biomedicine & Pharmacotherapy; vol. 127, 110195; pp. 1-7. (Year: 2020).*

Chen et al., Enhancement and destruction of antibody function by somatic mutation: unequal occurrence is controlled by V gene combinatorial associations. EMBO J. Jun. 15, 1995;14(12):2784-94. (Year: 1995).*

Edwards et al., The remarkable flexibility of the human antibody repertoire; isolation of over one thousand different antibodies to a single protein, BLyS. J Mol Biol. Nov. 14, 2003;334(1):103-18. (Year: 2003).*

Kussie, Paul H., "A Single Engineered Amino Acid Substitution Changes Antibody Fine Specificity", 1994, Journal of Immunology 152(1): pp. 146-152. (Year: 1994).*

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; (Year: 2017).*

Al-Lazikani et al., 1997, "Standard conformations for the canonical structures of immunoglobulins," J. Mol. Biol., 273(4):927-948.

Allen et al., 1989, "Acute eosinophilic pneumonia as a reversible cause of noninfectious respiratory failure," N. Engl. J. Med., 321(9):569-574.

Altschul et al., 1990, "Basic local alignment search tool," J. Mol. Biol., 215(3):403-410.

Altschul et al., 1997, "Gapped BLAST and PSI-BLAST: a new generation of protein database search programs," Nucleic Acids Res., 25(17):3389-3402.

Ashkenazi et al., 1991, "Protection against endotoxic shock by a tumor necrosis factor receptor immunoadhesin," Proc. Natl. Acad. Sci. USA, 88(23):10535-10539.

Baca et al., 1997, "Antibody humanization using monovalent phage display," J. Biol. Chem., 272(16):10678-10684.

Beck et al., 2008, "Trends in glycosylation, glycoanalysis and glycoengineering of therapeutic antibodies and Fc-fusion proteins," Curr. Pharm. Biotechnol., 9(6):482-501.

Bird et al., 1988, "Single-chain antigen-binding proteins," Science, 242(4877):423-426.

Bitter et al., 1987, "Expression and secretion vectors for yeast," Methods Enzymol., 153:516-544.

Blaise et al., 2004, "Construction and diversification of yeast cell surface displayed libraries by yeast mating: application to the affinity maturation of Fab antibody fragments," Gene., 342(2):211-218.

Boder et al., 1997, "Yeast surface display for screening combinatorial polypeptide libraries," Nat. Biotechnol., 15(6):553-557.

Boerner et al., 1991, "Production of antigen-specific human monoclonal antibodies from in vitro-primed human splenocytes," J. Immunol., 147(1):86-95.

Bond et al., 2005, "A structure-based database of antibody variable domain diversity," J. Mol. Biol., 348(3):699-709.

Bonner et al., 2009, "Location of secretory component on the Fc edge of dimeric IgA1 reveals insight into the role of secretory IgA1 in mucosal immunity," Mucosal. Immunol., 2(1):74-84 (Epub 2008).

Bonner et al., 2009, "The nonplanar secretory IgA2 and near planar secretory IgA1 solution structures rationalize their different mucosal immune responses," J. Biol. Chem., 284(8):5077-5087 (Epub 2008).

Bradbury et al., 2004, "Antibodies from phage antibody libraries," J. Immunol. Methods, 290(1-2):29-49.

Bruggemann et al., 1997, "Production of human antibody repertoires in transgenic mice," Curr. Opin. Biotechnol., 8(4):455-458.

Buchwald et al., 1980, "Long-term, continuous intravenous heparin administration by an implantable infusion pump in ambulatory patients with recurrent venous thrombosis," Surgery, 88(4):507-516.

Caldas et al., 2000, "Design and synthesis of germline-based hemi-humanized single-chain Fv against the CD18 surface antigen," Protein Eng., 13(5):353-360.

Carter et al., 1992, "Humanization of an anti-p185HER2 antibody for human cancer therapy," Proc. Natl. Acad. Sci. USA, 89(10):4285-4289.

Carter, 1986, "Site-directed mutagenesis," Biochem. J., 237(1):1-7.

Chao et al., 2006, "Isolating and engineering human antibodies using yeast surface display," Nat. Protoc., 1(2):755-768.

Chari et al., 1992, "Immunoconjugates containing novel maytansinoids: promising anticancer drugs," Cancer Res., 52(1):127-131.

(56) References Cited

OTHER PUBLICATIONS

Chen et al., 1999, "Selection and analysis of an optimized anti-VEGF antibody: crystal structure of an affinity-matured Fab in complex with antigen," J. Mol. Biol., 293(4):865-881.
Chothia et al., 1987, "Canonical structures for the hypervariable regions of immunoglobulins," J. Mol. Biol., 196(4):901-917.
Clackson et al., 1991, "Making antibody fragments using phage display libraries," Nature, 352(6336):624-628.
Cleek et al., 1997, "Biodegradable polymeric carriers for a bFGF antibody for cardiovascular application," Pro. Int. Symp. Control. Rel. Bioact. Mater., 24:853-854.
Cockett et al., 1990, "High level expression of tissue inhibitor of metalloproteinases in Chinese hamster ovary cells using glutamine synthetase gene amplification," Biotechnology (NY), 8(7):662-667.
Colbere-Garapin et al., 1981, "A new dominant hybrid selective marker for higher eukaryotic cells," J. Mol. Biol., 150(1):1-14.
Couto et al., 1995, "Anti-BA46 monoclonal antibody Mc3: humanization using a novel positional consensus and in vivo and in vitro characterization," Cancer Res., 55(8):1717-1722.
Couto et al., 1995, "Designing human consensus antibodies with minimal positional templates," Cancer Res., 55(23 Suppl):5973s-5977s.
Crouse et al., 1983, "Expression and amplification of engineered mouse dihydrofolate reductase minigenes," Mol. Cell. Biol., 3(2):257-266.
Dall'Acqua et al., 2005, "Antibody humanization by framework shuffling," Methods, 36(1):43-60.
Damschroder et al., 2007, "Framework shuffling of antibodies to reduce immunogenicity and manipulate functional and biophysical properties," Mol. Immunol., 44(11):3049-3060.
De Groot et al., 2006, "Evolutionary deimmunization: an ancillary mechanism for self-tolerance?" Cell Immunol., 244(2):148-153.
Dufner et al., 2006, "Harnessing phage and ribosome display for antibody optimisation," Trends Biotechnol., 24(11):523-529.
During et al., 1989, "Controlled release of dopamine from a polymeric brain implant: in vivo characterization," Ann. Neurol., 25(4):351-356.
Emmerson et al., 2011, "Enhancement of polymeric immunoglobulin receptor transcytosis by biparatopic VHH," PLoS One, 6(10):e26299.
Feldhaus et al., 2003, "Flow-cytometric isolation of human antibodies from a nonimmune *Saccharomyces cerevisiae* surface display library," Nat. Biotechnol., 21(2):163-170.
Foecking et al., 1986, "Powerful and versatile enhancer-promoter unit for mammalian expression vectors," Gene., 45(1):101-105.
Foote et al., 1992, "Antibody framework residues affecting the conformation of the hypervariable loops," J. Mol. Biol., 224(2):487-499.
Fukuda et al., 2006, "In vitro evolution of single-chain antibodies using mRNA display," Nucleic Acids Res., 34(19):e127 (8 pages).
GenBank Accession No. CR749533.1, 2008, "*Homo sapiens* mRNA; cDNA DKFZp686I21225 (from clone DKFZp686I21225)," Oct. 7, 2008 [retrieved on Jan. 7, 2023]. Retrieved from Internet: <https://www.ncbi.nlm.nih.gov/nuccore/CR749533> (3 pages).
GenBank Accession No. MN908947.3, 2020, "Severe acute respiratory syndrome coronavirus 2 isolate Wuhan-Hu-1, complete genome," Mar. 18, 2020 [retrieved on Jan. 8, 2023]. Retrieved from Internet: <https://www.ncbi.nlm.nih.gov/nuccore/MN908947> (11 pages).
GenBank Accession No. QHD43415.1, 2020, "orf1ab polyprotein [Severe acute respiratory syndrome coronavirus 2]," Mar. 18, 2020 [retrieved on Jan. 8, 2023]. Retrieved from Internet: <https://www.ncbi.nlm.nih.gov/protein/QHD43415> (8 pages).
GenBank Accession No. QHD43423.2, 2020, "nucleocapsid phosphoprotein [Severe acute respiratory syndrome coronavirus 2]," Mar. 18, 2020 [retrieved on Jan. 8, 2023]. Retrieved from Internet: <https://www.ncbi.nlm.nih.gov/protein/QHD43423> (2 pages).
GenBank Accession No. QHI42199.1, 2020, "ORF10 protein [Severe acute respiratory syndrome coronavirus 2]," Mar. 18, 2020 [retrieved on Jan. 8, 2023]. Retrieved from Internet: <https://www.ncbi.nlm.nih.gov/protein/QHI42199> (1 page).
Gentz et al., 1989, "Bioassay for trans-activation using purified human immunodeficiency virus tat-encoded protein: trans-activation requires mRNA synthesis," Proc. Natl. Acad. Sci. USA, 86(3):821-824.
Guex et al., 1997, "Swiss-Model and the Swiss-Pdb Viewer: an environment for comparative protein modeling," Electrophoresis, 18(15):2714-2723.
Hansson et al., 1999, "Evolution of differential substrate specificities in Mu class glutathione transferases probed by DNA shuffling," J. Mol. Biol., 287(2):265-276.
Harayama, 1998, "Artificial evolution by DNA shuffling," Trends Biotechnol., 16(2):76-82.
Henikoff et al., 1992, "Amino acid substitution matrices from protein blocks," Proc. Natl. Acad. Sci. USA, 89(22):10915-10919.
Ho et al., 2005, "In vitro antibody evolution targeting germline hot spots to increase activity of an anti-CD22 immunotoxin," J. Biol. Chem., 280(1):607-617 (Epub 2004).
Hofer et al., 2008, "An engineered selenocysteine defines a unique class of antibody derivatives," Proc. Natl. Acad. Sci. USA, 105(34):12451-12456.
Hofer et al., 2009, "Molecularly defined antibody conjugation through a selenocysteine interface," Biochemistry, 48(50):12047-12057.
Holliger et al., 1993, ""Diabodies": small bivalent and bispecific antibody fragments," Proc. Natl. Acad. Sci. USA, 90(14):6444-6448.
Honegger et al., 2001, "Yet another numbering scheme for immunoglobulin variable domains: an automatic modeling and analysis tool," J. Mol. Biol., 309(3):657-670.
Hoogenboom et al., 1992, "By-passing immunisation. Human antibodies from synthetic repertoires of germline VH gene segments rearranged in vitro," J. Mol. Biol., 227(2):381-388.
Hoogenboom, 2002, "Overview of antibody phage-display technology and its applications," Methods Mol. Biol., 178:1-37.
Hoogenboom, 2005, "Selecting and screening recombinant antibody libraries," Nat. Biotechnol., 23(9):1105-1116.
Howard III et al., 1989, "Intracerebral drug delivery in rats with lesion-induced memory deficits," J. Neurosurg., 71(1):105-112.
Hudecz, 2005, "Synthesis of peptide bioconjugates," Methods Mol. Biol., 298:209-223.
Hudson et al., 2003, "Engineered antibodies," Nat. Med., 9(1):129-134.
Huo et al., 2020, "Neutralization of SARS-CoV-2 by Destruction of the Prefusion Spike," Cell Host Microbe., 28(3):445-454.e6 and Erratum 28(3):497 (19 pages).
Huse et al., 1989, "Generation of a large combinatorial library of the immunoglobulin repertoire in phage lambda," Science, 246(4935):1275-1281.
Huston et al., 1988, "Protein engineering of antibody binding sites: recovery of specific activity in an anti-digoxin single-chain Fv analogue produced in *Escherichia coli*," Proc. Natl. Acad. Sci. USA, 85(16):5879-5883.
Inouye et al., 1985, "Up-promoter mutations in the lpp gene of *Escherichia coli*," Nucleic Acids Res., 13(9):3101-3110.
International Searching Authority, International Search Report and Written Opinion for International Patent Application No. PCT/US2020/044497 (Pub No. WO 2021025997) mailed Oct. 22, 2020 (11 pages).
International Searching Authority, International Search Report and Written Opinion for International Patent Application No. PCT/US2020/044505 (Pub No. WO 2021026000) mailed Dec. 3, 2020 (21 pages).
International Searching Authority, International Search Report and Written Opinion for International Patent Application No. PCT/US2021/044138 (Pub No. WO 2022031576) mailed Dec. 30, 2021 (14 pages).
International Searching Authority, International Search Report and Written Opinion for International Patent Application No. PCT/US2021/054381 (Pub No. WO 2022081460) mailed Feb. 23, 2022 (19 pages).
Jakobovits, 1995, "Production of fully human antibodies by transgenic mice," Curr. Opin. Biotechnol., 6(5):561-566.

(56) References Cited

OTHER PUBLICATIONS

Jones et al., 1986, "Replacing the complementarity-determining regions in a human antibody with those from a mouse," Nature, 321(6069):522-525.
Jones et al., 2009, "Deimmunization of monoclonal antibodies," Methods Mol. Biol., 525:405-423, xiv.
Junutula et al., 2008, "Rapid identification of reactive cysteine residues for site-specific labeling of antibody-Fabs," J. Immunol. Methods, 332(1-2):41-52.
Junutula et al., 2008, "Site-specific conjugation of a cytotoxic drug to an antibody improves the therapeutic index," Nat. Biotechnol., 26(8):925-932.
Juraszek et al., 2021, "Stabilizing the closed SARS-CoV-2 spike trimer," Nat. Commun., 12(1):244 (8 pages).
Kabat et al., 1977, "Unusual distributions of amino acids in complementarity-determining (hypervariable) segments of heavy and light chains of immunoglobulins and their possible roles in specificity of antibody-combining sites," J. Biol. Chem., 252(19):6609-6616.
Kabat, 1978, "The structural basis of antibody complementarity," Adv. Protein Chem., 32:1-75.
Kaetzel, 2001, "Polymeric Ig receptor: defender of the fort or Trojan horse?" Curr. Biol., 11(1):R35-R38.
Karlin et al., 1990, "Methods for assessing the statistical significance of molecular sequence features by using general scoring schemes," Proc. Natl. Acad. Sci. USA, 87(6):2264-2268.
Karlin et al., 1993, "Applications and statistics for multiple high-scoring segments in molecular sequences," Proc. Natl. Acad. Sci. USA, 90(12):5873-5877.
Kashmiri et al., 2005, "SDR grafting—a new approach to antibody humanization," Methods, 36(1):25-34.
Kirin et al., 2005, "Amino acid and peptide bioconjugates of copper(II) and zinc(II) complexes with a modified N,N-bis(2-picolyl)amine ligand," Inorg. Chem., 44(15):5405-5415.
Kohler et al., 1975, "Continuous cultures of fused cells secreting antibody of predefined specificity," Nature, 256(5517):495-497.
Kohler et al., 1976, "Derivation of specific antibody-producing tissue culture and tumor lines by cell fusion," Eur. J. Immunol., 6(7):511-519.
Kovtun et al., 2010, "Antibody-maytansinoid conjugates designed to bypass multidrug resistance," Cancer Res., 70(6):2528-2537.
Kwong et al., 2009, "*E. coli* expression and purification of Fab antibody fragments," Curr. Protoc. Protein Sci., Chapter 6:Unit 6.10 (14 pages).
Lam et al., 1997, "Microencapsulation of recombinant humanized monoclonal antibody for local delivery," Proc. Intl. Symp. Control Rel. Bioact. Mater, 24:759-760.
Langer et al., 1983, "Chemical and Physical Structure of Polymers as Carriers for Controlled Release of Bioactive Agents: A Review," Journal of Macromolecular Science—reviews in Macromolecular Chemistry and Physics, 23(1):61-126.
Langer, 1990, "New methods of drug delivery," Science, 249(4976):1527-1533.
Lazar et al., 2007, "A molecular immunology approach to antibody humanization and functional optimization," Mol. Immunol., 44(8):1986-1998 (Epub 2006).
Lefranc et al., 2003, "IMGT unique numbering for immunoglobulin and T cell receptor variable domains and Ig superfamily V-like domains," Dev. Comp. Immunol., 27(1):55-77.
Levy et al., 1985, "Inhibition of calcification of bioprosthetic heart valves by local controlled-release diphosphonate," Science, 228(4696):190-192.
Li et al., 2006, "Human antibodies for immunotherapy development generated via a human B cell hybridoma technology," Proc. Natl. Acad. Sci. USA, 103(10):3557-3562.
Logan et al., 1984, "Adenovirus tripartite leader sequence enhances translation of mRNAs late after infection," Proc. Natl. Acad. Sci. USA, 81(12):3655-3659.
Lorenzo et al., 1998, "PCR-based method for the introduction of mutations in genes cloned and expressed in vaccinia virus," Biotechniques, 24(2):308-313.
Lowy et al., 1980, "Isolation of transforming DNA: cloning the hamster aprt gene," Cell, 22(3):817-823.
Lu et al., 2003, "Tailoring in vitro selection for a picomolar affinity human antibody directed against vascular endothelial growth factor receptor 2 for enhanced neutralizing activity," J. Biol. Chem., 278(44):43496-43507.
Maclean et al., 1997, "Immunoliposomes as targeted delivery vehicles for cancer therapeutics (Review)," Int. J. Oncol., 11(2):325-332.
Malik et al., 2007, "Recent advances in protein and peptide drug delivery systems," Curr. Drug Deliv., 4(2):141-151.
Marks et al., 1991, "By-passing immunization. Human antibodies from V-gene libraries displayed on phage," J. Mol. Biol., 222(3):581-597.
Maruthachalam et al., 2020, "Discovery and characterization of single-domain antibodies for polymeric Ig receptor-mediated mucosal delivery of biologics," MAbs, 12(1):e1708030 (11 pages).
Merrifield, 1963, "Solid Phase Peptide Synthesis. I. The Synthesis of a Tetrapeptide," J. Am. Chem. Soc., 85(14):2149-2154.
Meulen et al., 2006, "Human monoclonal antibody combination against SARS coronavirus: synergy and coverage of escape mutants," PLoS Med., 3(7):e237 (9 pages).
Morea et al., 2000, "Antibody modeling: implications for engineering and design," Methods, 20(3):267-279.
Morgan et al., 1993, "Human gene therapy," Annu. Rev. Biochem., 62:191-217.
Morrison et al., 1984, "Chimeric human antibody molecules: mouse antigen-binding domains with human constant region domains," Proc. Natl. Acad. Sci. USA, 81(21):6851-6855.
Mulligan et al., 1981, "Selection for animal cells that express the *Escherichia coli* gene coding for xanthine-guanine phosphoribosyltransferase," Proc. Natl. Acad. Sci. USA, 78(4):2072-2076.
Mulligan, 1993, "The basic science of gene therapy," Science, 260(5110):926-932.
Muyldermans, 2001, "Single domain camel antibodies: current status," J. Biotechnol., 74(4):277-302.
Needleman et al., 1970, "A general method applicable to the search for similarities in the amino acid sequence of two proteins," J. Mol. Biol., 48(3):443-453.
Ning et al., 1996, "Intratumoral radioimmunotherapy of a human colon cancer xenograft using a sustained-release gel," Radiother Oncol., 39(2):179-189.
O'Hare et al., 1981, "Transformation of mouse fibroblasts to methotrexate resistance by a recombinant plasmid expressing a prokaryotic dihydrofolate reductase," Proc. Natl. Acad. Sci. USA, 78(3):1527-1531.
Padlan et al., 1995, "Identification of specificity-determining residues in antibodies," FASEB J., 9(1):133-139.
Padlan, 1991, "A possible procedure for reducing the immunogenicity of antibody variable domains while preserving their ligand-binding properties," Mol. Immunol., 28(4-5):489-498.
Park et al . . . , 2005, "Biodegradable polymers for microencapsulation of drugs," Molecules, 10(1):146-161.
Patten et al., 1997, "Applications of DNA shuffling to pharmaceuticals and vaccines," Curr. Opin. Biotechnol., 8(6):724-733.
Pearson et al., 1988, "Improved tools for biological sequence comparison," Proc. Natl. Acad. Sci. USA, 85(8):2444-2448.
Pedersen et al., 1994, "Comparison of surface accessible residues in human and murine immunoglobulin Fv domains. Implication for humanization of murine antibodies," J. Mol. Biol., 235(3):959-973.
Presta et al., 1993, "Humanization of an antibody directed against IgE," J. Immunol., 151(5):2623-2632.
Presta, 1992, "Antibody engineering," Curr. Op. Struct. Biol., 2:593-596.
Putney et al., 1998, "Improving protein therapeutics with sustained-release formulations," Nat. Biotechnol., 16(2):153-157.
Quiroz et al., 2011, "Engineering antibody fragments: replicating the immune system and beyond—Engineering antibody fragments: imitating and expanding the immune system," Biomedical Engineering Journal, 4(7):39-51 (in Spanish with English abstract).
Riechmann et al., 1988, "Reshaping human antibodies for therapy," Nature, 332(6162):323-327.

(56) References Cited

OTHER PUBLICATIONS

Roguska et al., 1994, "Humanization of murine monoclonal antibodies through variable domain resurfacing," Proc. Natl. Acad. Sci. USA, 91(3):969-973.
Roguska et al., 1996, "A comparison of two murine monoclonal antibodies humanized by CDR-grafting and variable domain resurfacing," Protein Eng., 9(10):895-904.
Rossotti et al., 2022, "Immunogenicity and humanization of single-domain antibodies," FEBS J., 289:4304-4327 (Epub 2021).
Ruther et al., 1983, "Easy identification of cDNA clones," EMBO J., 2(10):1791-1794.
Sali et al., 1993, "Comparative protein modelling by satisfaction of spatial restraints," J. Mol. Biol., 234(3):779-815.
Sandhu, 1994, "A rapid procedure for the humanization of monoclonal antibodies," Gene., 150(2):409-410.
Saunders, 2019, "Conceptual Approaches to Modulating Antibody Effector Functions and Circulation Half-Life," Front Immunol., 10:1296 (20 pages).
Schlapschy et al., 2004, "Functional humanization of an anti-CD30 Fab fragment for the immunotherapy of Hodgkin's lymphoma using an in vitro evolution approach," Protein Eng. Des. Sel., 17(12):847-860.
Sefton, 1987, "Implantable pumps," Crit. Rev. Biomed. Eng., 14(3):201-240.
Shusta et al., 1999, "Yeast polypeptide fusion surface display levels predict thermal stability and soluble secretion efficiency," J. Mol. Biol., 292(5):949-956.
Sims et al., 1993, "A humanized CD18 antibody can block function without cell destruction," J. Immunol., 151(4):2296-2308.
Smith et al., 1981, "Comparison of biosequences," Advances in Applied Mathematics, 2(4):482-489.
Song et al., 1996, "Antibody mediated lung targeting of long-circulating emulsions," PDA J. Pharm. Sci. Technol., 50(6):372-377.
Stadtmueller et al., 2016, "The structure and dynamics of secretory component and its interactions with polymeric immunoglobulins," Elife, e10640 (23 pages).
Starr et al., 2020, "Deep Mutational Scanning of SARS-CoV-2 Receptor Binding Domain Reveals Constraints on Folding and ACE2 Binding," Cell, 182(5):1295-1310.e20 (37 pages).
Starr et al., 2021, "Prospective mapping of viral mutations that escape antibodies used to treat COVID-19," Science, 371(6531):850-854.
Streltsov et al., 2004, "Structural evidence for evolution of shark Ig new antigen receptor variable domain antibodies from a cell-surface receptor," Proc. Natl. Acad. Sci. USA, 101(34):12444-12449.
Studnicka et al., 1994, "Human-engineered monoclonal antibodies retain full specific binding activity by preserving non-CDR complementarity-modulating residues," Protein Eng., 7(6):805-814.
Szybalska et al., 1962, "Genetics of human cell line. IV. DNA-mediated heritable transformation of a biochemical trait," Proc. Natl. Acad. Sci. USA, 48(12):2026-2034.
Tan et al., 2002, ""Superhumanized" antibodies: reduction of immunogenic potential by complementarity-determining region grafting with human germline sequences: application to an anti-CD28," J. Immunol., 169(2):1119-1125.
Tan et al., 2020, "A SARS-CoV-2 surrogate virus neutralization test based on antibody-mediated blockage of ACE2-spike protein-protein interaction," Nat. Biotechnol., 38(9):1073-1078.
Tan et al., 2021, "Early induction of functional SARS-CoV-2-specific T cells associates with rapid viral clearance and mild disease in COVID-19 patients," Cell Rep., 34(6):108728 and Supplementary Materials (18 pages).
Taylor et al., 1992, "A transgenic mouse that expresses a diversity of human sequence heavy and light chain immunoglobulins," Nucleic Acids Res., 20(23):6287-6295.
Terpe, 2003, "Overview of tag protein fusions: from molecular and biochemical fundamentals to commercial systems," Appl. Microbiol. Biotechnol., 60(5):523-533 (Epub 2002).
Tolstoshev, 1993, "Gene therapy, concepts, current trials and future directions," Annu. Rev. Pharmacol. Toxicol., 33:573-596.
Towler et al., 2004, "ACE2 X-ray structures reveal a large hinge-bending motion important for inhibitor binding and catalysis," J. Biol. Chem., 279(17):17996-18007.
Traunecker et al., 1988, "Soluble CD4 molecules neutralize human immunodeficiency virus type 1," Nature, 331(6151):84-86.
Turula et al., 2018, "The Role of the Polymeric Immunoglobulin Receptor and Secretory Immunoglobulins during Mucosal Infection and Immunity," Viruses, 10(5):237 (15 pages).
Van Dijk et al., 2001, "Human antibodies as next generation therapeutics," Curr. Opin. Chem. Biol., 5(4):368-374.
Van Heeke eta l., 1989, "Expression of human asparagine synthetase in *Escherichia coli*," J. Biol. Chem., 264(10):5503-5509.
Verhoeyen et al., 1988, "Reshaping human antibodies: grafting an antilysozyme activity," Science, 239(4847):1534-1536.
Vie et al., 1992, "Human fusion proteins between interleukin 2 and IgM heavy chain are cytotoxic for cells expressing the interleukin 2 receptor," Proc. Natl. Acad. Sci. USA, 89(23):11337-11341.
Walsh, 2010, "Post-translational modifications of protein biopharmaceuticals," Drug Discov. Today, 15(17-18):773-780.
Wang et al., 2020, "Clinical Characteristics of 138 Hospitalized Patients With 2019 Novel Coronavirus-Infected Pneumonia in Wuhan, China," JAMA, 323(11):1061-1069.
Wells et al., 1985, "Cassette mutagenesis: an efficient method for generation of multiple mutations at defined sites," Gene., 34(2-3):315-323.
Whitelegg et al., 2000, "WAM: an improved algorithm for modelling antibodies on the WEB," Protein Eng., 13(12):819-824.
Wigler et al., 1977, "Transfer of purified herpes virus thymidine kinase gene to cultured mouse cells," Cell, 11(1):223-232.
Wigler et al., 1980, "Transformation of mammalian cells with an amplifiable dominant-acting gene," Proc. Natl. Acad. Sci. USA, 77(6):3567-3570.
Wilson et al., 1984, "The structure of an antigenic determinant in a protein," Cell, 37(3):767-778.
Wilson et al., 2001, "The use of mRNA display to select high-affinity protein-binding peptides," Proc. Natl. Acad. Sci. USA, 98(7):3750-3755.
Wu et al., 1991, "Delivery systems for gene therapy," Biotherapy, 3(1):87-95.
Yuan et al., 2020, "A highly conserved cryptic epitope in the receptor binding domains of SARS-CoV-2 and SARS-CoV," Science, 368(6491):630-633.
Zheng et al., 1995, "Administration of noncytolytic IL-10/Fc in murine models of lipopolysaccharide-induced septic shock and allogeneic islet transplantation," J. Immunol., 154(10):5590-5600.
Zoller et al., 1982, "Oligonucleotide-directed mutagenesis using M13-derived vectors: an efficient and general procedure for the production of point mutations in any fragment of DNA," Nucleic Acids Res., 10(20):6487-6500.
Zoufaly et al., 2020, "Human recombinant soluble ACE2 in severe COVID-19," Lancet Respir. Med., 8(11):1154-1158.
Kaetzel, 2005, "The polymeric immunoglobulin receptor: bridging innate and adaptive immune responses at mucosal surfaces" Immunological Reviews, 206(1), 83-99.
McConnell et al., 2014, "A general approach to antibody thermostabilization" MABS, 6(5), 1274-1292.
Borrok MJ, DiGiandomenico A, Beyaz N, Marchetti GM, Barnes AS, Lekstrom KJ, Phipps SS, McCarthy MP, Wu H, Dall'Acqua WF, Tsui P, Gupta R. Enhancing IgG distribution to lung mucosal tissue improves protective effect of anti-Pseudomonas aeruginosa antibodies. JCI Insight. Jun. 2, 20181;3(12):e97844. 9 pages.
Ferkol T, Cohn LA, Phillips TE, Smith A, Davis PB. Targeted delivery of antiprotease to the epithelial surface of human tracheal xenografts. Am J Respir Crit Care Med. May 15, 2003;167(10):1374-9.
Lei C, Qian K, Li T, Zhang S, Fu W, Ding M, Hu S. Neutralization of SARS-CoV-2 spike pseudotyped virus by recombinant ACE2-Ig. Nat Commun. Apr. 2, 20204;11(1):2070. 5 pages.
White I, Tamot N, Doddareddy R, Ho J, Jiao Q, Harvilla PB, Yang TY, Geist B, Borrok MJ, Truppo MD, Ganesan R, Chowdhury P, Zwolak A. Bifunctional molecules targeting SARS-COV-2 spike

(56) References Cited

OTHER PUBLICATIONS and the polymeric Ig receptor display neutralization activity and mucosal enrichment. MAbs. Jan. 2021-Dec.;13(1):1987180. 11 pages.

* cited by examiner

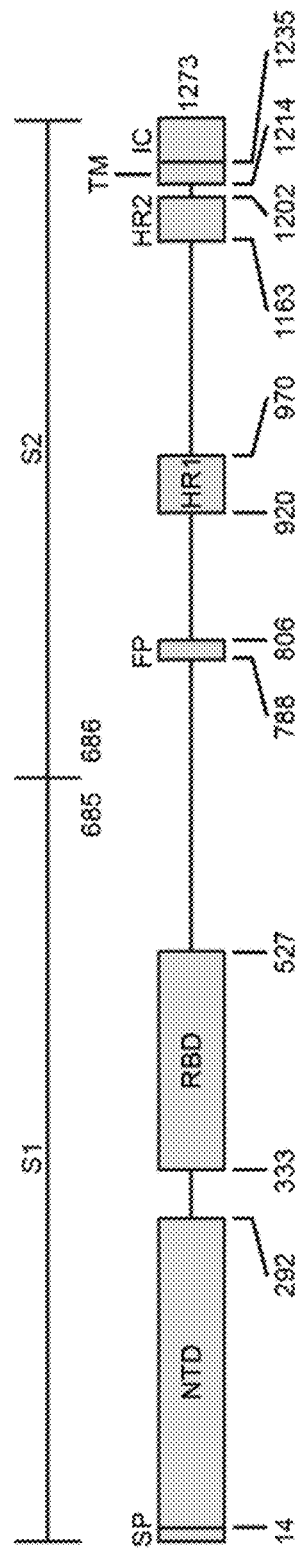
FIG. 2A
FIG. 2B
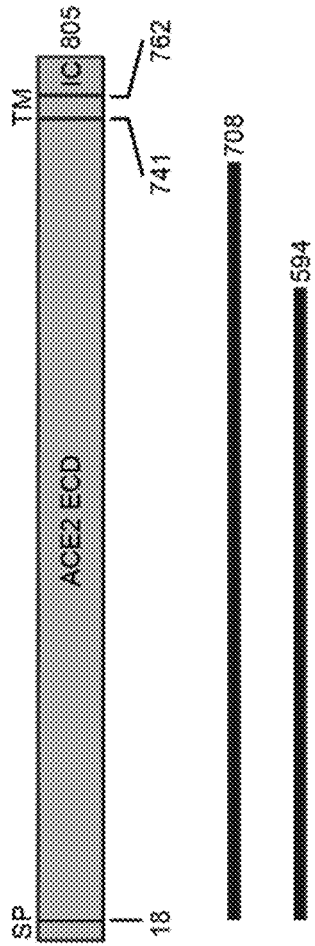
FIG. 2C human ACE2 ECD

```
 19 QSTIEEQAKTFLDKFNHEAEDLFYQSSLASWNYNTNITEENVQNMNNAGDKWSAFLKEQSTLAQMYPLQEIQNLTVKLQLQ   98
 99 ALQQNGSSVLSEDKSKRLNTILNTMSTIYSTGKVCNPDNPQECLLLEPGLNEIMANSLDYNERLWAWESWRSEVGKQLRPL  179
180 YEEYVVLKNEMARANHYEDYGDYWRGDYEVNGVDGYDYSRGQLIEDVEHTFEEIKPLYEHLHAYVRAKLMNAYPSYISPIG  260
261 CLPAHLLGDMWGRFWTNLYSLTVPFGQKPNIDVTDAMVDQAWDAQRIFKEAEKFFVSVGLPNMTQGFWENSMLTDPGNVQK  341
342 AVCHPTAWDLGKGDFRILMCTKVTMDDFLTAHHEMGHIQYDMAYAAQPFLLRNGANEGFHEAVGEIMSLSAATPKHLKSIG  422
423 LLSPDFQEDNETEINFLLKQALTIVGTLPFTYMLEKWRWMVFKGEIPKDQWMKKWWEMKREIVGVVEPVPHDETYCDPASL  503
504 FHVSNDYSFIRYYTRTLYQFQFQEALCQAAKHEGPLHKCDISNSTEAGQKLFNMLRLGKSEPWTLALENVVGAKNMNVRPL  584
585 LNYFEPLFTWLKDQNKNSFVGWSTDWSPYADQSIKVRISLKSALGDKAYEWNDNEMYLFRSSVAYAMRQYFLKVKNQMILF  665
666 GEEDVRVANLKPRISFNFFVTAPKNVSDIIPRTEVEKAIRMSRSRINDAFRLNDNSLEFLGIQPTLGPPNQPPVS         740
```

FIG. 2D

| Protein Name | Glyph | Description |
|---|---|---|
| CV19B308 |  | pIgR-VHH2-Fc-MSCD342-ACE2$_{18-611}$ |
| CV19B307 |  | pIgR-VHH2-Fc-MSCD342-ACE2$_{18-725}$ |
| CV19B301 |  | pIgR-VHH6-Fc-MSCD342-ACE2$_{18-725}$ |
| CV19B290 |  | null-VHH-Fc-MSCD342-ACE2$_{18-611}$ |
| CV19B289 |  | null-VHH-Fc-MSCD342-ACE2$_{18-725}$ |
| CV19B283 |  | pIgR-VHH2-MSCD342-ACE2$_{18-725}$-Fc |
| CV19B277 |  | pIgR-VHH6-MSCD342-ACE2$_{18-725}$-Fc |
| CV19B265 |  | null-VHH-MSCD342-ACE2$_{18-725}$-Fc |
| CR3022 |  | Pan-SARS-CoV mAb |
| D001 |  | SARS-CoV-2 neutralizing mAb |
| SAD-S35 |  | SARS-CoV-2 neutralizing mAb |

MATERIALS AND METHODS FOR MULTIDIRECTIONAL BIOTRANSPORTATION IN VIROTHERAPEUTICS

CROSS-REFERENCE TO RELATED APPLICATIONS

This application claims the benefit of U.S. Ser. No. 63/222,332, filed Jul. 15, 2021; U.S. Ser. No. 63/145,896, filed Feb. 4, 2021; U.S. Ser. No. 63/145,893, filed Feb. 4, 2021; U.S. Ser. No. 63/145,890, filed Feb. 4, 2021; U.S. Ser. No. 63/145,888, filed Feb. 4, 2021; U.S. Ser. No. 63/145,887, filed Feb. 4, 2021; U.S. Ser. No. 63/145,883, filed Feb. 4, 2021; U.S. Ser. No. 63/145,880, filed Feb. 4, 2021; U.S. Ser. No. 63/145,877, filed Feb. 4, 2021; U.S. Ser. No. 63/145,876, filed Feb. 4, 2021; U.S. Ser. No. 63/145,875, filed Feb. 4, 2021; U.S. Ser. No. 63/145,873, filed Feb. 4, 2021; U.S. Ser. No. 63/075,687, filed Sep. 8, 2020; U.S. Ser. No. 63/075,677, filed Sep. 8, 2020; U.S. Ser. No. 63/075,673, filed Sep. 8, 2020; U.S. Ser. No. 63/075,664, filed Sep. 8, 2020; U.S. Ser. No. 63/075,647, filed Sep. 8, 2020; U.S. Ser. No. 63/075,628, filed Sep. 8, 2020; U.S. Ser. No. 63/075,606, filed Sep. 8, 2020; U.S. Ser. No. 63/075,580, filed Sep. 8, 2020; U.S. Ser. No. 63/075,568, filed Sep. 8, 2020; U.S. Ser. No. 63/075,539, filed Sep. 8, 2020; U.S. Ser. No. 63/075,504, filed Sep. 8, 2020; U.S. Ser. No. 63/060,552, filed Aug. 3, 2020; U.S. Ser. No. 63/060,444, filed Aug. 3, 2020; U.S. Ser. No. 63/060,435, filed Aug. 3, 2020; U.S. Ser. No. 63/060,421, filed Aug. 3, 2020; U.S. Ser. No. 63/060,409, filed Aug. 3, 2020; U.S. Ser. No. 63/060,385, filed Aug. 3, 2020; U.S. Ser. No. 63/060,372, filed Aug. 3, 2020; U.S. Ser. No. 63/060,359, filed Aug. 3, 2020; U.S. Ser. No. 63/060,354, filed Aug. 3, 2020; U.S. Ser. No. 63/060,307, filed Aug. 3, 2020; and U.S. Ser. No. 63/060,293, filed Aug. 3, 2020, the disclosure of each of which is incorporated by reference herein in its entirety.

1. FIELD

Provided herein are multispecific molecules comprising one or more binding domain(s) that specifically bind to polymeric immunoglobulin receptor (pIgR), and optionally one or more binding domain(s) that specifically bind to a target of interest, such as severe acute respiratory syndrome coronavirus 2 (SARS-CoV-2) and related methods for the treatment of patients infected with SARS-CoV-2.

2. REFERENCE TO SEQUENCE LISTING SUBMITTED ELECTRONICALLY

This application contains a sequence listing, which is submitted electronically via EFS-Web as an ASCII formatted sequence listing with a file name of "14620-385-999_SEQ_LISTING.txt" and a creation date of Jul. 28, 2021 and having a size of 262,506 bytes. The sequence listing submitted via EFS-Web is part of the specification and is herein incorporated by reference in its entirety.

3. BACKGROUND

Viral infection is challenging to contain and treat. The Coronavirus Disease 2019 (COVID-19) pandemic caused by severe acute respiratory syndrome coronavirus 2 (SARS-CoV-2) has resulted in over 178 million infections and over 3.8 million deaths (as of Jul. 13, 2021). The global health and economic tolls of COVID-19 demonstrate the lack of a panoply of treatment strategies, including vaccines as well as therapeutic interventions. To date few approved treatments exist, and none have curative potential. Neutralizing antibodies against the SARS-CoV-2 spike glycoprotein have been identified but therapeutic options remain limited. Targeting of therapeutics is mostly undeveloped, including delivery of biologics to the lung mucosal space, where infection occurs. The lack of options presents a significant challenge.

4. SUMMARY

Accordingly, against this backdrop, there is a need for treatments that enable systemic administration of antibodies targeted to specific tissues and cells, for example, to the lung mucosa to treat COVID-19. In one aspect, provided herein is a multispecific molecule comprising: (a) a first binding domain that specifically binds to polymeric immunoglobulin receptor (pIgR), and (b) a second binding domain that specifically binds to SARS-CoV-2. In certain aspects, the molecule is a bispecific molecule.

In one aspect, the second binding domain of the multispecific molecule provided herein specifically binds to the surface of SARS-CoV-2. In another aspect, the second binding domain specifically binds to the spike glycoprotein on the surface of SARS-CoV-2. In certain aspects, the second binding domain specifically binds to the S1 subunit of the spike glycoprotein on the surface of SARS-CoV-2.

In another aspect, the second binding domain of the multispecific molecule provided herein comprises angiotensin-converting enzyme 2 (ACE2). In one aspect, the ACE2 comprises SEQ ID NO:194. In some embodiments, the second binding domain comprises the extracellular domain of ACE2. In one aspect, the extracellular domain of ACE2 comprises SEQ ID NO:134. In other embodiments, the second binding domain comprises a truncated extracellular domain of ACE2. In one aspect, the truncated extracellular domain of ACE2 comprises SEQ ID NO:120 or SEQ ID NO:121.

In one aspect, the first binding domain of the multispecific molecule provided herein comprises a single-domain antibody (VHH).

In one embodiment, the VHH comprises a complementarity determining region 1 (CDR1) having an amino acid sequence of SEQ ID NO:1, a CDR2 having an amino acid sequence of SEQ ID NO:2, and a CDR3 having an amino acid sequence of SEQ ID NO:3. In some embodiments, the VHH comprises an amino acid sequence of SEQ ID NO: 16.

In one embodiment, the VHH comprises a CDR1 having an amino acid sequence of SEQ ID NO:17, a CDR2 having an amino acid sequence of SEQ ID NO:18, and a CDR3 having an amino acid sequence of SEQ ID NO:19. In some embodiments, the VHH comprises an amino acid sequence of SEQ ID NO:32.

In one aspect of the multispecific molecule provided herein, the first binding domain specifically binds to pIgR that is present on the mucosal endothelium. In one embodiment the first binding domain specifically binds to pIgR that is present on the lung mucosal endothelium In another aspect of the multispecific molecule provided herein, the SARS-CoV-2 is neutralized when the molecule provided herein specifically binds to the pIgR and to SARS-CoV-2. In one embodiment, the molecule neutralizes SARS-CoV-2 with an $EC_{50}$ of less than about 4 nM. In a certain embodiment, the molecule neutralizes SARS-CoV-2 with an $EC_{50}$ of less than about 3 nM. In another embodiment, the molecule neutralizes SARS-CoV-2 with an $EC_{50}$ of less than about 1 nM. In another embodiment, the molecule neutralizes SARS-CoV-2 with an $EC_{50}$ of less than about 500 pM. In a certain embodiment, the molecule neutralizes SARS-CoV-2 with an $EC_{50}$ of less than about 100 pM.

In one aspect, provided herein is a pharmaceutical composition comprising: (a) a first binding domain that specifically binds to polymeric immunoglobulin receptor (pIgR), and (b) a second binding domain that specifically binds to SARS-CoV-2. In certain aspects of the pharmaceutical composition provided herein, the molecule is a bispecific molecule.

In one aspect, provided herein is a pharmaceutical composition comprising a multispecific molecule comprising: (a) a first binding domain that specifically binds to polymeric immunoglobulin receptor (pIgR), and (b) a second binding domain that specifically binds to a second target that is not pIgR, and a pharmaceutically acceptable carrier. In certain aspects of the pharmaceutical composition provided herein, the molecule is a bispecific molecule.

In one aspect of the pharmaceutical composition provided herein, the second binding domain of the multispecific molecule provided herein specifically binds to the surface of SARS-CoV-2. In another aspect of the pharmaceutical composition provided herein, the second binding domain specifically binds to the spike glycoprotein on the surface of SARS-CoV-2. In certain aspects of the pharmaceutical composition provided herein, the second binding domain specifically binds to the S1 subunit of the spike glycoprotein on the surface of SARS-CoV-2.

In another aspect of the pharmaceutical composition provided herein, the second binding domain of the multispecific molecule provided herein comprises angiotensin-converting enzyme 2 (ACE2). In one aspect of the pharmaceutical composition provided herein, the ACE2 comprises SEQ ID NO:194. In some embodiments of the pharmaceutical composition provided herein, the second binding domain comprises the extracellular domain of ACE2. In one aspect of the pharmaceutical composition provided herein, the extracellular domain of ACE2 comprises SEQ ID NO:134. In other embodiments of the pharmaceutical composition provided herein, the second binding domain comprises a truncated extracellular domain of ACE2. In one aspect of the pharmaceutical composition provided herein, the truncated extracellular domain of ACE2 comprises SEQ ID NO:120 or SEQ ID NO:121.

In one aspect of the pharmaceutical composition provided herein, the first binding domain of the multispecific molecule provided herein comprises a single-domain antibody (VHH).

In one embodiment of the pharmaceutical composition provided herein, the VHH comprises a complementarity determining region 1 (CDR1) having an amino acid sequence of SEQ ID NO:1, a CDR2 having an amino acid sequence of SEQ ID NO:2, and a CDR3 having an amino acid sequence of SEQ ID NO:3. In some embodiments of the pharmaceutical composition provided herein, the VHH comprises an amino acid sequence of SEQ ID NO:16.

In one embodiment of the pharmaceutical composition provided herein, the VHH comprises a CDR1 having an amino acid sequence of SEQ ID NO:17, a CDR2 having an amino acid sequence of SEQ ID NO:18, and a CDR3 having an amino acid sequence of SEQ ID NO:19. In some embodiments of the pharmaceutical composition provided herein, the VHH comprises an amino acid sequence of SEQ ID NO:32.

In one aspect of the pharmaceutical composition provided herein, the first binding domain specifically binds to pIgR that is present on the mucosal endothelium. In one embodiment of the pharmaceutical composition provided herein, the first binding domain specifically binds to pIgR that is present on the lung mucosal endothelium In another aspect of the pharmaceutical composition provided herein, the SARS-CoV-2 is neutralized when the molecule provided herein specifically binds to the pIgR and to SARS-CoV-2. In one embodiment of the pharmaceutical composition provided herein, the molecule neutralizes SARS-CoV-2 with an $EC_{50}$ of less than about 4 nM. In a certain embodiment of the pharmaceutical composition provided herein, the molecule neutralizes SARS-CoV-2 with an $EC_{50}$ of less than about 3 nM. In another embodiment of the pharmaceutical composition provided herein, the molecule neutralizes SARS-CoV-2 with an $EC_{50}$ of less than about 1 nM. In another embodiment of the pharmaceutical composition provided herein, the molecule neutralizes SARS-CoV-2 with an $EC_{50}$ of less than about 500 pM. In a certain embodiment of the pharmaceutical composition provided herein, the molecule neutralizes SARS-CoV-2 with an $EC_{50}$ of less than about 100 pM.

Also provided is a method of producing the pharmaceutical composition, comprising combining the molecule of the previous embodiments with a pharmaceutically acceptable carrier to obtain the pharmaceutical composition.

In one aspect, provided herein is a method of inhibiting viral entry into host cells or inhibiting proliferation of SARS-CoV-2, the method comprising contacting the SARS-CoV-2 with the multispecific molecule comprising: (a) a first binding domain that specifically binds to polymeric immunoglobulin receptor (pIgR), and (b) a second binding domain that specifically binds to SARS-CoV-2, wherein contacting SARS-CoV-2 with the molecule inhibits host cell entry or proliferation of SARS-CoV-2. In another aspect, provided herein is a method of inhibiting host cell entry or proliferation of target cells expressing the second target, the method comprising contacting the target cells with a multispecific molecule comprising: (a) a first binding domain that specifically binds to polymeric immunoglobulin receptor (pIgR), and (b) a second binding domain that specifically binds to a second target that is not pIgR, wherein contacting the target cells with the molecule inhibits host cell entry or proliferation of the target cells.

In one aspect, provided herein is a method for eliminating SARS-CoV-2 in a subject, administering to the subject an effective amount of a multispecific molecule comprising: (a) a first binding domain that specifically binds to polymeric immunoglobulin receptor (pIgR), and (b) a second binding domain that specifically binds to SARS-CoV-2. In some embodiments, the subject has COVID-19.

In one aspect, provided herein is a method of treating a disease caused all or in part by SARS-CoV-2 in a subject, comprising administering an effective amount of the multispecific molecule comprising: (a) a first binding domain that specifically binds to polymeric immunoglobulin receptor (pIgR), and (b) a second binding domain that specifically binds to SARS-CoV-2. In one embodiment, the disease is COVID-19.

In certain aspects of the methods provided herein, the molecule is a bispecific molecule. In one aspect of the methods provided herein, the second binding domain of the multispecific molecule provided herein specifically binds to the surface of SARS-CoV-2. In another aspect of the methods provided herein, the second binding domain specifically binds to the spike glycoprotein on the surface of SARS-CoV-2. In certain aspects of the methods provided herein, the second binding domain specifically binds to the S1 subunit of the spike glycoprotein on the surface of SARS-CoV-2.

In another aspect of the methods provided herein, the second binding domain of the multispecific molecule provided herein comprises angiotensin-converting enzyme 2 (ACE2). In one aspect of the methods provided herein, the ACE2 comprises SEQ ID NO:194. In some embodiments of the methods provided herein, the second binding domain comprises the extracellular domain of ACE2. In one aspect of the methods provided herein, the extracellular domain of ACE2 comprises SEQ ID NO:134. In other embodiments of the methods provided herein, the second binding domain comprises a truncated extracellular domain of ACE2. In one aspect of the methods provided herein, the truncated extracellular domain of ACE2 comprises SEQ ID NO:120 or SEQ ID NO:121.

In one aspect of the methods provided herein, the first binding domain of the multispecific molecule provided herein comprises a single-domain antibody (VHH).

In one embodiment of the methods provided herein, the VHH comprises a complementarity determining region 1 (CDR1) having an amino acid sequence of SEQ ID NO:1, a CDR2 having an amino acid sequence of SEQ ID NO:2, and a CDR3 having an amino acid sequence of SEQ ID NO:3. In some embodiments of the methods provided herein, the VHH comprises an amino acid sequence of SEQ ID NO:16.

In one embodiment of the methods provided herein, the VHH comprises a CDR1 having an amino acid sequence of SEQ ID NO:17, a CDR2 having an amino acid sequence of SEQ ID NO:18, and a CDR3 having an amino acid sequence of SEQ ID NO:19. In some embodiments of the methods provided herein, the VHH comprises an amino acid sequence of SEQ ID NO:32.

In one aspect of the methods provided herein, the first binding domain specifically binds to pIgR that is present on the mucosal endothelium. In one embodiment of the methods provided herein, the first binding domain specifically binds to pIgR that is present on the lung mucosal endothelium In another aspect of the methods provided herein, the SARS-CoV-2 is neutralized when the molecule provided herein specifically binds to the pIgR and to SARS-CoV-2. In one embodiment of the methods provided herein, the molecule neutralizes SARS-CoV-2 with an $EC_{50}$ of less than about 4 nM. In a certain embodiment of the methods provided herein, the molecule neutralizes SARS-CoV-2 with an $EC_{50}$ of less than about 3 nM. In another embodiment of the methods provided herein, the molecule neutralizes SARS-CoV-2 with an $EC_{50}$ of less than about 1 nM. In another embodiment of the methods provided herein, the molecule neutralizes SARS-CoV-2 with an $EC_{50}$ of less than about 500 pM. In a certain embodiment of the methods provided herein, the molecule neutralizes SARS-CoV-2 with an $EC_{50}$ of less than about 100 pM.

In some embodiments of the methods provided herein, the subject is a subject in need thereof. In some embodiments of the methods provided herein, the subject is a human.

In one aspect, provided herein is a system comprising a means for providing a first binding domain that specifically binds to polymeric immunoglobulin receptor (pIgR) and a second binding domain that specifically binds to a second target that is not pIgR.

In another aspect, provided herein is a system comprising a means for providing a first binding domain that specifically binds to polymeric immunoglobulin receptor (pIgR) and a second binding domain that specifically binds to surface of SARS-CoV-2.

In certain aspects of the systems provided herein, the molecule is a bispecific molecule. In one aspect of the systems provided herein, the second binding domain of the multispecific molecule provided herein specifically binds to the surface of SARS-CoV-2. In another aspect of the systems provided herein, the second binding domain specifically binds to the spike glycoprotein on the surface of SARS-CoV-2. In certain aspects of the systems provided herein, the second binding domain specifically binds to the S1 subunit of the spike glycoprotein on the surface of SARS-CoV-2.

In another aspect of the systems provided herein, the second binding domain of the multispecific molecule provided herein comprises angiotensin-converting enzyme 2 (ACE2). In one aspect of the systems provided herein, the ACE2 comprises SEQ ID NO:194. In some embodiments of the systems provided herein, the second binding domain comprises the extracellular domain of ACE2. In one aspect of the systems provided herein, the extracellular domain of ACE2 comprises SEQ ID NO:134. In other embodiments of the systems provided herein, the second binding domain comprises a truncated extracellular domain of ACE2. In one aspect of the systems provided herein, the truncated extracellular domain of ACE2 comprises SEQ ID NO:120 or SEQ ID NO:121.

In one aspect of the systems provided herein, the first binding domain of the multispecific molecule provided herein comprises a single-domain antibody (VHH).

In one embodiment of the systems provided herein, the VHH comprises a complementarity determining region 1 (CDR1) having an amino acid sequence of SEQ ID NO:1, a CDR2 having an amino acid sequence of SEQ ID NO:2, and a CDR3 having an amino acid sequence of SEQ ID NO:3. In some embodiments of the systems provided herein, the VHH comprises an amino acid sequence of SEQ ID NO:16.

In one embodiment of the systems provided herein, the VHH comprises a CDR1 having an amino acid sequence of SEQ ID NO:17, a CDR2 having an amino acid sequence of SEQ ID NO:18, and a CDR3 having an amino acid sequence of SEQ ID NO:19. In some embodiments of the systems provided herein, the VHH comprises an amino acid sequence of SEQ ID NO:32.

In one aspect of the systems provided herein, the first binding domain specifically binds to pIgR that is present on the mucosal endothelium. In one embodiment of the systems provided herein, the first binding domain specifically binds to pIgR that is present on the lung mucosal endothelium In another aspect of the systems provided herein, the SARS-CoV-2 is neutralized when the molecule provided herein specifically binds to the pIgR and to SARS-CoV-2. In one embodiment of the systems provided herein, the molecule neutralizes SARS-CoV-2 with an $EC_{50}$ of less than about 4 nM. In a certain embodiment of the systems provided herein, the molecule neutralizes SARS-CoV-2 with an $EC_{50}$ of less than about 3 nM. In another embodiment of the systems provided herein, the molecule neutralizes SARS-CoV-2 with an $EC_{50}$ of less than about 1 nM. In another embodiment of the systems provided herein, the molecule neutralizes SARS-CoV-2 with an $EC_{50}$ of less than about 500 pM. In a certain embodiment of the systems provided herein, the molecule neutralizes SARS-CoV-2 with an $EC_{50}$ of less than about 100 pM.

In another aspect, provided herein is a multispecific molecule comprising: (a) a first binding domain that specifically binds to polymeric immunoglobulin receptor (pIgR), and (b) a second binding domain that specifically binds to a second target that is not a pIgR. In another aspect, the molecule is a bispecific molecule. In one aspect, the first binding domain of the multispecific molecule provided herein comprises a single-domain antibody (VHH). In one embodiment, the VHH comprises a complementarity determining region 1 (CDR1) having an amino acid sequence of SEQ ID NO:1, a CDR2 having an amino acid sequence of SEQ ID NO:2, and a CDR3 having an amino acid sequence of SEQ ID NO:3. In some embodiments, the VHH comprises an amino acid sequence of SEQ ID NO:16. In one embodiment, the VHH comprises a CDR1 having an amino acid sequence of SEQ ID NO:17, a CDR2 having an amino acid sequence of SEQ ID NO:18, and a CDR3 having an amino acid sequence of SEQ ID NO: 19. In some embodiments, the VHH comprises an amino acid sequence of SEQ ID NO:32. In one aspect of the multispecific molecule provided herein, the first binding domain specifically binds to pIgR that is present on the mucosal endothelium. In one embodiment, the first binding domain specifically binds to pIgR that is present on the lung mucosal endothelium.

In one embodiment, the multispecific molecule provided herein comprises an Fc region from an IgG antibody. In one aspect, the IgG molecule is an IgG1, IgG2, IgG3, or IgG4 antibody.

In one embodiment of the multispecific molecule provided herein, the first binding domain specifically binds a pIgR antigen. In another embodiment, the first binding domain specifically binds an extracellular pIgR epitope. In one embodiment of the multispecific molecule provided herein, CDR1, CDR2, and CDR3 form a binding site for an antigen of the pIgR. In another embodiment, the CDR1, CDR2, and CDR3 form a binding site for an epitope of the pIgR.

In one aspect, the second target of the multispecific molecule provided herein is on the surface of a second cell. In another aspect, the second target is on the surface of a virus. In one aspect, the virus of SARS-CoV-2. In one aspect, the second target is the spike glycoprotein. In another aspect, the second target is the S1 subunit of the spike glycoprotein.

In another aspect, the second binding domain of the multispecific molecule provided herein comprises angiotensin-converting enzyme 2 (ACE2). In one aspect, the ACE2 comprises SEQ ID NO:194. In some embodiments, the second binding domain comprises the extracellular domain of ACE2. In one aspect, the extracellular domain of ACE2 comprises SEQ ID NO:134. In other embodiments, the second binding domain comprises a truncated extracellular domain of ACE2. In one aspect, the truncated extracellular domain of ACE2 comprises SEQ ID NO:120 or SEQ ID NO:121.

In one aspect, the second cell or virus is neutralized when the multispecific molecule provided herein specifically binds to the pIgR and to the second target on the surface of the second cell or virus. In one embodiment, the molecule neutralizes the second cell with an $EC_{50}$ of less than about 4 nM. In one embodiment, the molecule neutralizes the second cell or virus with an $EC_{50}$ of less than about 3 nM. In one embodiment, the molecule neutralizes the second cell or virus with an $EC_{50}$ of less than about 1 nM. In one embodiment, the molecule neutralizes the second cell or virus with an $EC_{50}$ of less than about 500 pM. In one embodiment, the molecule neutralizes the second cell or virus with an $EC_{50}$ of less than about 100 pM.

Provided herein, in one aspect, is a molecule comprising: a first means capable of binding pIgR on the mucosal endothelium; and a second means capable of binding a second target that is not pIgR. In one aspect, the second target is on the surface of a second cell.

In one embodiment, provided herein is a molecule comprising: a first means capable of binding pIgR on the mucosal endothelium; and a second means capable of binding a second target on the surface of a second cell or on the surface of a virus. In one embodiment, the virus is SARS-CoV-2.

In one aspect, provided herein is a nucleic acid encoding a multispecific molecule comprising: (a) a first binding domain that specifically binds to polymeric immunoglobulin receptor (pIgR), and (b) a second binding domain that specifically binds to SARS-CoV-2. In certain aspects of the nucleic acid provided herein, the molecule is a bispecific molecule.

In one aspect of the nucleic acid provided herein, the second binding domain of the multispecific molecule provided herein specifically binds to the surface of SARS-CoV-2. In another aspect of the nucleic acid provided herein, the second binding domain specifically binds to the spike glycoprotein on the surface of SARS-CoV-2. In certain aspects of the nucleic acid provided herein, the second binding domain specifically binds to the S1 subunit of the spike glycoprotein on the surface of SARS-CoV-2.

In another aspect of the nucleic acid provided herein, the second binding domain of the multispecific molecule provided herein comprises angiotensin-converting enzyme 2 (ACE2). In one aspect of the nucleic acid provided herein, the ACE2 comprises SEQ ID NO:194. In some embodiments of the nucleic acid provided herein, the second binding domain comprises the extracellular domain of ACE2. In one aspect of the nucleic acid provided herein, the extracellular domain of ACE2 comprises SEQ ID NO:134. In other embodiments of the nucleic acid provided herein, the second binding domain comprises a truncated extracellular domain of ACE2. In one aspect of the nucleic acid provided herein, the truncated extracellular domain of ACE2 comprises SEQ ID NO:120 or SEQ ID NO:121.

In one aspect of the nucleic acid provided herein, the first binding domain of the multispecific molecule provided herein comprises a single-domain antibody (VHH).

In one embodiment of the nucleic acid provided herein, the VHH comprises a complementarity determining region 1 (CDR1) having an amino acid sequence of SEQ ID NO:1, a CDR2 having an amino acid sequence of SEQ ID NO:2, and a CDR3 having an amino acid sequence of SEQ ID NO:3. In some embodiments of the nucleic acid provided herein, the VHH comprises an amino acid sequence of SEQ ID NO:16.

In one embodiment of the nucleic acid provided herein, the VHH comprises a CDR1 having an amino acid sequence of SEQ ID NO:17, a CDR2 having an amino acid sequence of SEQ ID NO:18, and a CDR3 having an amino acid sequence of SEQ ID NO:19. In some embodiments of the nucleic acid provided herein, the VHH comprises an amino acid sequence of SEQ ID NO:32.

In one aspect of the nucleic acid provided herein, the first binding domain specifically binds to pIgR that is present on the mucosal endothelium. In one embodiment of the nucleic acid provided herein, the first binding domain specifically binds to pIgR that is present on the lung mucosal endothelium In another aspect of the nucleic acid provided herein, the SARS-CoV-2 is neutralized when the molecule provided herein specifically binds to the pIgR and to SARS-CoV-2. In one embodiment of the nucleic acid provided herein, the molecule neutralizes SARS-CoV-2 with an $EC_{50}$ of less than about 4 nM. In a certain embodiment of the nucleic acid provided herein, the molecule neutralizes SARS-CoV-2 with an $EC_{50}$ of less than about 3 nM. In another embodiment of the nucleic acid provided herein, the molecule neutralizes SARS-CoV-2 with an $EC_{50}$ of less than about 1 nM. In another embodiment of the nucleic acid provided herein, the molecule neutralizes SARS-CoV-2 with an $EC_{50}$ of less than about 500 pM. In a certain embodiment of the nucleic acid provided herein, the molecule neutralizes SARS-CoV-2 with an $EC_{50}$ of less than about 100 pM.

Also provided is a vector comprising the nucleic acid described herein. In one aspect, also provided is a host cell comprising the vector provided herein. In another aspect, provided herein is a kit comprising the vector and packaging for the same.

In one aspect, provided herein is a pharmaceutical composition comprising the molecule of any one of the previous embodiments, and a pharmaceutically acceptable carrier. In another aspect, provided herein is a pharmaceutical composition comprising the means for delivering the molecule of any one of the previous embodiments, and a pharmaceutically acceptable carrier. Also provided is a method of producing the pharmaceutical composition, comprising combining the molecule with a pharmaceutically acceptable carrier to obtain the pharmaceutical composition.

In one aspect, provided herein is a method of inhibiting host cell entry or proliferation of target cells expressing the second target, the method comprising contacting the target cells with the molecule of any of the previous embodiments, wherein contacting the target cells with the molecule inhibits host cell entry or proliferation of the target cells.

In another aspect, provided herein is a method for eliminating target cells expressing the second target in a subject, comprising administering an effective amount of the molecule of any of the previous embodiments to the subject. In one aspect, the subject has COVID-19. In one aspect, the subject is a subject in need thereof. In another aspect, the subject is a human.

In one aspect, provided herein is a method of treating a disease caused all or in part by cells expressing the second target in a subject, comprising administering an effective amount of the molecule of any of the previous embodiments to the subject. In one aspect, the disease is COVID-19. In one aspect, the subject is a subject in need thereof. In another aspect, the subject is a human.

In one aspect, provided herein is a system comprising a means for providing a first binding domain that specifically binds to polymeric immunoglobulin receptor (pIgR) and a second binding domain that specifically binds to a second target that is not pIgR.

In another aspect, provided herein is a process for making a molecule that specifically binds to more than one target molecule, the process comprising: a step for performing a function of obtaining a binding domain capable of binding to pIgR on mucosal endothelium; a step for performing a function of obtaining a binding domain capable of binding to a second target on a second cell or on a virus; and a step for performing a function of providing a molecule capable of binding to a pIgR antigen on mucosal endothelium and a second target on a second cell or on a virus. In some embodiments of the process, the step for performing a function of obtaining a binding domain capable of binding to a second target is repeated n times and further comprising n steps for performing a function of providing a binding domain capable of binding to a pIgR on mucosal endothelium and n number of target molecules, wherein n is at least 2. In some embodiments of the process, the second target is on the surface of the second cell. In some embodiments of the process, the second target is on the surface of a virus. In some embodiments of the process, the virus is SARS-CoV-2.

In some embodiments of the process, the binding domain capable of binding to pIgR specifically binds a pIgR antigen. In other embodiments of the process, the binding domain capable of binding to pIgR specifically binds a pIgR epitope. In some embodiments of the process, the binding domain capable of binding to a second target is an antigen. In some embodiments of the process, the binding domain capable of binding to a second target is an epitope of the second target.

5. BRIEF DESCRIPTION OF THE DRAWINGS

The foregoing summary, as well as the following detailed description of specific embodiments of the present application, will be better understood when read in conjunction with the appended drawings. It should be understood, however, that the application is not limited to the precise embodiments shown in the drawings.

FIG. 1 shows summary of the mechanism of pIgR-based targeted transport. SARS-CoV-2 viral entry occurs upon binding of the RBD domain of its spike glycoprotein to the ACE2 receptor on target cells. Bispecific molecules gain access to the lung mucosa through pIgR-mediated transport and bind/neutralize SARS-CoV-2 by binding the RBD domain through their ACE2 ECD moiety in a steric mechanism.

FIGS. 2A-2E provide description of SARS-CoV-2 spike glycoprotein and ACE2. FIG. 2A shows the domain architecture of the spike glycoprotein showing the S1 and S2 furin-cleavage products: SP—signal peptide, NTD—N-terminal domain, RBD—receptor-binding domain, FP—fusion peptide, HR1—heptad repeat 1, HR2—heptad repeat 2, TM—transmembrane domain, IC—intracellular domain. Domain boundaries are numbered. FIG. 2B shows the sequence alignment of the RBD domains of SARS-CoV-2 and SARS-CoV. Residues which interact (based on 5 Å cutoff from PDB ID 6M0J) are underlined. FIG. 2C shows domain architecture of the ACE2 enzyme. Constructs used to generate the bispecific molecules are indicated below. FIG. 2D shows the sequence of the human ACE2 ECD. Residues which interact with SARS-CoV-2 spike glycoprotein are underlined. FIG. 2E shows a cartoon representation of the crystal structure of SARS-CoV-2 spike glycoprotein RBD bound to ACE2 (PBD ID 6MOJ).

FIG. 3 shows the bispecific molecules that were generated with VHH2/6 and the extracellular domain (ECD) from ACE2.

FIGS. 4A-4B show Surface Biolayer Interferometry-based binding of bispecific molecules to spike glycoprotein and to pIgR. Antibodies and antigens are indicated in the graphs. Graphs represent magnitude of response (nm) over time. Association and dissociation are displayed along with fitted curves. FIG. 4A describes the binding of the bispecific molecules to pIgR and to wild-type spike glycoprotein and FIG. 4B describes the binding to the spike glycoprotein variants Y435F, N439K, N501Y, and D614G.

FIGS. 5A-5B show that the bispecific molecules display specific functional activity against SARS-CoV-2. In FIG. 5A, the neutralizing ability is plotted vs. molecule concentration. Molecules are indicated in the graph. FIG. 5B shows PBMC-mediated ADCC of MDCK-pIgR cells is plotted as green area per well (normalized to 0 h) vs concentration of bispecific molecules (nM). Molecules are indicated in the legend.

Figure 8:
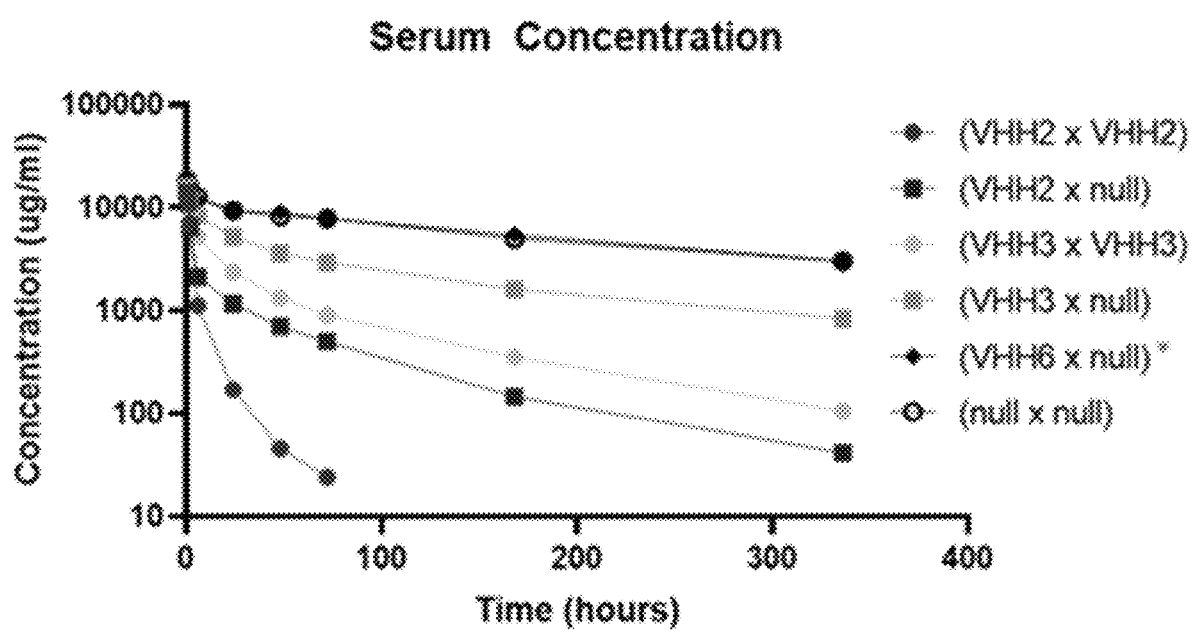

FIG. 8 shows pharmacokinetic analysis of anti-pIgR VHH-Fc molecules. Serum concentration (pg/mL) is plotted vs time after injection (h). Antibodies were formatted as VHH-Fc fusions having a heterodimeric Fc. Each VHH-Fc was co-expressed with its complementary VHH-Fc fusion having either the same VHH or a null VHH (EGFW55).

Figure 9A:
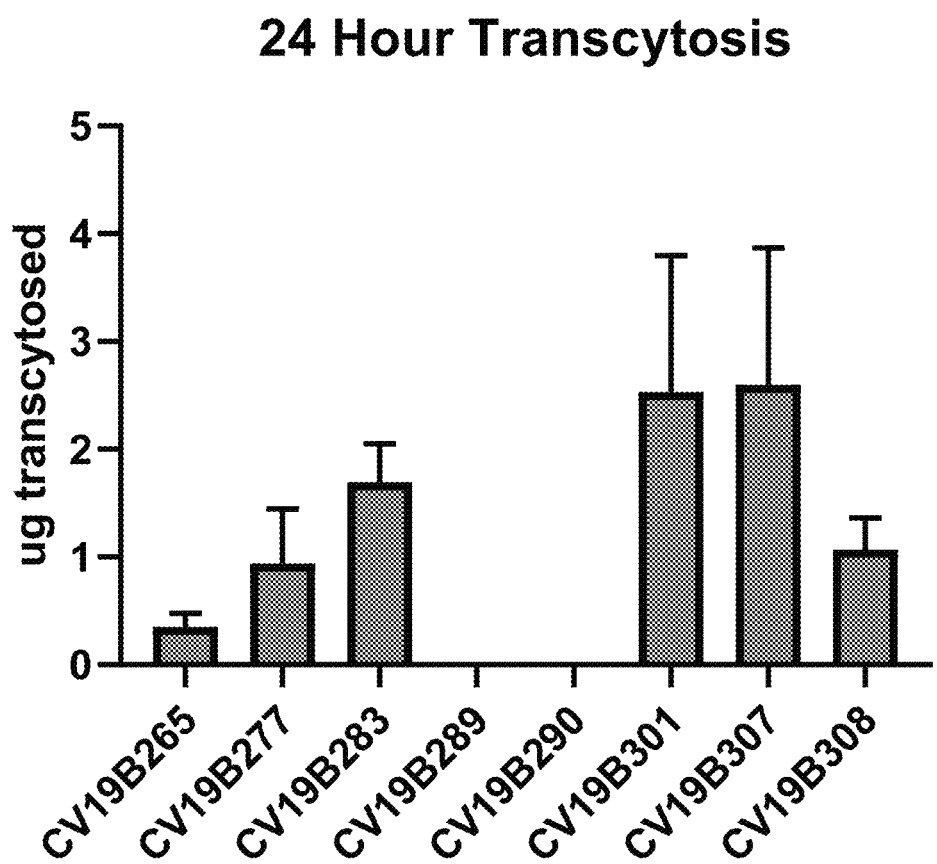
Figure 9B:
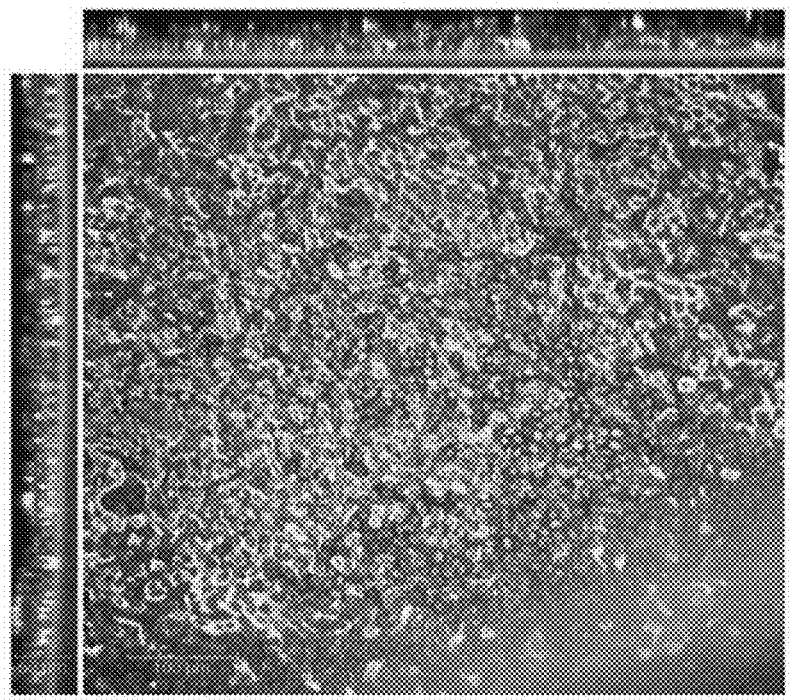
Figure 9C:
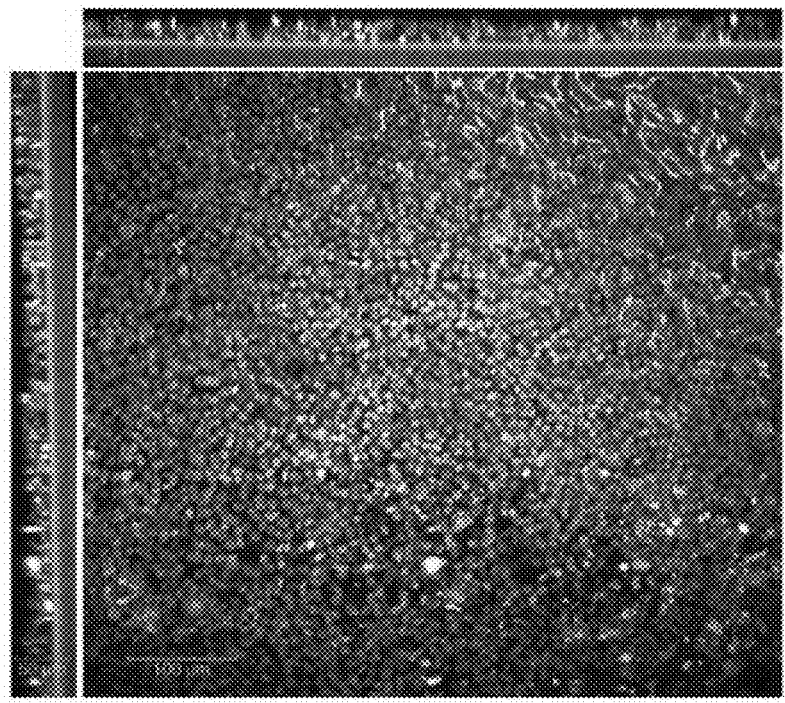

FIGS. 9A-9C show transcytosis in lung microtissues. FIG. 9A shows transcytosis of bispecific fusion molecules in EpiAirway tissue model in 24 hours post application. For each sample, 20 µg of protein was added to the basolateral well, and after 24 hr, the mucosal surface was washed and the levels of transcytosed molecules were quantified. Levels are shown in total micrograms transcytosed in a 24 hr period. Error bars represent standard error and are representative of at least 2 independent experiments. FIG. 9B shows confocal image showing the human epiairway microtissue for CV19B307. Staining shows: blue (nuclei), green (anti-VHH), and red (pIgR). Scale bars show 50 µm (insets) and 100 µm (main image). FIG. 9C shows confocal image showing the human epiairway microtissue for CV19B290. Staining shows: blue (nuclei), green (anti-VHH), and red (pIgR). Scale bars show 50 µm (insets) and 100 µm (main image).

6. DETAILED DESCRIPTION

The present disclosure is based, in part, on the surprising finding that multispecific molecules comprising a first binding domain that binds to polymeric immunoglobulin receptor (pIgR), and a second binding domain that binds to SARS-CoV-2 can efficiently transcytose across the lung epithelium where they are able to bind and neutralize SARS-CoV-2. The compositions and methods of the invention thus provide an avenue for systemic administration of proteins targeted to the lung mucosa to treat COVID-19.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

It should also be understood that the terms "about," "approximately," "generally," "substantially," and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

As used herein, the term "polynucleotide," synonymously referred to as "nucleic acid molecule," "nucleotides" or "nucleic acids," refers to any polyribonucleotide or polydeoxyribonucleotide, which can be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

As used herein, the term "vector" is a replicon in which another nucleic acid segment can be operably inserted so as to bring about the replication or expression of the segment.

As used herein, the term "host cell" refers to a cell comprising a nucleic acid molecule of the invention. The "host cell" can be any type of cell, e.g., a primary cell, a cell in culture, or a cell from a cell line. In one embodiment, a "host cell" is a cell transfected with a nucleic acid molecule disclosed herein. In another embodiment, a "host cell" is a progeny or potential progeny of such a transfected cell. A progeny of a cell may or may not be identical to the parent cell, e.g., due to mutations or environmental influences that can occur in succeeding generations or integration of the nucleic acid molecule into the host cell genome.

The term "expression" as used herein, refers to the biosynthesis of a gene product. The term encompasses the transcription of a gene into RNA. The term also encompasses translation of RNA into one or more polypeptides, and further encompasses all naturally occurring post-transcriptional and post-translational modifications. The expressed bispecific molecule can be within the cytoplasm of a host cell, into the extracellular milieu such as the growth medium of a cell culture or anchored to the cell membrane.

As used herein, the terms "peptide," "polypeptide," or "protein" can refer to a molecule comprised of amino acids and can be recognized as a protein by those of skill in the art. The conventional one-letter or three-letter code for amino acid residues is used herein. The terms "peptide," "polypeptide," and "protein" can be used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The peptide sequences described herein are written according to the usual convention whereby the N-terminal region of the peptide is on the left and the C-terminal region is on the right. Although isomeric forms of the amino acids are known, it is the L-form of the amino acid that is represented unless otherwise expressly indicated.

As used herein, the term "antibody" is used in a broad sense and includes immunoglobulin or antibody molecules including human, humanized, composite and chimeric antibodies and antibody fragments that are monoclonal or polyclonal. In general, antibodies are proteins or peptide chains that exhibit binding specificity to a specific antigen. Antibody structures are well known. Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Accordingly, the antibodies provided herein can be of any of the five major classes or corresponding sub-classes. In specific embodiments, the antibodies provided herein are IgG1, IgG2, IgG3 or IgG4. Antibody light chains of vertebrate species can be assigned to one of two clearly distinct types, namely kappa and lambda, based on the amino acid sequences of their constant domains. Accordingly, the antibodies provided herein can contain a kappa or lambda light chain constant domain. According to particular embodiments, the antibodies disclosed herein include heavy and/or light chain constant regions from rat or human antibodies.

In addition to the heavy and light constant domains, antibodies contain an antigen-binding region that is made up of a light chain variable region (VL) and a heavy chain variable region (VH), each of which contains three domains (i.e., complementarity determining regions 1 (CDR1), CDR2 and CDR3. A "CDR" refers to one of three hypervariable regions (HCDR1, HCDR2 or HCDR3) within the non-framework region of the immunoglobulin (Ig or antibody) VH β-sheet framework, or one of three hypervariable regions (LCDR1, LCDR2 or LCDR3) within the non-framework region of the antibody VL β-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., *J. Biol. Chem.* 252:6609-6616 (1977); Kabat, *Adv. Prot. Chem.* 32:1-75 (1978)). CDR region sequences also have been defined structurally by Chothia as those residues that are not part of the conserved β-sheet framework, and thus are able to adapt different conformations (Chothia and Lesk, *J. Mol. Biol.* 196:901-917 (1987)). Both terminologies are well recognized in the art. CDR region sequences have also been defined by AbM, Contact and IMGT. Exemplary CDR region sequences are illustrated herein, for example, in the Sequence Listing, and tables provided in the Examples below. The positions of CDRs within a canonical antibody variable region have been determined by comparison of numerous structures (Al-Lazikani et al., *J. Mol. Biol.* 273: 927-948 (1997); Morea et al., *Methods* 20:267-279 (2000)). Because the number of residues within a hypervariable region varies in different antibodies, additional residues relative to the canonical positions are conventionally numbered with a, b, c and so forth next to the residue number in the canonical variable region numbering scheme (Al-Lazikani et al., supra (1997)). Such nomenclature is similarly well known to those skilled in the art.

The light chain variable region CDR1 domain is interchangeably referred to herein as LCDR1 or VL CDR1. The light chain variable region CDR2 domain is interchangeably referred to herein as LCDR2 or VL CDR2. The light chain variable region CDR3 domain is interchangeably referred to herein as LCDR3 or VL CDR3. The heavy chain variable region CDR1 domain is interchangeably referred to herein as HCDR1 or VH CDR1. The heavy chain variable region CDR2 domain is interchangeably referred to herein as HCDR2 or VH CDR2. The heavy chain variable region CDR1 domain is interchangeably referred to herein as HCDR3 or VH CDR3.

The term "hypervariable region", such as a VH or VL, when used herein refers to the regions of an antibody variable region that are hypervariable in sequence and/or form structurally defined loops. Generally, antibodies comprise six hypervariable regions; three in the VH (HCDR1, HCDR2, HCDR3), and three in the VL (LCDR1, LCDR2, LCDR3). A number of hypervariable region delineations are in use and are encompassed herein. The "Kabat" CDRs are based on sequence variability and are the most commonly used (see, e.g., Kabat et al., *Sequences of Proteins of Immunological Interest,* 5th Ed. Public Health Service, National Institutes of Health, Bethesda, MD (1991)). "Chothia" refers instead to the location of the structural loops (see, e.g., Chothia and Lesk, *J. Mol. Biol.* 196:901-917 (1987)). The end of the Chothia CDR-HCDR1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The "AbM" hypervariable regions represent a compromise between the Kabat CDRs and Chothia structural loops, and are used by Oxford Molecular's AbM antibody modeling software (see, e.g., Martin, in *Antibody Engineering,* Vol. 2, Chapter 3, Springer Verlag). "Contact" hypervariable regions are based on an analysis of the available complex crystal structures.

Recently, a universal numbering system has been developed and widely adopted, ImMunoGeneTics (IMGT) Information System® (Lafranc et al., *Dev. Comp. Immunol.* 27(1):55-77 (2003)). IMGT is an integrated information system specializing in immunoglobulins (IG), T cell receptors (TR) and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues and are readily identified. This information can be used in grafting and replacement of CDR residues from immunoglobulins of one species into an acceptor framework from, typically, a human antibody. An additional numbering system (AHon) has been developed by Honegger and Plückthun, *J. Mol. Biol.* 309: 657-670 (2001). Correspondence between the numbering system, including, for example, the Kabat numbering and the IMGT unique numbering system, is well known to one skilled in the art (see, e.g., Kabat, supra; Chothia and Lesk, supra; Martin, supra; Lefranc et al., supra). An Exemplary system, shown herein, combines Kabat and Chothia.

|  | Exemplary | IMGT | Kabat | AbM | Chothia | Contact |
| --- | --- | --- | --- | --- | --- | --- |
| $V_H$ CDR1 | 26-35 | 27-38 | 31-35 | 26-35 | 26-32 | 30-35 |
| $V_H$ CDR2 | 50-65 | 56-65 | 50-65 | 50-58 | 53-55 | 47-58 |
| $V_H$ CDR3 | 95-102 | 105-117 | 95-102 | 95-102 | 96-101 | 93-101 |
| $V_L$ CDR1 | 24-34 | 27-38 | 24-34 | 24-34 | 26-32 | 30-36 |
| $V_L$ CDR2 | 50-56 | 56-65 | 50-56 | 50-56 | 50-52 | 46-55 |
| $V_L$ CDR3 | 89-97 | 105-117 | 89-97 | 89-97 | 91-96 | 89-96 |

Hypervariable regions may comprise "extended hypervariable regions" as follows: 24-36 or 24-34 (LCDR1), 46-56 or 50-56 (LCDR2) and 89-97 or 89-96 (LCDR3) in the VL and 26-35 or 26-35A (HCDR1), 50-65 or 49-65 (HCDR2) and 93-102, 94-102, or 95-102 (HCDR3) in the VH. CDR sequences, reflecting each of the above numbering schemes, are provided herein, including in the Sequence Listing.

The term "constant region" or "constant domain" refers to a carboxy terminal portion of the light and heavy chain which is not directly involved in binding of the antibody to antigen but exhibits various effector function, such as interaction with the Fc receptor. The terms refer to the portion of an immunoglobulin molecule having a more conserved amino acid sequence relative to the other portion of the immunoglobulin, the variable region, which contains the antigen binding site. The constant region may contain the CH1, CH2 and CH3 regions of the heavy chain and the CL region of the light chain.

The term "framework" or "FR" residues are those variable region residues flanking the CDRs. FR residues are present, for example, in chimeric, humanized, human, domain antibodies, diabodies, linear antibodies, and bispecific antibodies. FR residues are those variable domain residues other than the hypervariable region residues or CDR residues.

As used herein, the term an "isolated antibody" refers to an antibody which is substantially free of other antibodies having different antigenic specificities (e.g., an isolated antibody that specifically binds to a target antigen is substantially free of antibodies that do not bind to the target antigen; an isolated antibody that specifically binds to a second target antigen is substantially free of antibodies that do not bind to the second target antigen. In addition, an isolated antibody is substantially free of other cellular material and/or chemicals.

As used herein, the term "monoclonal antibody" refers to an antibody obtained from a population of substantially homogeneous antibodies, i.e., the individual antibodies comprising the population are identical except for possible naturally occurring mutations that can be present in minor amounts. The monoclonal antibodies disclosed herein can be made by the hybridoma method, phage display technology, single lymphocyte gene cloning technology, or by recombinant DNA methods. For example, the monoclonal antibodies can be produced by a hybridoma, which includes a B cell obtained from a transgenic nonhuman animal, such as a transgenic mouse or rat, having a genome comprising a human heavy chain transgene and a light chain transgene.

As used herein, the term "antigen-binding fragment" refers to an antibody fragment such as, for example, a diabody, a Fab, a Fab', a F(ab')2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdAb) an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the heavy chain. According to other particular embodiments, the antigen-binding fragment comprises Fab and F(ab').

As used herein, the term "single-chain antibody" refers to a conventional single-chain antibody in the field, which comprises a heavy chain variable region and a light chain variable region connected by a short peptide of about 15 to about 20 amino acids.

As used herein, the term "single domain antibody" or "sdAb" refers to a single monomeric variable antibody domain and which is capable of antigen binding (e.g., single domain antibodies that bind to pIgR). Single domain antibodies include VHH domains as described herein. The single domain antibodies provided herein transport from an apical surface to a basolateral surface (reverse transcytosis) as well as from the basolateral to apical side (transcytosis). Examples of single domain antibodies include, but are not limited to, antibodies naturally devoid of light chains such as those from Camelidae species (e.g., llama), single domain antibodies derived from conventional 4-chain antibodies, engineered antibodies and single domain scaffolds other than those derived from antibodies. Single domain antibodies may be derived from any species including, but not limited to mouse, human, camel, llama, goat, rabbit, and bovine. For example, a single domain antibody can be derived from antibodies raised in Camelidae species, for example in camel, llama, dromedary, alpaca and guanaco, as described herein. Other species besides Camelidae may produce heavy chain antibodies naturally devoid of light chain; VHHs derived from such other species are within the scope of the disclosure. In some embodiments, the single domain antibody (e.g., VHH) provided herein has a structure of FR1-CDR1-FR2-CDR2-FR3-CDR3-FR4. Single domain antibodies may be genetically fused or chemically conjugated to another molecule (e.g., an agent) as described herein.

As used herein, the term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide.

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "chimeric antibody" refers to an antibody wherein the amino acid sequence of the immunoglobulin molecule is derived from two or more species. The variable region of both the light and heavy chains often corresponds to the variable region of an antibody derived from one species of mammal (e.g., mouse, rat, rabbit, etc.) having the desired specificity, affinity, and capability, while the constant regions correspond to the sequences of an antibody derived from another species of mammal (e.g., human) to avoid eliciting an immune response in that species.

As used herein, the term "multispecific molecule" refers to a molecule that comprises multiple binding domains, each capable of specifically binding a target molecule, ligand or fragments thereof. As such, while a multispecific molecule can be a multispecific antibody, its binding domains are not limited to antibodies, fragments thereof or any other antibody-related molecules comprised of antibody components (i.e. scFvs), but include binding domains that are non-antibody proteins and fragments thereof, including recombinant antigens, that can specifically bind another protein, ligand of fragment thereof. In an embodiment, a multispecific molecule can comprise a first binding domain comprising an immunoglobulin variable domain sequence which has binding specificity for a first epitope (e.g., an epitope on a pIgR) and a second binding domain that specifically binds to target protein of interest, or fragment thereof (e.g. the extracellular domain of angiotensin-converting enzyme 2 (ACE2).

The term "bispecific molecule" refers to a molecule that has two binding domains, each capable of specifically binding a target protein, ligand or fragments thereof. As such, while a bispecific molecule can be a bispecific antibody, its binding domains are not limited to antibodies, fragments thereof or any other antibody-related molecules comprised of antibody components (i.e. scFvs), but include binding domains that are non-antibody proteins, ligands and fragments thereof, including recombinant antigens, that can specifically bind another protein. In an embodiment, a bispecific molecule can comprise a first binding domain comprising an immunoglobulin variable domain sequence which has binding specificity for a first epitope (e.g., an epitope on a pIgR) and a second binding domain that specifically binds to target protein of interest, or fragment thereof (e.g. the extracellular domain of angiotensin-converting enzyme 2 (ACE2).

As used herein, the term "multispecific antibody" refers to an antibody that comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes do not overlap or do not substantially overlap. In an embodiment, the first and second epitopes are on different antigens, e.g., the different proteins (or different subunits of a multimeric protein). In an embodiment, a multispecific antibody comprises a third, fourth, or fifth immunoglobulin variable domain. In an embodiment, a multispecific antibody is a bispecific antibody molecule, a trispecific antibody molecule, or a tetraspecific antibody molecule.

As used herein, the term "bispecific antibody" refers to a multispecific antibody that binds no more than two epitopes or two antigens. A bispecific antibody is characterized by a first immunoglobulin variable domain sequence which has binding specificity for a first epitope (e.g., an epitope on a pIgR) and a second immunoglobulin variable domain sequence that has binding specificity for a second epitope. In an embodiment, the first and second epitopes are on different antigens, e.g., the different proteins (or different subunits of a multimeric protein). In an embodiment, a bispecific antibody comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody comprises a single domain antibody, or fragment thereof, having binding specificity for a first epitope and an antibody, or any fragment thereof, having binding specificity for a second epitope. In an embodiment, a bispecific antibody comprises a scFv, or fragment thereof, having binding specificity for a first epitope, and a scFv, or fragment thereof, having binding specificity for a second epitope.

The terms "binds" or "binding" refer to an interaction between molecules including, for example, to form a complex. The term "binding domain" refers to a portion of a multispecific or bispecific molecule responsible for a specific binding interaction with another molecule or ligand. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions, or forces. The strength of the total non-covalent interactions between a single antigen-binding site on an antibody and a single epitope of a target molecule, such as an antigen, is the affinity of the antibody or functional fragment for that epitope. The ratio of dissociation rate ($k_{off}$) to association rate ($k_{on}$) of a binding molecule (e.g., an antibody) to a monovalent antigen ($k_{off}/k_{on}$) is the dissociation constant $K_D$, which is inversely related to affinity. The lower the $K_D$ value, the higher the affinity of the antibody. The value of $K_D$ varies for different complexes of binding molecules and their ligands (i.e. antibody and antigen) and depends on both $k_{on}$ and $k_{off}$. A binding domain that can specifically bind the target with a KD of 1×10-7 M or less, such as 1×10-8 M or less, 5×10-9 M or less, 1×10-9 M or less, 5×10-10 M or less, or 1×10-10 M or less. The dissociation constant $K_D$ for an antibody provided herein can be determined using any method provided herein or any other method well known to those skilled in the art. The affinity at one binding site does not always reflect the true strength of the interaction between an antibody and an antigen. When complex antigens containing multiple, repeating antigenic determinants, such as a polyvalent antigen, come in contact with antibodies containing multiple binding sites, the interaction of antibody with antigen at one site will increase the probability of a reaction at a second site. The strength of such multiple interactions between a multivalent antibody and antigen is called the avidity.

In connection with the binding molecules described herein terms such as "bind to," "that specifically bind to," and analogous terms are also used interchangeably herein and refer to binding molecules of antigen binding domains that specifically bind to an antigen, such as a polypeptide. A binding molecule or antigen binding domain that binds to or specifically binds to an antigen may be cross-reactive with related antigens. In certain embodiments, a binding molecule or antigen binding domain that binds to or specifically binds to an antigen does not cross-react with other antigens. A binding molecule or antigen binding domain that binds to or specifically binds to an antigen can be identified, for example, by immunoassays, Octet®, Biacore®, or other techniques known to those of skill in the art. In some embodiments, a binding molecule or antigen binding domain binds to or specifically binds to an antigen when it binds to an antigen with higher affinity than to any cross-reactive antigen as determined using experimental techniques, such as radioimmunoassays (RIA) and enzyme linked immunosorbent assays (ELISAs). Typically, a specific or selective reaction will be at least twice background signal or noise and may be more than 10 times background. See, e.g., *Fundamental Immunology* 332-36 (Paul ed., 2d ed. 1989) for a discussion regarding binding specificity. In certain embodiments, the extent of binding of a binding molecule or antigen binding domain to a "non-target" protein is less than about 10% of the binding of the binding molecule or antigen binding domain to its particular target antigen, for example, as determined by fluorescence activated cell sorting (FACS) analysis or RIA. With regard terms such as "specific binding," "specifically binds to," or "is specific for" means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. A binding molecule or antigen binding domain that binds to an antigen includes one that is capable of binding the antigen with sufficient affinity such that the binding molecule is useful, for example, as a diagnostic agent in targeting the antigen. In certain embodiments, a binding molecule or antigen binding domain that binds to an antigen has an equilibrium dissociation constant ($K_D$) of less than or equal to 800 nM, 600 nM, 550 nM, 500 nM, 300 nM, 250 nM, 100 nM, 50 nM, 10 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM. In certain embodiments, a binding molecule or antigen binding domain binds to an epitope of an antigen that is conserved among the antigen from different species (e.g., between human and cyno species).

"Binding affinity" generally refers to the strength of the sum total of noncovalent interactions between a single binding site of a molecule (e.g., a binding protein such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a binding molecule X for its binding partner Y can generally be represented by the equilibrium dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative embodiments include the following. In one embodiment, the "$K_D$" or "$K_D$ value" may be measured by assays known in the art, for example by a binding assay. The $K_D$ may be measured in a RIA, for example, performed with the Fab version of an antibody of interest and its antigen (Chen et al., 1999, J. Mol Biol 293:865-81). The $K_D$ or $K_D$ value may also be measured by using biolayer interferometry (BLI) or surface plasmon resonance (SPR) assays by Octet®, using, for example, an Octet® Red96 system, or by Biacore®, using, for example, a Biacore® TM-2000 or a Biacore® TM-3000. An "on-rate" or "rate of association" or "association rate" or "$k_{on}$" may also be determined with the same biolayer interferometry (BLI) or surface plasmon resonance (SPR) techniques described above using, for example, the Octet® Red96, the Biacore® TM-2000, or the Biacore® TM-3000 system.

In certain embodiments, the binding molecules or antigen binding domains can comprise "chimeric" sequences in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., 1984, Proc. Natl. Acad. Sci. USA 81:6851-55). Chimeric sequences may include humanized sequences.

In certain embodiments, the binding molecules or antigen binding domains can comprise portions of "humanized" forms of nonhuman (e.g., camelid, murine, non-human primate) antibodies that include sequences from human immunoglobulins (e.g., recipient antibody) in which the native CDR residues are replaced by residues from the corresponding CDR of a nonhuman species (e.g., donor antibody) such as camelid, mouse, rat, rabbit, or nonhuman primate having the desired specificity, affinity, and capacity. In some instances, one or more FR region residues of the human immunoglobulin sequences are replaced by corresponding nonhuman residues. Furthermore, humanized antibodies can comprise residues that are not found in the recipient antibody or in the donor antibody. These modifications are made to further refine antibody performance. A humanized antibody heavy or light chain can comprise substantially all of at least one or more variable regions, in which all or substantially all of the CDRs correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. For further details, see, Jones et al., 1986, Nature 321:522-25; Riechmann et al., 1988, Nature 332:323-29; Presta, 1992, Curr. Op. Struct. Biol. 2:593-96; Carter et al., 1992, Proc. Natl. Acad. Sci. USA 89:4285-89; U.S. Pat. Nos. 6,800,738; 6,719,971; 6,639,055; 6,407,213; and 6,054,297.

As used herein, the term "SARS-CoV-2" refers to the virus responsible for coronavirus disease 2019 (COVID-19). The SARS-CoV-2 genome comprises of around 30,000 nucleotides organized into specific genes encoding structural proteins and nonstructural proteins. The full-length viral nucleotide sequence of the reference SARS-CoV-2 is provided by GenBank Accession Number MN908947. Structural proteins include spike (S), envelope (E), membrane (M), and nucleocapsid (N) proteins. Surface S glycoprotein is involved in the interaction with the host's angiotensin-converting enzyme 2 (ACE2) receptor and plays an important role in rapid human to human transmission. A defined receptor-binding domain (RBD) on S mediates this interaction. Nonstructural proteins, which are generated as cleavage products of the open reading frame 1ab (ORF 1ab) viral polyproteins, assemble to facilitate viral replication and transcription. RNA-dependent RNA polymerase, also known as Nsp12, is the key component that regulates viral RNA synthesis with the assistance of Nsp7 and Nsp8. In addition, five accessory proteins are encoded by ORF3a, ORF6, ORF7a ORF8, and ORF10 genes. Reference full length SARS-CoV-2 amino acid sequence are provided by GenBank Accession Numbers QHD43415-QHD43423, QHI42199.

As used herein, the terms "angiotensin-converting enzyme 2" and "ACE 2" refer to a protein that has a multiplicity of physiological roles that revolve around its trivalent function: a negative regulator of the renin-angiotensin system, facilitator of amino acid transport, and the severe acute respiratory syndrome-coronavirus (SARS-CoV) and SARS-CoV-2 receptor. ACE2 is widely expressed, including, in the lungs, cardiovascular system, gut, kidneys, central nervous system, and adipose tissue. ACE2 has been identified as the SARS-CoV-2 receptor, providing a critical link between immunity, inflammation, ACE2, and cardiovascular disease. The viral spike (S) protein of SARS-CoV-2 binds to ACE2 as a cellular receptor, leading to host cell entry of the virus in concert with S-protein priming by the host cell protease TMPRSS2.

The term "$K_D$" refers to the dissociation constant, which is obtained from the ratio of $k_d$ to $k_a$ (i.e., $k_d/k_a$) and is expressed as a molar concentration (M). $K_D$ values for antibodies can be determined using methods in the art in view of the present disclosure. For example, the $K_D$ of a protein, for example, an antibody, can be determined by using surface plasmon resonance, such as by using a biosensor system, e.g., a Biacore® system, or by using biolayer interferometry technology, such as an Octet RED96 system.

The smaller the value of the $K_D$ of an antibody, the higher affinity that the protein binds to a ligand.

Techniques and procedures described or referenced herein include those that are generally well understood and/or commonly employed using conventional methodology by those skilled in the art, such as, for example, the widely utilized methodologies described in Sambrook et al., Molecular Cloning: A Laboratory Manual (3d ed. 2001); Current Protocols in Molecular Biology (Ausubel et al. eds., 2003); Therapeutic Monoclonal Antibodies: From Bench to Clinic (An ed. 2009); Monoclonal Antibodies: *Methods and Protocols* (Albitar ed. 2010); and *Antibody Engineering* Vols 1 and 2 (Kontermann and Dübel eds., 2d ed. 2010).

Unless otherwise defined herein, technical and scientific terms used in the present description have the meanings that are commonly understood by those of ordinary skill in the art. For purposes of interpreting this specification, the following description of terms will apply and whenever appropriate, terms used in the singular will also include the plural and vice versa. In the event that any description of a term set forth conflicts with any document incorporated herein by reference, the description of the term set forth below shall control.

Provided herein is a multispecific molecule comprising: (a) a first binding domain that specifically binds to polymeric immunoglobulin receptor (pIgR), and (b) a second binding domain that specifically binds to a second target that is not pIgR. In some embodiments, the molecule is a bispecific molecule.

In some embodiments, the multispecific molecule comprises (a) a first binding domain that specifically binds to polymeric immunoglobulin receptor (pIgR), and (b) a second binding domain that specifically binds to SARS-CoV-2.

As provided herein, the multispecific molecule can comprise an Fc region from an IgG antibody. In some embodiments, the multispecific molecule can comprise an Fc region from an IgG1, IgG2, IgG3, or IgG4 antibody. In some embodiments, the multispecific molecule can comprise an Fc region, which is a silent Fc region or a modified Fc region, that has a genetically engineered Fc domain with key mutations that abrogate binding of Fc receptors and abolish antibody directed cytotoxicity (ADCC) effector function.

In some embodiments, the second binding domain is genetically fused or chemically conjugated to the C-terminus of the Fc region. In some embodiments, the ACE2 extracellular binding domain is genetically fused or chemically conjugated to the C-terminus of the Fc region. In some embodiments, the truncated ACE2 extracellular binding domain is genetically fused or chemically conjugated to the C-terminus of the Fc region. In other embodiments, the second binding domain is genetically fused or chemically conjugated to the N-terminus of the Fc region. In some embodiments, the ACE2 extracellular binding domain is genetically fused or chemically conjugated to the N-terminus of the Fc region. In some embodiments, the truncated ACE2 extracellular binding domain is genetically fused or chemically conjugated to the N-terminus of the Fc region.

In various embodiments, the first binding domain is genetically fused or chemically conjugated to the second binding domain. Genetic fusion may be accomplished by placing a linker (e.g., a polypeptide) between the first binding domain and the second binding domain. In various embodiments, the first binding domain is genetically fused or chemically conjugated to the Fc region. Genetic fusion may be accomplished by placing a linker (e.g., a polypeptide) between the first binding domain and the Fc region. In various embodiments, the second binding domain is genetically fused or chemically conjugated to the Fc region. Genetic fusion may be accomplished by placing a linker (e.g., a polypeptide) between the second binding domain and the Fc region.

In one aspect, the hinge region may be a flexible linker comprising a sequence selected from the group consisting of EPKTPKPQPQPQLQPQPNPTTESKSPK (SEQ ID NO:195), (EAAAK)n (SEQ ID NO:196), (GGGGS)n (SEQ ID NO:197) and (GGGS)n (SEQ ID NO:198), wherein n is an integer from 1 to 20. In one aspect, the flexible linker comprises SEQ ID NO:119.

In some embodiments, the hinge region comprises the sequence EPKTPKPQPQPQLQPQPNPTTESKSPK (SEQ ID NO:195). In some embodiments, the hinge region comprises an amino acid sequence having at least 50, at least 55, at least 60, at least 65, at least 70, at least 75, at least 80, at least 85, at least 90, at least 95, at least 98 or at least 99%, sequence identity with EPKTPKPQPQPQLQPQPNPTTESKSPK (SEQ ID NO:195). In one embodiment, the hinge region comprises an amino acid sequence having at least 50% sequence identity with EPKTPKPQPQPQLQPQPNPTTESKSPK (SEQ ID NO:195). In one embodiment, the hinge region comprises an amino acid sequence having at least 55% sequence identity with EPKTPKPQPQPQLQPQPNPTTESKSPK (SEQ ID NO:195). In one embodiment, the hinge region comprises an amino acid sequence having at least 60% sequence identity with EPKTPKPQPQPQLQPQPNPTTESKSPK (SEQ ID NO:195). In one embodiment, the hinge region comprises an amino acid sequence having at least 65% sequence identity with EPKTPKPQPQPQLQPQPNPTTESKSPK (SEQ ID NO:195). In one embodiment, the hinge region comprises an amino acid sequence having at least 70% sequence identity with EPKTPKPQPQPQLQPQPNPTTESKSPK (SEQ ID NO:195). In one embodiment, the hinge region comprises an amino acid sequence having at least 75% sequence identity with EPKTPKPQPQPQLQPQPNPTTESKSPK (SEQ ID NO:195). In one embodiment, the hinge region comprises an amino acid sequence having at least 80% sequence identity with EPKTPKPQPQPQLQPQPNPTTESKSPK (SEQ ID NO:195). In one embodiment, the hinge region comprises an amino acid sequence having at least 85% sequence identity with EPKTPKPQPQPQLQPQPNPTTESKSPK (SEQ ID NO:195). In one embodiment, the hinge region comprises an amino acid sequence having at least 90% sequence identity with EPKTPKPQPQPQLQPQPNPTTESKSPK (SEQ ID NO:195). In one embodiment, the hinge region comprises an amino acid sequence having at least 95% sequence identity with EPKTPKPQPQPQLQPQPNPTTESKSPK (SEQ ID NO:195). In one embodiment, the hinge region comprises an amino acid sequence having at least 98% sequence identity with EPKTPKPQPQPQLQPQPNPTTESKSPK (SEQ ID NO:195). In one embodiment, the hinge region comprises an amino acid sequence having at least 99% sequence identity with EPKTPKPQPQPQLQPQPNPTTESKSPK (SEQ ID NO:195).

In some embodiments, the hinge region comprises the sequence EPKSCDKTHTCPPCP (SEQ ID NO: 100). In some embodiments, the hinge region comprises an amino acid sequence having at least 50, at least 55, at least 60, at least 65, at least 70, at least 75, at least 80, at least 85, at least 90, at least 95, at least 98 or at least 99%, sequence identity with EPKSCDKTHTCPPCP (SEQ ID NO: 100). In one embodiment, the hinge region comprises an amino acid sequence having at least 50% sequence identity with EPKSCDKTHTCPPCP (SEQ ID NO: 100). In one embodiment, the hinge region comprises an amino acid sequence having at least 55% sequence identity with EPKSCDKTHTCPPCP (SEQ ID NO: 100). In one embodiment, the hinge region comprises an amino acid sequence having at least 60% sequence identity with EPKSCDKTHTCPPCP (SEQ ID NO: 100). In one embodiment, the hinge region comprises an amino acid sequence having at least 65% sequence identity with EPKSCDKTHTCPPCP (SEQ ID NO: 100). In one embodiment, the hinge region comprises an amino acid sequence having at least 70% sequence identity with EPKSCDKTHTCPPCP (SEQ ID NO: 100). In one embodiment, the hinge region comprises an amino acid sequence having at least 75% sequence identity with EPKSCDKTHTCPPCP (SEQ ID NO: 100). In one embodiment, the hinge region comprises an amino acid sequence having at least 80% sequence identity with EPKSCDKTHTCPPCP (SEQ ID NO: 100). In one embodiment, the hinge region comprises an amino acid sequence having at least 85% sequence identity with EPKSCDKTHTCPPCP (SEQ ID NO: 100). In one embodiment, the hinge region comprises an amino acid sequence having at least 90% sequence identity with EPKSCDKTHTCPPCP (SEQ ID NO: 100). In one embodiment, the hinge region comprises an amino acid sequence having at least 95% sequence identity with EPKSCDKTHTCPPCP (SEQ ID NO: 100). In one embodiment, the hinge region comprises an amino acid sequence having at least 98% sequence identity with EPKSCDKTHTCPPCP (SEQ ID NO: 100). In one embodiment, the hinge region comprises an amino acid sequence having at least 99% sequence identity with EPKSCDKTHTCPPCP (SEQ ID NO: 100).

In some embodiments, the hinge region comprises the sequence ERKCCVECPPCP (SEQ ID NO:199). In one embodiment, the hinge region comprises an amino acid sequence having at least 50, at least 55, at least 60, at least 65, at least 70, at least 75, at least 80, at least 85, at least 90, at least 95, at least 98 or at least 99%, sequence identity with ERKCCVECPPCP (SEQ ID NO:199). In one embodiment, the hinge region comprises an amino acid sequence having at least 50% sequence identity with ERKCCVECPPCP (SEQ ID NO:199). In one embodiment, the hinge region comprises an amino acid sequence having at least 55% sequence identity with ERKCCVECPPCP (SEQ ID NO:199). In one embodiment, the hinge region comprises an amino acid sequence having at least 60% sequence identity with ERKCCVECPPCP (SEQ ID NO:199). In one embodiment, the hinge region comprises an amino acid sequence having at least 65% sequence identity with ERKCCVECPPCP (SEQ ID NO:199). In one embodiment, the hinge region comprises an amino acid sequence having at least 70% sequence identity with ERKCCVECPPCP (SEQ ID NO:199). In one embodiment, the hinge region comprises an amino acid sequence having at least 75% sequence identity with ERKCCVECPPCP (SEQ ID NO:199). In one embodiment, the hinge region comprises an amino acid sequence having at least 80% sequence identity with ERKCCVECPPCP (SEQ ID NO:199). In one embodiment, the hinge region comprises an amino acid sequence having at least 85% sequence identity with ERKCCVECPPCP (SEQ ID NO:199). In one embodiment, the hinge region comprises an amino acid sequence having at least 90% sequence identity with ERKCCVECPPCP (SEQ ID NO:199). In one embodiment, the hinge region comprises an amino acid sequence having at least 95% sequence identity with ERKCCVECPPCP (SEQ ID NO:199). In one embodiment, the hinge region comprises an amino acid sequence having at least 98% sequence identity with ERKCCVECPPCP (SEQ ID NO:199). In one embodiment, the hinge region comprises an amino acid sequence having at least 99% sequence identity with ERKCCVECPPCP (SEQ ID NO:199).

In some embodiments, the hinge region comprises the sequence ELKTPLGDTTHTCPRCP(EPKSCDTPPPCPRCP)3 (SEQ ID NO:200). In some embodiments, the hinge region comprises an amino acid sequence having at least 50, at least 55, at least 60, at least 65, at least 70, at least 75, at least 80, at least 85, at least 90, at least 95, at least 98 or at least 99%, sequence identity with ELKTPLGDTTHTCPRCP(EPKSCDTPPPCPRCP)3 (SEQ ID NO:200). In one embodiment, the hinge region comprises an amino acid sequence having at least 50% sequence identity with ELKTPLGDTTHTCPRCP(EPKSCDTPPPCPRCP)3 (SEQ ID NO:200). In one embodiment, the hinge region comprises an amino acid sequence having at least 55% sequence identity with ELKTPLGDTTHTCPRCP(EPKSCDTPPPCPRCP)3 (SEQ ID NO:200). In one embodiment, the hinge region comprises an amino acid sequence having at least 60% sequence identity with ELKTPLGDTTHTCPRCP(EPKSCDTPPPCPRCP)3 (SEQ ID NO:200). In one embodiment, the hinge region comprises an amino acid sequence having at least 65% sequence identity with ELKTPLGDTTHTCPRCP(EPKSCDTPPPCPRCP)3 (SEQ ID NO:200). In one embodiment, the hinge region comprises an amino acid sequence having at least 70% sequence identity with ELKTPLGDTTHTCPRCP (EPKSCDTPPPCPRCP)3 (SEQ ID NO:200). In one embodiment, the hinge region comprises an amino acid sequence having at least 75% sequence identity with ELKTPLGDTTHTCPRCP(EPKSCDTPPPCPRCP)3 (SEQ ID NO:200). In one embodiment, the hinge region comprises an amino acid sequence having at least 80% sequence identity with ELKTPLGDTTHTCPRCP (EPKSCDTPPPCPRCP)3 (SEQ ID NO:200). In one embodiment, the hinge region comprises an amino acid sequence having at least 85% sequence identity with ELKTPLGDTTHTCPRCP(EPKSCDTPPPCPRCP)3 (SEQ ID NO:200). In one embodiment, the hinge region comprises an amino acid sequence having at least 90% sequence identity with ELKTPLGDTTHTCPRCP (EPKSCDTPPPCPRCP)3 (SEQ ID NO:200). In one embodiment, the hinge region comprises an amino acid sequence having at least 95% sequence identity with ELKTPLGDTTHTCPRCP(EPKSCDTPPPCPRCP)3 (SEQ ID NO:200). In one embodiment, the hinge region comprises an amino acid sequence having at least 98% sequence identity with ELKTPLGDTTHTCPRCP (EPKSCDTPPPCPRCP)3 (SEQ ID NO:200). In one embodiment, the hinge region comprises an amino acid sequence having at least 99% sequence identity with ELKTPLGDTTHTCPRCP(EPKSCDTPPPCPRCP)3 (SEQ ID NO:200).

In some embodiments, the hinge region comprises the sequence ESKYGPPCPSCP (SEQ ID NO: 201). In some embodiments, the hinge region comprises an amino acid sequence having at least 50, at least 55, at least 60, at least 65, at least 70, at least 75, at least 80, at least 85, at least 90, at least 95, at least 98 or at least 99%, sequence identity with ESKYGPPCPSCP (SEQ ID NO: 201). In one embodiment, the hinge region comprises an amino acid sequence having at least 50% sequence identity with ESKYGPPCPSCP (SEQ ID NO: 201). In one embodiment, the hinge region comprises an amino acid sequence having at least 55% sequence identity with ESKYGPPCPSCP (SEQ ID NO: 201). In one embodiment, the hinge region comprises an amino acid sequence having at least 60% sequence identity with ESKYGPPCPSCP (SEQ ID NO: 201). In one embodiment, the hinge region comprises an amino acid sequence having at least 65% sequence identity with ESKYGPPCPSCP (SEQ ID NO: 201). In one embodiment, the hinge region comprises an amino acid sequence having at least 70% sequence identity with ESKYGPPCPSCP (SEQ ID NO: 201). In one embodiment, the hinge region comprises an amino acid sequence having at least 75% sequence identity with ESKYGPPCPSCP (SEQ ID NO: 201). In one embodiment, the hinge region comprises an amino acid sequence having at least 80% sequence identity with ESKYGPPCPSCP (SEQ ID NO: 201). In one embodiment, the hinge region comprises an amino acid sequence having at least 85% sequence identity with ESKYGPPCPSCP (SEQ ID NO: 201). In one embodiment, the hinge region comprises an amino acid sequence having at least 90% sequence identity with ESKYGPPCPSCP (SEQ ID NO: 201). In one embodiment, the hinge region comprises an amino acid sequence having at least 95% sequence identity with ESKYGPPCPSCP (SEQ ID NO: 201). In one embodiment, the hinge region comprises an amino acid sequence having at least 98% sequence identity with ESKYGPPCPSCP (SEQ ID NO: 201). In one embodiment, the hinge region comprises an amino acid sequence having at least 99% sequence identity with ESKYGPPCPSCP (SEQ ID NO: 201).

In one aspect, the hinge region comprises SEQ ID NO:100. In one aspect, the hinge region comprises SEQ ID NO:101. In one aspect, the hinge region comprises SEQ ID NO:102. In one aspect, the hinge region comprises SEQ ID NO:103. In one aspect, the hinge region comprises SEQ ID NO:104. In another aspect, the hinge region comprises SEQ ID NO:105.

In some embodiments, the second binding domain specifically binds to the surface of SARS-CoV-2. In some embodiments, the second binding domain specifically binds to a structural protein on the surface of SARS-CoV-2, for example, the spike protein S, the small envelope protein E, the matrix protein M or the unexposed nucleocapsid protein N. In some embodiments, the second binding domain specifically binds to the spike protein S of SARS-CoV-2. In some embodiments, the second binding domain specifically binds to the small envelope protein E of SARS-CoV-2. In some embodiments, the second binding domain specifically binds to the matrix protein M of SARS-CoV-2. In some embodiments, the second binding domain specifically binds to the unexposed nucleocapsid protein N of SARS-CoV-2. In additional embodiments, the second binding domain specifically binds to the spike glycoprotein on the surface of SARS-CoV-2. In further embodiments, second binding domain specifically binds to the S1 subunit of the spike glycoprotein on the surface of SARS-CoV-2.

In some embodiments, the second binding domain comprises a protein or fragment thereof that specifically binds to the surface of SARS-CoV-2. In some embodiments, the second binding domain comprises a protein or fragment thereof that specifically binds to a structural protein on the surface of SARS-CoV-2, for example, the spike protein S, the small envelope protein E, the matrix protein M or the unexposed nucleocapsid protein N. In some embodiments, the second binding domain comprises a protein or fragment thereof that specifically binds to the spike protein S of SARS-CoV-2. In some embodiments, the second binding domain comprises a protein or fragment thereof that specifically binds to the small envelope protein E of SARS-CoV-2. In some embodiments, the second binding domain comprises a protein or fragment thereof that specifically binds to the matrix protein M of SARS-CoV-2. In some embodiments, the second binding domain comprises a protein or fragment thereof that specifically binds to the unexposed nucleocapsid protein N of SARS-CoV-2. In additional embodiments, the second binding domain comprises a protein or fragment thereof that specifically binds to the spike glycoprotein on the surface of SARS-CoV-2. In further embodiments, second binding domain comprises a protein or fragment thereof that specifically binds to the S1 subunit of the spike glycoprotein on the surface of SARS-CoV-2. In additional embodiments, the second binding domain comprises a protein or fragment thereof that specifically binds to the spike glycoprotein on the surface of SARS-CoV-2. In further embodiments, second binding domain comprises a protein or fragment thereof that specifically binds to the S1 subunit of the spike glycoprotein on the surface of SARS-CoV-2. In some embodiments, the second binding domain comprise a protein. In some embodiments, the second binding domain comprise a fragment of the protein.

In some embodiments, the second binding domain comprising a protein or fragment thereof that specifically binds to the spike glycoprotein on the surface of SARS-CoV-2 comprises angiotensin-converting enzyme 2 (ACE2) or a fragment thereof. In some embodiments, the second binding domain comprising a protein or fragment thereof specifically binds to the spike glycoprotein on the surface of SARS-CoV-2 comprises the extracellular domain of ACE2 designated SEQ ID NO:134, or a fragment thereof. In some embodiments, the second binding domain comprising a protein or fragment thereof that specifically binds to the spike glycoprotein on the surface of SARS-CoV-2 comprises a truncated extracellular domain of ACE2 designated SEQ ID NO:120 or SEQ ID NO:121. In some embodiments, the second binding domain comprise a protein. In some embodiments, the second binding domain comprise a fragment of the protein.

In some embodiments, the second binding domain comprises an antibody or antigen-binding fragment thereof that specifically binds to the surface of SARS-CoV-2. In some embodiments, the second binding domain comprises an antibody or antigen-binding fragment thereof that specifically binds to a structural antibody on the surface of SARS-CoV-2, for example, the spike protein S, the small envelope protein E, the matrix protein M or the unexposed nucleocapsid protein N. In some embodiments, the second binding domain comprises an antibody or antigen-binding fragment thereof that specifically binds to the spike protein S of SARS-CoV-2. In some embodiments, the second binding domain comprises an antibody or antigen-binding fragment thereof that specifically binds to the small envelope protein E of SARS-CoV-2. In some embodiments, the second binding domain comprises an antibody or antigen-binding fragment thereof that specifically binds to the matrix protein M of SARS-CoV-2. In some embodiments, the second binding domain comprises an antibody or antigen-binding fragment thereof that specifically binds to the unexposed nucleocapsid protein N of SARS-CoV-2. In additional embodiments, the second binding domain comprises an antibody or antigen-binding fragment thereof that specifically binds to the spike glycoprotein on the surface of SARS-CoV-2. In further embodiments, second binding domain comprises an antibody or antigen-binding fragment thereof that specifically binds to the S1 subunit of the spike glycoprotein on the surface of SARS-CoV-2. In one embodiment, the second binding domain comprises an antibody. In another embodiment, the second binding domain comprises an antigen-binding fragment of the antibody.

In some embodiments, the second binding domain comprises an antigen-binding fragment that specifically binds to the surface of SARS-CoV-2 as described directly above. In some embodiments, the antigen binding fragment is a diabody. In some embodiments, the antigen binding fragment is a Fab. In some embodiments, the antigen binding fragment is a Fab'. In some embodiments, the antigen binding fragment is a F(ab')2. In some embodiments, the antigen binding fragment is a Fv fragment. In some embodiments, the antigen binding fragment is a disulfide stabilized Fv fragment (dsFv). In some embodiments, the antigen binding fragment is a (dsFv)$_2$. In some embodiments, the antigen binding fragment is a bispecific dsFv (dsFv-dsFv'). In some embodiments, the antigen binding fragment is a disulfide stabilized diabody (ds diabody). In some embodiments, the antigen binding fragment is a single-chain antibody molecule (scFv). In some embodiments, the antigen binding fragment is a single domain antibody (sdAb). In some embodiments, the antigen binding fragment is an scFv dimer (bivalent diabody). In some embodiments, the antigen binding fragment is a multispecific antibody formed from a portion of an antibody comprising one or more CDRs. In some embodiments, the antigen binding fragment is a camelized single domain antibody. In some embodiments, the antigen binding fragment is a nanobody. In some embodiments, the antigen binding fragment is a domain antibody. In some embodiments, the antigen binding fragment is a bivalent domain antibody. In some embodiments, the antigen binding fragment is an antibody fragment that binds to an antigen but does not comprise a complete antibody structure.

In some embodiments, the first binding domain comprises a single-domain antibody (VHH) capable of binding to polymeric immunoglobulin receptor (pIgR), that can act as a delivery domain for therapeutic agents. In various embodiments, the VHH domains provided herein bind to human pIgR (Genbank ID: CR749533) (see Turula, H. & Wobus, C. E. The Role of the Polymeric Immunoglobulin Receptor and Secretory Immunoglobulins during Mucosal Infection and Immunity. Viruses 10 (2018)). Human pIgR (hpIgR) is an 82 kDa, single-pass transmembrane receptor containing a 620-residue extracellular domain (ECD), a 23-residue transmembrane domain and a 103-residue intracellular domain.

pIgR transports soluble polymeric forms of IgA and IgM into apical mucosal tissues from the basolateral side of the epithelium. The process of transporting polymeric immunoglobulins from the basolateral to apical side is transcytosis. Following transcytosis, the pIgR ECD that contains five domains (secretory component) is proteolytically cleaved and released into mucus with or without IgA. In addition to transcytosis, pIgR has several different functions that include, but are not limited to, conferring stability to IgA, immune exclusion, anti-inflammatory properties and homeostasis of commensals in the mucosal immune system.

Approximately 75% of total daily antibody production (approximately 3-5 g) is directed to IgA molecules. In humans, there are two Cα genes encoding IgA subclass: IgA1 and IgA2 (IgA2m(1) and (2) allotypes). IgA1 has elongated hinge region absent in IgA2, that contains several O-glycan sites and is susceptible to proteolytic cleavage. Endogenous IgA is present in various forms in a compartment-dependent manner. Monomeric IgA (mIgA) is the predominant form in serum (at a concentration of 1-3 mg/mL), primarily as IgA1 (about 90%) produced in bone marrow. Dimeric IgA (dIgA) is formed via S-S bridging of the C-terminal Fc tailpiece with J chain. dIgA is produced locally at target site of action and transported across mucosal surface into secretions of respiratory, GI and genitourinary tracts. Secretory IgA (S-IgA) is formed via dIgA complex with extracellular domain of polymeric Ig receptor (pIgR). Cleavage of secretory component (SC) at the mucosal surface of epithelial cells releases S-IgA.

The polymeric immunoglobulin receptor (pIgR) binds to soluble dimeric IgA via Fc and J-chain mediated interactions. pIgR does not bind or transport IgG molecules across mucosal epithelium. Though IgG molecules lack a lumen-targeted active transport mechanism, conferring pIgR-binding abilities to IgG can mediate selective transport of IgG antibodies into the mucosal lumen.

In some embodiments, the single domain antibody (e.g., VHH domain) provided herein competes with IgA binding to the pIgR. In some embodiments, the single domain antibody (e.g., VHH domain) provided herein promotes IgA binding to the pIgR. In some embodiments, the $K_D$ of the binding of the single domain antibody (e.g., VHH domain) provided herein to pIgR is from 4 to 525 nM. In some embodiments, the $K_D$ of the binding of the single domain antibody (e.g., VHH domain) provided herein to pIgR is less than 525 nM. In some embodiments, the $K_D$ of the binding of the single domain antibody (e.g., VHH domain) provided herein to pIgR is less than 400 nM. In some embodiments, the $K_D$ of the binding of the single domain antibody (e.g., VHH domain) provided herein to pIgR is less than 350 nM. In some embodiments, the $K_D$ of the binding of the single domain antibody (e.g., VHH domain) provided herein to pIgR is less than 300 nM. In some embodiments, the $K_D$ of the binding of the single domain antibody (e.g., VHH domain) provided herein to pIgR is less than 250 nM. In some embodiments, the $K_D$ of the binding of the single domain antibody (e.g., VHH domain) provided herein to pIgR is less than 200 nM. In some embodiments, the $K_D$ of the binding of the single domain antibody (e.g., VHH domain) provided herein to pIgR is less than 150 nM. In some embodiments, the $K_D$ of the binding of the single domain antibody (e.g., VHH domain) provided herein to pIgR is less than 100 nM. In some embodiments, the $K_D$ of the binding of the single domain antibody (e.g., VHH domain) provided herein to pIgR is less than 50 nM. In some embodiments, the $K_D$ of the binding of the single domain antibody (e.g., VHH domain) provided herein to pIgR is from 4 to 525 nM. In some embodiments, the $K_D$ of the binding of the single domain antibody (e.g., VHH domain) provided herein to pIgR is from 4 to 34 nM. Intermediate ranges are also contemplated. For example, in some embodiments, the $K_D$ of the binding of the single domain antibody (e.g., VHH domain) provided herein to pIgR is from 4 to 50 nM. in some embodiments, the $K_D$ of the binding of the single domain antibody (e.g., VHH domain) provided herein to pIgR is from 4 to 100 nM. In some embodiments, the $K_D$ of the binding of the single domain antibody (e.g., VHH domain) provided herein to pIgR is from 4 to 200 nM. in some embodiments, the $K_D$ of the binding of the single domain antibody (e.g., VHH domain) provided herein to pIgR is from 4 to 300 nM. In some embodiments, the $K_D$ of the binding of the single domain antibody (e.g., VHH domain) provided herein to pIgR is from 4 to 400 nM. In some embodiments, the $K_D$ of the binding of the single domain antibody (e.g., VHH domain) provided herein to pIgR is from 50 to 100 nM. In some embodiments, the $K_D$ of the binding of the single domain antibody (e.g., VHH domain) provided herein to pIgR is from 50 to 200 nM. In some embodiments, the $K_D$ of the binding of the single domain antibody (e.g., VHH domain) provided herein to pIgR is from 50 to 300 nM. In some embodiments, the $K_D$ of the binding of the single domain antibody (e.g., VHH domain) provided herein to pIgR is from 50 to 400 nM.

In some embodiments, the $T_m$ of the single domain antibody (e.g., VHH domain) is from 53 to 77° C. In some embodiments, the $T_m$ of the single domain antibody (e.g., VHH domain) is from 53.9 to 76.4° C. In some embodiments, the $T_m$ of the single domain antibody (e.g., VHH domain) is from 61 to 77° C. In some embodiments, the $T_m$ of the single domain antibody (e.g., VHH domain) is from 61 to 71° C.

In a specific embodiment, the single domain antibody is a VHH domain.

In one aspect, provided herein is a multispecific molecule comprising a first binding domain comprising a VHH that binds to domain 1 of pIgR, wherein the VHH comprises the CDR1, CDR2 and/or CDR3 sequence of VHH2. In some embodiments, the VHH comprises a complementarity determining region 1 (CDR1) having an amino acid sequence of SEQ ID NO:1, a CDR2 having an amino acid sequence of SEQ ID NO:2, and/or a CDR3 having an amino acid sequence of SEQ ID NO:3. In some embodiments, the VHH comprises a CDR1 having an amino acid sequence of SEQ ID NO:4, a CDR2 having an amino acid sequence of SEQ ID NO:5, and/or a CDR3 having an amino acid sequence of SEQ ID NO:6. In some embodiments, the VHH comprises a CDR1 having an amino acid sequence of SEQ ID NO:7, a CDR2 having an amino acid sequence of SEQ ID NO:8, and/or a CDR3 having an amino acid sequence of SEQ ID NO:9. In some embodiments, the VHH comprises a CDR1 having an amino acid sequence of SEQ ID NO:10, a CDR2 having an amino acid sequence of SEQ ID NO:11, and/or a CDR3 having an amino acid sequence of SEQ ID NO:12. In some embodiments, the VHH comprises a CDR1 having an amino acid sequence of SEQ ID NO:13, a CDR2 having an amino acid sequence of SEQ ID NO:14, and/or a CDR3 having an amino acid sequence of SEQ ID NO:15. In some embodiments, the VHH comprises a CDR1 having an amino acid sequence of SEQ ID NO:7, a CDR2 having an amino acid sequence of SEQ ID NO:8, and/or a CDR3 having an amino acid sequence of SEQ ID NO:191. In some embodiments, the VHH comprises an amino acid sequence of SEQ ID NO:16.

In one aspect, provided herein is a multispecific molecule comprising a first binding domain comprising a VHH domain that binds to domain 2 of pIgR, wherein the VHH domain comprises the CDR1, CDR2 and/or CDR3 sequence of VHH6. In some embodiments, the VHH comprises a CDR1 having an amino acid sequence of SEQ ID NO:17, a CDR2 having an amino acid sequence of SEQ ID NO:18, and/or a CDR3 having an amino acid sequence of SEQ ID NO:19. In some embodiments, the VHH comprises a CDR1 having an amino acid sequence of SEQ ID NO:20, a CDR2 having an amino acid sequence of SEQ ID NO:21, and/or a CDR3 having an amino acid sequence of SEQ ID NO:22. In some embodiments, the VHH comprises a CDR1 having an amino acid sequence of SEQ ID NO:23, a CDR2 having an amino acid sequence of SEQ ID NO:24, and/or a CDR3 having an amino acid sequence of SEQ ID NO:25. In some embodiments, the VHH comprises a CDR1 having an amino acid sequence of SEQ ID NO:26, a CDR2 having an amino acid sequence of SEQ ID NO:27, and/or a CDR3 having an amino acid sequence of SEQ ID NO:28. In some embodiments, the VHH comprises a CDR1 having an amino acid sequence of SEQ ID NO:29, a CDR2 having an amino acid sequence of SEQ ID NO:30, and/or a CDR3 having an amino acid sequence of SEQ ID NO:31. In some embodiments, the VHH comprises a CDR1 having an amino acid sequence of SEQ ID NO:23, a CDR2 having an amino acid sequence of SEQ ID NO:192, and/or a CDR3 having an amino acid sequence of SEQ ID NO:193. In some embodiments, the VHH comprises an amino acid sequence of SEQ ID NO:32.

In one aspect, provided herein is a multispecific molecule comprising a first binding domain comprising a VHH that binds to domain 1 of pIgR, wherein the VHH comprises the CDR1, CDR2 or CDR3 sequence of VHH2. In some embodiments, the VHH comprises a complementarity determining region 1 (CDR1) having an amino acid sequence of SEQ ID NO:1, a CDR2 having an amino acid sequence of SEQ ID NO:2, or a CDR3 having an amino acid sequence of SEQ ID NO:3. In some embodiments, the VHH comprises a CDR1 having an amino acid sequence of SEQ ID NO:4, a CDR2 having an amino acid sequence of SEQ ID NO:5, or a CDR3 having an amino acid sequence of SEQ ID NO:6. In some embodiments, the VHH comprises a CDR1 having an amino acid sequence of SEQ ID NO:7, a CDR2 having an amino acid sequence of SEQ ID NO:8, or a CDR3 having an amino acid sequence of SEQ ID NO:9. In some embodiments, the VHH comprises a CDR1 having an amino acid sequence of SEQ ID NO:10, a CDR2 having an amino acid sequence of SEQ ID NO:11, or a CDR3 having an amino acid sequence of SEQ ID NO:12. In some embodiments, the VHH comprises a CDR1 having an amino acid sequence of SEQ ID NO:13, a CDR2 having an amino acid sequence of SEQ ID NO:14, or a CDR3 having an amino acid sequence of SEQ ID NO:15. In some embodiments, the VHH comprises a CDR1 having an amino acid sequence of SEQ ID NO:7, a CDR2 having an amino acid sequence of SEQ ID NO:8, or a CDR3 having an amino acid sequence of SEQ ID NO:191. In some embodiments, the VHH comprises an amino acid sequence of SEQ ID NO:16.

In one aspect, provided herein is a multispecific molecule comprising a first binding domain comprising a VHH domain that binds to domain 2 of pIgR, wherein the VHH domain comprises the CDR1, CDR2 or CDR3 sequence of VHH6. In some embodiments, the VHH comprises a CDR1 having an amino acid sequence of SEQ ID NO:17, a CDR2 having an amino acid sequence of SEQ ID NO:18, or a CDR3 having an amino acid sequence of SEQ ID NO:19. In some embodiments, the VHH comprises a CDR1 having an amino acid sequence of SEQ ID NO:20, a CDR2 having an amino acid sequence of SEQ ID NO:21, or a CDR3 having an amino acid sequence of SEQ ID NO:22. In some embodiments, the VHH comprises a CDR1 having an amino acid sequence of SEQ ID NO:23, a CDR2 having an amino acid sequence of SEQ ID NO:24, or a CDR3 having an amino acid sequence of SEQ ID NO:25. In some embodiments, the VHH comprises a CDR1 having an amino acid sequence of SEQ ID NO:26, a CDR2 having an amino acid sequence of SEQ ID NO:27, or a CDR3 having an amino acid sequence of SEQ ID NO:28. In some embodiments, the VHH comprises a CDR1 having an amino acid sequence of SEQ ID NO:29, a CDR2 having an amino acid sequence of SEQ ID NO:30, or a CDR3 having an amino acid sequence of SEQ ID NO:31. In some embodiments, the VHH comprises a CDR1 having an amino acid sequence of SEQ ID NO:23, a CDR2 having an amino acid sequence of SEQ ID NO:192, or a CDR3 having an amino acid sequence of SEQ ID NO:193. In some embodiments, the VHH comprises an amino acid sequence of SEQ ID NO:32.

In one aspect, provided herein is a multispecific molecule comprising a first binding domain comprising a VHH that binds to domain 1 of pIgR, wherein the VHH comprises the CDR1, CDR2 and CDR3 sequence of VHH2. In some embodiments, the VHH comprises a complementarity determining region 1 (CDR1) having an amino acid sequence of SEQ ID NO:1, a CDR2 having an amino acid sequence of SEQ ID NO:2, and a CDR3 having an amino acid sequence of SEQ ID NO:3. In some embodiments, the VHH comprises a CDR1 having an amino acid sequence of SEQ ID NO:4, a CDR2 having an amino acid sequence of SEQ ID NO:5, and a CDR3 having an amino acid sequence of SEQ ID NO:6. In some embodiments, the VHH comprises a CDR1 having an amino acid sequence of SEQ ID NO:7, a CDR2 having an amino acid sequence of SEQ ID NO:8, and a CDR3 having an amino acid sequence of SEQ ID NO:9. In some embodiments, the VHH comprises a CDR1 having an amino acid sequence of SEQ ID NO:10, a CDR2 having an amino acid sequence of SEQ ID NO:11, and a CDR3 having an amino acid sequence of SEQ ID NO:12. In some embodiments, the VHH comprises a CDR1 having an amino acid sequence of SEQ ID NO:13, a CDR2 having an amino acid sequence of SEQ ID NO:14, and a CDR3 having an amino acid sequence of SEQ ID NO:15. In some embodiments, the VHH comprises a CDR1 having an amino acid sequence of SEQ ID NO:7, a CDR2 having an amino acid sequence of SEQ ID NO:8, and a CDR3 having an amino acid sequence of SEQ ID NO:191. In some embodiments, the VHH comprises an amino acid sequence of SEQ ID NO:16.

In one aspect, provided herein is a multispecific molecule comprising a first binding domain comprising a VHH domain that binds to domain 2 of pIgR, wherein the VHH domain comprises the CDR1, CDR2 and CDR3 sequence of VHH6. In some embodiments, the VHH comprises a CDR1 having an amino acid sequence of SEQ ID NO:17, a CDR2 having an amino acid sequence of SEQ ID NO:18, and a CDR3 having an amino acid sequence of SEQ ID NO:19. In some embodiments, the VHH comprises a CDR1 having an amino acid sequence of SEQ ID NO:20, a CDR2 having an amino acid sequence of SEQ ID NO:21, and a CDR3 having an amino acid sequence of SEQ ID NO:22. In some embodiments, the VHH comprises a CDR1 having an amino acid sequence of SEQ ID NO:23, a CDR2 having an amino acid sequence of SEQ ID NO:24, and a CDR3 having an amino acid sequence of SEQ ID NO:25. In some embodiments, the VHH comprises a CDR1 having an amino acid sequence of SEQ ID NO:26, a CDR2 having an amino acid sequence of SEQ ID NO:27, and a CDR3 having an amino acid sequence of SEQ ID NO:28. In some embodiments, the VHH comprises a CDR1 having an amino acid sequence of SEQ ID NO:29, a CDR2 having an amino acid sequence of SEQ ID NO:30, and a CDR3 having an amino acid sequence of SEQ ID NO:31. In some embodiments, the VHH comprises a CDR1 having an amino acid sequence of SEQ ID NO:23, a CDR2 having an amino acid sequence of SEQ ID NO:192, and a CDR3 having an amino acid sequence of SEQ ID NO:193. In some embodiments, the VHH comprises an amino acid sequence of SEQ ID NO:32.

In one aspect, provided herein is a multispecific molecule comprising a first binding domain comprising a VHH that binds to domain 1 of pIgR, wherein the VHH comprises the CDR1, CDR2 or CDR3 sequence of VHH2. In some embodiments, the VHH comprises a CDR1 having an amino acid sequence having at least 95% identity to an amino acid sequence of SEQ ID NO:1, a CDR2 having an amino acid sequence having at least 95% identity to an amino acid sequence of SEQ ID NO:2, or a CDR3 having an amino acid sequence having at least 95% identity to an amino acid sequence of SEQ ID NO:3. In some embodiments, the VHH comprises a CDR1 having an amino acid sequence having at least 95% identity to an amino acid sequence of SEQ ID NO:4, a CDR2 having an amino acid sequence having at least 95% identity to an amino acid sequence of SEQ ID NO:5, or a CDR3 having an amino acid sequence having at least 95% identity to an amino acid sequence of SEQ ID NO:6. In some embodiments, the VHH comprises a CDR1 having an amino acid sequence having at least 95% identity to an amino acid sequence of SEQ ID NO:7, a CDR2 having an amino acid sequence having at least 95% identity to an amino acid sequence of SEQ ID NO:8, or a CDR3 having an amino acid sequence having at least 95% identity to an amino acid sequence of SEQ ID NO:9. In some embodiments, the VHH comprises a CDR1 having an amino acid sequence having at least 95% identity to an amino acid sequence of SEQ ID NO:10, a CDR2 having an amino acid sequence having at least 95% identity to an amino acid sequence of SEQ ID NO:11, or a CDR3 having an amino acid sequence having at least 95% identity to an amino acid sequence of SEQ ID NO:12. In some embodiments, the VHH comprises a CDR1 having an amino acid sequence having at least 95% identity to an amino acid sequence of SEQ ID NO:13, a CDR2 having an amino acid sequence having at least 95% identity to an amino acid sequence of SEQ ID NO:14, or a CDR3 having an amino acid sequence having at least 95% identity to an amino acid sequence of SEQ ID NO:15. In some embodiments, the VHH comprises a CDR1 having an amino acid sequence having at least 95% identity to an amino acid sequence of SEQ ID NO:7, a CDR2 having an amino acid sequence having at least 95% identity to an amino acid sequence of SEQ ID NO:8, or a CDR3 having an amino acid sequence having at least 95% identity to an amino acid sequence of SEQ ID NO:191. In some embodiments, the VHH comprises an amino acid sequence having at least 95% identity to an amino acid sequence of SEQ ID NO:16.

In one aspect, provided herein is a multispecific molecule comprising a first binding domain comprising a VHH domain that binds to domain 2 of pIgR, wherein the VHH domain comprises the CDR1, CDR2 or CDR3 sequence of VHH6. In some embodiments, the VHH comprises a CDR1 having an amino acid sequence having at least 95% identity to an amino acid sequence of SEQ ID NO:17, a CDR2 having an amino acid sequence having at least 95% identity to an amino acid sequence of SEQ ID NO:18, or a CDR3 having an amino acid sequence having at least 95% identity to an amino acid sequence of SEQ ID NO:19. In some embodiments, the VHH comprises a CDR1 having an amino acid sequence having at least 95% identity to an amino acid sequence of SEQ ID NO:20, a CDR2 having an amino acid sequence having at least 95% identity to an amino acid sequence of SEQ ID NO:21, or a CDR3 having an amino acid sequence having at least 95% identity to an amino acid sequence of SEQ ID NO:22. In some embodiments, the VHH comprises a CDR1 having an amino acid sequence having at least 95% identity to an amino acid sequence of SEQ ID NO:23, a CDR2 having an amino acid sequence having at least 95% identity to an amino acid sequence of SEQ ID NO:24, or a CDR3 having an amino acid sequence having at least 95% identity to an amino acid sequence of SEQ ID NO:25. In some embodiments, the VHH comprises a CDR1 having an amino acid sequence having at least 95% identity to an amino acid sequence of SEQ ID NO:26, a CDR2 having an amino acid sequence having at least 95% identity to an amino acid sequence of SEQ ID NO:27, or a CDR3 having an amino acid sequence having at least 95% identity to an amino acid sequence of SEQ ID NO:28. In some embodiments, the VHH comprises a CDR1 having an amino acid sequence having at least 95% identity to an amino acid sequence of SEQ ID NO:29, a CDR2 having an amino acid sequence having at least 95% identity to an amino acid sequence of SEQ ID NO:30, or a CDR3 having an amino acid sequence having at least 95% identity to an amino acid sequence of SEQ ID NO:31. In some embodiments, the VHH comprises a CDR1 having an amino acid sequence having at least 95% identity to an amino acid sequence of SEQ ID NO:23, a CDR2 having an amino acid sequence having at least 95% identity to an amino acid sequence of SEQ ID NO:192, or a CDR3 having an amino acid sequence having at least 95% identity to an amino acid sequence of SEQ ID NO:193. In some embodiments, the VHH comprises an amino acid sequence having at least 95% identity to an amino acid sequence of SEQ ID NO:32.

In one aspect, provided herein is a multispecific molecule comprising a first binding domain comprising a VHH that binds to domain 1 of pIgR, wherein the VHH comprises the CDR1, CDR2 and CDR3 sequence of VHH2. In some embodiments, the VHH comprises a complementarity determining region 1 (CDR1) having an amino acid sequence having at least 95% identity to an amino acid sequence of SEQ ID NO:1, a CDR2 having an amino acid sequence having at least 95% identity to an amino acid sequence of SEQ ID NO:2, and a CDR3 having an amino acid sequence having at least 95% identity to an amino acid sequence of SEQ ID NO:3. In some embodiments, the VHH comprises a CDR1 having an amino acid sequence having at least 95% identity to an amino acid sequence of SEQ ID NO:4, a CDR2 having an amino acid sequence having at least 95% identity to an amino acid sequence of SEQ ID NO:5, and a CDR3 having an amino acid sequence having at least 95% identity to an amino acid sequence of SEQ ID NO:6. In some embodiments, the VHH comprises a CDR1 having an amino acid sequence having at least 95% identity to an amino acid sequence of SEQ ID NO:7, a CDR2 having an amino acid sequence having at least 95% identity to an amino acid sequence of SEQ ID NO:8, and a CDR3 having an amino acid sequence having at least 95% identity to an amino acid sequence of SEQ ID NO:9. In some embodiments, the VHH comprises a CDR1 having an amino acid sequence having at least 95% identity to an amino acid sequence of SEQ ID NO:10, a CDR2 having an amino acid sequence having at least 95% identity to an amino acid sequence of SEQ ID NO:11, and a CDR3 having an amino acid sequence having at least 95% identity to an amino acid sequence of SEQ ID NO:12. In some embodiments, the VHH comprises a CDR1 having an amino acid sequence having at least 95% identity to an amino acid sequence of SEQ ID NO:13, a CDR2 having an amino acid sequence having at least 95% identity to an amino acid sequence of SEQ ID NO:14, and a CDR3 having an amino acid sequence having at least 95% identity to an amino acid sequence of SEQ ID NO:15. In some embodiments, the VHH comprises a CDR1 having an amino acid sequence having at least 95% identity to an amino acid sequence of SEQ ID NO:7, a CDR2 having an amino acid sequence having at least 95% identity to an amino acid sequence of SEQ ID NO:8, and a CDR3 having an amino acid sequence having at least 95% identity to an amino acid sequence of SEQ ID NO:191. In some embodiments, the VHH comprises an amino acid sequence having at least 95% identity to an amino acid sequence of SEQ ID NO:16.

In one aspect, provided herein is a multispecific molecule comprising a first binding domain comprising a VHH domain that binds to domain 2 of pIgR, wherein the VHH domain comprises the CDR1, CDR2 and CDR3 sequence of VHH6. In some embodiments, the VHH comprises a CDR1 having an amino acid sequence having at least 95% identity to an amino acid sequence of SEQ ID NO:17, a CDR2 having an amino acid sequence having at least 95% identity to an amino acid sequence of SEQ ID NO:18, and a CDR3 having an amino acid sequence having at least 95% identity to an amino acid sequence of SEQ ID NO:19. In some embodiments, the VHH comprises a CDR1 having an amino acid sequence having at least 95% identity to an amino acid sequence of SEQ ID NO:20, a CDR2 having an amino acid sequence having at least 95% identity to an amino acid sequence of SEQ ID NO:21, and a CDR3 having an amino acid sequence having at least 95% identity to an amino acid sequence of SEQ ID NO:22. In some embodiments, the VHH comprises a CDR1 having an amino acid sequence having at least 95% identity to an amino acid sequence of SEQ ID NO:23, a CDR2 having an amino acid sequence having at least 95% identity to an amino acid sequence of SEQ ID NO:24, and a CDR3 having an amino acid sequence having at least 95% identity to an amino acid sequence of SEQ ID NO:25. In some embodiments, the VHH comprises a CDR1 having an amino acid sequence having at least 95% identity to an amino acid sequence of SEQ ID NO:26, a CDR2 having an amino acid sequence having at least 95% identity to an amino acid sequence of SEQ ID NO:27, and a CDR3 having an amino acid sequence having at least 95% identity to an amino acid sequence of SEQ ID NO:28. In some embodiments, the VHH comprises a CDR1 having an amino acid sequence having at least 95% identity to an amino acid sequence of SEQ ID NO:29, a CDR2 having an amino acid sequence having at least 95% identity to an amino acid sequence of SEQ ID NO:30, and a CDR3 having an amino acid sequence having at least 95% identity to an amino acid sequence of SEQ ID NO:31. In some embodiments, the VHH comprises a CDR1 having an amino acid sequence having at least 95% identity to an amino acid sequence of SEQ ID NO:23, a CDR2 having an amino acid sequence having at least 95% identity to an amino acid sequence of SEQ ID NO:192, and a CDR3 having an amino acid sequence having at least 95% identity to an amino acid sequence of SEQ ID NO:193. In some embodiments, the VHH comprises an amino acid sequence having at least 95% identity to an amino acid sequence of SEQ ID NO:32.

In some embodiments, the VH CDR1, VH CDR2, VH CDR3, VL CDR1, VL CDR2, and VL CDR3 sequences are according to the Kabat numbering system. In some embodiments, the VH CDR1, VH CDR2, VH CDR3, VL CDR1, VL CDR2, and VL CDR3 sequences are according to the Chothia numbering system. In some embodiments, the VH CDR1, VH CDR2, VH CDR3, VL CDR1, VL CDR2, and VL CDR3 sequences are according to the Exemplary numbering system. In some embodiments, the VH CDR1, VH CDR2, VH CDR3, VL CDR1, VL CDR2, and VL CDR3 sequences are according to the Contact numbering system. In some embodiments, the VH CDR1, VH CDR2, VH CDR3, VL CDR1, VL CDR2, and VL CDR3 sequences are according to the IMGT numbering system. In some embodiments, the VH CDR1, VH CDR2, VH CDR3, VL CDR1, VL CDR2, and VL CDR3 sequences are according to the AbM numbering system. Exemplary sets of 6 CDRs (VH CDR1-3 and VL CDR1-3) of certain antibody embodiments are provided herein. Other sets of CDRs are contemplated and within the scope of the antibody embodiments provided herein.

In some embodiments, the first binding domain comprises a VHH domain that specifically binds an extracellular pIgR epitope. In some embodiments, CDR1, CDR2, and CDR3 of the VHH domain form a binding site for an antigen of the pIgR. In some embodiments, CDR1, CDR2, and CDR3 of the VHH domain form a binding site for an epitope of the pIgR.

In some embodiments, the VHH domain of a multispecific molecule of the invention binds to a pIgR is present on the mucosal endothelium. In additional embodiments, the VHH domain of a multispecific molecule of the invention binds to pIgR is present on respiratory tissue. In additional embodiments, the VHH domain of a multispecific molecule of the invention binds to pIgR is present on the lung endothelium.

In one aspect, the SARS-CoV-2 is neutralized when the multispecific molecule specifically binds to the pIgR and to SARS-CoV-2. In some embodiments, the multispecific molecule neutralizes SARS-CoV-2 with an $EC_{50}$ of less than about 4 nM. In some embodiments, the multispecific molecule neutralizes SARS-CoV-2 with an $EC_{50}$ of less than about 3 nM. In some embodiments, the multispecific molecule neutralizes SARS-CoV-2 with an $EC_{50}$ of less than about 1 nM. In some embodiments, the multispecific molecule neutralizes SARS-CoV-2 with an $EC_{50}$ of less than about 500 pM. In some embodiments, the multispecific molecule neutralizes SARS-CoV-2 with an $EC_{50}$ of less than about 100 pM.

In certain embodiments, the $EC_{50}$ is less than about 1 nM. In one embodiment, the $EC_{50}$ is less than about 0.9 nM. In one embodiment, the $EC_{50}$ is less than about 0.8 nM. In one embodiment, the $EC_{50}$ is less than about 0.7 nM. In one embodiment, the $EC_{50}$ is less than about 0.6 nM. In one embodiment, the $EC_{50}$ is less than about 0.5 nM. In one embodiment, the $EC_{50}$ is less than about 0.4 nM. In one embodiment, the $EC_{50}$ is less than about 0.300 nM. In one embodiment, the $EC_{50}$ is less than about 0.2 nM. In one embodiment, the $EC_{50}$ is less than about 0.19 nM. In one embodiment, the $EC_{50}$ is less than about 0.18 nM. In one embodiment, the $EC_{50}$ is less than about 0.17 nM. In one embodiment, the $EC_{50}$ is less than about 0.16 nM. In one embodiment, the $EC_{50}$ is less than about 0.15 nM. In one embodiment, the $EC_{50}$ is less than about 0.14 nM. In one embodiment, the $EC_{50}$ is less than about 0.13 nM. In one embodiment, the $EC_{50}$ is less than about 0.12 nM. In one embodiment, the $EC_{50}$ is less than about 0.11 nM. In one embodiment, the $EC_{50}$ is less than about 0.1 nM. In one embodiment, the $EC_{50}$ is less than about 0.09 nM. In one embodiment, the $EC_{50}$ is less than about 0.08 nM. In one embodiment, the $EC_{50}$ is less than about 0.07 nM. In one embodiment, the $EC_{50}$ is less than about 0.06 nM. In one embodiment, the $EC_{50}$ is less than about 0.05 nM. In one embodiment, the $EC_{50}$ is less than about 0.04 nM. In one embodiment, the $EC_{50}$ is less than about 0.03 nM. In one embodiment, the $EC_{50}$ is less than about 0.02 nM. In one embodiment, the $EC_{50}$ is less than about 0.01 nM.

In certain embodiments, the $EC_{50}$ is less than about 1 pM. In one embodiment, the $EC_{50}$ is less than about 0.9 pM. In one embodiment, the $EC_{50}$ is less than about 0.8 pM. In one embodiment, the $EC_{50}$ is less than about 0.7 pM. In one embodiment, the $EC_{50}$ is less than about 0.6 pM. In one embodiment, the $EC_{50}$ is less than about 0.5 pM. In one embodiment, the $EC_{50}$ is less than about 0.4 pM. In one embodiment, the $EC_{50}$ is less than about 0.300 pM. In one embodiment, the $EC_{50}$ is less than about 0.2 pM. In one embodiment, the $EC_{50}$ is less than about 0.19 pM. In one embodiment, the $EC_{50}$ is less than about 0.18 pM. In one embodiment, the $EC_{50}$ is less than about 0.17 pM. In one embodiment, the $EC_{50}$ is less than about 0.16 pM. In one embodiment, the $EC_{50}$ is less than about 0.15 pM. In one embodiment, the $EC_{50}$ is less than about 0.14 pM. In one embodiment, the $EC_{50}$ is less than about 0.13 pM. In one embodiment, the $EC_{50}$ is less than about 0.12 pM. In one embodiment, the $EC_{50}$ is less than about 0.11 pM. In one embodiment, the $EC_{50}$ is less than about 0.1 pM. In one embodiment, the $EC_{50}$ is less than about 0.09 pM. In one embodiment, the $EC_{50}$ is less than about 0.08 pM. In one embodiment, the $EC_{50}$ is less than about 0.07 pM. In one embodiment, the $EC_{50}$ is less than about 0.06 pM. In one embodiment, the $EC_{50}$ is less than about 0.05 pM. In one embodiment, the $EC_{50}$ is less than about 0.04 pM. In one embodiment, the $EC_{50}$ is less than about 0.03 pM. In one embodiment, the $EC_{50}$ is less than about 0.02 pM. In one embodiment, the $EC_{50}$ is or less than about 0.01 pM. In certain embodiments, the $EC_{50}$ is less than about 1000 pM. In one embodiment, the $EC_{50}$ is less than about 900 pM. In one embodiment, the $EC_{50}$ is less than about 800 pM. In one embodiment, the $EC_{50}$ is less than about 700 pM. In one embodiment, the $EC_{50}$ is less than about 600 pM. In one embodiment, the $EC_{50}$ is less than about 500 pM. In one embodiment, the $EC_{50}$ is less than about 400 pM. In one embodiment, the $EC_{50}$ is less than about 300 pM. In one embodiment, the $EC_{50}$ is less than about 200 pM. In one embodiment, the $EC_{50}$ is less than about 190 pM. In one embodiment, the $EC_{50}$ is less than about 180 pM. In one embodiment, the $EC_{50}$ is less than about 170 pM. In one embodiment, the $EC_{50}$ is less than about 160 pM. In one embodiment, the $EC_{50}$ is less than about 150 pM. In one embodiment, the $EC_{50}$ is less than about 140 pM. In one embodiment, the $EC_{50}$ is less than about 130 pM. In one embodiment, the $EC_{50}$ is less than about 120 pM. In one embodiment, the $EC_{50}$ is less than about 110 pM. In one embodiment, the $EC_{50}$ is less than about 100 pM. In one embodiment, the $EC_{50}$ is less than about 90 pM. In one embodiment, the $EC_{50}$ is less than about 80 pM. In one embodiment, the $EC_{50}$ is less than about 70 pM. In one embodiment, the $EC_{50}$ is less than about 60 pM. In one embodiment, the $EC_{50}$ is less than about 50 pM. In one embodiment, the $EC_{50}$ is less than about 40 pM. In one embodiment, the $EC_{50}$ is less than about 30 pM. In one embodiment, the $EC_{50}$ is less than about 20 pM. In one embodiment, the $EC_{50}$ is less than about 10 pM.

Also provided are methods of inhibiting host cell entry or proliferation of SARS-CoV-2, the method comprising contacting the SARS-CoV-2 with a multispecific molecule described herein, wherein contacting SARS-CoV-2 with the multispecific molecule inhibits host cell entry or proliferation of SARS-CoV-2. In one embodiment, provided is a method of inhibiting host cell entry of SARS-CoV-2, the method comprising contacting the SARS-CoV-2 with a multispecific molecule described herein, wherein contacting SARS-CoV-2 with the multispecific molecule inhibits the host cell entry of the SARS-CoV-2. In one embodiment, provided is a method of inhibiting proliferation of SARS-CoV-2, the method comprising contacting the SARS-CoV-2 with a multispecific molecule described herein, wherein contacting SARS-CoV-2 with the multispecific molecule inhibits the proliferation of the SARS-CoV-2.

Also provided are methods for eliminating SARS-CoV-2 in a subject, comprising administering an effective amount of the multispecific molecule described herein to a subject. In some embodiments, the subject has COVID-19.

Also provided are methods of treating a disease caused all or in part by SARS-CoV-2 in a subject, comprising administering an effective amount of the multispecific molecule described herein to the subject. In some embodiments, the disease is COVID-19.

In some embodiments, the multispecific molecules described herein are administered to a subject in need thereof. In some embodiments, the subject is human. In yet other embodiments, the multispecific molecule is administered to the subject via oral delivery, buccal delivery, nasal delivery or inhalation delivery. In one embodiment, the multispecific molecule is administered to the subject via oral delivery. In one embodiment, the multispecific molecule is administered to the subject via buccal delivery. In one embodiment, the multispecific molecule is administered to the subject via nasal delivery. In one embodiment, the multispecific molecule is administered to the subject via inhalation delivery.

In yet other embodiments, provided herein is use of a multispecific molecule provided herein for treating a disease or disorder in subject, wherein optionally the therapeutic molecule is administered to the subject via oral delivery, buccal delivery, nasal delivery or inhalation delivery. In one embodiment, the multispecific molecule is administered to the subject via oral delivery. In one embodiment, the multispecific molecule is administered to the subject via buccal delivery. In one embodiment, the multispecific molecule is administered to the subject via nasal delivery. In one embodiment, the multispecific molecule is administered to the subject via inhalation delivery.

Also provided is a system comprising a means for providing a first binding domain that specifically binds to polymeric immunoglobulin receptor (pIgR) and a second binding domain that specifically binds to a surface of SARS-CoV-2. In some embodiments, the second binding domain specifically binds to a structural protein on the surface of SARS-CoV-2, for example, the spike protein S, the small envelope protein E, the matrix protein M or the unexposed nucleocapsid protein N. In one embodiment, the second binding domain specifically binds to the spike protein S of SARS-CoV-2. In one embodiment, the second binding domain specifically binds to the small envelope protein E of SARS-CoV-2. In one embodiment, the second binding domain specifically binds to the matrix protein M of SARS-CoV-2. In one embodiment, the second binding domain specifically binds to unexposed nucleocapsid protein N of SARS-CoV-2. In additional embodiments, the second binding domain specifically binds to the spike glycoprotein on the surface of SARS-CoV-2. In further embodiments, second binding domain specifically binds to the S1 subunit of the spike glycoprotein on the surface of SARS-CoV-2.

Also provided is a multispecific molecule comprising: a first means capable of binding pIgR on the mucosal endothelium; and a second means capable of binding a second target that is not pIgR.

Also provided is a molecule comprising: a first means capable of binding pIgR on the mucosal endothelium; and a second means capable of binding a second target on the surface of a second cell or on a virus. In one embodiment, the second target is on the surface of a second cell. In one embodiment, the second target is on the surface of a virus. In some embodiments, the virus is SARS-CoV-2.

Also provided are nucleic acid molecules encoding the multispecific molecules described herein. Also provided are vectors nucleic acid molecules encoding the multispecific molecules described herein. Also provided are kits comprising the vector and packaging for the same. Also provided are host cells comprising the vectors containing the nucleic acid molecules encoding the multispecific molecules described herein.

Also provided is a process for making a molecule that specifically binds to more than one target molecule, the process comprising: a step for performing a function of obtaining a binding domain capable of binding to pIgR on mucosal endothelium; a step for performing a function of obtaining a binding domain capable of binding to a second target on a second cell or on a virus; and a step for performing a function of providing a molecule capable of binding to a pIgR antigen on lung endothelium and a second target on a second cell or on a virus. In some embodiments, the step for performing a function of obtaining a binding domain capable of binding to a second target is repeated n times and further comprising n steps for performing a function of providing a binding domain capable of binding to a pIgR on mucosal endothelium and n number of target molecules, wherein n is at least 2.

In some embodiments, the multispecific molecules provided herein can comprise a binding domain comprising a protein or fragment thereof that specifically binds to a ligand of interest.

In some embodiments, the multispecific molecules provided herein can comprise a binding domain comprising a diabody, a cross-body, or a bispecific antibody obtained via a controlled Fab arm exchange as those described herein.

In some embodiments, the multispecific molecules comprise IgG-like molecules with complementarity CH3 domains that promote heterodimerization; recombinant IgG-like dual targeting molecules, wherein the two sides of the molecule each contain the Fab fragment or part of the Fab fragment of at least two different antibodies; IgG fusion molecules, wherein full length IgG antibodies are fused to an extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; scFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

In some embodiments, IgG-like molecules with complementarity CH3 domains molecules include the Triomab/Quadroma (Trion Pharma/Fresenius Biotech), the Knobs-into-Holes (Genentech), CrossMAbs (Roche) and the electrostatically-matched (Amgen), the LUZ-Y (Genentech), the Strand Exchange Engineered Domain body (SEEDbody) (EMD Serono), the Biclonic (Merus), the Azymetric™ platform (Zymeworks) and the DuoBody (Genmab A/S).

In some embodiments, recombinant IgG-like dual targeting molecules include Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer).

In some embodiments, IgG fusion molecules include Dual Variable Domain (DVD)-Ig (Abbott), IgG-like Bispecific (InnClone/Eli Lilly), Ts2Ab (MedImmune/AZ) and BsAb (Zymogenetics), HERCULES (Biogen Idec) and TvAb (Roche).

In some embodiments, Fc fusion molecules can include ScFv/Fc Fusions (Academic Institution), SCORPION (Emergent BioSolutions/Trubion, Zymogenetics/BMS), Dual Affinity Retargeting Technology (Fc-DART) (MacroGenics) and Dual(ScFv)$_2$-Fab (National Research Center for Antibody Medicine—China).

In some embodiments, Fab fusion bispecific antibodies include F(ab)$_2$ (Medarex/AMGEN), Dual-Action or Bis-Fab (Genentech), Dock-and-Lock (DNL) (ImmunoMedics), Bivalent Bispecific (Biotecnol) and Fab-Fv (UCB-Celltech). ScFv-, diabody-based, and domain antibodies, include but are not limited to, Bispecific T Cell Engager (BiTE) (Micromet), Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies.

Full length bispecific antibodies provided herein can be generated for example using Fab arm exchange (or half molecule exchange) between two mono specific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy-chain disulfide bonds in the hinge regions of the parent mono specific antibodies are reduced. The resulting free cysteines of one of the parent monospecific antibodies form an inter heavy-chain disulfide bond with cysteine residues of a second parent mono specific antibody molecule and simultaneously CH3 domains of the parent antibodies release and reform by dissociation-association. The CH3 domains of the Fab arms can be engineered to favor heterodimerization over homodimerization resulting in a bispecific antibody having two Fab arms or half molecules which each binding a distinct epitope.

"Homodimerization" as used herein refers to an interaction of two heavy chains having identical CH3 amino acid sequences. "Homodimer" as used herein refers to an antibody having two heavy chains with identical CH3 amino acid sequences.

"Heterodimerization" as used herein refers to an interaction of two heavy chains having non-identical CH3 amino acid sequences. "Heterodimer" as used herein refers to an antibody having two heavy chains with non-identical CH3 amino acid sequences.

The "knob-in-hole" strategy (see, e.g., PCT Publ. No. WO2006/028936) can be used to generate full length bispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob." Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S L368A_Y407V.

Other strategies such as promoting heavy chain heterodimerization using electrostatic interactions by substituting positively charged residues at one CH3 surface and negatively charged residues at a second CH3 surface can be used, as described in US Pat. Publ. No. US2010/0015133; US Pat. Publ. No. US2009/0182127; US Pat. Publ. No. US2010/028637; or US Pat. Publ. No. US2011/0123532. In other strategies, heterodimerization can be promoted by the following substitutions (expressed as modified position in the first CH3 domain of the first heavy chain/modified position in the second CH3 domain of the second heavy chain): L351Y_F405AY407V/T394W, T3661_K392M_T394W/F405A_Y407V, T366L_K392M_T394W/F405A_Y407V, L351Y_Y407A/T366A_K409F, L351Y_Y407A/T366V K409F Y407A/T366A_K409F, or T350V_L351Y_F405A_Y407V/T350V_T366L_K392L_T394W as described in U.S. Pat. Publ. No. US2012/0149876 or U.S. Pat. Publ. No. US2013/0195849.

In addition to methods described above, bispecific antibodies provided herein can be generated in vitro in a cell-free environment by introducing asymmetrical mutations in the CH3 regions of two mono specific homodimeric antibodies and forming the bispecific heterodimeric antibody from two parent monospecific homodimeric antibodies in reducing conditions to allow disulfide bond isomerization according to methods described in PCT Pat. Publ. No. WO2011/131746. In the methods, the first monospecific bivalent antibody and the second monospecific bivalent antibody are engineered to have certain substitutions at the CH3 domain that promotes heterodimer stability; the antibodies are incubated together under reducing conditions sufficient to allow the cysteines in the hinge region to undergo disulfide bond isomerization; thereby generating the bispecific antibody by Fab arm exchange. The incubation conditions can optionally be restored to non-reducing conditions. Exemplary reducing agents that can be used are 2-mercaptoethylamine (2-MEA), dithiothreitol (DTT), dithioerythritol (DTE), glutathione, tris (2-carboxyethyl) phosphine (TCEP), L-cysteine and beta-mercaptoethanol, preferably a reducing agent selected from the group consisting of: 2-mercaptoethylamine, dithiothreitol and tris (2-carboxyethyl) phosphine. For example, incubation for at least 90 min at a temperature of at least 20° C. in the presence of at least 25 mM 2-MEA or in the presence of at least 0.5 mM dithiothreitol at a pH from 5-8, for example at pH of 7.0 or at pH of 7.4 can be used.

In certain embodiments, the $EC_{50}$ is less than about 1 pM, less than about 0.9 pM, less than about 0.8 pM, less than about 0.7 pM, less than about 0.6 pM, less than about 0.5 pM, less than about 0.4 pM, less than about 0.300 pM, less than about 0.2 pM, less than about 0.19 pM, less than about 0.18 pM, less than about 0.17 pM, less than about 0.16 pM, less than about 0.15 pM, less than about 0.14 pM, less than about 0.13 pM, less than about 0.12 pM, less than about 0.11 pM, less than about 0.1 pM, less than about 0.09 pM, less than about 0.08 pM, less than about 0.07 pM, less than about 0.06 pM, less than about 0.05 pM, less than about 0.04 pM, less than about 0.03 pM, less than about 0.02 pM, or less than about 0.01 pM. In certain embodiments, the $EC_{50}$ is less than about 1000 pM, less than about 900 pM, less than about 800 pM, less than about 700 pM, less than about 600 pM, less than about 500 pM, less than about 400 pM, less than about 300 pM, less than about 200 pM, less than about 190 pM, less than about 180 pM, less than about 170 pM, less than about 160 pM, less than about 150 pM, less than about 140 pM, less than about 130 pM, less than about 120 pM, less than about 110 pM, less than about 100 pM, less than about 90 pM, less than about 80 pM, less than about 70 pM, less than about 60 pM, less than about 50 pM, less than about 40 pM, less than about 30 pM, less than about 20 pM, or less than about 10 pM.

In certain embodiments, the concentration of the bispecific antibody or antigen-binding fragment thereof is about 0.000005 ng/mL, about 0.00005 ng/mL, about 0.0005 ng/mL, about 0.005 ng/mL, about 0.01 ng/mL, about 0.02 ng/mL, about 0.03 ng/mL, about 0.04 ng/mL, about 0.05 ng/mL, about 0.06 ng/mL, about 0.07 ng/mL, about 0.08 ng/mL, about 0.09 ng/mL, about 0.1 ng/mL, about 0.5 ng/mL, about 1.0 ng/mL, about 10 ng/mL, about 20 ng/mL about, about 30 ng/mL about 40 ng/mL, about 50 ng/mL, about 60 ng/mL, about 70 ng/mL, about 80 ng/mL, about 90 ng/mL, about 100 ng/mL, or about 1000 ng/mL.

In some embodiments, the first binding domain is human. In some embodiments, the second binding domain is human. In other embodiments, both the first binding domain and the second binding domain are human. In some embodiments, the first binding domain is humanized. In some embodiments, the second binding domain is humanized. In other embodiments, both the first binding domain and the second binding domain are humanized. In other embodiments, the first binding domain is human and the second binding domain is humanized. In other embodiments, the first binding domain is humanized and the second binding domain is human.

In some embodiments, the bispecific molecule is an IgG antibody. In some embodiments, the IgG antibody is an IgG1 antibody. In some embodiments, the IgG antibody is an IgG2 antibody. In some embodiments, the IgG antibody is an IgG3 antibody. In some embodiments, the IgG antibody is an IgG4 antibody.

In some embodiments, the bispecific molecule is multivalent. In some embodiments, the bispecific antibody is capable of binding at least three antigens. In some embodiments, the bispecific antibody is capable of binding at least five antigens.

In another general aspect, the provided herein is a vector comprising an isolated nucleic acid encoding a multispecific molecule or fragment thereof disclosed herein. In another general aspect, provided is a vector comprising an isolated nucleic acid encoding a bispecific molecule or fragment thereof disclosed herein.

It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding antibodies provided herein can be altered without changing the amino acid sequences of the proteins.

Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to embodiments provided herein. Such techniques are well known to those skilled in the art in view of the present disclosure.

In another general aspect, provided is a host cell comprising an isolated nucleic acid encoding a monoclonal antibody and/or bispecific antibody or an antigen-binding fragment thereof provided herein. Any host cell known to those skilled in the art in view of the present disclosure can be used for recombinant expression of antibodies or antigen-binding fragments thereof provided herein. In some embodiments, the host cells are *E. coli* TG1 or BL21 cells (for expression of, e.g., an scFv or Fab antibody), CHO-DG44 or CHO-K1 cells or HEK293 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, provided is a method of producing a multispecific molecule or fragment thereof disclosed herein. The methods comprise culturing a cell comprising a nucleic acid encoding the multispecific molecule or fragment thereof under conditions to produce a multispecific molecule or fragment thereof disclosed herein and recovering the multispecific molecule or fragment thereof from the cell or cell culture (e.g., from the supernatant). Expressed multispecific molecules or fragments thereof can be harvested from the cells and purified according to conventional techniques known in the art and as described herein.

In another general aspect, provided is a method of producing a bispecific molecule or fragment thereof disclosed herein. The methods comprise culturing a cell comprising a nucleic acid encoding the bispecific molecule or fragment thereof under conditions to produce a bispecific molecule or fragment thereof disclosed herein and recovering the bispecific molecule or fragment thereof from the cell or cell culture (e.g., from the supernatant). Expressed bispecific molecules or fragments thereof can be harvested from the cells and purified according to conventional techniques known in the art and as described herein.

Pharmaceutical Compositions

In another aspect, also provided are pharmaceutical compositions comprising the multispecific molecules described herein, and a pharmaceutically acceptable carrier.

In another aspect, also provided are pharmaceutical compositions comprising the means for delivering the multispecific molecules described herein, and a pharmaceutically acceptable carrier.

Also provided are methods of producing a pharmaceutical composition comprising combining the multispecific molecules described herein with a pharmaceutically acceptable carrier to obtain the pharmaceutical composition. The term "pharmaceutical composition" as used herein means a product comprising a multispecific molecule provided herein together with a pharmaceutically acceptable carrier. Therefore, a pharmaceutical composition can comprise a multispecific molecule comprising: (a) a first binding domain that specifically binds to polymeric immunoglobulin receptor (pIgR), and (b) a second binding domain that specifically binds to SARS-CoV-2. In another aspect, a pharmaceutical composition can comprise a multispecific molecule comprising: (a) a first binding domain that specifically binds to polymeric immunoglobulin receptor (pIgR), and (b) a second binding domain that specifically binds to SARS-CoV-2. Multispecific molecules provided herein and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition provided herein. According to particular embodiments, in view of the present disclosure, any pharmaceutically acceptable carrier suitable for use in an antibody pharmaceutical composition can be used herein.

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carriers can be used in formulating the pharmaceutical compositions provided herein.

In one embodiment of the invention, the pharmaceutical composition is a liquid formulation. A preferred example of a liquid formulation is an aqueous formulation, i.e., a formulation comprising water. The liquid formulation can comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition can be formulated as an injectable which can be injected, for example, via an injection device (e.g., a syringe or an infusion pump). The injection can be delivered subcutaneously, intramuscularly, intraperitoneally, intravitreally, or intravenously, for example.

In another embodiment, the pharmaceutical composition is a solid formulation, e.g., a freeze-dried or spray-dried composition, which can be used as is, or whereto the physician or the patient adds solvents, and/or diluents prior to use. Solid dosage forms can include tablets, such as compressed tablets, and/or coated tablets, and capsules (e.g., hard or soft gelatin capsules). The pharmaceutical composition can also be in the form of sachets, dragees, powders, granules, lozenges, or powders for reconstitution, for example.

The dosage forms can be immediate release, in which case they can comprise a water-soluble or dispersible carrier, or they can be delayed release, sustained release, or modified release, in which case they can comprise water-insoluble polymers that regulate the rate of dissolution of the dosage form in the gastrointestinal tract or under the skin.

In other embodiments, the pharmaceutical composition can be delivered intranasally, intrabuccally, or sublingually.

The pH in an aqueous formulation can be between pH 3 and pH 10. In one embodiment provided herein, the pH of the formulation is from about 7.0 to about 9.5. In another embodiment provided herein, the pH of the formulation is from about 3.0 to about 7.0.

In another embodiment provided herein, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer can be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments provided herein.

In another embodiment provided herein, the pharmaceutical composition comprises a preservative. Non-limiting examples of preservatives include: benzethonium chloride, benzoic acid, benzyl alcohol, bronopol, butyl 4-hydroxybenzoate, chlorobutanol, chlorocresol, chlorohexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative can be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments provided herein.

In another embodiment provided herein, the pharmaceutical composition comprises an isotonic agent. Non-limiting examples of isotonic agents include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars can include mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethyl-cellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. The isotonic agent can be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative provided herein.

In another embodiment provided herein, the pharmaceutical composition comprises a chelating agent. Non-limiting examples of chelating agents include citric acid, aspartic acid, salts of ethylenediaminetetraacetic acid (EDTA), and mixtures thereof. The chelating agent can be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments of the invention.

In another embodiment provided herein, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment provided herein, the pharmaceutical composition comprises a stabilizer, wherein said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer can be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments provided herein.

In further embodiments provided herein, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant can, for example, be selected from the group consisting of anionic surfactants, cationic surfactants, nonionic surfactants, and/or zwitterionic surfactants. The surfactant can be present individually or in the aggregate, in a concentration from about 0.1 mg/ml to about 20 mg/ml. Pharmaceutical compositions comprising each one of these specific surfactants constitute alternative embodiments provided herein.

In a further embodiment provided herein, the pharmaceutical composition comprises one or more protease inhibitors, such as, e.g., EDTA, and/or benzamidine hydrochloric acid (HCl). The protease inhibitor can be present individually or in the aggregate, in a concentration from about 0.1 mg/ml to about 20 mg/ml. Pharmaceutical compositions comprising each one of these specific protease inhibitors constitute alternative embodiments provided herein.

In another general aspect, provided is a method of producing a pharmaceutical composition comprising a multispecific molecule, antibody or antigen-binding fragment thereof disclosed herein, comprising combining a multispecific molecule, antibody or antigen-binding fragment thereof with a pharmaceutically acceptable carrier to obtain the pharmaceutical composition.

Methods of Use

According to some embodiments, the described multispecific molecule can be provided in a buffered composition for storage or use. Suitable buffers for the storage of the described multispecific molecule would serve to maintain the stability of the molecule by minimizing deterioration while stored, not promoting aggregation of the molecule, or minimizing adhesion to the storage vessel.

In one aspect, provided herein is a method for eliminating SARS-CoV-2 in a subject, comprising administering an effective amount of the multispecific molecule provided herein to the subject. In one aspect, provided herein is a method of treating a disease caused all or in part by SARS-CoV-2 in a subject, comprising administering an effective amount of the multispecific molecule provided herein to the subject. In one embodiment, the disease is COVID-19.

In one aspect, provided herein is a method for eliminating SARS-CoV-1 in a subject, comprising administering an effective amount of the multispecific molecule provided herein to the subject. In one aspect, provided herein is a method of treating a disease caused all or in part by SARS-CoV-1 in a subject, comprising administering an effective amount of the multispecific molecule provided herein to the subject. In one embodiment, the disease is SARS.

In one aspect, provided herein is a method of treating a disease wherein host cell entry is facilitated by binding of a viral surface protein to ACE2, comprising administering an effective amount of the multispecific molecule provided herein to the subject. In another aspect, provided herein is a method of treating a disease wherein host cell entry is facilitated by binding of a SARS-CoV-1 surface protein to ACE2, comprising administering an effective amount of the multispecific molecule provided herein to the subject. In another aspect, provided herein is a method of treating a disease wherein host cell entry is facilitated by binding of a SARS-CoV-2 surface protein to ACE2, comprising administering an effective amount of the multispecific molecule provided herein to the subject.

In another aspect, provided herein is a method for eliminating target cells expressing the second target in a subject, comprising administering an effective amount of the multispecific molecule provided herein to the subject. In one aspect, provided herein is a method of treating a disease caused all or in part by cells expressing the second target in a subject, comprising administering an effective amount of the multispecific molecule provided herein to the subject.

The some embodiments, the disease is a cancer, an inflammatory disease, inflammatory bowel disease, pneumonia, cystic fibrosis, lung infection, asthma, tuberculosis, chronic obstructive pulmonary disease (COPD), bronchitis and emphysema, Crohn's disease, ulcerative colitis, cystitis, overactive bladder disease, sinus infection, gastrointestinal ulcer, adenomyosis, uterine inflammation, hepatobiliary disease, or hepatitis. In one embodiment, the disease is a SARS-CoV-2-mediated disease. In one aspect, the disease is COVID-19.

In one aspect, the subject is a subject in need thereof. In another aspect, the subject is a human.

As used herein, the term "effective amount" refers to an amount of an active ingredient or component that elicits the desired biological or medicinal response in a subject.

According to particular embodiments, an effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

According to particular embodiments, the compositions described herein are formulated to be suitable for the intended route of administration to a subject. For example, the compositions described herein can be formulated to be suitable for intravenous, subcutaneous, or intramuscular administration.

As used herein, the terms "treat," "treating," and "treatment" are all intended to refer to an amelioration or reversal of at least one measurable physical parameter related to a cancer, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition, such as a tumor or more preferably a cancer. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

In some embodiments, multispecific molecule provided herein is used in combination with a supplemental therapy.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

7. EMBODIMENTS

This invention provides the following non-limiting embodiments.

In one set of embodiments, provided are:

A1. A multispecific molecule comprising: (a) a first binding domain that specifically binds to polymeric immunoglobulin receptor (pIgR), and (b) a second binding domain that specifically binds to SARS-CoV-2.

A2. The molecule of embodiment A1, wherein the molecule is a bispecific molecule.

A3. The molecule of any one of embodiments A1 or A2, wherein the second binding domain specifically binds to the surface of SARS-CoV-2.

A4. The molecule of any one of embodiments A1 to A3, wherein the second binding domain specifically binds to the spike glycoprotein on the surface of SARS-CoV-2.

A5. The molecule of any one of embodiments A1 to A4, wherein the second binding domain specifically binds to the S1 subunit of the spike glycoprotein on the surface of SARS-CoV-2.

A6. The molecule of any one of embodiments A1 to A5, wherein the second binding domain comprises angiotensin-converting enzyme 2 (ACE2).

A7. The molecule of any one of embodiments A1 to A5, wherein the second binding domain comprises the extracellular domain of ACE2.

A8. The molecule of any one of embodiments A1 to A5, wherein the second binding domain comprises a truncated extracellular domain of ACE2.

A9. The molecule of embodiment A6, wherein ACE2 comprises SEQ ID NO:194.

A10. The molecule of embodiment A7, wherein the extracellular domain of ACE2 comprises SEQ ID NO:134.

A11. The molecule of embodiment A8, wherein the truncated extracellular domain of ACE2 comprises SEQ ID NO:120 or SEQ ID NO:121.

A12. The molecule of any one of embodiments A1 to A11, wherein the first binding domain comprises a single-domain molecule (VHH).

A13. The molecule of embodiment A12, wherein the VHH comprises a complementarity determining region 1 (CDR1) having an amino acid sequence of SEQ ID NO:1, a CDR2 having an amino acid sequence of SEQ ID NO:2, and a CDR3 having an amino acid sequence of SEQ ID NO:3.

A14. The molecule of embodiment A13, wherein the VHH comprises an amino acid sequence of SEQ ID NO:16.

A15. The molecule of embodiment A12, wherein the VHH comprises a CDR1 having an amino acid sequence of SEQ ID NO:17, a CDR2 having an amino acid sequence of SEQ ID NO:18, and a CDR3 having an amino acid sequence of SEQ ID NO:19.

A16. The molecule of embodiment A15, wherein the VHH comprises an amino acid sequence of SEQ ID NO:32.

A17. The molecule of any one of embodiments A1 to A16, wherein the first binding domain specifically binds to pIgR that is present on the mucosal endothelium.

A18. The molecule of embodiment A17, wherein the first binding domain specifically binds to pIgR that is present on the lung mucosal endothelium.

A19. The molecule of any one of embodiments A1 to A18, wherein the SARS-CoV-2 is neutralized when the molecule specifically binds to the pIgR and to SARS-CoV-2.

A20. The molecule of embodiment A19, wherein the molecule neutralized SARS-CoV-2 with an $EC_{50}$ of less than about 4 nM.

A21. The molecule of embodiment A19, wherein the molecule neutralized SARS-CoV-2 with an $EC_{50}$ of less than about 3 nM.

A22. The molecule of embodiment A19, wherein the molecule neutralized SARS-CoV-2 with an $EC_{50}$ of less than about 1 nM.

A23. The molecule of embodiment A19, wherein the molecule neutralized SARS-CoV-2 with an $EC_{50}$ of less than about 500 pM.

A24. The molecule of embodiment A19, wherein the molecule neutralized SARS-CoV-2 with an $EC_{50}$ of less than about 100 pM.

A25. The molecule of any one of embodiments A1 to A24, wherein the molecule comprises an Fc region from an IgG antibody.

A26. The molecule of embodiment A25, wherein the IgG molecule is an IgG1, IgG2, IgG3, or IgG4 antibody.

A27. The molecule of any one of embodiments A1 to A26, wherein the first binding domain specifically binds a pIgR antigen.

A28. The molecule of any one of embodiments A1 to A26, wherein the first binding domain specifically binds an extracellular pIgR epitope.

A29. The molecule of any one of embodiments A1 to A26, wherein CDR1, CDR2, and CDR3 form a binding site for an antigen of the pIgR.

A30. The molecule of any one of embodiments A1 to A26, wherein the CDR1, CDR2, and CDR3 form a binding site for an epitope of the pIgR.

In a second set of embodiments, provided are:

B1. A pharmaceutical composition comprising a multi-specific molecule comprising: (a) a first binding domain that specifically binds to polymeric immunoglobulin receptor (pIgR), and (b) a second binding domain that specifically binds to SARS-CoV-2, and a pharmaceutically acceptable carrier.

B2. The pharmaceutical composition of embodiment B1, wherein the molecule is a bispecific molecule.

B3. The pharmaceutical composition of any one of embodiments B1 or B2, wherein the second binding domain specifically binds to the surface of SARS-CoV-2.

B4. The pharmaceutical composition of any one of embodiments B1 to B3, wherein the second binding domain specifically binds to the spike glycoprotein on the surface of SARS-CoV-2.

B5. The pharmaceutical composition of any one of embodiments B1 to B4, wherein the second binding domain specifically binds to the S1 subunit of the spike glycoprotein on the surface of SARS-CoV-2.

B6. The pharmaceutical composition of any one of embodiments B1 to B5, wherein the second binding domain comprises angiotensin-converting enzyme 2 (ACE2).

B7. The pharmaceutical composition of any one of embodiments B1 to B5, wherein the second binding domain comprises the extracellular domain of ACE2.

B8. The pharmaceutical composition of any one of embodiments B1 to B5, wherein the second binding domain comprises a truncated extracellular domain of ACE2.

B9. The pharmaceutical composition of embodiment B6, wherein ACE2 comprises SEQ ID NO:194.

B10. The pharmaceutical composition of embodiment B7, wherein the extracellular domain of ACE2 comprises SEQ ID NO:134.

B11. The pharmaceutical composition of embodiment B8, wherein the truncated extracellular domain of ACE2 comprises SEQ ID NO:120 or SEQ ID NO:121.

B12. The pharmaceutical composition of any one of embodiments B1 to B11, wherein the first binding domain comprises a single-domain molecule (VHH).

B13. The pharmaceutical composition of embodiment B12, wherein the VHH comprises a complementarity determining region 1 (CDR1) having an amino acid sequence of SEQ ID NO:1, a CDR2 having an amino acid sequence of SEQ ID NO:2, and a CDR3 having an amino acid sequence of SEQ ID NO:3.

B14. The pharmaceutical composition of embodiment B13, wherein the VHH comprises an amino acid sequence of SEQ ID NO:16.

B15. The pharmaceutical composition of embodiment B12, wherein the VHH comprises a CDR1 having an amino acid sequence of SEQ ID NO:17, a CDR2 having an amino acid sequence of SEQ ID NO:18, and a CDR3 having an amino acid sequence of SEQ ID NO:19.

B16. The pharmaceutical composition of embodiment B15, wherein the VHH comprises an amino acid sequence of SEQ ID NO:32.

B17. The pharmaceutical composition of any one of embodiments B1 to B16, wherein the first binding domain specifically binds to pIgR that is present on the mucosal endothelium.

B18. The pharmaceutical composition of embodiment B17, wherein the first binding domain specifically binds to pIgR that is present on the lung mucosal endothelium.

B19. The pharmaceutical composition of any one of embodiments B1 to B18, wherein the SARS-CoV-2 is neutralized when the molecule specifically binds to the pIgR and to SARS-CoV-2.

B20. The pharmaceutical composition of embodiment B19, wherein the molecule neutralized SARS-CoV-2 with an EC50 of less than about 4 nM.

B21. The pharmaceutical composition of embodiment B19, wherein the molecule neutralized SARS-CoV-2 with an EC50 of less than about 3 nM.

B22. The pharmaceutical composition of embodiment B19, wherein the molecule neutralized SARS-CoV-2 with an EC50 of less than about 1 nM.
B23. The pharmaceutical composition of embodiment B19, wherein the molecule neutralized SARS-CoV-2 with an EC50 of less than about 500 pM.
B24. The pharmaceutical composition of embodiment B19, wherein the molecule neutralized SARS-CoV-2 with an EC50 of less than about 100 pM.
B25. A pharmaceutical composition comprising the means for delivering the molecule of any one of embodiments B1 to B24, and a pharmaceutically acceptable carrier.
B26. A method of producing the pharmaceutical composition of embodiment B25, comprising combining the molecule with a pharmaceutically acceptable carrier to obtain the pharmaceutical composition.

In a third set of embodiments, provided are:

C1. A method of inhibiting host cell entry or proliferation of SARS-CoV-2, the method comprising contacting the SARS-CoV-2 with a multispecific molecule comprising: (a) a first binding domain that specifically binds to polymeric immunoglobulin receptor (pIgR), and (b) a second binding domain that specifically binds to SARS-CoV-2, wherein contacting SARS-CoV-2 with the molecule inhibits host cell entry or proliferation of SARS-CoV-2.
C2. The method of embodiment C1, wherein the molecule is a bispecific molecule.
C3. The method of any one of embodiments C1 or C2, wherein the second binding domain specifically binds to the surface of SARS-CoV-2.
C4. The method of any one of embodiments C1 to C3, wherein the second binding domain specifically binds to the spike glycoprotein on the surface of SARS-CoV-2.
C5. The method of any one of embodiments C1 to C4, wherein the second binding domain specifically binds to the S1 subunit of the spike glycoprotein on the surface of SARS-CoV-2.
C6. The method of any one of embodiments C1 to C5, wherein the second binding domain comprises angiotensin-converting enzyme 2 (ACE2).
C7. The method of any one of embodiments C1 to C5, wherein the second binding domain comprises the extracellular domain of ACE2.
C8. The method of any one of embodiments C1 to C5, wherein the second binding domain comprises a truncated extracellular domain of ACE2.
C9. The method of embodiment C6, wherein ACE2 comprises SEQ ID NO:194.
C10. The method of embodiment C7, wherein the extracellular domain of ACE2 comprises SEQ ID NO:134.
C11. The method of embodiment C8, wherein the truncated extracellular domain of ACE2 comprises SEQ ID NO:120 or SEQ ID NO:121.
C12. The method of any one of embodiments C1 to C11, wherein the first binding domain comprises a single-domain molecule (VHH).
C13. The method of embodiment C12, wherein the VHH comprises a complementarity determining region 1 (CDR1) having an amino acid sequence of SEQ ID NO:1, a CDR2 having an amino acid sequence of SEQ ID NO:2, and a CDR3 having an amino acid sequence of SEQ ID NO:3.
C14. The method of embodiment C13, wherein the VHH comprises an amino acid sequence of SEQ ID NO:16.
C15. The method of embodiment C12, wherein the VHH comprises a CDR1 having an amino acid sequence of SEQ ID NO:17, a CDR2 having an amino acid sequence of SEQ ID NO:18, and a CDR3 having an amino acid sequence of SEQ ID NO:19.
C16. The method of embodiment C15, wherein the VHH comprises an amino acid sequence of SEQ ID NO:32.
C17. The method of any one of embodiments C1 to C16, wherein the first binding domain specifically binds to pIgR that is present on the mucosal endothelium.
C18. The method of embodiment C17, wherein the first binding domain specifically binds to pIgR that is present on the lung mucosal endothelium.
C19. The method of any one of embodiments C1 to C18, wherein the SARS-CoV-2 is neutralized when the molecule specifically binds to the pIgR and to SARS-CoV-2.
C20. The method of embodiment C19, wherein the molecule neutralized SARS-CoV-2 with an $EC_{50}$ of less than about 4 nM.
C21. The method of embodiment C19, wherein the molecule neutralized SARS-CoV-2 with an $EC_{50}$ of less than about 3 nM.
C22. The method of embodiment C19, wherein the molecule neutralized SARS-CoV-2 with an $EC_{50}$ of less than about 1 nM.
C23. The method of embodiment C19, wherein the molecule neutralized SARS-CoV-2 with an $EC_{50}$ of less than about 500 pM.
C24. The method of embodiment C19, wherein the molecule neutralized SARS-CoV-2 with an $EC_{50}$ of less than about 100 pM.
C25. The method of any one of embodiments C1 to C24, wherein the subject has COVID-19.
C26. A method for eliminating SARS-CoV-2 in a subject, comprising administering to the subject an effective amount of a multispecific molecule comprising: (a) a first binding domain that specifically binds to polymeric immunoglobulin receptor (pIgR), and (b) a second binding domain that specifically binds to SARS-CoV-2.
C27. The method of embodiment C26, wherein the molecule is a bispecific molecule.
C28. The method of any one of embodiments C26 or C27, wherein the second binding domain specifically binds to the surface of SARS-CoV-2.
C29. The method of any one of embodiments C26 to C28, wherein the second binding domain specifically binds to the spike glycoprotein on the surface of SARS-CoV-2.
C30. The method of any one of embodiments C26 to C29, wherein the second binding domain specifically binds to the S1 subunit of the spike glycoprotein on the surface of SARS-CoV-2.
C31. The method of any one of embodiments C26 to C30, wherein the second binding domain comprises angiotensin-converting enzyme 2 (ACE2).
C32. The method of any one of embodiments C26 to C30, wherein the second binding domain comprises the extracellular domain of ACE2.
C33. The method of any one of embodiments C26 to C30, wherein the second binding domain comprises a truncated extracellular domain of ACE2.
C34. The method of embodiment C31, wherein ACE2 comprises SEQ ID NO:194.
C35. The method of embodiment C32, wherein the extracellular domain of ACE2 comprises SEQ ID NO:134.

C36. The method of embodiment C33, wherein the truncated extracellular domain of ACE2 comprises SEQ ID NO:120 or SEQ ID NO:121.

C37. The method of any one of embodiments C26 to C36, wherein the first binding domain comprises a single-domain molecule (VHH).

C38. The method of embodiment C37, wherein the VHH comprises a complementarity determining region 1 (CDR1) having an amino acid sequence of SEQ ID NO:1, a CDR2 having an amino acid sequence of SEQ ID NO:2, and a CDR3 having an amino acid sequence of SEQ ID NO:3.

C39. The method of embodiment C38, wherein the VHH comprises an amino acid sequence of SEQ ID NO:16.

C40. The method of embodiment C37, wherein the VHH comprises a CDR1 having an amino acid sequence of SEQ ID NO:17, a CDR2 having an amino acid sequence of SEQ ID NO:18, and a CDR3 having an amino acid sequence of SEQ ID NO:19.

C41. The method of embodiment C40, wherein the VHH comprises an amino acid sequence of SEQ ID NO:32.

C42. The method of any one of embodiments C37 to C41, wherein the first binding domain specifically binds to pIgR that is present on the mucosal endothelium.

C43. The method of embodiment C42, wherein the first binding domain specifically binds to pIgR that is present on the lung mucosal endothelium.

C44. The method of any one of embodiments C26 to C43, wherein the SARS-CoV-2 is neutralized when the molecule specifically binds to the pIgR and to SARS-CoV-2.

C45. The method of embodiment C44, wherein the molecule neutralized SARS-CoV-2 with an $EC_{50}$ of less than about 4 nM.

C46. The method of embodiment C44, wherein the molecule neutralized SARS-CoV-2 with an $EC_{50}$ of less than about 3 nM.

C47. The method of embodiment C44, wherein the molecule neutralized SARS-CoV-2 with an $EC_{50}$ of less than about 1 nM.

C48. The method of embodiment C44, wherein the molecule neutralized SARS-CoV-2 with an $EC_{50}$ of less than about 500 pM.

C49. The method of embodiment C44, wherein the molecule neutralized SARS-CoV-2 with an $EC_{50}$ of less than about 100 pM.

C50. The method of any one of embodiments C26 to C44, wherein the subject has COVID-19.

In a fourth set of embodiments, provided are:

D1. A method of treating a disease caused all or in part by SARS-CoV-2 in a subject, comprising administering to the subject an effective amount of a multispecific molecule comprising: (a) a first binding domain that specifically binds to polymeric immunoglobulin receptor (pIgR), and (b) a second binding domain that specifically binds to SARS-CoV-2.

D2. The method of embodiment D1, wherein the molecule is a bispecific molecule.

D3. The method of any one of embodiments D1 or D2, wherein the second binding domain specifically binds to the surface of SARS-CoV-2.

D4. The method of any one of embodiments D1 to D3, wherein the second binding domain specifically binds to the spike glycoprotein on the surface of SARS-CoV-2.

D5. The method of any one of embodiments D1 to D4, wherein the second binding domain specifically binds to the S1 subunit of the spike glycoprotein on the surface of SARS-CoV-2.

D6. The method of any one of embodiments D1 to D5, wherein the second binding domain comprises angiotensin-converting enzyme 2 (ACE2).

D7. The method of any one of embodiments D1 to D5, wherein the second binding domain comprises the extracellular domain of ACE2.

D8. The method of any one of embodiments D1 to D5, wherein the second binding domain comprises a truncated extracellular domain of ACE2.

D9. The method of embodiment D6, wherein ACE2 comprises SEQ ID NO:194.

D10. The method of embodiment D7, wherein the extracellular domain of ACE2 comprises SEQ ID NO:134.

D11. The method of embodiment D8, wherein the truncated extracellular domain of ACE2 comprises SEQ ID NO:120 or SEQ ID NO:121.

D12. The method of any one of embodiments D1 to D11, wherein the first binding domain comprises a single-domain molecule (VHH).

D13. The method of embodiment D12, wherein the VHH comprises a complementarity determining region 1 (CDR1) having an amino acid sequence of SEQ ID NO:1, a CDR2 having an amino acid sequence of SEQ ID NO:2, and a CDR3 having an amino acid sequence of SEQ ID NO:3.

D14. The method of embodiment D13, wherein the VHH comprises an amino acid sequence of SEQ ID NO:16.

D15. The method of embodiment D12, wherein the VHH comprises a CDR1 having an amino acid sequence of SEQ ID NO:17, a CDR2 having an amino acid sequence of SEQ ID NO:18, and a CDR3 having an amino acid sequence of SEQ ID NO:19.

D16. The method of embodiment D15, wherein the VHH comprises an amino acid sequence of SEQ ID NO:32.

D17. The method of any one of embodiments D1 to D16, wherein the first binding domain specifically binds to pIgR that is present on the mucosal endothelium.

D18. The method of embodiment D17, wherein the first binding domain specifically binds to pIgR that is present on the lung mucosal endothelium.

D19. The method of any one of embodiments D1 to D18, wherein the SARS-CoV-2 is neutralized when the molecule specifically binds to the pIgR and to SARS-CoV-2.

D20. The method of embodiment D19, wherein the molecule neutralized SARS-CoV-2 with an $EC_{50}$ of less than about 4 nM.

D21. The method of embodiment D19, wherein the molecule neutralized SARS-CoV-2 with an $EC_{50}$ of less than about 3 nM.

D22. The method of embodiment D19, wherein the molecule neutralized SARS-CoV-2 with an $EC_{50}$ of less than about 1 nM.

D23. The method of embodiment D19, wherein the molecule neutralized SARS-CoV-2 with an $EC_{50}$ of less than about 500 pM.

D24. The method of embodiment D19, wherein the molecule neutralized SARS-CoV-2 with an $EC_{50}$ of less than about 100 pM.

D25. The method of any one of embodiments D1 to D24, wherein the disease is COVID-19.

D26. The method of any one of embodiments D1 to D25, wherein the subject is a subject in need thereof.

D27. The method of any one of embodiments D1 to D26, wherein the subject is a human.

In fifth set of embodiments, provided are:

E1. A system comprising a means for providing a first binding domain that specifically binds to polymeric immunoglobulin receptor (pIgR) and a second binding domain that specifically binds to surface of SARS-CoV-2.

E2. The system of embodiment E1, wherein the means comprises a bispecific molecule.

E3. The system of any one of embodiments E1 or E2, wherein the second binding domain specifically binds to the surface of SARS-CoV-2.

E4. The system of any one of embodiments E1 to E3, wherein the second binding domain specifically binds to the spike glycoprotein on the surface of SARS-CoV-2.

E5. The system of any one of embodiments E1 to E4, wherein the second binding domain specifically binds to the S1 subunit of the spike glycoprotein on the surface of SARS-CoV-2.

E6. The system of any one of embodiments E1 to E5, wherein the second binding domain comprises angiotensin-converting enzyme 2 (ACE2).

E7. The system of any one of embodiments E1 to E5, wherein the second binding domain comprises the extracellular domain of ACE2.

E8. The system of any one of embodiments E1 to E5, wherein the second binding domain comprises a truncated extracellular domain of ACE2.

E9. The system of embodiment E6, wherein ACE2 comprises SEQ ID NO:194.

E10. The system of embodiment E7, wherein the extracellular domain of ACE2 comprises SEQ ID NO:134.

E11. The system of embodiment E8, wherein the truncated extracellular domain of ACE2 comprises SEQ ID NO:120 or SEQ ID NO:121.

E12. The system of any one of embodiments E1 to E11, wherein the first binding domain comprises a single-domain molecule (VHH).

E13. The system of embodiment E12, wherein the VHH comprises a complementarity determining region 1 (CDR1) having an amino acid sequence of SEQ ID NO:1, a CDR2 having an amino acid sequence of SEQ ID NO:2, and a CDR3 having an amino acid sequence of SEQ ID NO:3.

E14. The system of embodiment E13, wherein the VHH comprises an amino acid sequence of SEQ ID NO:16.

E15. The system of embodiment E12, wherein the VHH comprises a CDR1 having an amino acid sequence of SEQ ID NO:17, a CDR2 having an amino acid sequence of SEQ ID NO:18, and a CDR3 having an amino acid sequence of SEQ ID NO:19.

E16. The system of embodiment E15, wherein the VHH comprises an amino acid sequence of SEQ ID NO:32.

E17. The system of any one of embodiments E1 to E16, wherein the first binding domain specifically binds to pIgR that is present on the mucosal endothelium.

E18. The system of embodiment E17, wherein the first binding domain specifically binds to pIgR that is present on the lung mucosal endothelium.

E19. The system of any one of embodiments E1 to E18, wherein the SARS-CoV-2 is neutralized when the molecule specifically binds to the pIgR and to SARS-CoV-2.

E20. The system of embodiment E19, wherein the molecule neutralized SARS-CoV-2 with an $EC_{50}$ of less than about 4 nM.

E21. The system of embodiment E19, wherein the molecule neutralized SARS-CoV-2 with an $EC_{50}$ of less than about 3 nM.

E22. The system of embodiment E19, wherein the molecule neutralized SARS-CoV-2 with an $EC_{50}$ of less than about 1 nM.

E23. The system of embodiment E19, wherein the molecule neutralized SARS-CoV-2 with an $EC_{50}$ of less than about 500 pM.

E24. The system of embodiment E19, wherein the molecule neutralized SARS-CoV-2 with an $EC_{50}$ of less than about 100 pM.

E25. A system comprising a means for providing a first binding domain that specifically binds to pIgR and a second binding domain that specifically binds to a second target that is not pIgR.

E26. The system of embodiment E25, wherein the means comprises a bispecific molecule.

E27. The molecule of any one of embodiments E25 or E26 wherein the first binding domain comprises a single-domain molecule (VHH).

E28. The system of embodiment E27, wherein the VHH comprises a complementarity determining region 1 (CDR1) having an amino acid sequence of SEQ ID NO:1, a CDR2 having an amino acid sequence of SEQ ID NO:2, and a CDR3 having an amino acid sequence of SEQ ID NO:3.

E29. The system of embodiment E28, wherein the VHH comprises an amino acid sequence of SEQ ID NO:16.

E30. The system of embodiment E27, wherein the VHH comprises a CDR1 having an amino acid sequence of SEQ ID NO:17, a CDR2 having an amino acid sequence of SEQ ID NO:18, and a CDR3 having an amino acid sequence of SEQ ID NO:19.

E31. The system of embodiment E30, wherein the VHH comprises an amino acid sequence of SEQ ID NO:32.

E32. The system of any one of embodiments E25 to E31, wherein the first binding domain specifically binds to pIgR that is present on the mucosal endothelium.

E33. The system of embodiment E32, wherein the first binding domain specifically binds to pIgR that is present on the lung mucosal endothelium.

E34. The system of any one of embodiments E1 to E18 and E25 to E32, wherein the molecule comprises an Fc region from an IgG antibody.

E35. The system of embodiment E34, wherein the IgG molecule is an IgG1, IgG2, IgG3, or IgG4 antibody.

E36. The system of any one of embodiments E1 to E18 and E25 to E35, wherein the first binding domain specifically binds a pIgR antigen.

E37. The system of any one of embodiments E1 to E18 and E25 to E35, wherein the first binding domain specifically binds an extracellular pIgR epitope.

E38. The system of any one of embodiments E1 to E18 and E25 to E35, wherein CDR1, CDR2, and CDR3 form a binding site for an antigen of the pIgR.

E39. The system of any one of embodiments E1 to E18 and E25 to E35, wherein the CDR1, CDR2, and CDR3 form a binding site for an epitope of the pIgR.

E40. The system of any one of embodiments E25 to E39, wherein the second target is on the surface of a second cell.

E41. The system of any one of embodiments E25 to E40, wherein the second target is on the surface of a virus.

E42. The system of any one of embodiments E25 to E41, wherein the second target is on the surface of SARS-CoV-2.

E43. The system of any one of embodiments E25 to E42, wherein the second target is the spike glycoprotein.

E44. The system of embodiment E43, wherein the second target is the S1 subunit of the spike glycoprotein.

E45. The system of any one of embodiments E25 to E44, wherein the second binding domain comprises angiotensin-converting enzyme 2 (ACE2).

E46. The system of any one of embodiments E25 to E44, wherein the second binding domain comprises the extracellular domain of ACE2.

E47. The system of any one of embodiments E25 to E44, wherein the second binding domain comprises a truncated extracellular domain of ACE2.

E48. The system of embodiment E45, wherein ACE2 comprises SEQ ID NO:194.

E49. The system of embodiment E46, wherein the extracellular domain of ACE2 comprises SEQ ID NO:134.

E50. The system of embodiment E47, wherein the truncated extracellular domain of ACE2 comprises SEQ ID NO:120 or SEQ ID NO:121.

E51. The system of any one of embodiments E40 to E50, wherein the second cell or virus is neutralized when the molecule specifically binds to the pIgR and to the second target on the surface of the second cell or virus.

E52. The system of embodiment E51, wherein the molecule neutralized the second cell or virus with an $EC_{50}$ of less than about 4 nM.

E53. The system of embodiment E51, wherein the molecule neutralized the second cell or virus with an $EC_{50}$ of less than about 3 nM.

E54. The system of embodiment E51, wherein the molecule neutralized the second cell or virus with an $EC_{50}$ of less than about 1 nM.

E55. The system of embodiment E51, wherein the molecule neutralized the second cell or virus with an $EC_{50}$ of less than about 500 pM.

E56. The system of embodiment E51, wherein the molecule neutralized the second cell or virus with an $EC_{50}$ of less than about 100 pM.

In sixth set of embodiments, provided are:

F1. A method of inhibiting host cell entry or proliferation of target cells expressing the second target, the method comprising contacting the target cells with a multispecific molecule comprising: (a) a first binding domain that specifically binds to polymeric immunoglobulin receptor (pIgR), and (b) a second binding domain that specifically binds to a second target that is not pIgR, wherein contacting the target cells with the molecule inhibits host cell entry or proliferation of the target cells.

F2. The molecule of embodiment F1, wherein the molecule is a bispecific molecule.

F3. The molecule of any one of embodiments F1 or F2, wherein the first binding domain comprises a single-domain molecule (VHH).

F4. The molecule of embodiment F3, wherein the VHH comprises a complementarity determining region 1 (CDR1) having an amino acid sequence of SEQ ID NO:1, a CDR2 having an amino acid sequence of SEQ ID NO:2, and a CDR3 having an amino acid sequence of SEQ ID NO:3.

F5. The molecule of embodiment F4, wherein the VHH comprises an amino acid sequence of SEQ ID NO:16.

F6. The molecule of embodiment F3, wherein the VHH comprises a CDR1 having an amino acid sequence of SEQ ID NO:17, a CDR2 having an amino acid sequence of SEQ ID NO:18, and a CDR3 having an amino acid sequence of SEQ ID NO:19.

F7. The molecule of embodiment F6, wherein the VHH comprises an amino acid sequence of SEQ ID NO:32.

F8. The molecule of any one of embodiments F1 to F7, wherein the first binding domain specifically binds to pIgR that is present on the mucosal endothelium.

F9. The molecule of embodiment F8, wherein the first binding domain specifically binds to pIgR that is present on the lung mucosal endothelium.

F10. The molecule of any one of embodiments F1 to F9, wherein the molecule comprises an Fc region from an IgG antibody.

F11. The molecule of embodiment F10, wherein the IgG molecule is an IgG1, IgG2, IgG3, or IgG4 antibody.

F12. The molecule of any one of embodiments F1 to F11, wherein the first binding domain specifically binds a pIgR antigen.

F13. The molecule of any one of embodiments F1 to F11, wherein the first binding domain specifically binds an extracellular pIgR epitope.

F14. The molecule of any one of embodiments F1 to F11, wherein CDR1, CDR2, and CDR3 form a binding site for an antigen of the pIgR.

F15. The molecule of any one of embodiments F1 to F11, wherein the CDR1, CDR2, and CDR3 form a binding site for an epitope of the pIgR.

F16. The molecule of any one of embodiments F1 to F15, wherein the second target is on the surface of a second cell.

F17. The molecule of any one of embodiments F1 to F16, wherein the second target is on the surface of a virus.

F18. The molecule of any one of embodiments F1 to F17, wherein the second target is on the surface of SARS-CoV-2.

F19. The molecule of any one of embodiments F1 to F18, wherein the second target is the spike glycoprotein.

F20. The molecule of embodiment F19, wherein the second target is the S1 subunit of the spike glycoprotein.

F21. The molecule of any one of embodiments F1 to F20, wherein the second binding domain comprises angiotensin-converting enzyme 2 (ACE2).

F22. The molecule of any one of embodiments F1 to F20, wherein the second binding domain comprises the extracellular domain of ACE2.

F23. The molecule of any one of embodiments F1 to F20, wherein the second binding domain comprises a truncated extracellular domain of ACE2.

F24. The molecule of embodiment F21, wherein ACE2 comprises SEQ ID NO:194.

F25. The molecule of embodiment F22, wherein the extracellular domain of ACE2 comprises SEQ ID NO:134.

F26. The molecule of embodiment F23, wherein the truncated extracellular domain of ACE2 comprises SEQ ID NO:120 or SEQ ID NO:121.

F27. The molecule of any one of embodiments F16 to F26, wherein the second cell or virus is neutralized when the molecule specifically binds to the pIgR and to the second target on the surface of the second cell or virus.

F28. The molecule of embodiment F27, wherein the molecule neutralized the second cell or virus with an $EC_{50}$ of less than about 4 nM.

F29. The molecule of embodiment F27, wherein the molecule neutralized the second cell or virus with an $EC_{50}$ of less than about 3 nM.

F30. The molecule of embodiment F27, wherein the molecule neutralized the second cell or virus with an $EC_{50}$ of less than about 1 nM.

F31. The molecule of embodiment F27, wherein the molecule neutralized the second cell or virus with an $EC_{50}$ of less than about 500 pM.

F32. The molecule of embodiment F27, wherein the molecule neutralized the second cell or virus with an $EC_{50}$ of less than about 100 pM.

In a seventh set of embodiments, provided are:

G1. A molecule comprising: a first means capable of binding pIgR on the mucosal endothelium; and a second means capable of binding a second target that is not pIgR.

G2. The molecule of embodiment G1, wherein the molecule is a bispecific molecule.

G3. The molecule of any one of embodiments G1 or G2, wherein the second means specifically binds to the surface of SARS-CoV-2.

G4. The molecule of any one of embodiments G1 to G3, wherein the second means specifically binds to the spike glycoprotein on the surface of SARS-CoV-2.

G5. The molecule of any one of embodiments G1 to G4, wherein the second means specifically binds to the S1 subunit of the spike glycoprotein on the surface of SARS-CoV-2.

G6. The molecule of any one of embodiments G1 to G5, wherein the second means comprises angiotensin-converting enzyme 2 (ACE2).

G7. The molecule of any one of embodiments G1 to G5, wherein the second means comprises the extracellular domain of ACE2.

G8. The molecule of any one of embodiments G1 to G5, wherein the second means comprises a truncated extracellular domain of ACE2.

G9. The molecule of embodiment G6, wherein ACE2 comprises SEQ ID NO:194.

G10. The molecule of embodiment G7, wherein the extracellular domain of ACE2 comprises SEQ ID NO:134.

G11. The molecule of embodiment G8, wherein the truncated extracellular domain of ACE2 comprises SEQ ID NO:120 or SEQ ID NO:121.

G12. The molecule of any one of embodiments G1 to G11, wherein the first means comprises a single-domain molecule (VHH).

G13. The molecule of embodiment G12, wherein the VHH comprises a complementarity determining region 1 (CDR1) having an amino acid sequence of SEQ ID NO:1, a CDR2 having an amino acid sequence of SEQ ID NO:2, and a CDR3 having an amino acid sequence of SEQ ID NO:3.

G14. The molecule of embodiment G13, wherein the VHH comprises an amino acid sequence of SEQ ID NO:16.

G15. The molecule of embodiment G12, wherein the VHH comprises a CDR1 having an amino acid sequence of SEQ ID NO:17, a CDR2 having an amino acid sequence of SEQ ID NO:18, and a CDR3 having an amino acid sequence of SEQ ID NO:19.

G16. The molecule of embodiment G15, wherein the VHH comprises an amino acid sequence of SEQ ID NO:32.

G17. The molecule of any one of embodiments G1 to G16, wherein the first binding domain specifically binds to pIgR that is present on the mucosal endothelium.

G18. The molecule of embodiment G17, wherein the first binding domain specifically binds to pIgR that is present on the lung mucosal endothelium.

G19. The molecule of any one of embodiments G3 to G18, wherein the SARS-CoV-2 is neutralized when the molecule specifically binds to the pIgR and to SARS-CoV-2.

G20. The molecule of embodiment G19, wherein the molecule neutralized SARS-CoV-2 with an $EC_{50}$ of less than about 4 nM.

G21. The molecule of embodiment G19, wherein the molecule neutralized SARS-CoV-2 with an $EC_{50}$ of less than about 3 nM.

G22. The molecule of embodiment G19, wherein the molecule neutralized SARS-CoV-2 with an $EC_{50}$ of less than about 1 nM.

G23. The molecule of embodiment G19, wherein the molecule neutralized SARS-CoV-2 with an $EC_{50}$ of less than about 500 pM.

G24. The molecule of embodiment G19, wherein the molecule neutralized SARS-CoV-2 with an $EC_{50}$ of less than about 100 pM.

G25. A molecule comprising: a first means capable of binding pIgR on the mucosal endothelium; and a second means capable of binding a second target on the surface of a second cell or on the surface of a virus.

G26. The molecule of embodiment G25, wherein the second means is capable of binding a second target on the surface of a virus.

G27. The molecule of embodiment G26, wherein the virus is SARS-CoV-2.

G28. The molecule of embodiment G25, wherein the molecule is a bispecific molecule.

G29. The molecule of any one of embodiments G25 to G27, wherein the second means specifically binds to the surface of SARS-CoV-2.

G30. The molecule of any one of embodiments G25 to G29, wherein the second means specifically binds to the spike glycoprotein on the surface of SARS-CoV-2.

G31. The molecule of any one of embodiments G25 to G30, wherein the second means specifically binds to the S1 subunit of the spike glycoprotein on the surface of SARS-CoV-2.

G32. The molecule of any one of embodiments G25 to G31, wherein the second means comprises angiotensin-converting enzyme 2 (ACE2).

G33. The molecule of any one of embodiments G25 to G31, wherein the second means comprises the extracellular domain of ACE2.

G34. The molecule of any one of embodiments G25 to G31, wherein the second means comprises a truncated extracellular domain of ACE2.

G35. The molecule of embodiment G32, wherein ACE2 comprises SEQ ID NO:194.

G36. The molecule of embodiment G33, wherein the extracellular domain of ACE2 comprises SEQ ID NO:134.

G37. The molecule of embodiment G34, wherein the truncated extracellular domain of ACE2 comprises SEQ ID NO:120 or SEQ ID NO:121.

G38. The molecule of any one of embodiments G25 to G37, wherein the first means comprises a single-domain molecule (VHH).

G39. The molecule of embodiment G38, wherein the VHH comprises a complementarity determining region 1 (CDR1) having an amino acid sequence of SEQ ID NO:1, a CDR2 having an amino acid sequence of SEQ ID NO:2, and a CDR3 having an amino acid sequence of SEQ ID NO:3.

G40. The molecule of embodiment G39, wherein the VHH comprises an amino acid sequence of SEQ ID NO:16.

G41. The molecule of embodiment G38, wherein the VHH comprises a CDR1 having an amino acid sequence of SEQ ID NO:17, a CDR2 having an amino acid sequence of SEQ ID NO:18, and a CDR3 having an amino acid sequence of SEQ ID NO:19.

G42. The molecule of embodiment G41, wherein the VHH comprises an amino acid sequence of SEQ ID NO:32.

G43. The molecule of any one of embodiments G25 to G42, wherein the first binding domain specifically binds to pIgR that is present on the mucosal endothelium.

G44. The molecule of embodiment G43, wherein the first binding domain specifically binds to pIgR that is present on the lung mucosal endothelium.

G45. The molecule of any one of embodiments G27 to G44, wherein the SARS-CoV-2 is neutralized when the molecule specifically binds to the pIgR and to SARS-CoV-2.

G46. The molecule of embodiment G45, wherein the molecule neutralized SARS-CoV-2 with an $EC_{50}$ of less than about 4 nM.

G47. The molecule of embodiment G45, wherein the molecule neutralized SARS-CoV-2 with an $EC_{50}$ of less than about 3 nM.

G48. The molecule of embodiment G45, wherein the molecule neutralized SARS-CoV-2 with an $EC_{50}$ of less than about 1 nM.

G49. The molecule of embodiment G45, wherein the molecule neutralized SARS-CoV-2 with an $EC_{50}$ of less than about 500 pM.

G50. The molecule of embodiment G45, wherein the molecule neutralized SARS-CoV-2 with an $EC_{50}$ of less than about 100 pM.

In an eighth set of embodiments, provided are:

H1. A nucleic acid encoding a multispecific molecule comprising: (a) a first binding domain that specifically binds to polymeric immunoglobulin receptor (pIgR), and (b) a second binding domain that specifically binds to SARS-CoV-2.

H2. The nucleic acid of embodiment H1, wherein the molecule is a bispecific molecule.

H3. The nucleic acid of any one of embodiments H1 or H2, wherein the second binding domain specifically binds to the surface of SARS-CoV-2.

H4. The nucleic acid of any one of embodiments H1 to H3, wherein the second binding domain specifically binds to the spike glycoprotein on the surface of SARS-CoV-2.

H5. The nucleic acid of any one of embodiments H1 to H4, wherein the second binding domain specifically binds to the S1 subunit of the spike glycoprotein on the surface of SARS-CoV-2.

H6. The nucleic acid of any one of embodiments H1 to H5, wherein the second binding domain comprises angiotensin-converting enzyme 2 (ACE2).

H7. The nucleic acid of any one of embodiments H1 to H5, wherein the second binding domain comprises the extracellular domain of ACE2.

H8. The nucleic acid of any one of embodiments H1 to H5, wherein the second binding domain comprises a truncated extracellular domain of ACE2.

H9. The nucleic acid of embodiment H6, wherein ACE2 comprises SEQ ID NO:194.

H10. The nucleic acid of embodiment H7, wherein the extracellular domain of ACE2 comprises SEQ ID NO:134.

H11. The nucleic acid of embodiment H8, wherein the truncated extracellular domain of ACE2 comprises SEQ ID NO:120 or SEQ ID NO:121.

H12. The nucleic acid of any one of embodiments H1 to H11, wherein the first binding domain comprises a single-domain molecule (VHH).

H13. The nucleic acid of embodiment H12, wherein the VHH comprises a complementarity determining region 1 (CDR1) having an amino acid sequence of SEQ ID NO:1, a CDR2 having an amino acid sequence of SEQ ID NO:2, and a CDR3 having an amino acid sequence of SEQ ID NO:3.

H14. The nucleic acid of embodiment H13, wherein the VHH comprises an amino acid sequence of SEQ ID NO:16.

H15. The nucleic acid of embodiment H12, wherein the VHH comprises a CDR1 having an amino acid sequence of SEQ ID NO:17, a CDR2 having an amino acid sequence of SEQ ID NO:18, and a CDR3 having an amino acid sequence of SEQ ID NO:19.

H16. The nucleic acid of embodiment H15, wherein the VHH comprises an amino acid sequence of SEQ ID NO:32.

H17. The nucleic acid of any one of embodiments H1 to H16, wherein the first binding domain specifically binds to pIgR that is present on the mucosal endothelium.

H18. The nucleic acid of embodiment H17, wherein the first binding domain specifically binds to pIgR that is present on the lung mucosal endothelium.

H19. The nucleic acid of any one of embodiments H1 to H18, wherein the SARS-CoV-2 is neutralized when the molecule specifically binds to the pIgR and to SARS-CoV-2.

H20. The nucleic acid of embodiment H19, wherein the molecule neutralized SARS-CoV-2 with an $EC_{50}$ of less than about 4 nM.

H21. The nucleic acid of embodiment H19, wherein the molecule neutralized SARS-CoV-2 with an $EC_{50}$ of less than about 3 nM.

H22. The nucleic acid of embodiment H19, wherein the molecule neutralized SARS-CoV-2 with an $EC_{50}$ of less than about 1 nM.

H23. The nucleic acid of embodiment H19, wherein the molecule neutralized SARS-CoV-2 with an $EC_{50}$ of less than about 500 pM.

H24. The nucleic acid of embodiment H19, wherein the molecule neutralized SARS-CoV-2 with an $EC_{50}$ of less than about 100 pM.

H25. A vector comprising the nucleic acid of any one of embodiments H1 to H24.

H26. A host cell comprising the vector of embodiment H25.

H27. A kit comprising the vector of embodiment H25 and packaging for the same.

In a ninth set of embodiments, provided are:

I1. A pharmaceutical composition comprising a multispecific molecule comprising: (a) a first binding domain that specifically binds to polymeric immunoglobulin receptor (pIgR), and (b) a second binding domain that specifically binds to a second target that is not pIgR, and a pharmaceutically acceptable carrier.

I2. The pharmaceutical composition of embodiment I1, wherein the molecule is a bispecific molecule.

I3. The pharmaceutical composition of any one of embodiments I1 or I2, wherein the first binding domain comprises a single-domain molecule (VHH).

I4. The pharmaceutical composition of embodiment I3, wherein the VHH comprises a complementarity determining region 1 (CDR1) having an amino acid sequence of SEQ ID NO:1, a CDR2 having an amino acid sequence of SEQ ID NO:2, and a CDR3 having an amino acid sequence of SEQ ID NO:3.

I5. The pharmaceutical composition of embodiment I4, wherein the VHH comprises an amino acid sequence of SEQ ID NO:16.

I6. The pharmaceutical composition of embodiment I3, wherein the VHH comprises a CDR1 having an amino acid sequence of SEQ ID NO:17, a CDR2 having an amino acid sequence of SEQ ID NO:18, and a CDR3 having an amino acid sequence of SEQ ID NO:19.

I7. The pharmaceutical composition of embodiment I6, wherein the VHH comprises an amino acid sequence of SEQ ID NO:32.

I8. The pharmaceutical composition of any one of embodiments I1 to I7, wherein the first binding domain specifically binds to pIgR that is present on the mucosal endothelium.

I9. The pharmaceutical composition of embodiment I8, wherein the first binding domain specifically binds to pIgR that is present on the lung mucosal endothelium.

I10. The pharmaceutical composition of any one of embodiments I1 to I9, wherein the molecule comprises an Fc region from an IgG antibody.

I11. The pharmaceutical composition of embodiment I10, wherein the IgG molecule is an IgG1, IgG2, IgG3, or IgG4 antibody.

I12. The pharmaceutical composition of any one of embodiments I1 to I11, wherein the first binding domain specifically binds a pIgR antigen.

I13. The pharmaceutical composition of any one of embodiments I1 to I11, wherein the first binding domain specifically binds an extracellular pIgR epitope.

I14. The pharmaceutical composition of any one of embodiments I1 to I11, wherein CDR1, CDR2, and CDR3 form a binding site for an antigen of the pIgR.

I15. The pharmaceutical composition of any one of embodiments I1 to I11, wherein the CDR1, CDR2, and CDR3 form a binding site for an epitope of the pIgR.

I16. The pharmaceutical composition of any one of embodiments I1 to I15, wherein the second target is on the surface of a second cell.

I17. The pharmaceutical composition of any one of embodiments I1 to I16, wherein the second target is on the surface of a virus.

I18. The pharmaceutical composition of any one of embodiments I1 to I17, wherein the second target is on the surface of SARS-CoV-2.

I19. The pharmaceutical composition of any one of embodiments I1 to I18, wherein the second target is the spike glycoprotein.

I20. The pharmaceutical composition of embodiment I19, wherein the second target is the S1 subunit of the spike glycoprotein.

I21. The pharmaceutical composition of any one of embodiments I1 to I20, wherein the second binding domain comprises angiotensin-converting enzyme 2 (ACE2).

I22. The pharmaceutical composition of any one of embodiments I1 to I20, wherein the second binding domain comprises the extracellular domain of ACE2.

I23. The pharmaceutical composition of any one of embodiments I1 to I20, wherein the second binding domain comprises a truncated extracellular domain of ACE2.

I24. The pharmaceutical composition of embodiment I21, wherein ACE2 comprises SEQ ID NO:194.

I25. The pharmaceutical composition of embodiment I22, wherein the extracellular domain of ACE2 comprises SEQ ID NO:134.

I26. The pharmaceutical composition of embodiment I23, wherein the truncated extracellular domain of ACE2 comprises SEQ ID NO:120 or SEQ ID NO:121.

I27. The pharmaceutical composition of any one of embodiments I16 to I26, wherein the second cell or virus is neutralized when the molecule specifically binds to the pIgR and to the second target on the surface of the second cell or virus.

I28. The pharmaceutical composition of embodiment I27, wherein the molecule neutralized the second cell or virus with an $EC_{50}$ of less than about 4 nM.

I29. The pharmaceutical composition of embodiment I27, wherein the molecule neutralized the second cell or virus with an $EC_{50}$ of less than about 3 nM.

I30. The pharmaceutical composition of embodiment I27, wherein the molecule neutralized the second cell or virus with an $EC_{50}$ of less than about 1 nM.

I31. The pharmaceutical composition of embodiment I27, wherein the molecule neutralized the second cell or virus with an $EC_{50}$ of less than about 500 pM.

I32. The pharmaceutical composition of embodiment I27, wherein the molecule neutralized the second cell or virus with an $EC_{50}$ of less than about 100 pM.

I33. A pharmaceutical composition comprising the means for delivering the molecule of any one of embodiments I1 to I32, and a pharmaceutically acceptable carrier.

I34. A method of producing the pharmaceutical composition of any one of embodiments I1 to I33, comprising combining the molecule with a pharmaceutically acceptable carrier to obtain the pharmaceutical composition.

In a tenth set of embodiments, provided are:

J1. A method of inhibiting host cell entry or proliferation of target cells expressing the second target, the method comprising contacting the target cells with a multispecific molecule comprising: (a) a first binding domain that specifically binds to polymeric immunoglobulin receptor (pIgR), and (b) a second binding domain that specifically binds to a second target that is not pIgR, wherein contacting the target cells with the molecule inhibits host cell entry or proliferation of the target cells.

J2. The molecule of embodiment J1, wherein the molecule is a bispecific molecule.

J3. The molecule of any one of embodiments J1 or J2, wherein the first binding domain comprises a single-domain molecule (VHH).

J4. The molecule of embodiment J3, wherein the VHH comprises a complementarity determining region 1 (CDR1) having an amino acid sequence of SEQ ID NO:1, a CDR2 having an amino acid sequence of SEQ ID NO:2, and a CDR3 having an amino acid sequence of SEQ ID NO:3.

J5. The molecule of embodiment J4, wherein the VHH comprises an amino acid sequence of SEQ ID NO:16.

J6. The molecule of embodiment J3, wherein the VHH comprises a CDR1 having an amino acid sequence of SEQ ID NO:17, a CDR2 having an amino acid sequence of SEQ ID NO:18, and a CDR3 having an amino acid sequence of SEQ ID NO:19.

J7. The molecule of embodiment J6, wherein the VHH comprises an amino acid sequence of SEQ ID NO:32.

J8. The molecule of any one of embodiments J1 to J7, wherein the first binding domain specifically binds to pIgR that is present on the mucosal endothelium.

J9. The molecule of embodiment J8, wherein the first binding domain specifically binds to pIgR that is present on the lung mucosal endothelium.

J10. The molecule of any one of embodiments J1 to J9, wherein the molecule comprises an Fc region from an IgG antibody.

J11. The molecule of embodiment J10, wherein the IgG molecule is an IgG1, IgG2, IgG3, or IgG4 antibody.

J12. The molecule of any one of embodiments J1 to J11, wherein the first binding domain specifically binds a pIgR antigen.

J13. The molecule of any one of embodiments J1 to J11, wherein the first binding domain specifically binds an extracellular pIgR epitope.

J14. The molecule of any one of embodiments J1 to J11, wherein CDR1, CDR2, and CDR3 form a binding site for an antigen of the pIgR.

J15. The molecule of any one of embodiments J1 to J11, wherein the CDR1, CDR2, and CDR3 form a binding site for an epitope of the pIgR.

J16. The molecule of any one of embodiments J1 to J15, wherein the second target is on the surface of a second cell.

J17. The molecule of any one of embodiments J1 to J16, wherein the second target is on the surface of a virus.

J18. The molecule of any one of embodiments J1 to J17, wherein the second target is on the surface of SARS-CoV-2.

J19. The molecule of any one of embodiments J1 to J18, wherein the second target is the spike glycoprotein.

J20. The molecule of embodiment J19, wherein the second target is the S1 subunit of the spike glycoprotein.

J21. The molecule of any one of embodiments J1 to J20, wherein the second binding domain comprises angiotensin-converting enzyme 2 (ACE2).

J22. The molecule of any one of embodiments J1 to J20, wherein the second binding domain comprises the extracellular domain of ACE2.

J23. The molecule of any one of embodiments J1 to J20, wherein the second binding domain comprises a truncated extracellular domain of ACE2.

J24. The molecule of embodiment J21, wherein ACE2 comprises SEQ ID NO:194.

J25. The molecule of embodiment J22, wherein the extracellular domain of ACE2 comprises SEQ ID NO:134.

J26. The molecule of embodiment J23, wherein the truncated extracellular domain of ACE2 comprises SEQ ID NO:120 or SEQ ID NO:121.

J27. The molecule of any one of embodiments J16 to J26, wherein the second cell or virus is neutralized when the molecule specifically binds to the pIgR and to the second target on the surface of the second cell or virus.

J28. The molecule of embodiment J27, wherein the molecule neutralized the second cell or virus with an $EC_{50}$ of less than about 4 nM.

J29. The molecule of embodiment J27, wherein the molecule neutralized the second cell or virus with an $EC_{50}$ of less than about 3 nM.

J30. The molecule of embodiment J27, wherein the molecule neutralized the second cell or virus with an $EC_{50}$ of less than about 1 nM.

J31. The molecule of embodiment J27, wherein the molecule neutralized the second cell or virus with an $EC_{50}$ of less than about 500 pM.

J32. The molecule of embodiment J27, wherein the molecule neutralized the second cell or virus with an $EC_{50}$ of less than about 100 pM.

In an eleventh set of embodiments, provided are:

K1. A process for making a molecule that specifically binds to more than one target molecule, the process comprising:
- a step for performing a function of obtaining a binding domain capable of binding to pIgR on mucosal endothelium;
- a step for performing a function of obtaining a binding domain capable of binding to a second target on a second cell or virus; and
- a step for performing a function of providing a molecule capable of binding to a pIgR antigen on mucosal endothelium and a second target on a second cell or virus.

K2. The process of embodiment K1, wherein the step for performing a function of obtaining a binding domain capable of binding to a second target is repeated n times and further comprising n steps for performing a function of providing a binding domain capable of binding to a pIgR on mucosal endothelium and n number of target molecules, wherein n is at least 2.

K3. The process of any one of embodiments K1 or K2, wherein the second target is on the surface of the second cell or on the surface of a virus.

K4. The process of any one of embodiments K1 to K3, wherein the second target is on the surface of a virus.

K5. The process of any one of embodiments K1 to K4, wherein the virus is SARS-CoV-2.

K6. The process of any one of embodiments K1 to K5, wherein the binding domain capable of binding to pIgR specifically binds a pIgR antigen.

K7. The process of any one of embodiments K1 to K5, wherein the binding domain capable of binding to pIgR specifically binds a pIgR epitope.

K8. The process of any one of embodiments K1 to K7, wherein the binding domain capable of binding to a second target is an antigen.

K9. The process of any one of embodiments K1 to K7, wherein the binding domain capable of binding to a second target is an epitope of the second target.

Particular embodiments of this invention are described herein. Upon reading the foregoing description, variations of the disclosed embodiments may become apparent to individuals working in the art, and it is expected that those skilled artisans may employ such variations as appropriate.

Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. A number of embodiments of the invention have been described. Nevertheless, it will be understood that various modifications may be made without departing from the spirit and scope of the invention. Accordingly, the descriptions in the Examples section are intended to illustrate but not limit the scope of invention described in the claims.

8. EXAMPLES

Figure 1:
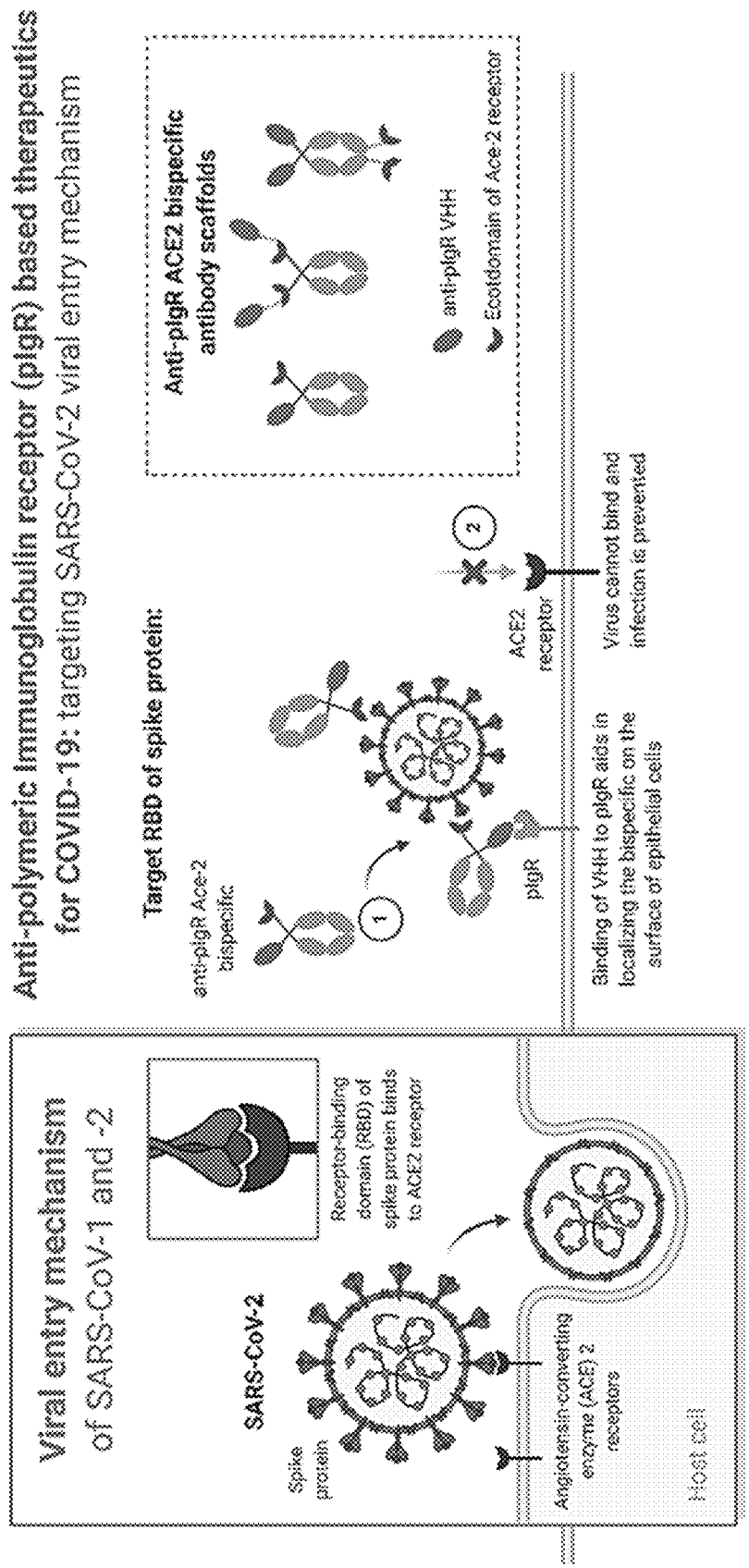

The mechanism of action of the pIgR-mediated transport of SARS-CoV-2 neutralizing agents is described in the schematic outlined in FIG. 1.

Example 1: Methods and Materials

Construct Design

Constructs were designed fusing anti-pIgR VHHs to the N-terminus of the heavy chain of each mAb with a 2(G4S) linker. Null controls were designed in IgG1 mAbs as well as N-terminal VHH fusions bearing a null VHH binder. Additionally, constructs were designed using human ACE2 in conjunction with anti-pIgR VHHs. Human ACE2 ECD (18-725 AA) as well as a truncated variant (18-611 AA) were designed. These molecules consisted of two formats: VHH-2(G4S)-ACE2-Fc, and VHH-Fc-2(G4S)-ACE2. DNA sequences for variable regions and ACE2 were codon-optimized for CHO expression and cloned into Lonza-pEE6.4 (heavy chains) or Lonza-pEE12.4 (light chains).

Expression and Purification of Bispecific Molecules

Expression plasmids encoding bispecific molecules were transfected into EXPICHO cells according to manufacturer's instructions. Cell supernatants were harvested after 6-7 days by centrifugation (4,000 g, 15 min), passed through a 0.45 μm filter, and purified by MABSELECT™ SURE™ (ThermoFisher) chromatography on an ÄKTA express system using phosphate-buffered saline (PBS) as running buffer and 0.1 M sodium acetate, pH 3.5 as elution buffer. Eluted fractions were immediately neutralized using 25% (v/v) 2 M Tris-HCl pH 7.0, dialyzed to PBS, sterilized by 0.22 m filtration and stored at 4° C. Protein concentration was determined by UV-visible spectroscopy. Final yields ranged from 7 mg to 22 mg protein after 35 mL expression.

Bio-Layer Interferometry

Binding kinetics were measured between molecules and either pIgR or spike glycoprotein by immobilizing his-tagged pIgR or SARS-CoV-2 RBD to anti-His (HIS2) biosensors. Antigen-coated tips were then exposed to each protein for a 90 second association step, followed by a 90 second dissociation step. Association and dissociation rates were measured by the shift in wavelength (nm). All proteins and antigens were diluted to concentration of 10 μg/mL in 1×PBS at 25° C. Data were collected with Octet Data Acquisition (ForteBio) and analyzed using Octet Data Analysis (ForteBio). Data were processed using GRAPHPAD Prism software.

Functional Surrogate Neutralization Assay Analysis

The bispecific molecules were prepared by serial dilution in assay buffer (3% BSA+PBS). Samples were incubated with 0.1 μg/mL of biotinylated spike glycoprotein at 1:1 (v/v) for 1 hr with shaking. After incubation, 25 mL of the mixture was added to Streptavidin Gold multi-array 96-well plates (MESO SCALE DISCOVERY) and incubated for 1 hr with shaking. After incubation, 25 μL of ruthenium labeled ACE2 at 2 μg/mL was added and incubated for 1 hr with shaking. Plates were washed with PBS prior to addition of 150 μL of 2×MSD read buffer to read the plate on Mesoscale Sector S 600 reader. MSD data was analyzed and $IC_{50}$ values were calculated using GRAPHPAD Prism software.

ADCC Analysis

Figure 5A:
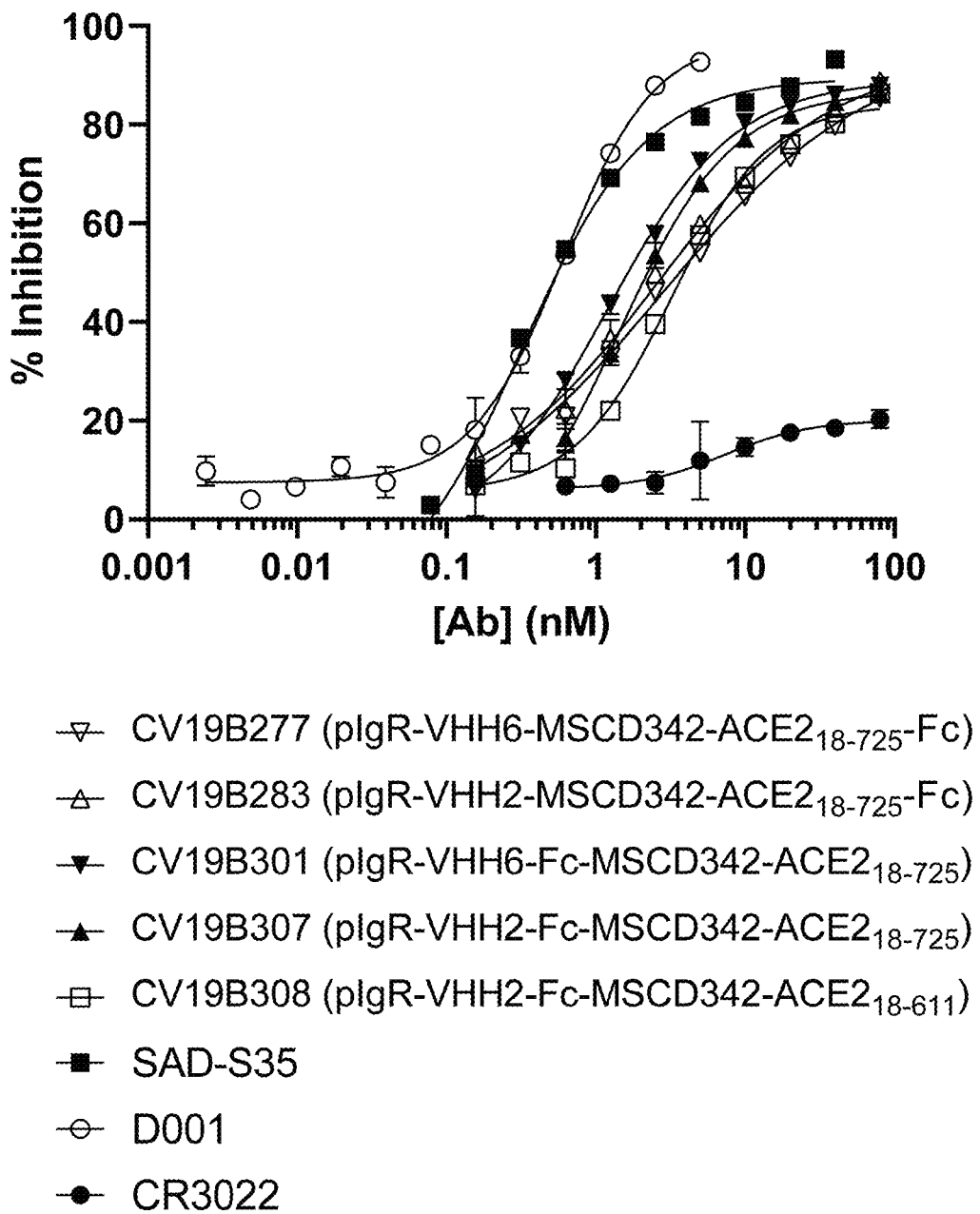
Figure 5B:
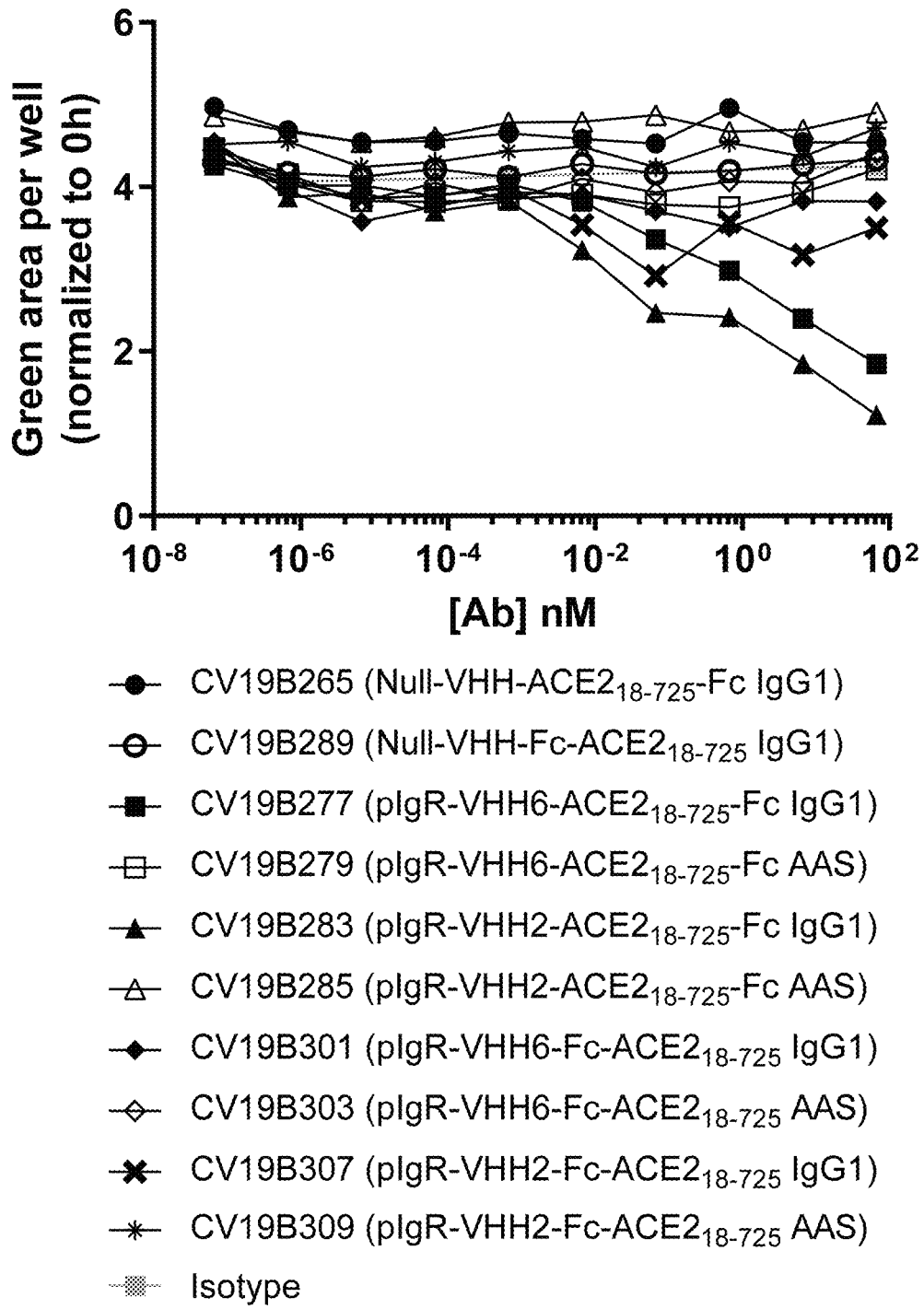

MDCK cells (ATCC) were transfected with human pIgR and Nuclight green and used as target cells. MDCK cells were cultured in EMEM supplemented with 10% FBS, 1×NEAA, and 5 μg/ml Puromycin. PBMC effector cells were obtained from Hemacare. Percentages of T cells (CD3+), B cells (CD19+), and NK cells (CD56+16+) were enumerated by flow cytometry (FIGS. 5A-5C). PBMCs were incubated overnight in RPMI-1640 supplemented with 10% FBS and 1×NEAA at a density of 1×106 cells/mL. MDCK cells were plated at 10,000 cells/well in 100 μL of assay media and incubated 1 hr at 37° C. with 5% CO2. Bispecific Antibodies were added at 10 μg/mL and diluted 10-fold per well. Equal volumes of PBMCs and MDCK cells were then incubated with antibody for 72 hr at 37° C., 5% CO2 inside an INCUCYTE. Cell lysis was measured by total green area per well after incubation.

Pharmacokinetic Analysis

Female C57BL/6 mice were injected with VHH-Fc test antibodies intravenously via tail vein at a dose of 5 mg/kg into 5 animals per group. Time points were taken at 0.02, 0.04, 0.08, 0.25, 1, 2, 3, 7, and 14 days. At each time point, 20 l of whole blood was obtained via tail snip into micro EDTA tubes. Blood collected was diluted 10× in LOW-CROSS buffer (Candor; cat #100500), inverted to mix, and kept on wet ice during collection. Immediately after all samples were collected at a specific timepoint, diluted samples were centrifuged at 1500×g for 2 minutes and supernatants collected and frozen until analysis. The PK study was approved by the Institutional Animal Care and Use Committee at Janssen Research & Development, LLC. All experiments were performed in compliance with the guidelines of the committee.

For detection of the VHH-Fc test antibodies in mouse diluted whole blood, an electrochemiluminescent immunoassay (ECLIA) was used. Streptavidin Gold multi-array 96-well plates (MESOSCALE DISCOVERY®) were blocked with 1% BSA in 1× dPBS for 30 minutes. The capture reagent, biotinylated rabbit anti-camelid VHH mAb (GenScript®; cat #A01995), was diluted to 0.5 μg/mL and 40 μL combined with 10 μL of diluted standards, controls, and samples in the assay plate for 60 minutes. Plates were washed in PBS-buffered saline with Tween 20 (PBST) and 50 μL/well of ruthenium-labeled anti-human Fc mAb (Janssen R&D) diluted to 0.5 μg/mL was added and incubated for 60 minutes. Following another wash step, 150 μL/well of 1× Read Buffer T (MSD; cat #R92TD) was added and plates were read in a MSD Sector Imager 600 plate reader. Final sample concentrations of the VHH-Fc antibodies were back-calculated from representative standard curves using a 5-parameter non-linear regression with $1/y^2$ weighting in Watson LIMS 7.6 analysis software.

Terminal half-life ($T_{1/2}$) calculations of the elimination phase (P phase) for PK studies were determined using the 1-phase exponential decay model fitted by non-linear regression of natural log concentration versus time using Prism version 8.0 software. The least squares nonlinear decay model was weighted by the inverse of the fitted concentration. Half-life calculations of the elimination phase (β phase) were determined using the formula $T_{1/2}=\ln 2/\beta$, where β is the −slope of the line fitted by the least square regression analysis starting after first dose. The terminal half-life value for an antibody was determined by taking the average of the $T_{1/2}$ values calculated for each animal within the test group.

Transcytosis Activity in EpiAirway Tissue System

Tissue models were obtained from Mattek Corporation and maintained according to manufacturer's instructions. 40 μg of test and control VHH-mFc molecules were added to 2 ml of EPIAIRWAY media in the basolateral chamber and 100 μL of samples were collected from the basolateral and apical chambers at 0 and 24 hours. EpiAirway TEER buffer (120 μl) was used to collect the mucus from the apical chambers. The amount of VHH present in basolateral media and apical mucus was quantified by electrochemiluminescence. Streptavidin-coated MSD plates were bound up with a biotinylated anti-VHH antibody (Genscript A01995) at 2 μg/ml in PBS for 2 hours at RT at 1000 rpm, washed 3× with PBT, incubated with blocking buffer for 1 hour at RT, incubated with VHH-mFc containing media/mucus (at different dilutions) for 1 hour at RT at 1000 rpm, washed 3× with PBT, incubated with ruthenylatedanti-human-Fc antibody (Clone R10Z8E9, labeled in-house) at 2 ug/ml in PBS for 1 hour at RT with 1000 rpm, washed 3× with PBT and read plates in 150 μL reading buffer using the MSD imager. The amount of VHH in basolateral and apical chambers were calculated by plotting ECLU against VHH-mFc standard curves in Prism (GRAPHPAD).

Confocal Imaging

Immunofluorescence and confocal microscopy were used to track the amount of pIgR and VHH retained across the EpiAirway microtissue 24 h post-treatment. Tissue samples were rinsed 3× with phosphate-buffered saline (PBS) prior to fixing to remove unbound antibodies and mucus. A 10% formalin solution was added to a final volume of 0.4 mL to the apical chamber and samples were fixed for 20 min at room temperature. The fixing reagent was removed by aspiration and chamber was washed 3× with 2 mL PBS supplemented with 1% Triton-X100 (v/v) (PBST) at room temperature. Primary antibodies against pIgR (R&D Systems, MAB27171) and VHH domains (Genscript, A01995) were diluted to 5 μg/mL final concentration in PBST supplemented with 10% fetal bovine serum (FBS) and 500 μL was applied to the apical and basolateral chamber for 2 h at room temperature. Both chambers were washed 2× with 2 mL PBST at room temperature, and incubated with secondary antibodies (100 μL apical, 500 μL basolateral) diluted in PBST for 2 h. The secondary antibody mix contained Alexa-Fluor 647-labeled anti-mouse antibody (Invitrogen A28181, 1:1,000 dilution), Alexa-Flour 488-labeled streptavidin (Invitrogen, S32357, 1:100 dilution) and DAPI (GENETEX GTX16206, 1:1,000 dilution) diluted in PBST with 10% FBS. Transwells were washed 2× with PBST and placed in 6 well glass bottom plates for imaging with PBS added to each chamber to prevent desiccation of sample. Fixed, permeabilized and stained tissues were imaged at 20× resolution (40 planes, 1.6 μm z-slice) using an OPERA PHENIX confocal laser microscope. Image analysis was performed using the HARMONY suite, fluorescence readouts were corrected for membrane autofluorescence, normalized by mean fluorescence intensity for each color channel. Representative images from a total of three separate experiments per condition were reported.

Example 2. Preparation of Anti-Pigr Based Bispecific Molecules

Figure 2E:
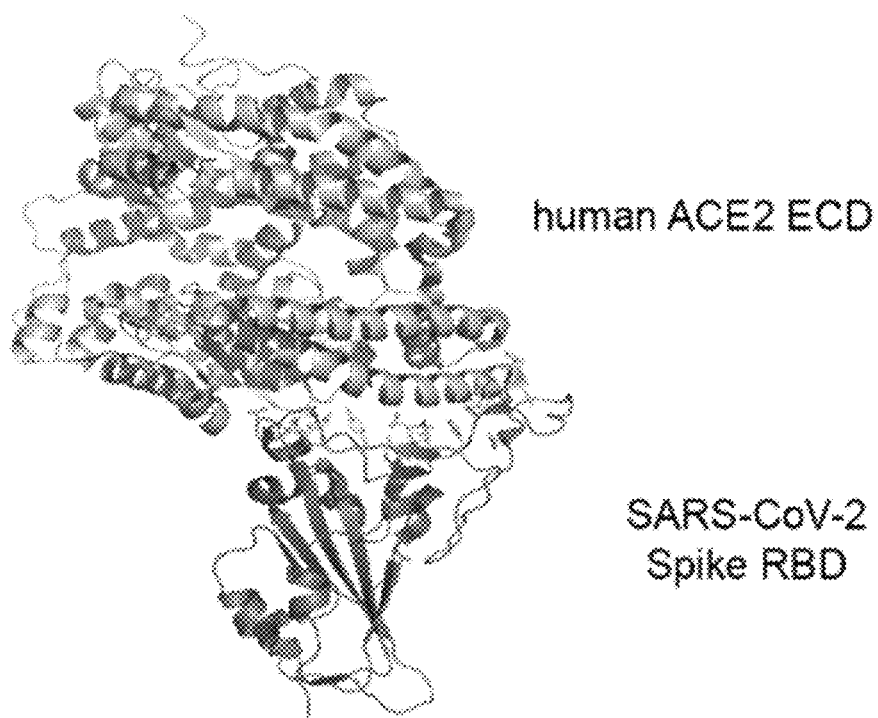
Figure 3:
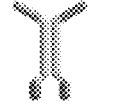
Figure 3:
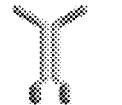
Figure 3:
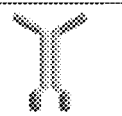
Figure 3:
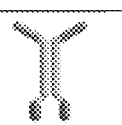
Figure 3:
Figure 3:
Figure 3:
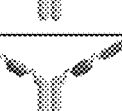
Figure 3:
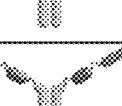
Figure 3:
Figure 3:
Figure 3:

To generate bispecific molecules that engage both pIgR and the receptor-binding domain (RBD) of the SARS-CoV-2 spike glycoprotein, which includes all residues required for binding to ACE2 (FIGS. 2A and 2B), a panel of heavy chain only (VHH) antibodies which could bind human pIgR with affinities ranging from ~4-500 nM that were previously identified were used (Maruthachalam et al. MAbs 12, 1708030 (2020)). Of these, VHH2 and VHH6 were included in this analysis since VHH2 displayed cross-reactivity to mouse pIgR and both displayed strong transcytosis in both an MDCK monolayer-based assay and in a human epithelial airway model. The sequences included are shown in Tables 1, 2 and 3.

TABLE 1

CDR Sequences of VHH2 (Kabat).

| Antibody | HCDR1 | SEQ ID NO: | HCDR2 | SEQ ID NO: | HCDR3 | SEQ ID NO: |
|---|---|---|---|---|---|---|
| VHH2 | SYRMG | 4 | AIDWNGRGTY YRYYADSVKG | 5 | TTVLTDPR VLNEYAT | 6 |

TABLE 2

CDR Sequences of VHH6 (Kabat).

| Antibody | HCDR1 | SEQ ID NO: | HCDR2 | SEQ ID NO: | HCDR3 | SEQ ID NO: |
|---|---|---|---|---|---|---|
| VHH6 | SDAMG | 20 | FISGGGTTTYADSVKG | 21 | PLTSR | 22 |

TABLE 3

VH sequences of VHH2 and VHH6.

| Antibody | VH Amino Acid Sequence | SEQ ID NO: |
|---|---|---|
| VHH2 | EVQVVESGGGLVQAGGSLKLACAAPGLTFSS YRMGWFRQAPGQEREFVAAIDWNGRGTYYRY YADSVKGRSTISRDNAKNTVYLQMNSLKPED TAVYYCAATTVLTDPRVLNEYATWGQGTQVT VSS | 16 |
| VHH6 | EVQLVESGGGLVQAGGSLRLSCAVSGSSVSS DAMGWYRQAPGNQRAWVAFISGGGTTTYADS VKGRFTISRDNTKNTVYLHMNSLKPEDTAVY YCNHPLTSRWGQGTQVTVSS | 32 |

To mediate binding to the SARS-CoV-2 spike glycoprotein, two antibodies were identified, which were reported to display neutralization activity—D001 (Sino Biological cat. #40150-D001) and SAD-S35 (Acro Biosystems cat. #SAD-S35). CR3022 was included as a positive control for binding although this antibody does not neutralize SARS-CoV-2. Bispecific molecules were generated with VHH2/6 and the extracellular domain (ECD) from ACE2 (FIGS. 2A-2E, FIG. 3).

Two truncations of the ACE2 ECD were used: residues 18-611 and 18-725, which begin just after the native signal peptide (FIGS. 2C and 2D). The short truncation was based on analysis of the crystal structure of ACE2 (PDB ID 1R42), which suggested that both constructs could form stable molecules (Towler, P. et al. J Biol Chem 279, 17996-18007 (2004)). The ACE2 ECD was attached to either the N- or C-terminus of the Fc while the anti-pIgR VHH moieties were formatted only on the N-terminus of the bi-functional molecules to avoid binding with preformed antibodies in human sera (Rossotti, M. et al. FEBS J, 15809 (2021)). All molecules featured a human IgG1-based constant region.

Figure 4A:
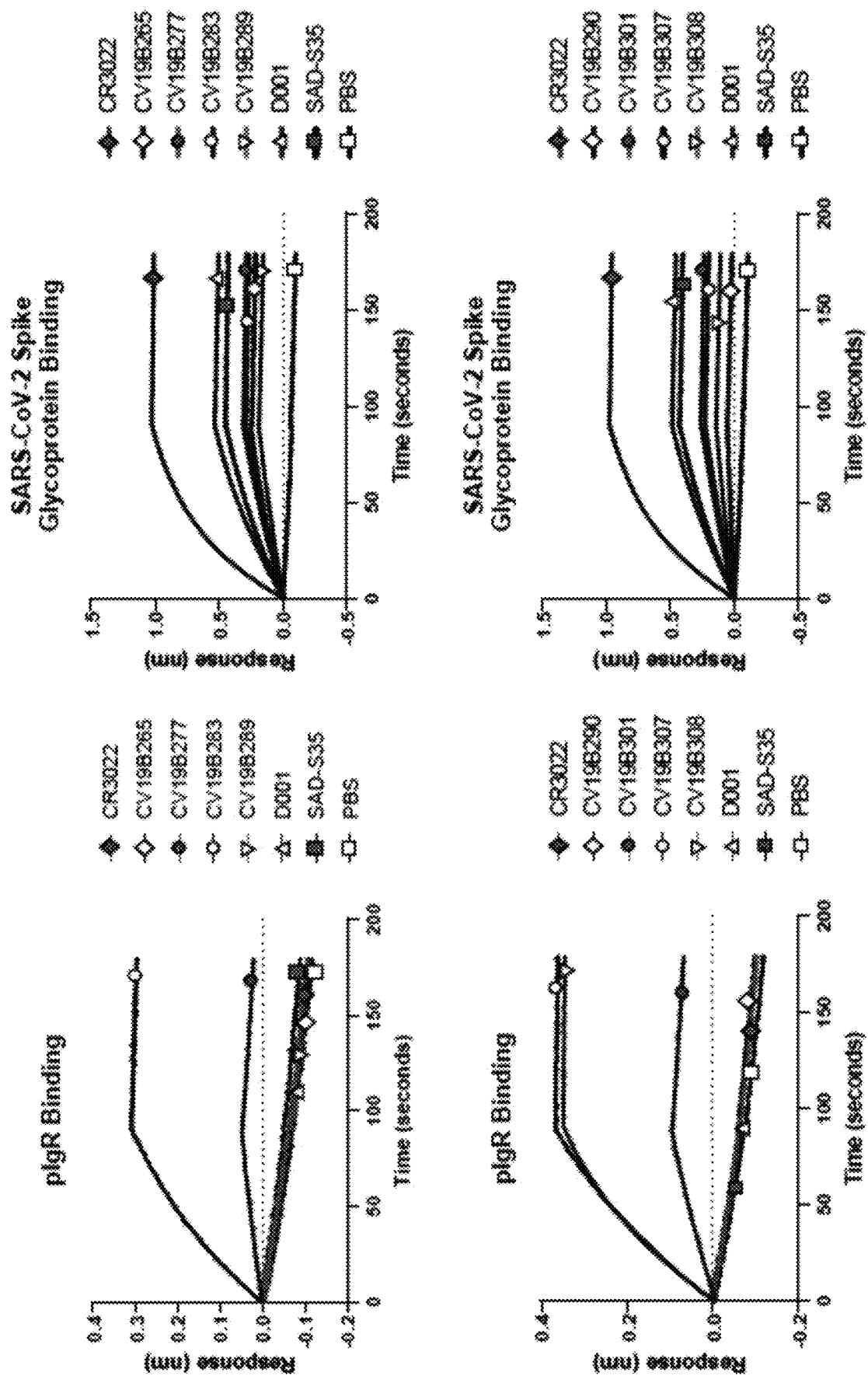
Figure 4B:
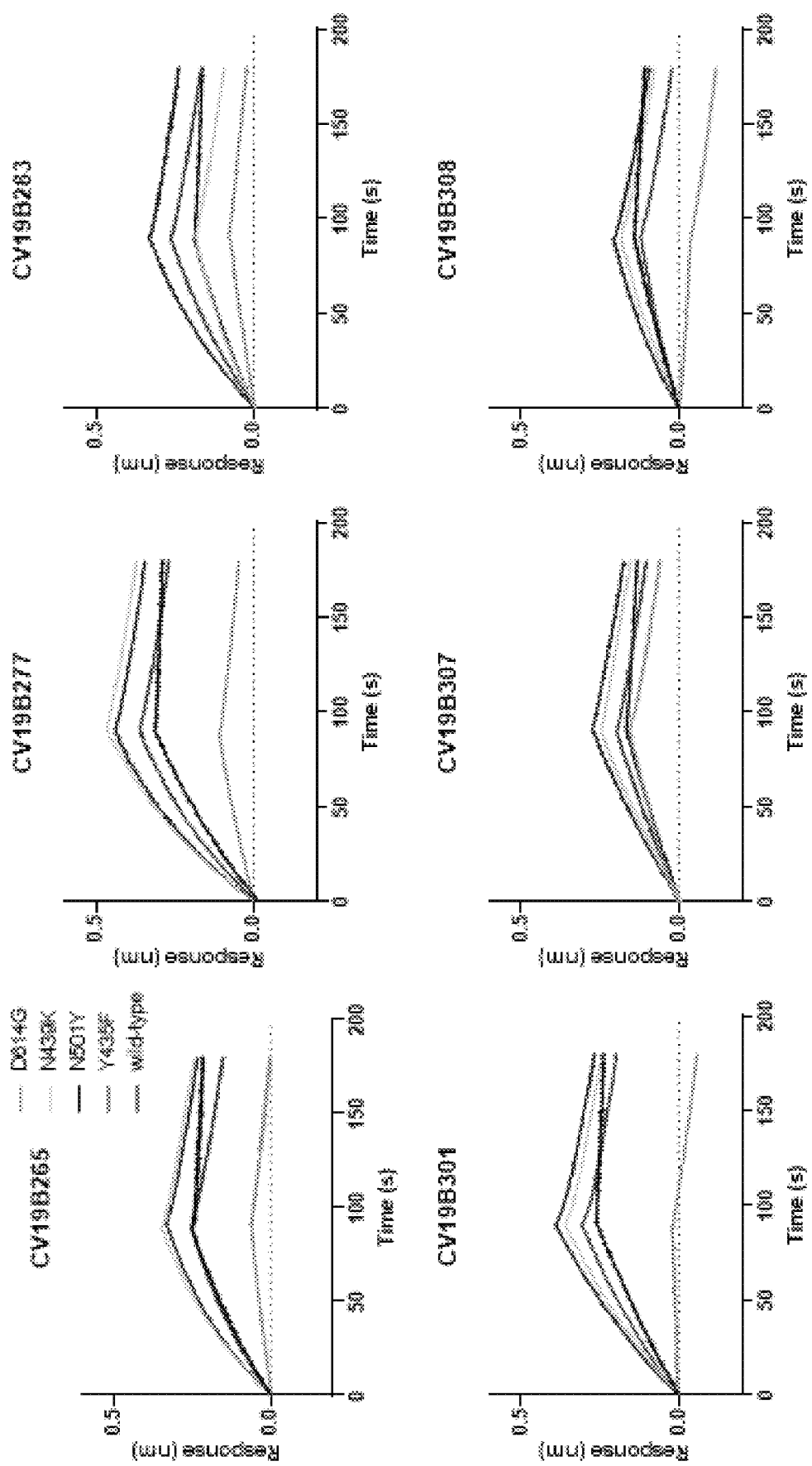
Figure 4B:
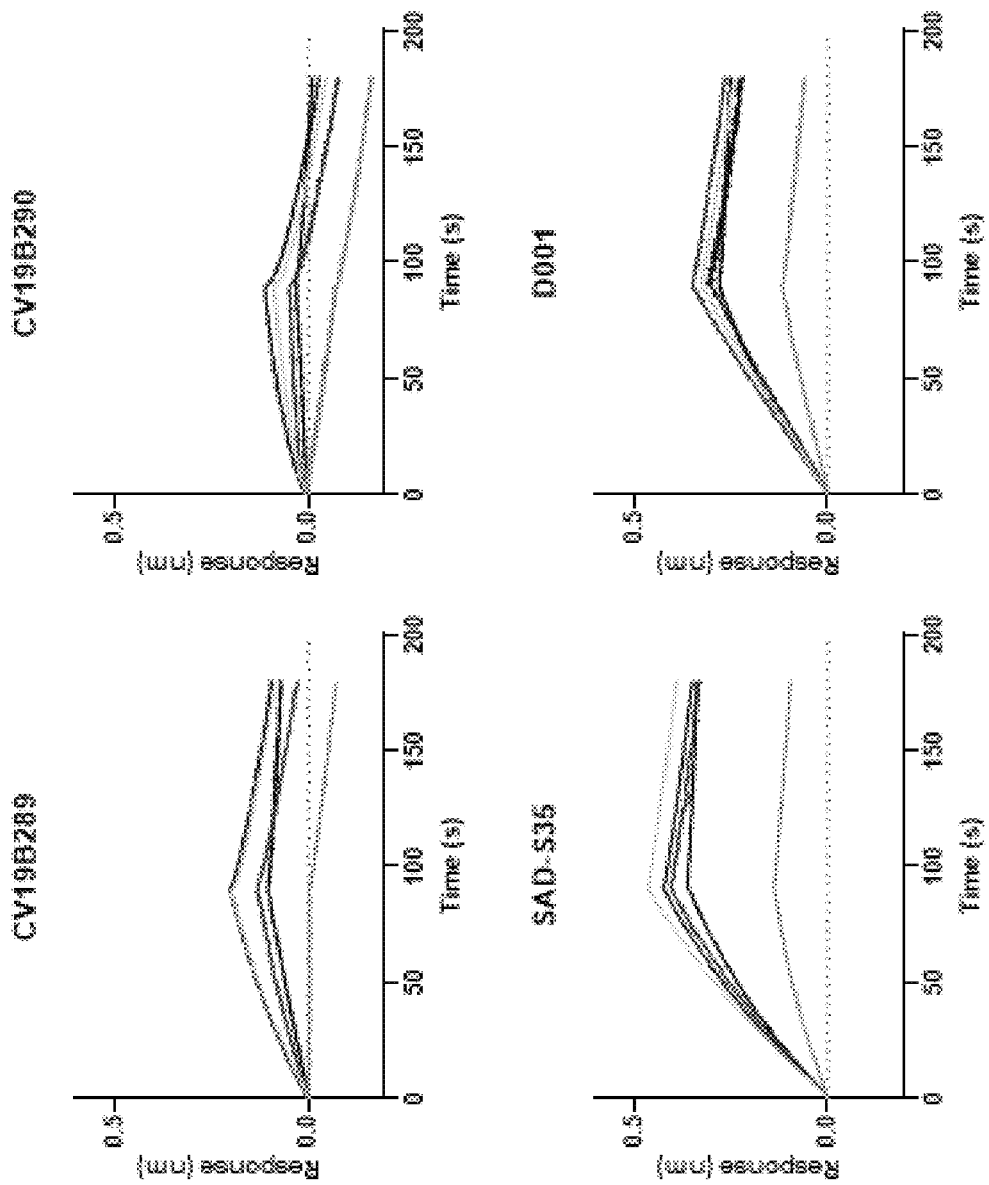

Example 3. Binding Properties of Anti-PIGR/Anti-ACE2 Bispecific Molecules to PIGR and Spike Glycoprotein All molecules with binding moieties of ACE218-611, ACE218-725 exhibited binding to COVID-19 RBD, including CR3022, D001 and SAD-S35 (Tan, X. et al. bioRxiv, (2020)) (FIGS. 4A-4B). CR3022 was reported to bind SARS-CoV-2 spike glycoprotein with $K_D$=115 nM (Yuan, M. et al. Science 368, 630-633, (2020)). Relative $K_D$ values, based on surface biolayer interferometry, are reported herein (Table 4).

CR3022 bound with the highest apparent affinity to spike glycoprotein, and the two neutralizing mAbs (D001 and SAD-S35) bound ~12-fold weaker (Table 4).

ated with increased infectivity of SARS-CoV-2 and can prevent neutralization by some monoclonal antibodies (Starr, T. N. et al. bioRxiv, (2020)). For example, mutations at N439 were shown to modulate interaction with REGN-COV2, and is thus likely to represent part of an important epitope for neutralization (Starr, T. N. et al. Science 371, 850-854, (2021)). All molecules tested here showed qualitatively similar binding to the spike glycoprotein variants Y435F, N439K, and N501Y as to wild-type spike glycoprotein (FIGS. 4A-4B). The D614G mutation stabilized the "closed" structure of the spike glycoprotein, and was shown to decrease the ability of ACE2 to bind the spike glycoprotein (Juraszek, J. et al. Nat Commun 12, 244, (2021)). Consistently, both the ACE2 bi-functional molecule and the mAbs all showed modest decrease in binding to the D614G variant. Interestingly, one bi-functional molecule, CV19B307 displayed similar ability to bind all variants, including the D614G variant.

All the mAbs and bispecific molecules featuring the null VHH (CV19B265, CV19B289, and CV19B290) failed to bind pIgR, as expected (FIGS. 4A-4B and Table 4). Bispecific molecules containing VHH2 (CV19B283, CV19B307, and CV19B308) bound to pIgR with $K_D$ values ~5 nM,

TABLE 4

Binding kinetic values from surface biolayer interferometry

| | SARS-CoV-2 spike | | | | pIgR | | | |
|---|---|---|---|---|---|---|---|---|
| Protein | $k_{on}$ (min$^{-1}$ nM$^{-1}$) | $k_{off}$ (min$^{-1}$) | $K_D$ (nM) | Relative Kd (compared to CR3022) | $k_{on}$ (min$^{-1}$ nM$^{-1}$) | $k_{off}$ (min$^{-1}$) | $K_D$ (nM) | Relative $K_D$ (VHH2) |
| CV19B277 | 32157 | 0.0008426 | 26.2 | 22 | 39.9 | 0.008349 | 2 × 10$^5$ | 142857 |
| CV19B308 | 2975 | 0.003050 | 1.025 × 10$^3$ | 854 | 63861 | 8.646 × 10$^{-5}$ | 1.4 | 1 |
| CV19B307 | 8646 | 0.001496 | 173.1 | 144 | 44364 | 0.0002236 | 5.0 | 4 |
| CV19B301 | 10783 | 0.001092 | 101.2 | 84 | 13406 | 0.003557 | 265.3 | 190 |
| CV19B290 | 37.88 | 0.008619 | 2.28 × 10$^5$ | 190000 | NB | NB | NB | NB |
| CV19B289 | 15478 | 0.002270 | 146.7 | 122 | NB | NB | NB | NB |
| CV19B283 | 28303 | 0.0009639 | 34.1 | 28 | 5.1 × 10$^4$ | 0.0004055 | 7.8 | 6 |
| CV19B265 | 37364 | 0.001704 | 45.6 | 38 | NB | NB | NB | NB |
| CR3022 | 109803 | 0.0001340 | 1.2 | 1 | NB | NB | NB | NB |
| D001 | 43749 | 0.0006574 | 15.0 | 13 | NB | NB | NB | NB |
| SAD-S35 | 37484 | 0.0005347 | 14.3 | 12 | NB | NB | NB | NB |

Bispecific molecules featuring the VHH-ACE2-Fc architecture (CV19B265, CV19B277, CV19B283, and CV19B289) bound to the SARS-CoV-2 spike glycoprotein with similar affinities, each ~2-3-fold weaker than D001 and SAD-S35. The two molecules featuring the negative control VHH, targeted against mouse EGFR, (CV19B265 and CV19B289) displayed off-rates of binding ~5-fold faster than the mAbs and the bi-functional molecules featuring VHH2 (CV19B277 and CV19B283). Bispecific molecules featuring the ACE2 ECD attached to the C-terminus of the Fc (CV19B290, CV19B301, CV19B307, and CV19B308) displayed a wide range of affinities for spike glycoprotein. CV19B290 featured the short truncation of ACE2 and displayed the weakest binding.

The emergence of SARS-CoV-2 variants has led to question of whether neutralizing monoclonal antibodies would retain activity (Korber, B. et al. Lancet Respir Med 8, 1154-1158, (2020); Starr, T. N. et al. Science 371, 850-854, (2021)), whereas recombinant ACE2 is expected to effectively neutralize all variants since ACE2 is the native receptor for SARS-CoV-2. Thus, the abilities of the ACE2 bifunctional molecules to bind to the Y435F, N439K, N501Y, and D614G variants was tested, which are associconsistent with our previous findings (Maruthachalam et al. MAbs 12, 1708030, (2020)). Bispecific molecules containing VHH6 (CV19B277 and CV19B301) bound with Kd~0.2 µM and 265 nM, respectively.

Figure 7:
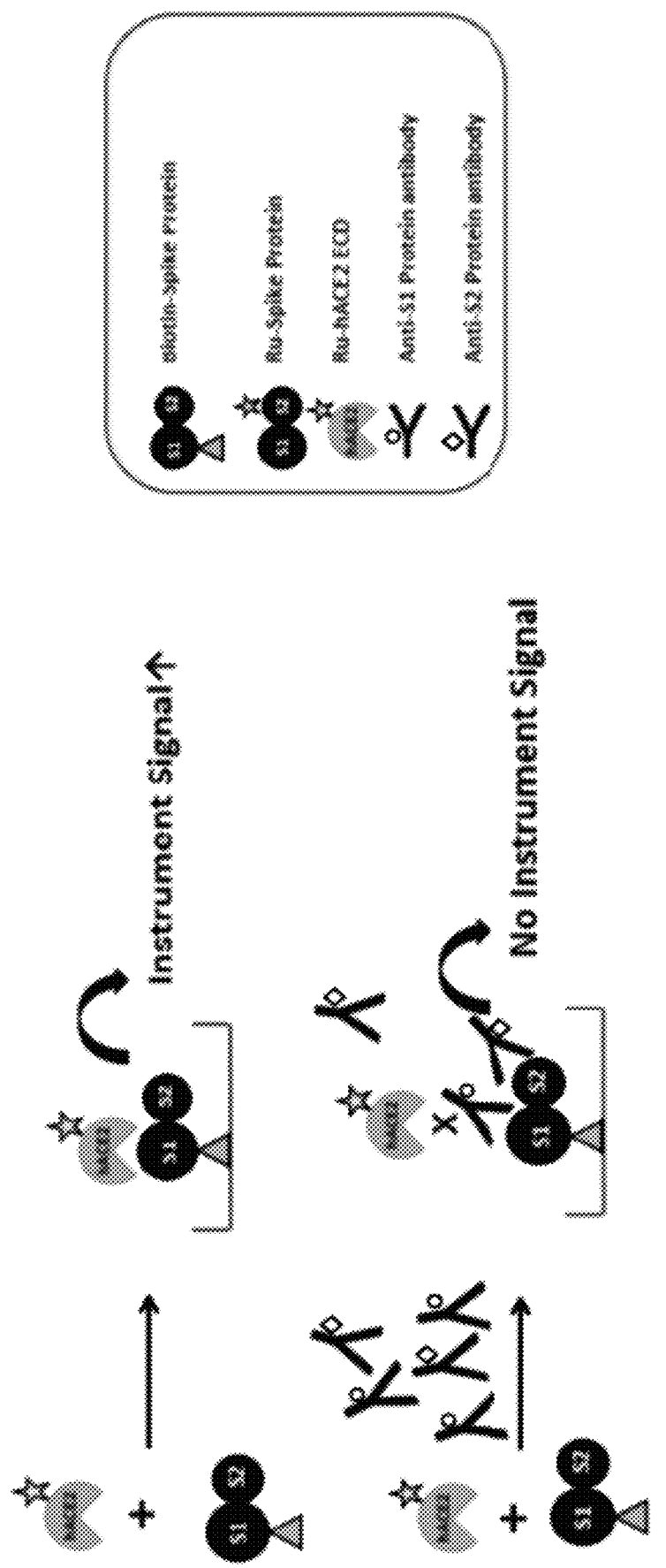
FIG. 7 shows a graphical depiction of the assay used to identify neutralizing antibodies by competitive and inhibitory non-cell-based surrogate neutralization immunoassay by using SARS-COV-2 trimer spike and ACE2 proteins as reagents.

Example 4. Anti-PIGR/Anti-ACE2 Bispecific Molecules Display Anti-SARS-CoV-2 Activity and Design-Dependent ADCC Activity Molecules were tested for their abilities to compete binding between SARS-CoV-2 S-protein and ACE2 using an MSD-based surrogate neutralization assay modified from previous report (FIG. 5A, FIG. 7 and Table 5) (Tan, C. W. et al. Nat Biotechnol 38, 1073-1078, (2020)). This immunoassay based surrogate neutralization assay has shown good correlation with the infectivity-based neutralization assay. D001 displayed inhibitory activity with IC$_{50}$=0.2 nM, while CR3022, an anti-SARS-CoV antibody known to lack the ability to neutralize SARS-CoV-2 (Huo, J. et al. Cell Host Microbe, (2020); ter Meulen, J. et al. PLoS Med 3, (2006)), failed to compete. All bispecific molecules featuring the ACE2 ECD displayed surrogate neutralization ability, with IC$_{50}$ ranging from 1-3 nM, with maximum activity within 4-10-fold to that of D001.

TABLE 5

IC$_{50}$ Values for SARS-CoV-2 competition

| Antibody | IC$_{50}$ in nM |
|---|---|
| CV19B277 | 2.876 |
| CV19B283 | 1.512 |
| CV19B301 | 1.195 |
| CV19B307 | 1.424 |
| CV19B308 | 3.206 |
| CR3022 | N/A |
| SAD-S35 | 0.3233 |
| D001 | 0.2991 |

Figure 6C:
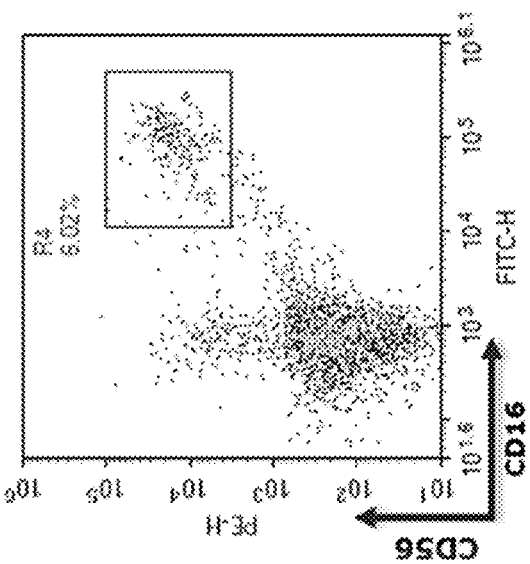
FIGS. 6A-6C show flow cytometric gating criteria for characterization of PBMC effector cell components. Live cells were selected by FSC vs SSC (FIG. 6A), B cells by CD19 expression, T cells by CD3 expression (FIG. 6B), and NK cells by CD56 and CD16 expression (FIG. 6C).
Figure 6B:
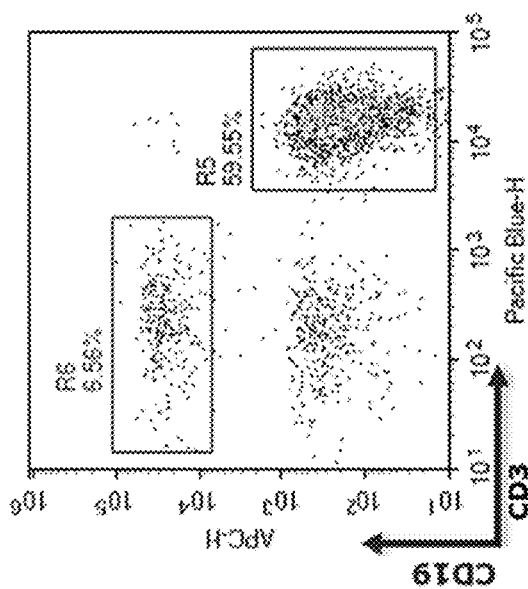
Figure 6A:
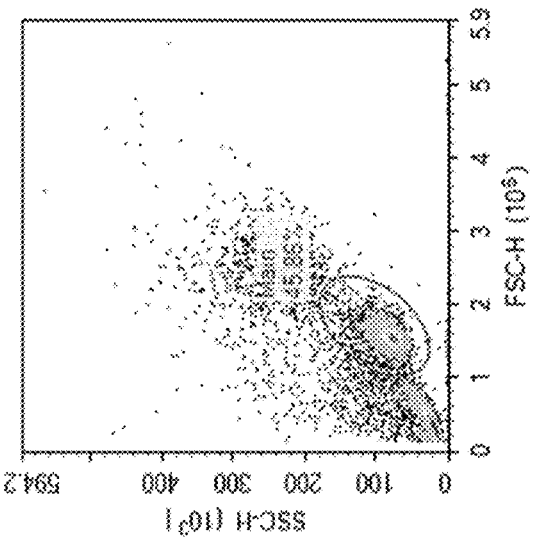

Thus, competition with SARS-CoV-2 S-protein appeared to be universal to all bispecific molecules featuring the ACE2 moiety. The bispecific molecules were designed to target pIgR on mucosal epithelial cells and co-transcytose across epithelial layers. However, targeting pIgR with an antibody featuring an active Fc region posed the risk of inducing antibody-dependent cellular cytotoxicity (ADCC) against the epithelial cells, resulting in potential undesirable toxicity. The ability of the bispecific molecules to mediate ADCC by PBMCs, against pIgR-expressing MDCK cells (FIG. 5B) was assessed. PBMC samples were comprised of ~7% CD19+ B cells, 60% CD3+ T cells, and 6% CD56+, CD16+ NK cells (FIGS. 6A-6C). Each bispecific molecule was formatted on both an active and "silent" Fc region, in which the Fc was mutated with L234A, L235A, and D265S to disrupt interaction with Fcγ receptors (Saunders, K. O. Front Immunol 10, 1296, (2019)). Two control molecules harboring the ACE2 ECD and a non-binding control VHH failed to mediate ADCC. Bispecific molecules featuring anti-pIgR VHH moieties on a silent Fc also failed to mediate ADCC, due to their inability to bind Fcγ receptors on NK cells. Interestingly, of the bispecific molecules having an active Fc, only those in which the VHH was fused in tandem with the ACE2 ECD on the N-terminus of the Fc displayed weak ADCC activity (CV19B277 and CV19B283). Other bispecific molecules in which the anti-pIgR VHH was fused onto the N-terminus of the Fc with the ACE2 ECD C-terminal of the Fc (CV19B301 and CV19B307) failed to mediate ADCC, despite binding pIgR on the MDCK cells and having an active Fc. This suggested that either the presence of the C-terminal ACE2 ECD inhibited ADCC or that this architecture allowed transcytosis rates to exceed the binding rate for Fcγ receptor engagement.

Example 5. PIGR Engagement LED to Serum Clearance and Mucosal Enrichment

The anti-pIgR VHH modules could mediate transcytosis across both MDCK cell bilayers and in a human epithelial microtissue model (Maruthachalam et al. MAbs 12, 1708030 (2020)), and thus it was assessed whether this pIgR-mediated transcytosis could occur in vivo. VHH2, VHH3, and VHH6 were selected for pharmacokinetic analysis in either monovalent or bivalent format in C57BL/6 mice (FIG. 8 and Table 6).

TABLE 6

Pharmacokinetic properties of anti-pIgR VHH modules in C57BL/6 mice.

| Sample | $C_{max}$ (μg/mL) | $AUC_{last}$ (μg · day/mL) | $AUC_{inf}$ (μg · day/mL) | $V_z$ (mL/kg) | CL (mL/day/kg) | $T_{1/2}$ (day) |
|---|---|---|---|---|---|---|
| (VHH2 x VHH2) | 13.82 ± 1.02 | 1.95 ± 0.25 | 1.97 ± 0.25 | 999.61 ± 263.15 | 1284.27 ± 179.51 | 0.55 ± 0.15 |
| (VHH2 x null) | 14.11 ± 0.98 | 6.00 ± 0.72 | 6.17 ± 0.71 | 1888.48 ± 349.58 | 409.42 ± 47.81 | 3.18 ± 0.27 |
| (VHH3 x VHH3) | 14.80 ± 3.50 | 11.60 ± 1.54 | 12.13 ± 1.57 | 1085.97 ± 173.33 | 208.66 ± 24.28 | 3.60 ± 0.35 |
| (VHH3 x null) | 16.05 ± 4.85 | 32.56 ± 8.14 | 39.98 ± 10.48 | 588.35 ± 130.00 | 65.23 ± 12.91 | 6.26 ± 0.64 |
| (VHH6 x null) | 17.63 ± 1.33 | 83.78 ± 6.99 | 120.50 ± 16.99 | 246.53 ± 28.49 | 21.06 ± 2.75 | 8.26 ± 1.61 |
| (null x null) | 18.39 ± 1.32 | 81.23 ± 11.50 | 116.95 ± 24.13 | 255.97 ± 30.37 | 22.22 ± 5.18 | 8.18 ± 1.28 |

Although VHH2 and VHH6 were used in the bispecific molecules, VHH2 and VHH3 were selected for mouse studies for their abilities to cross react with mouse pIgR. As expected, a monovalent VHH6 displayed a serum half-life of ~8.2 d, consistent with that of the null VHH-Fc ($T_{1/2}$~8.2 d). Conversely, molecules harboring a single copy of the mouse pIgR cross-reactive VHH2 and VHH3 modules displayed rapid serum clearance, with $T_{1/2}$~3.2 d and 6 d, respectively. Bivalent versions of these modules displayed even faster serum clearance, having $T_{1/2}$ values of 0.55 d and 3.6 d, respectively. The VHH2-based molecules were cleared more rapidly than VHH3-based molecules, despite having similar affinity to pIgR.

The EPIAIRWAY 3D model (MatTEK Life Sciences), an established lung tissue model engineered from primary human tracheal bronchial cells, was used to test the transcytosis activity of anti-pIgR VHH-Fc molecules to the mucosal lumen (FIG. 9A). As expected, bispecific molecules featuring the null-VHH, which does not bind pIgR, did not effectively transcytose (CV19B289, CV19B290, and CV19B265). Conversely, bispecific molecules that could bind pIgR displayed higher luminal MSD signals, indicating higher transcytosis. Indeed, protein recovery from the mucosal extract appeared to result through active cross-tissue transport as shown by confocal imaging (FIGS. 9B and 9C). Staining for both pIgR and anti-VHH at 24 hr showed that CV19B307 (VHH2) was localized throughout the tissue while CV19B290 (null VHH) failed to transcytose through the tissue at all.

Interestingly, bispecific molecules in which the anti-pIgR VHH domains were fused directly to the N-terminus of the Fc (CV19B301, CV19B307, and CV19B308) appeared to transcytose more effectively than bispecific molecules in which the anti-pIgR VHH was fused in tandem with the ACE2 ECD on the N-terminus of the Fc (CV19B277 and CV19B283). In the case of CV19B301 and CV19B307, approximately 6% of the total protein was recovered in the mucociliary milieu, compared to ~0.3% for the bispecific molecules featuring the null VHH, or ~16-fold enrichment in the mucosa. Although the amount of protein retained in the basal chamber was not measured, a large amount of bispecific molecule was retained within the tissue space and non-recoverable from the mucosal extract, and this molecule would ultimately be fated for mucosal secretion (FIG. 9B). The binding affinity of the anti-pIgR VHH had less impact on transcytosis, although the bispecific molecule featuring the shorter ACE2 fragment (CV19B308) displayed somewhat weaker transcytosis. Based on transcytosis ability, the two most optimal bispecific molecules were CV19B301 and CV19B307, having mucosal enrichment >16-fold compared to CD19B265 (null VHH).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

What is claimed is:

1. A multispecific molecule comprising: (a) a first binding domain that specifically binds to polymeric immunoglobulin receptor (pIgR), and (b) a second binding domain that specifically binds to SARS-COV-2, wherein the first binding domain comprises a single-domain antibody (VHH) comprising:
   (a) a CDR1 comprising the amino acid sequence of SEQ ID NO:1, a CDR2 comprising the amino acid sequence of SEQ ID NO:2, and a CDR3 comprising the amino acid sequence of SEQ ID NO:3;
   (b) a CDR1 comprising the amino acid sequence of SEQ ID NO:4, a CDR2 comprising the amino acid sequence of SEQ ID NO:5, and a CDR3 comprising the amino acid sequence of SEQ ID NO:6;
   (c) a CDR1 comprising the amino acid sequence of SEQ ID NO:7, a CDR2 comprising the amino acid sequence of SEQ ID NO:8, and a CDR3 comprising the amino acid sequence of SEQ ID NO:9;
   (d) a CDR1 comprising the amino acid sequence of SEQ ID NO: 10, a CDR2 comprising the amino acid sequence of SEQ ID NO: 11, and a CDR3 comprising the amino acid sequence of SEQ ID NO:12;
   (e) a CDR1 comprising the amino acid sequence of SEQ ID NO:13, a CDR2 comprising the amino acid sequence of SEQ ID NO:14, and a CDR3 comprising the amino acid sequence of SEQ ID NO:15;
   (f) a CDR1 comprising the amino acid sequence of SEQ ID NO:17, a CDR2 comprising the amino acid sequence of SEQ ID NO: 18, and a CDR3 comprising the amino acid sequence of SEQ ID NO:19;
   (g) a CDR1 comprising the amino acid sequence of SEQ ID NO:20, a CDR2 comprising the amino acid sequence of SEQ ID NO:21, and a CDR3 comprising the amino acid sequence of SEQ ID NO:22;
   (h) a CDR1 comprising the amino acid sequence of SEQ ID NO:23, a CDR2 comprising the amino acid sequence of SEQ ID NO:24, and a CDR3 comprising the amino acid sequence of SEQ ID NO:25;
   (i) a CDR1 comprising the amino acid sequence of SEQ ID NO:26, a CDR2 comprising the amino acid sequence of SEQ ID NO:27, and a CDR3 comprising the amino acid sequence of SEQ ID NO:28; or
   (j) a CDR1 comprising the amino acid sequence of SEQ ID NO:29, a CDR2 comprising the amino acid sequence of SEQ ID NO:30, and a CDR3 comprising the amino acid sequence of SEQ ID NO:31;
   and wherein the second binding domain comprises a peptide comprising:
   (a) angiotensin-converting enzyme 2 (ACE2);
      comprising the amino acid sequence of SEQ ID NO: 194;
   (b) the extracellular domain of ACE2;
      comprising the amino acid sequence of SEQ ID NO: 134; or
   (c) a truncated extracellular domain of ACE2;
      comprising the amino acid sequence of SEQ ID NO: 120 or the amino acid sequence of SEQ ID NO: 121.

2. The molecule of claim 1, wherein the molecule is a bispecific molecule.

3. The molecule of claim 1, wherein the second binding domain specifically binds to the surface of SARS-COV-2.

4. The molecule of claim 1, wherein the first binding domain comprises a VHH comprising:
   (a) a complementarity determining region 1 (CDR1) comprising the amino acid sequence of SEQ ID NO:1, a CDR2 comprising the amino acid sequence of SEQ ID NO:2, and a CDR3 comprising the amino acid sequence of SEQ ID NO:3; further wherein the VHH comprises the amino acid sequence of SEQ ID NO:16; or
   (b) a CDR1 comprising the amino acid sequence of SEQ ID NO:17, a CDR2 comprising the amino acid sequence of SEQ ID NO:18, and a CDR3 comprising the amino acid sequence of SEQ ID NO:19; further wherein the VHH comprises the amino acid sequence of SEQ ID NO:32.

5. The molecule of claim 1, wherein the first binding domain specifically binds to pIgR that is present on the mucosal endothelium.

6. The molecule of claim 1, wherein the SARS-COV-2 is neutralized when the molecule specifically binds to the pIgR and to SARS-COV-2.

7. A nucleic acid encoding the molecule of claim 1.

8. A vector comprising the nucleic acid of claim 7.

9. A host cell comprising the vector of claim 8.

10. A kit comprising the vector of claim 8 and packaging.

11. A pharmaceutical composition comprising the molecule of claim 1, and a pharmaceutically acceptable carrier.

12. A method of producing a pharmaceutical composition comprising combining the molecule of claim 1 with a pharmaceutically acceptable carrier to obtain the pharmaceutical composition.

13. A method of inhibiting host cell entry or proliferation of target cells expressing SARS-COV-2, the method comprising contacting the target cells with the molecule of claim 1, wherein contacting the target cells with the molecule inhibits host cell entry or proliferation of the target cells.

14. A method of treating SARS-COV-2 or COVID-19 in a subject, comprising administering an effective amount of the molecule of claim 1 to the subject.

15. The molecule of claim 3, wherein the second binding domain specifically binds to the spike glycoprotein on the surface of SARS-COV-2.

16. The molecule of claim 3, wherein the second binding domain specifically binds to the S1 subunit of the spike glycoprotein on the surface of SARS-COV-2.

17. The molecule of claim 5, wherein the first binding domain specifically binds to pIgR that is present on the lung mucosal endothelium.

18. The molecule of claim 6, wherein SARS-COV-2 is neutralized with an $EC_{50}$ of (a) less than about 4 nM; (b) less than about 3 nM; (c) less than about 1 nM; (d) less than about 500 pM; or (e) less than about 100 pM.

* * * * *

```
                       SEQUENCE LISTING

<160> NUMBER OF SEQ ID NOS: 201

<210> SEQ ID NO 1
    <211> LENGTH: 8
    <212> TYPE: PRT
    <213> ORGANISM: Artificial Sequence
    <220> FEATURE:
    <223> OTHER INFORMATION: VHH2 CDR1 (IMGT)

<400> SEQUENCE: 1

Gly Leu Thr Phe Ser Ser Tyr Arg
    1               5

<210> SEQ ID NO 2
    <211> LENGTH: 11
    <212> TYPE: PRT
    <213> ORGANISM: Artificial Sequence
    <220> FEATURE:
    <223> OTHER INFORMATION: VHH2 CDR2 (IMGT)

<400> SEQUENCE: 2

Ile Asp Trp Asn Gly Arg Gly Thr Tyr Tyr Arg
    1               5                   10

<210> SEQ ID NO 3
    <211> LENGTH: 17
    <212> TYPE: PRT
    <213> ORGANISM: Artificial Sequence
    <220> FEATURE:
    <223> OTHER INFORMATION: VHH2 CDR3 (IMGT)

<400> SEQUENCE: 3

Ala Ala Thr Thr Val Leu Thr Asp Pro Arg Val Leu Asn Glu Tyr Ala
    1               5                   10                  15

Thr

<210> SEQ ID NO 4
    <211> LENGTH: 5
    <212> TYPE: PRT
    <213> ORGANISM: Artificial Sequence
    <220> FEATURE:
    <223> OTHER INFORMATION: VHH2 CDR1 (Kabat)

<400> SEQUENCE: 4

Ser Tyr Arg Met Gly
    1               5
```

```
<210> SEQ ID NO 5
<211> LENGTH: 20
<212> TYPE: PRT
<213> ORGANISM: Artificial Sequence
<220> FEATURE:
<223> OTHER INFORMATION: VHH2 CDR2 (Kabat)

<400> SEQUENCE: 5

Ala Ile Asp Trp Asn Gly Arg Gly Thr Tyr Tyr Arg Tyr Tyr Ala Asp
1               5                   10                  15

Ser Val Lys Gly
            20

<210> SEQ ID NO 6
<211> LENGTH: 15
<212> TYPE: PRT
<213> ORGANISM: Artificial Sequence
<220> FEATURE:
<223> OTHER INFORMATION: VHH2 CDR3 (Kabat)

<400> SEQUENCE: 6

Thr Thr Val Leu Thr Asp Pro Arg Val Leu Asn Glu Tyr Ala Thr
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: VHH2 CDR1 (Chothia)

<400> SEQUENCE: 7

Gly Leu Thr Phe Ser Ser Tyr
1               5

<210> SEQ ID NO 8
<211> LENGTH: 9
<212> TYPE: PRT
<213> ORGANISM: Artificial Sequence
<220> FEATURE:
<223> OTHER INFORMATION: VHH2 CDR2 (Chothia)

<400> SEQUENCE: 8

Asp Trp Asn Gly Arg Gly Thr Tyr Tyr
1               5

<210> SEQ ID NO 9
<211> LENGTH: 14
<212> TYPE: PRT
<213> ORGANISM: Artificial Sequence
<220> FEATURE:
<223> OTHER INFORMATION: VHH2 CDR3 (Chothia)

<400> SEQUENCE: 9

Thr Thr Val Leu Thr Asp Pro Arg Val Leu Asn Glu Tyr Ala
1               5                   10

<210> SEQ ID NO 10
<211> LENGTH: 6
<212> TYPE: PRT
<213> ORGANISM: Artificial Sequence
<220> FEATURE:
<223> OTHER INFORMATION: VHH2 CDR1 (Contact)

<400> SEQUENCE: 10

Ser Ser Tyr Arg Met Gly
1               5
```

```
<210> SEQ ID NO 11
<211> LENGTH: 16
<212> TYPE: PRT
<213> ORGANISM: Artificial Sequence
<220> FEATURE:
<223> OTHER INFORMATION: VHH2 CDR2 (Contact)

<400> SEQUENCE: 11

Phe Val Ala Ala Ile Asp Trp Asn Gly Arg Gly Thr Tyr Tyr Arg Tyr
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: VHH2 CDR3 (Contact)

<400> SEQUENCE: 12

Ala Ala Thr Thr Val Leu Thr Asp Pro Arg Val Leu Asn Glu Tyr Ala
1               5                   10                  15

<210> SEQ ID NO 13
<211> LENGTH: 10
<212> TYPE: PRT
<213> ORGANISM: Artificial Sequence
<220> FEATURE:
<223> OTHER INFORMATION: VHH2 CDR1 (AbM)

<400> SEQUENCE: 13

Gly Leu Thr Phe Ser Ser Tyr Arg Met Gly
1               5                   10

<210> SEQ ID NO 14
<211> LENGTH: 13
<212> TYPE: PRT
<213> ORGANISM: Artificial Sequence
<220> FEATURE:
<223> OTHER INFORMATION: VHH2 CDR2 (AbM)

<400> SEQUENCE: 14

Ala Ile Asp Trp Asn Gly Arg Gly Thr Tyr Tyr Arg Tyr
1               5                   10

<210> SEQ ID NO 15
<211> LENGTH: 15
<212> TYPE: PRT
<213> ORGANISM: Artificial Sequence
<220> FEATURE:
<223> OTHER INFORMATION: VHH2 CDR3 (AbM)

<400> SEQUENCE: 15

Thr Thr Val Leu Thr Asp Pro Arg Val Leu Asn Glu Tyr Ala Thr
1               5                   10                  15

<210> SEQ ID NO 16
<211> LENGTH: 127
<212> TYPE: PRT
<213> ORGANISM: Artificial Sequence
<220> FEATURE:
<223> OTHER INFORMATION: VHH2 - VH amino acid sequence

<400> SEQUENCE: 16

Glu Val Gln Val Val Glu Ser Gly Gly Gly Leu Val Gln Ala Gly Gly
1               5                   10                  15
```

```
Ser Leu Lys Leu Ala Cys Ala Ala Pro Gly Leu Thr Phe Ser Ser Tyr
            20                  25                  30

Arg Met Gly Trp Phe Arg Gln Ala Pro Gly Gln Glu Arg Glu Phe Val
        35                  40                  45

Ala Ala Ile Asp Trp Asn Gly Arg Gly Thr Tyr Tyr Arg Tyr Tyr Ala
    50                  55                  60

Asp Ser Val Lys Gly Arg Ser Thr Ile Ser Arg Asp Asn Ala Lys Asn
65                  70                  75                  80

Thr Val Tyr Leu Gln Met Asn Ser Leu Lys Pro Glu Asp Thr Ala Val
                85                  90                  95

Tyr Tyr Cys Ala Ala Thr Thr Val Leu Thr Asp Pro Arg Val Leu Asn
            100                 105                 110

Glu Tyr Ala Thr Trp Gly Gln Gly Thr Gln Val Thr Val Ser Ser
        115                 120                 125
```

<210> SEQ ID NO 17
<211> LENGTH: 8
<212> TYPE: PRT
<213> ORGANISM: Artificial Sequence
<220> FEATURE:
<223> OTHER INFORMATION: VHH6 CDR1 (IMGT)

<400> SEQUENCE: 17

```
Gly Ser Ser Val Ser Ser Asp Ala
1               5
```

<210> SEQ ID NO 18
<211> LENGTH: 7
<212> TYPE: PRT
<213> ORGANISM: Artificial Sequence
<220> FEATURE:
<223> OTHER INFORMATION: VHH6 CDR2 (IMGT)

<400> SEQUENCE: 18

```
Ile Ser Gly Gly Gly Thr Thr
1               5
```

<210> SEQ ID NO 19
<211> LENGTH: 7
<212> TYPE: PRT
<213> ORGANISM: Artificial Sequence
<220> FEATURE:
<223> OTHER INFORMATION: VHH6 CDR3 (IMGT)

<400> SEQUENCE: 19

```
Asn His Pro Leu Thr Ser Arg
1               5
```

<210> SEQ ID NO 20
<211> LENGTH: 5
<212> TYPE: PRT
<213> ORGANISM: Artificial Sequence
<220> FEATURE:
<223> OTHER INFORMATION: VHH6 CDR1 (Kabat)

<400> SEQUENCE: 20

```
Ser Asp Ala Met Gly
1               5
```

<210> SEQ ID NO 21
<211> LENGTH: 16
<212> TYPE: PRT
<213> ORGANISM: Artificial Sequence
<220> FEATURE:

<223> OTHER INFORMATION: VHH6 CDR2 (Kabat)

<400> SEQUENCE: 21

Phe Ile Ser Gly Gly Gly Thr Thr Thr Tyr Ala Asp Ser Val Lys Gly
1               5                   10                  15

<210> SEQ ID NO 22
<211> LENGTH: 5
<212> TYPE: PRT
<213> ORGANISM: Artificial Sequence
<220> FEATURE:
<223> OTHER INFORMATION: VHH6 CDR3 (Kabat)

<400> SEQUENCE: 22

Pro Leu Thr Ser Arg
1               5

<210> SEQ ID NO 23
<211> LENGTH: 7
<212> TYPE: PRT
<213> ORGANISM: Artificial Sequence
<220> FEATURE:
<223> OTHER INFORMATION: VHH6 CDR1 (Chothia)

<400> SEQUENCE: 23

Gly Ser Ser Val Ser Ser Asp
1               5

<210> SEQ ID NO 24
<211> LENGTH: 5
<212> TYPE: PRT
<213> ORGANISM: Artificial Sequence
<220> FEATURE:
<223> OTHER INFORMATION: VHH6 CDR2 (Chothia)

<400> SEQUENCE: 24

Ser Gly Gly Gly Thr
1               5

<210> SEQ ID NO 25
<211> LENGTH: 4
<212> TYPE: PRT
<213> ORGANISM: Artificial Sequence
<220> FEATURE:
<223> OTHER INFORMATION: VHH6 CDR3 (Chothia)

<400> SEQUENCE: 25

Pro Leu Thr Ser
1

<210> SEQ ID NO 26
<211> LENGTH: 6
<212> TYPE: PRT
<213> ORGANISM: Artificial Sequence
<220> FEATURE:
<223> OTHER INFORMATION: VHH6 CDR1 (Contact)

<400> SEQUENCE: 26

Ser Ser Asp Ala Met Gly
1               5

<210> SEQ ID NO 27
<211> LENGTH: 12
<212> TYPE: PRT
<213> ORGANISM: Artificial Sequence
<220> FEATURE:
<223> OTHER INFORMATION: VHH6 CDR2 (Contact)

```
<400> SEQUENCE: 27

Trp Val Ala Phe Ile Ser Gly Gly Gly Thr Thr Thr
1               5                   10

<210> SEQ ID NO 28
<211> LENGTH: 6
<212> TYPE: PRT
<213> ORGANISM: Artificial Sequence
<220> FEATURE:
<223> OTHER INFORMATION: VHH6 CDR3 (Contact)

<400> SEQUENCE: 28

Asn His Pro Leu Thr Ser
1               5

<210> SEQ ID NO 29
<211> LENGTH: 10
<212> TYPE: PRT
<213> ORGANISM: Artificial Sequence
<220> FEATURE:
<223> OTHER INFORMATION: VHH6 CDR1 (AbM)

<400> SEQUENCE: 29

Gly Ser Ser Val Ser Ser Asp Ala Met Gly
1               5                   10

<210> SEQ ID NO 30
<211> LENGTH: 9
<212> TYPE: PRT
<213> ORGANISM: Artificial Sequence
<220> FEATURE:
<223> OTHER INFORMATION: VHH6 CDR2 (AbM)

<400> SEQUENCE: 30

Phe Ile Ser Gly Gly Gly Thr Thr Thr
1               5

<210> SEQ ID NO 31
<211> LENGTH: 5
<212> TYPE: PRT
<213> ORGANISM: Artificial Sequence
<220> FEATURE:
<223> OTHER INFORMATION: VHH6 CDR3 (AbM)

<400> SEQUENCE: 31

Pro Leu Thr Ser Arg
1               5

<210> SEQ ID NO 32
<211> LENGTH: 113
<212> TYPE: PRT
<213> ORGANISM: Artificial Sequence
<220> FEATURE:
<223> OTHER INFORMATION: VHH6 - VH amino acid sequence

<400> SEQUENCE: 32

Glu Val Gln Leu Val Glu Ser Gly Gly Gly Leu Val Gln Ala Gly Gly
1               5                   10                  15

Ser Leu Arg Leu Ser Cys Ala Val Ser Gly Ser Ser Val Ser Ser Asp
            20                  25                  30

Ala Met Gly Trp Tyr Arg Gln Ala Pro Gly Asn Gln Arg Ala Trp Val
        35                  40                  45

Ala Phe Ile Ser Gly Gly Gly Thr Thr Thr Tyr Ala Asp Ser Val Lys
    50                  55                  60
```

```
Gly Arg Phe Thr Ile Ser Arg Asp Asn Thr Lys Asn Thr Val Tyr Leu
65                  70                  75                  80

His Met Asn Ser Leu Lys Pro Glu Asp Thr Ala Val Tyr Tyr Cys Asn
                85                  90                  95

His Pro Leu Thr Ser Arg Trp Gly Gln Gly Thr Gln Val Thr Val Ser
            100                 105                 110

Ser

<210> SEQ ID NO 33
<211> LENGTH: 8
<212> TYPE: PRT
<213> ORGANISM: Artificial Sequence
<220> FEATURE:
<223> OTHER INFORMATION: D001 VH CDR1 (IMGT)

<400> SEQUENCE: 33

Gly Tyr Ser Phe Thr Asn Tyr Tyr
1               5

<210> SEQ ID NO 34
<211> LENGTH: 8
<212> TYPE: PRT
<213> ORGANISM: Artificial Sequence
<220> FEATURE:
<223> OTHER INFORMATION: D001 VH CDR2 (IMGT)

<400> SEQUENCE: 34

Ile Asp Pro Phe Asn Gly Gly Thr
1               5

<210> SEQ ID NO 35
<211> LENGTH: 13
<212> TYPE: PRT
<213> ORGANISM: Artificial Sequence
<220> FEATURE:
<223> OTHER INFORMATION: D001 VH CDR3 (IMGT)

<400> SEQUENCE: 35

Ala Arg Ser Glu Tyr Asp Pro Tyr Tyr Val Met Asp Tyr
1               5                   10

<210> SEQ ID NO 36
<211> LENGTH: 6
<212> TYPE: PRT
<213> ORGANISM: Artificial Sequence
<220> FEATURE:
<223> OTHER INFORMATION: D001 VL CDR1 (IMGT)

<400> SEQUENCE: 36

Gln Ser Ile Ser Ser Asn
1               5

<210> SEQ ID NO 37
<211> LENGTH: 3
<212> TYPE: PRT
<213> ORGANISM: Artificial Sequence
<220> FEATURE:
<223> OTHER INFORMATION: D001 VL CDR2 (IMGT)

<400> SEQUENCE: 37

Tyr Ala Ser
1

<210> SEQ ID NO 38
```

```
<211> LENGTH: 9
<212> TYPE: PRT
<213> ORGANISM: Artificial Sequence
<220> FEATURE:
<223> OTHER INFORMATION: D001 VL CDR3 (IMGT)

<400> SEQUENCE: 38

Gln Gln Thr Asn Phe Trp Pro Tyr Thr
1               5

<210> SEQ ID NO 39
<211> LENGTH: 5
<212> TYPE: PRT
<213> ORGANISM: Artificial Sequence
<220> FEATURE:
<223> OTHER INFORMATION: D001 VH CDR1 (Kabat)

<400> SEQUENCE: 39

Asn Tyr Tyr Ile His
1               5

<210> SEQ ID NO 40
<211> LENGTH: 17
<212> TYPE: PRT
<213> ORGANISM: Artificial Sequence
<220> FEATURE:
<223> OTHER INFORMATION: D001 VH CDR2 (Kabat)

<400> SEQUENCE: 40

Tyr Ile Asp Pro Phe Asn Gly Gly Thr Ser Asp Asn Leu Lys Phe Lys
1               5                   10                  15

Gly

<210> SEQ ID NO 41
<211> LENGTH: 11
<212> TYPE: PRT
<213> ORGANISM: Artificial Sequence
<220> FEATURE:
<223> OTHER INFORMATION: D001 VH CDR3 (Kabat)

<400> SEQUENCE: 41

Ser Glu Tyr Asp Pro Tyr Tyr Val Met Asp Tyr
1               5                   10

<210> SEQ ID NO 42
<211> LENGTH: 11
<212> TYPE: PRT
<213> ORGANISM: Artificial Sequence
<220> FEATURE:
<223> OTHER INFORMATION: D001 VL CDR1 (Kabat)

<400> SEQUENCE: 42

Arg Ala Ser Gln Ser Ile Ser Ser Asn Leu His
1               5                   10

<210> SEQ ID NO 43
<211> LENGTH: 7
<212> TYPE: PRT
<213> ORGANISM: Artificial Sequence
<220> FEATURE:
<223> OTHER INFORMATION: D001 VL CDR2 (Kabat)

<400> SEQUENCE: 43

Tyr Ala Ser Gln Ser Ile Ser
1               5
```

```
<210> SEQ ID NO 44
<211> LENGTH: 9
<212> TYPE: PRT
<213> ORGANISM: Artificial Sequence
<220> FEATURE:
<223> OTHER INFORMATION: D001 VL CDR3 (Kabat)

<400> SEQUENCE: 44

Gln Gln Thr Asn Phe Trp Pro Tyr Thr
1               5

<210> SEQ ID NO 45
<211> LENGTH: 7
<212> TYPE: PRT
<213> ORGANISM: Artificial Sequence
<220> FEATURE:
<223> OTHER INFORMATION: D001 VH CDR1 (Chothia)

<400> SEQUENCE: 45

Gly Tyr Ser Phe Thr Asn Tyr
1               5

<210> SEQ ID NO 46
<211> LENGTH: 6
<212> TYPE: PRT
<213> ORGANISM: Artificial Sequence
<220> FEATURE:
<223> OTHER INFORMATION: D001 VH CDR2 (Chothia)

<400> SEQUENCE: 46

Asp Pro Phe Asn Gly Gly
1               5

<210> SEQ ID NO 47
<211> LENGTH: 10
<212> TYPE: PRT
<213> ORGANISM: Artificial Sequence
<220> FEATURE:
<223> OTHER INFORMATION: D001 VH CDR3 (Chothia)

<400> SEQUENCE: 47

Ser Glu Tyr Asp Pro Tyr Tyr Val Met Asp
1               5                   10

<210> SEQ ID NO 48
<211> LENGTH: 7
<212> TYPE: PRT
<213> ORGANISM: Artificial Sequence
<220> FEATURE:
<223> OTHER INFORMATION: D001 VL CDR1 (Chothia)

<400> SEQUENCE: 48

Ser Gln Ser Ile Ser Ser Asn
1               5

<210> SEQ ID NO 49
<211> LENGTH: 3
<212> TYPE: PRT
<213> ORGANISM: Artificial Sequence
<220> FEATURE:
<223> OTHER INFORMATION: D001 VL CDR2 (Chothia)

<400> SEQUENCE: 49

Tyr Ala Ser
1

<210> SEQ ID NO 50
```

```
<211> LENGTH: 6
<212> TYPE: PRT
<213> ORGANISM: Artificial Sequence
<220> FEATURE:
<223> OTHER INFORMATION: D001 VL CDR3 (Chothia)

<400> SEQUENCE: 50

Thr Asn Phe Trp Pro Tyr
1               5

<210> SEQ ID NO 51
<211> LENGTH: 6
<212> TYPE: PRT
<213> ORGANISM: Artificial Sequence
<220> FEATURE:
<223> OTHER INFORMATION: D001 VH CDR1 (Contact)

<400> SEQUENCE: 51

Thr Asn Tyr Tyr Ile His
1               5

<210> SEQ ID NO 52
<211> LENGTH: 13
<212> TYPE: PRT
<213> ORGANISM: Artificial Sequence
<220> FEATURE:
<223> OTHER INFORMATION: D001 VH CDR2 (Contact)

<400> SEQUENCE: 52

Trp Ile Gly Tyr Ile Asp Pro Phe Asn Gly Gly Thr Ser
1               5                   10

<210> SEQ ID NO 53
<211> LENGTH: 12
<212> TYPE: PRT
<213> ORGANISM: Artificial Sequence
<220> FEATURE:
<223> OTHER INFORMATION: D001 VH CDR3 (Contact)

<400> SEQUENCE: 53

Ala Arg Ser Glu Tyr Asp Pro Tyr Tyr Val Met Asp
1               5                   10

<210> SEQ ID NO 54
<211> LENGTH: 7
<212> TYPE: PRT
<213> ORGANISM: Artificial Sequence
<220> FEATURE:
<223> OTHER INFORMATION: D001 VL CDR1 (Contact)

<400> SEQUENCE: 54

Ser Ser Asn Leu His Trp Tyr
1               5

<210> SEQ ID NO 55
<211> LENGTH: 10
<212> TYPE: PRT
<213> ORGANISM: Artificial Sequence
<220> FEATURE:
<223> OTHER INFORMATION: D001 VL CDR2 (Contact)

<400> SEQUENCE: 55

Leu Leu Ile Lys Tyr Ala Ser Gln Ser Ile
1               5                   10

<210> SEQ ID NO 56
<211> LENGTH: 8
```

```
<212> TYPE: PRT
<213> ORGANISM: Artificial Sequence
<220> FEATURE:
<223> OTHER INFORMATION: D001 VL CDR3 (Contact)

<400> SEQUENCE: 56

Gln Gln Thr Asn Phe Trp Pro Tyr
1               5

<210> SEQ ID NO 57
<211> LENGTH: 10
<212> TYPE: PRT
<213> ORGANISM: Artificial Sequence
<220> FEATURE:
<223> OTHER INFORMATION: D001 VH CDR1 (AbM)

<400> SEQUENCE: 57

Gly Tyr Ser Phe Thr Asn Tyr Tyr Ile His
1               5                   10

<210> SEQ ID NO 58
<211> LENGTH: 10
<212> TYPE: PRT
<213> ORGANISM: Artificial Sequence
<220> FEATURE:
<223> OTHER INFORMATION: D001 VH CDR2 (AbM)

<400> SEQUENCE: 58

Tyr Ile Asp Pro Phe Asn Gly Gly Thr Ser
1               5                   10

<210> SEQ ID NO 59
<211> LENGTH: 11
<212> TYPE: PRT
<213> ORGANISM: Artificial Sequence
<220> FEATURE:
<223> OTHER INFORMATION: D001 VH CDR3 (AbM)

<400> SEQUENCE: 59

Ser Glu Tyr Asp Pro Tyr Tyr Val Met Asp Tyr
1               5                   10

<210> SEQ ID NO 60
<211> LENGTH: 11
<212> TYPE: PRT
<213> ORGANISM: Artificial Sequence
<220> FEATURE:
<223> OTHER INFORMATION: D001 VL CDR1 (AbM)

<400> SEQUENCE: 60

Arg Ala Ser Gln Ser Ile Ser Ser Asn Leu His
1               5                   10

<210> SEQ ID NO 61
<211> LENGTH: 7
<212> TYPE: PRT
<213> ORGANISM: Artificial Sequence
<220> FEATURE:
<223> OTHER INFORMATION: D001 VL CDR2 (AbM)

<400> SEQUENCE: 61

Tyr Ala Ser Gln Ser Ile Ser
1               5

<210> SEQ ID NO 62
<211> LENGTH: 9
<212> TYPE: PRT
```

```
<213> ORGANISM: Artificial Sequence
<220> FEATURE:
<223> OTHER INFORMATION: D001 VL CDR3 (AbM)

<400> SEQUENCE: 62

Gln Gln Thr Asn Phe Trp Pro Tyr Thr
1               5

<210> SEQ ID NO 63
<211> LENGTH: 120
<212> TYPE: PRT
<213> ORGANISM: Artificial Sequence
<220> FEATURE:
<223> OTHER INFORMATION: D001 - VH amino acid sequence

<400> SEQUENCE: 63

Gln Val Gln Leu Gln Gln Ser Gly Pro Glu Leu Met Lys Pro Gly Ala
1               5                   10                  15

Ser Val Lys Ile Ser Cys Lys Ala Ser Gly Tyr Ser Phe Thr Asn Tyr
                20                  25                  30

Tyr Ile His Trp Val Lys Gln Ser His Gly Lys Ser Leu Glu Trp Ile
            35                  40                  45

Gly Tyr Ile Asp Pro Phe Asn Gly Gly Thr Ser Asp Asn Leu Lys Phe
    50                  55                  60

Lys Gly Ala Ala Thr Leu Thr Val Asp Lys Ser Ser Ser Thr Ala Tyr
65                  70                  75                  80

Met His Leu Ser Ser Leu Thr Ser Glu Asp Ser Ala Val Tyr Tyr Cys
                85                  90                  95

Ala Arg Ser Glu Tyr Asp Pro Tyr Tyr Val Met Asp Tyr Trp Gly Gln
            100                 105                 110

Gly Thr Ser Val Thr Val Ser Ser
        115                 120

<210> SEQ ID NO 64
<211> LENGTH: 107
<212> TYPE: PRT
<213> ORGANISM: Artificial Sequence
<220> FEATURE:
<223> OTHER INFORMATION: D001 - VL amino acid sequence

<400> SEQUENCE: 64

Glu Ile Val Leu Thr Gln Ser Pro Asp Thr Leu Ser Val Thr Pro Gly
1               5                   10                  15

Asp Ser Val Ser Leu Ser Cys Arg Ala Ser Gln Ser Ile Ser Ser Asn
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Ile Tyr Phe Cys Gln Gln Thr Asn Phe Trp Pro Tyr
                85                  90                  95

Thr Phe Gly Gly Gly Thr Lys Leu Glu Ile Lys
            100                 105

<210> SEQ ID NO 65
<211> LENGTH: 8
<212> TYPE: PRT
<213> ORGANISM: Artificial Sequence
```

<220> FEATURE:
<223> OTHER INFORMATION: CR3022 VH CDR1 (IMGT)

<400> SEQUENCE: 65

Gly Tyr Gly Phe Ile Thr Tyr Trp
1               5

<210> SEQ ID NO 66
<211> LENGTH: 8
<212> TYPE: PRT
<213> ORGANISM: Artificial Sequence
<220> FEATURE:
<223> OTHER INFORMATION: CR3022 VH CDR2 (IMGT)

<400> SEQUENCE: 66

Ile Tyr Pro Gly Asp Ser Glu Thr
1               5

<210> SEQ ID NO 67
<211> LENGTH: 12
<212> TYPE: PRT
<213> ORGANISM: Artificial Sequence
<220> FEATURE:
<223> OTHER INFORMATION: CR3022 VH CDR3 (IMGT)

<400> SEQUENCE: 67

Ala Gly Gly Ser Gly Ile Ser Thr Pro Met Asp Val
1               5                   10

<210> SEQ ID NO 68
<211> LENGTH: 12
<212> TYPE: PRT
<213> ORGANISM: Artificial Sequence
<220> FEATURE:
<223> OTHER INFORMATION: CR3022 VL CDR1 (IMGT)

<400> SEQUENCE: 68

Gln Ser Val Leu Tyr Ser Ser Ile Asn Lys Asn Tyr
1               5                   10

<210> SEQ ID NO 69
<211> LENGTH: 3
<212> TYPE: PRT
<213> ORGANISM: Artificial Sequence
<220> FEATURE:
<223> OTHER INFORMATION: CR3022 VL CDR2 (IMGT)

<400> SEQUENCE: 69

Trp Ala Ser
1

<210> SEQ ID NO 70
<211> LENGTH: 9
<212> TYPE: PRT
<213> ORGANISM: Artificial Sequence
<220> FEATURE:
<223> OTHER INFORMATION: CR3022 VL CDR3 (IMGT)

<400> SEQUENCE: 70

Gln Gln Tyr Tyr Ser Thr Pro Tyr Thr
1               5

<210> SEQ ID NO 71
<211> LENGTH: 5
<212> TYPE: PRT
<213> ORGANISM: Artificial Sequence
<220> FEATURE:

<223> OTHER INFORMATION: CR3022 VH CDR1 (Kabat)

<400> SEQUENCE: 71

Thr Tyr Trp Ile Gly
1               5

<210> SEQ ID NO 72
<211> LENGTH: 17
<212> TYPE: PRT
<213> ORGANISM: Artificial Sequence
<220> FEATURE:
<223> OTHER INFORMATION: CR3022 VH CDR2 (Kabat)

<400> SEQUENCE: 72

Ile Ile Tyr Pro Gly Asp Ser Glu Thr Arg Tyr Ser Pro Ser Phe Gln
1               5                   10                  15

Gly

<210> SEQ ID NO 73
<211> LENGTH: 10
<212> TYPE: PRT
<213> ORGANISM: Artificial Sequence
<220> FEATURE:
<223> OTHER INFORMATION: CR3022 VH CDR3 (Kabat)

<400> SEQUENCE: 73

Gly Ser Gly Ile Ser Thr Pro Met Asp Val
1               5                   10

<210> SEQ ID NO 74
<211> LENGTH: 17
<212> TYPE: PRT
<213> ORGANISM: Artificial Sequence
<220> FEATURE:
<223> OTHER INFORMATION: CR3022 VL CDR1 (Kabat)

<400> SEQUENCE: 74

Lys Ser Ser Gln Ser Val Leu Tyr Ser Ser Ile Asn Lys Asn Tyr Leu
1               5                   10                  15

Ala

<210> SEQ ID NO 75
<211> LENGTH: 7
<212> TYPE: PRT
<213> ORGANISM: Artificial Sequence
<220> FEATURE:
<223> OTHER INFORMATION: CR3022 VL CDR2 (Kabat)

<400> SEQUENCE: 75

Trp Ala Ser Thr Arg Glu Ser
1               5

<210> SEQ ID NO 76
<211> LENGTH: 9
<212> TYPE: PRT
<213> ORGANISM: Artificial Sequence
<220> FEATURE:
<223> OTHER INFORMATION: CR3022 VL CDR3 (Kabat)

<400> SEQUENCE: 76

Gln Gln Tyr Tyr Ser Thr Pro Tyr Thr
1               5

<210> SEQ ID NO 77
<211> LENGTH: 7

```
<212> TYPE: PRT
<213> ORGANISM: Artificial Sequence
<220> FEATURE:
<223> OTHER INFORMATION: CR3022 VH CDR1 (Chothia)

<400> SEQUENCE: 77

Gly Tyr Gly Phe Ile Thr Tyr
1               5

<210> SEQ ID NO 78
<211> LENGTH: 6
<212> TYPE: PRT
<213> ORGANISM: Artificial Sequence
<220> FEATURE:
<223> OTHER INFORMATION: CR3022 VH CDR2 (Chothia)

<400> SEQUENCE: 78

Tyr Pro Gly Asp Ser Glu
1               5

<210> SEQ ID NO 79
<211> LENGTH: 9
<212> TYPE: PRT
<213> ORGANISM: Artificial Sequence
<220> FEATURE:
<223> OTHER INFORMATION: CR3022 VH CDR3 (Chothia)

<400> SEQUENCE: 79

Gly Ser Gly Ile Ser Thr Pro Met Asp
1               5

<210> SEQ ID NO 80
<211> LENGTH: 13
<212> TYPE: PRT
<213> ORGANISM: Artificial Sequence
<220> FEATURE:
<223> OTHER INFORMATION: CR3022 VL CDR1 (Chothia)

<400> SEQUENCE: 80

Ser Gln Ser Val Leu Tyr Ser Ser Ile Asn Lys Asn Tyr
1               5                   10

<210> SEQ ID NO 81
<211> LENGTH: 3
<212> TYPE: PRT
<213> ORGANISM: Artificial Sequence
<220> FEATURE:
<223> OTHER INFORMATION: CR3022 VL CDR2 (Chothia)

<400> SEQUENCE: 81

Trp Ala Ser
1

<210> SEQ ID NO 82
<211> LENGTH: 6
<212> TYPE: PRT
<213> ORGANISM: Artificial Sequence
<220> FEATURE:
<223> OTHER INFORMATION: CR3022 VL CDR3 (Chothia)

<400> SEQUENCE: 82

Tyr Tyr Ser Thr Pro Tyr
1               5

<210> SEQ ID NO 83
<211> LENGTH: 6
<212> TYPE: PRT
```

```
<213> ORGANISM: Artificial Sequence
<220> FEATURE:
<223> OTHER INFORMATION: CR3022 VH CDR1 (Contact)

<400> SEQUENCE: 83

Ile Thr Tyr Trp Ile Gly
1               5

<210> SEQ ID NO 84
<211> LENGTH: 13
<212> TYPE: PRT
<213> ORGANISM: Artificial Sequence
<220> FEATURE:
<223> OTHER INFORMATION: CR3022 VH CDR2 (Contact)

<400> SEQUENCE: 84

Trp Met Gly Ile Ile Tyr Pro Gly Asp Ser Glu Thr Arg
1               5                   10

<210> SEQ ID NO 85
<211> LENGTH: 11
<212> TYPE: PRT
<213> ORGANISM: Artificial Sequence
<220> FEATURE:
<223> OTHER INFORMATION: CR3022 VH CDR3 (Contact)

<400> SEQUENCE: 85

Ala Gly Gly Ser Gly Ile Ser Thr Pro Met Asp
1               5                   10

<210> SEQ ID NO 86
<211> LENGTH: 13
<212> TYPE: PRT
<213> ORGANISM: Artificial Sequence
<220> FEATURE:
<223> OTHER INFORMATION: CR3022 VL CDR1 (Contact)

<400> SEQUENCE: 86

Leu Tyr Ser Ser Ile Asn Lys Asn Tyr Leu Ala Trp Tyr
1               5                   10

<210> SEQ ID NO 87
<211> LENGTH: 10
<212> TYPE: PRT
<213> ORGANISM: Artificial Sequence
<220> FEATURE:
<223> OTHER INFORMATION: CR3022 VL CDR2 (Contact)

<400> SEQUENCE: 87

Leu Leu Ile Tyr Trp Ala Ser Thr Arg Glu
1               5                   10

<210> SEQ ID NO 88
<211> LENGTH: 8
<212> TYPE: PRT
<213> ORGANISM: Artificial Sequence
<220> FEATURE:
<223> OTHER INFORMATION: CR3022 VL CDR3 (Contact)

<400> SEQUENCE: 88

Gln Gln Tyr Tyr Ser Thr Pro Tyr
1               5

<210> SEQ ID NO 89
<211> LENGTH: 10
<212> TYPE: PRT
<213> ORGANISM: Artificial Sequence
```

```
<220> FEATURE:
<223> OTHER INFORMATION: CR3022 VH CDR1 (AbM)

<400> SEQUENCE: 89

Gly Tyr Gly Phe Ile Thr Tyr Trp Ile Gly
1               5                   10

<210> SEQ ID NO 90
<211> LENGTH: 10
<212> TYPE: PRT
<213> ORGANISM: Artificial Sequence
<220> FEATURE:
<223> OTHER INFORMATION: CR3022 VH CDR2 (AbM)

<400> SEQUENCE: 90

Ile Ile Tyr Pro Gly Asp Ser Glu Thr Arg
1               5                   10

<210> SEQ ID NO 91
<211> LENGTH: 10
<212> TYPE: PRT
<213> ORGANISM: Artificial Sequence
<220> FEATURE:
<223> OTHER INFORMATION: CR3022 VH CDR3 (AbM)

<400> SEQUENCE: 91

Gly Ser Gly Ile Ser Thr Pro Met Asp Val
1               5                   10

<210> SEQ ID NO 92
<211> LENGTH: 17
<212> TYPE: PRT
<213> ORGANISM: Artificial Sequence
<220> FEATURE:
<223> OTHER INFORMATION: CR3022 VL CDR1 (AbM)

<400> SEQUENCE: 92

Lys Ser Ser Gln Ser Val Leu Tyr Ser Ser Ile Asn Lys Asn Tyr Leu
1               5                   10                  15

Ala

<210> SEQ ID NO 93
<211> LENGTH: 7
<212> TYPE: PRT
<213> ORGANISM: Artificial Sequence
<220> FEATURE:
<223> OTHER INFORMATION: CR3022 VL CDR2 (AbM)

<400> SEQUENCE: 93

Trp Ala Ser Thr Arg Glu Ser
1               5

<210> SEQ ID NO 94
<211> LENGTH: 9
<212> TYPE: PRT
<213> ORGANISM: Artificial Sequence
<220> FEATURE:
<223> OTHER INFORMATION: CR3022 VL CDR3 (AbM)

<400> SEQUENCE: 94

Gln Gln Tyr Tyr Ser Thr Pro Tyr Thr
1               5

<210> SEQ ID NO 95
<211> LENGTH: 119
<212> TYPE: PRT
```

```
<213> ORGANISM: Artificial Sequence
<220> FEATURE:
<223> OTHER INFORMATION: CR3022 - VH amino acid sequence

<400> SEQUENCE: 95

Gln Met Gln Leu Val Gln Ser Gly Thr Glu Val Lys Lys Pro Gly Glu
1               5                   10                  15

Ser Leu Lys Ile Ser Cys Lys Gly Ser Gly Tyr Gly Phe Ile Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Glu Thr Arg Tyr Ser Pro Ser Phe
50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Ile Tyr Tyr Cys
                85                  90                  95

Ala Gly Gly Ser Gly Ile Ser Thr Pro Met Asp Val Trp Gly Gln Gly
            100                 105                 110

Thr Thr Val Thr Val Ser Ser
        115

<210> SEQ ID NO 96
<211> LENGTH: 113
<212> TYPE: PRT
<213> ORGANISM: Artificial Sequence
<220> FEATURE:
<223> OTHER INFORMATION: CR3022 - VL amino acid sequence

<400> SEQUENCE: 96

Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Ile Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Val Glu Ile
            100                 105                 110

Lys

<210> SEQ ID NO 97
<211> LENGTH: 98
<212> TYPE: PRT
<213> ORGANISM: Artificial Sequence
<220> FEATURE:
<223> OTHER INFORMATION: huIgG1_G1m(17) CH1

<400> SEQUENCE: 97

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 98
<211> LENGTH: 98
<212> TYPE: PRT
<213> ORGANISM: Artificial Sequence
<220> FEATURE:
<223> OTHER INFORMATION: huIgG1_G1m(17) AAS CH1

<400> SEQUENCE: 98

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 99
<211> LENGTH: 98
<212> TYPE: PRT
<213> ORGANISM: Artificial Sequence
<220> FEATURE:
<223> OTHER INFORMATION: huIgG1_G1m(17) JAWA CH1

<400> SEQUENCE: 99

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 100
<211> LENGTH: 15
<212> TYPE: PRT
<213> ORGANISM: Artificial Sequence

```
<220> FEATURE:
<223> OTHER INFORMATION: huIgG1_G1m(17) hinge region

<400> SEQUENCE: 100

Glu Pro Lys Ser Cys Asp Lys Thr His Thr Cys Pro Pro Cys Pro
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: huIgG1_G1m(17) AAS hinge region

<400> SEQUENCE: 101

Glu Pro Lys Ser Cys Asp Lys Thr His Thr Cys Pro Pro Cys Pro
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: huIgG1_G1m(17) JAWA hinge region

<400> SEQUENCE: 102

Glu Pro Lys Ser Cys Asp Lys Thr His Thr Cys Pro Pro Cys Pro
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: huIgG1_G1m(17)-Fc_C220S hinge region

<400> SEQUENCE: 103

Glu Pro Lys Ser Ser Asp Lys Thr His Thr Cys Pro Pro Cys Pro
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: huIgG1_G1m(17)-Fc_C220S AAS hinge region

<400> SEQUENCE: 104

Glu Pro Lys Ser Ser Asp Lys Thr His Thr Cys Pro Pro Cys Pro
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: huIgG1_G1m(17)-Fc_C220S JAWA hinge region

<400> SEQUENCE: 105

Glu Pro Lys Ser Ser Asp Lys Thr His Thr Cys Pro Pro Cys Pro
1               5                   10                  15

<210> SEQ ID NO 106
<211> LENGTH: 110
<212> TYPE: PRT
<213> ORGANISM: Artificial Sequence
<220> FEATURE:
```

<223> OTHER INFORMATION: huIgG1_G1m(17) CH2

<400> SEQUENCE: 106

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 107
<211> LENGTH: 110
<212> TYPE: PRT
<213> ORGANISM: Artificial Sequence
<220> FEATURE:
<223> OTHER INFORMATION: huIgG1_G1m(17) AAS CH2

<400> SEQUENCE: 107

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Ser Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 108
<211> LENGTH: 110
<212> TYPE: PRT
<213> ORGANISM: Artificial Sequence
<220> FEATURE:
<223> OTHER INFORMATION: huIgG1_G1m(17) JAWA CH2

<400> SEQUENCE: 108

Ala Pro Glu Leu Leu Gly Gly Pro Ser Val Phe Leu Phe Pro Pro Lys
1               5                   10                  15

Pro Glu Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His

```
                65                  70                  75                  80
Gln Asp Trp Leu Asn Gly Lys Glu Tyr Lys Cys Lys Val Ser Asn Lys
                    85                  90                  95

Ala Leu Pro Ala Pro Ile Glu Lys Thr Ile Ser Lys Ala Lys
                100                 105                 110

<210> SEQ ID NO 109
<211> LENGTH: 110
<212> TYPE: PRT
<213> ORGANISM: Artificial Sequence
<220> FEATURE:
<223> OTHER INFORMATION: huIgG1_G1m(17)-Fc_C220S CH2

<400> SEQUENCE: 109

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                    85                  90                  95

Ala Leu Pro Ala Pro Ile Glu Lys Thr Ile Ser Lys Ala Lys
                100                 105                 110

<210> SEQ ID NO 110
<211> LENGTH: 110
<212> TYPE: PRT
<213> ORGANISM: Artificial Sequence
<220> FEATURE:
<223> OTHER INFORMATION: huIgG1_G1m(17)-Fc_C220S AAS CH2

<400> SEQUENCE: 110

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Ser Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                    85                  90                  95

Ala Leu Pro Ala Pro Ile Glu Lys Thr Ile Ser Lys Ala Lys
                100                 105                 110

<210> SEQ ID NO 111
<211> LENGTH: 110
<212> TYPE: PRT
<213> ORGANISM: Artificial Sequence
<220> FEATURE:
<223> OTHER INFORMATION: huIgG1_G1m(17)-Fc_C220S JAWA CH2

<400> SEQUENCE: 111
```

Ala Pro Glu Leu Leu Gly Gly Pro Ser Val Phe Leu Phe Pro Pro Lys
1               5                   10                  15

Pro Glu Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 112
<211> LENGTH: 107
<212> TYPE: PRT
<213> ORGANISM: Artificial Sequence
<220> FEATURE:
<223> OTHER INFORMATION: huIgG1_G1m(17) CH3

<400> SEQUENCE: 112

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 113
<211> LENGTH: 107
<212> TYPE: PRT
<213> ORGANISM: Artificial Sequence
<220> FEATURE:
<223> OTHER INFORMATION: huIgG1_G1m(17) AAS CH3

<400> SEQUENCE: 113

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr

```
                85                  90                  95

Thr Gln Lys Ser Leu Ser Leu Ser Pro Gly Lys
            100                 105

<210> SEQ ID NO 114
<211> LENGTH: 107
<212> TYPE: PRT
<213> ORGANISM: Artificial Sequence
<220> FEATURE:
<223> OTHER INFORMATION: huIgG1_G1m(17) JAWA CH3

<400> SEQUENCE: 114

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Arg Gln Lys Ser Leu Ser Leu Ser Pro Gly Lys
            100                 105

<210> SEQ ID NO 115
<211> LENGTH: 107
<212> TYPE: PRT
<213> ORGANISM: Artificial Sequence
<220> FEATURE:
<223> OTHER INFORMATION: huIgG1_G1m(17)-Fc_C220S CH3

<400> SEQUENCE: 115

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 116
<211> LENGTH: 107
<212> TYPE: PRT
<213> ORGANISM: Artificial Sequence
<220> FEATURE:
<223> OTHER INFORMATION: huIgG1_G1m(17)-Fc_C220S AAS CH3

<400> SEQUENCE: 116

Gly Gln Pro Arg Glu Pro Gln Val Tyr Thr Leu Pro Pro Ser Arg Glu
1               5                   10                  15
```

```
Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105
```

<210> SEQ ID NO 117
<211> LENGTH: 107
<212> TYPE: PRT
<213> ORGANISM: Artificial Sequence
<220> FEATURE:
<223> OTHER INFORMATION: huIgG1_G1m(17)-Fc_C220S JAWA CH3

<400> SEQUENCE: 117

```
Gly Gln Pro Arg Glu Pro Gln Val Tyr Thr Leu Pro Pro Ser Arg Glu
 1               5                  10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Arg Gln Lys Ser Leu Ser Leu Ser Pro Gly Lys
            100                 105
```

<210> SEQ ID NO 118
<211> LENGTH: 107
<212> TYPE: PRT
<213> ORGANISM: Artificial Sequence
<220> FEATURE:
<223> OTHER INFORMATION: huKappa_Km(3) CL

<400> SEQUENCE: 118

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

-continued

<210> SEQ ID NO 119
<211> LENGTH: 10
<212> TYPE: PRT
<213> ORGANISM: Artificial Sequence
<220> FEATURE:
<223> OTHER INFORMATION: 2(G4S) linker

<400> SEQUENCE: 119

Gly Gly Gly Gly Ser Gly Gly Gly Gly Ser
1               5                   10

<210> SEQ ID NO 120
<211> LENGTH: 708
<212> TYPE: PRT
<213> ORGANISM: Homo sapiens
<220> FEATURE:
<223> OTHER INFORMATION: ACE2-18-725 (truncated)

<400> SEQUENCE: 120

Gln Ser Thr Ile Glu Glu Gln Ala Lys Thr Phe Leu Asp Lys Phe Asn
1               5                   10                  15

His Glu Ala Glu Asp Leu Phe Tyr Gln Ser Ser Leu Ala Ser Trp Asn
            20                  25                  30

Tyr Asn Thr Asn Ile Thr Glu Glu Asn Val Gln Asn Met Asn Asn Ala
        35                  40                  45

Gly Asp Lys Trp Ser Ala Phe Leu Lys Glu Gln Ser Thr Leu Ala Gln
    50                  55                  60

Met Tyr Pro Leu Gln Glu Ile Gln Asn Leu Thr Val Lys Leu Gln Leu
65                  70                  75                  80

Gln Ala Leu Gln Gln Asn Gly Ser Ser Val Leu Ser Glu Asp Lys Ser
                85                  90                  95

Lys Arg Leu Asn Thr Ile Leu Asn Thr Met Ser Thr Ile Tyr Ser Thr
            100                 105                 110

Gly Lys Val Cys Asn Pro Asp Asn Pro Gln Glu Cys Leu Leu Leu Glu
        115                 120                 125

Pro Gly Leu Asn Glu Ile Met Ala Asn Ser Leu Asp Tyr Asn Glu Arg
    130                 135                 140

Leu Trp Ala Trp Glu Ser Trp Arg Ser Glu Val Gly Lys Gln Leu Arg
145                 150                 155                 160

Pro Leu Tyr Glu Glu Tyr Val Val Leu Lys Asn Glu Met Ala Arg Ala
                165                 170                 175

Asn His Tyr Glu Asp Tyr Gly Asp Tyr Trp Arg Gly Asp Tyr Glu Val
            180                 185                 190

Asn Gly Val Asp Gly Tyr Asp Tyr Ser Arg Gly Gln Leu Ile Glu Asp
        195                 200                 205

Val Glu His Thr Phe Glu Glu Ile Lys Pro Leu Tyr Glu His Leu His
    210                 215                 220

Ala Tyr Val Arg Ala Lys Leu Met Asn Ala Tyr Pro Ser Tyr Ile Ser
225                 230                 235                 240

Pro Ile Gly Cys Leu Pro Ala His Leu Leu Gly Asp Met Trp Gly Arg
                245                 250                 255

Phe Trp Thr Asn Leu Tyr Ser Leu Thr Val Pro Phe Gly Gln Lys Pro
            260                 265                 270

Asn Ile Asp Val Thr Asp Ala Met Val Asp Gln Ala Trp Asp Ala Gln
        275                 280                 285

```
Arg Ile Phe Lys Glu Ala Glu Lys Phe Phe Val Ser Val Gly Leu Pro
    290             295             300
Asn Met Thr Gln Gly Phe Trp Glu Asn Ser Met Leu Thr Asp Pro Gly
305             310             315             320
Asn Val Gln Lys Ala Val Cys His Pro Thr Ala Trp Asp Leu Gly Lys
            325             330             335
Gly Asp Phe Arg Ile Leu Met Cys Thr Lys Val Thr Met Asp Asp Phe
            340             345             350
Leu Thr Ala His His Glu Met Gly His Ile Gln Tyr Asp Met Ala Tyr
        355             360             365
Ala Ala Gln Pro Phe Leu Leu Arg Asn Gly Ala Asn Glu Gly Phe His
370             375             380
Glu Ala Val Gly Glu Ile Met Ser Leu Ser Ala Thr Pro Lys His
385             390             395             400
Leu Lys Ser Ile Gly Leu Leu Ser Pro Asp Phe Gln Glu Asp Asn Glu
            405             410             415
Thr Glu Ile Asn Phe Leu Leu Lys Gln Ala Leu Thr Ile Val Gly Thr
            420             425             430
Leu Pro Phe Thr Tyr Met Leu Glu Lys Trp Arg Trp Met Val Phe Lys
        435             440             445
Gly Glu Ile Pro Lys Asp Gln Trp Met Lys Lys Trp Trp Glu Met Lys
450             455             460
Arg Glu Ile Val Gly Val Val Glu Pro Val Pro His Asp Glu Thr Tyr
465             470             475             480
Cys Asp Pro Ala Ser Leu Phe His Val Ser Asn Asp Tyr Ser Phe Ile
            485             490             495
Arg Tyr Tyr Thr Arg Thr Leu Tyr Gln Phe Gln Phe Gln Glu Ala Leu
        500             505             510
Cys Gln Ala Ala Lys His Glu Gly Pro Leu His Lys Cys Asp Ile Ser
        515             520             525
Asn Ser Thr Glu Ala Gly Gln Lys Leu Phe Asn Met Leu Arg Leu Gly
    530             535             540
Lys Ser Glu Pro Trp Thr Leu Ala Leu Glu Asn Val Val Gly Ala Lys
545             550             555             560
Asn Met Asn Val Arg Pro Leu Leu Asn Tyr Phe Glu Pro Leu Phe Thr
            565             570             575
Trp Leu Lys Asp Gln Asn Lys Asn Ser Phe Val Gly Trp Ser Thr Asp
        580             585             590
Trp Ser Pro Tyr Ala Asp Gln Ser Ile Lys Val Arg Ile Ser Leu Lys
        595             600             605
Ser Ala Leu Gly Asp Lys Ala Tyr Glu Trp Asn Asp Asn Glu Met Tyr
    610             615             620
Leu Phe Arg Ser Ser Val Ala Tyr Ala Met Arg Gln Tyr Phe Leu Lys
625             630             635             640
Val Lys Asn Gln Met Ile Leu Phe Gly Glu Glu Asp Val Arg Val Ala
            645             650             655
Asn Leu Lys Pro Arg Ile Ser Phe Asn Phe Phe Val Thr Ala Pro Lys
            660             665             670
Asn Val Ser Asp Ile Ile Pro Arg Thr Glu Val Glu Lys Ala Ile Arg
        675             680             685
Met Ser Arg Ser Arg Ile Asn Asp Ala Phe Arg Leu Asn Asp Asn Ser
690             695             700
Leu Glu Phe Leu
```

<210> SEQ ID NO 121
<211> LENGTH: 594
<212> TYPE: PRT
<213> ORGANISM: Homo sapiens
<220> FEATURE:
<223> OTHER INFORMATION: ACE2-18-611 (truncated)

<400> SEQUENCE: 121

```
Gln Ser Thr Ile Glu Glu Gln Ala Lys Thr Phe Leu Asp Lys Phe Asn
1               5                   10                  15

His Glu Ala Glu Asp Leu Phe Tyr Gln Ser Ser Leu Ala Ser Trp Asn
            20                  25                  30

Tyr Asn Thr Asn Ile Thr Glu Glu Asn Val Gln Asn Met Asn Asn Ala
        35                  40                  45

Gly Asp Lys Trp Ser Ala Phe Leu Lys Glu Gln Ser Thr Leu Ala Gln
    50                  55                  60

Met Tyr Pro Leu Gln Glu Ile Gln Asn Leu Thr Val Lys Leu Gln Leu
65                  70                  75                  80

Gln Ala Leu Gln Gln Asn Gly Ser Ser Val Leu Ser Glu Asp Lys Ser
                85                  90                  95

Lys Arg Leu Asn Thr Ile Leu Asn Thr Met Ser Thr Ile Tyr Ser Thr
            100                 105                 110

Gly Lys Val Cys Asn Pro Asp Asn Pro Gln Glu Cys Leu Leu Leu Glu
        115                 120                 125

Pro Gly Leu Asn Glu Ile Met Ala Asn Ser Leu Asp Tyr Asn Glu Arg
    130                 135                 140

Leu Trp Ala Trp Glu Ser Trp Arg Ser Glu Val Gly Lys Gln Leu Arg
145                 150                 155                 160

Pro Leu Tyr Glu Glu Tyr Val Val Leu Lys Asn Glu Met Ala Arg Ala
                165                 170                 175

Asn His Tyr Glu Asp Tyr Gly Asp Tyr Trp Arg Gly Asp Tyr Glu Val
            180                 185                 190

Asn Gly Val Asp Gly Tyr Asp Tyr Ser Arg Gly Gln Leu Ile Glu Asp
        195                 200                 205

Val Glu His Thr Phe Glu Glu Ile Lys Pro Leu Tyr Glu His Leu His
    210                 215                 220

Ala Tyr Val Arg Ala Lys Leu Met Asn Ala Tyr Pro Ser Tyr Ile Ser
225                 230                 235                 240

Pro Ile Gly Cys Leu Pro Ala His Leu Leu Gly Asp Met Trp Gly Arg
                245                 250                 255

Phe Trp Thr Asn Leu Tyr Ser Leu Thr Val Pro Phe Gly Gln Lys Pro
            260                 265                 270

Asn Ile Asp Val Thr Asp Ala Met Val Asp Gln Ala Trp Asp Ala Gln
        275                 280                 285

Arg Ile Phe Lys Glu Ala Glu Lys Phe Phe Val Ser Val Gly Leu Pro
    290                 295                 300

Asn Met Thr Gln Gly Phe Trp Glu Asn Ser Met Leu Thr Asp Pro Gly
305                 310                 315                 320

Asn Val Gln Lys Ala Val Cys His Pro Thr Ala Trp Asp Leu Gly Lys
                325                 330                 335

Gly Asp Phe Arg Ile Leu Met Cys Thr Lys Val Thr Met Asp Asp Phe
            340                 345                 350

Leu Thr Ala His His Glu Met Gly His Ile Gln Tyr Asp Met Ala Tyr
```

```
                355                 360                 365
Ala Ala Gln Pro Phe Leu Leu Arg Asn Gly Ala Asn Glu Gly Phe His
    370                 375                 380

Glu Ala Val Gly Glu Ile Met Ser Leu Ser Ala Thr Pro Lys His
385                 390                 395                 400

Leu Lys Ser Ile Gly Leu Leu Ser Pro Asp Phe Gln Glu Asp Asn Glu
                405                 410                 415

Thr Glu Ile Asn Phe Leu Leu Lys Gln Ala Leu Thr Ile Val Gly Thr
                420                 425                 430

Leu Pro Phe Thr Tyr Met Leu Glu Lys Trp Arg Trp Met Val Phe Lys
                435                 440                 445

Gly Glu Ile Pro Lys Asp Gln Trp Met Lys Lys Trp Trp Glu Met Lys
            450                 455                 460

Arg Glu Ile Val Gly Val Val Glu Pro Val Pro His Asp Glu Thr Tyr
465                 470                 475                 480

Cys Asp Pro Ala Ser Leu Phe His Val Ser Asn Asp Tyr Ser Phe Ile
                485                 490                 495

Arg Tyr Tyr Thr Arg Thr Leu Tyr Gln Phe Gln Phe Gln Glu Ala Leu
                500                 505                 510

Cys Gln Ala Ala Lys His Glu Gly Pro Leu His Lys Cys Asp Ile Ser
                515                 520                 525

Asn Ser Thr Glu Ala Gly Gln Lys Leu Phe Asn Met Leu Arg Leu Gly
                530                 535                 540

Lys Ser Glu Pro Trp Thr Leu Ala Leu Glu Asn Val Val Gly Ala Lys
545                 550                 555                 560

Asn Met Asn Val Arg Pro Leu Leu Asn Tyr Phe Glu Pro Leu Phe Thr
                565                 570                 575

Trp Leu Lys Asp Gln Asn Lys Asn Ser Phe Val Gly Trp Ser Thr Asp
                580                 585                 590

Trp Ser

<210> SEQ ID NO 122
<211> LENGTH: 1077
<212> TYPE: PRT
<213> ORGANISM: Artificial Sequence
<220> FEATURE:
<223> OTHER INFORMATION: pIgR-VHH2-MSCD342-ACE2-18-725-Fc HC1 AA

<400> SEQUENCE: 122

Glu Val Gln Val Val Glu Ser Gly Gly Gly Leu Val Gln Ala Gly Gly
1               5                   10                  15

Ser Leu Lys Leu Ala Cys Ala Ala Pro Gly Leu Thr Phe Ser Ser Tyr
                20                  25                  30

Arg Met Gly Trp Phe Arg Gln Ala Pro Gly Gln Glu Arg Glu Phe Val
            35                  40                  45

Ala Ala Ile Asp Trp Asn Gly Arg Gly Thr Tyr Tyr Arg Tyr Tyr Ala
        50                  55                  60

Asp Ser Val Lys Gly Arg Ser Thr Ile Ser Arg Asp Asn Ala Lys Asn
65                  70                  75                  80

Thr Val Tyr Leu Gln Met Asn Ser Leu Lys Pro Glu Asp Thr Ala Val
                85                  90                  95

Tyr Tyr Cys Ala Ala Thr Thr Val Leu Thr Asp Pro Arg Val Leu Asn
                100                 105                 110

Glu Tyr Ala Thr Trp Gly Gln Gly Thr Gln Val Thr Val Ser Ser Gly
            115                 120                 125
```

```
Gly Gly Gly Ser Gly Gly Gly Ser Gln Ser Thr Ile Glu Glu Gln
            130             135             140
Ala Lys Thr Phe Leu Asp Lys Phe Asn His Glu Ala Glu Asp Leu Phe
145                 150                 155                 160
Tyr Gln Ser Ser Leu Ala Ser Trp Asn Tyr Asn Thr Asn Ile Thr Glu
                165                 170                 175
Glu Asn Val Gln Asn Met Asn Asn Ala Gly Asp Lys Trp Ser Ala Phe
            180                 185                 190
Leu Lys Glu Gln Ser Thr Leu Ala Gln Met Tyr Pro Leu Gln Glu Ile
    195                 200                 205
Gln Asn Leu Thr Val Lys Leu Gln Leu Gln Ala Leu Gln Gln Asn Gly
    210                 215                 220
Ser Ser Val Leu Ser Glu Asp Lys Ser Lys Arg Leu Asn Thr Ile Leu
225                 230                 235                 240
Asn Thr Met Ser Thr Ile Tyr Ser Thr Gly Lys Val Cys Asn Pro Asp
                245                 250                 255
Asn Pro Gln Glu Cys Leu Leu Leu Glu Pro Gly Leu Asn Glu Ile Met
            260                 265                 270
Ala Asn Ser Leu Asp Tyr Asn Glu Arg Leu Trp Ala Trp Glu Ser Trp
    275                 280                 285
Arg Ser Glu Val Gly Lys Gln Leu Arg Pro Leu Tyr Glu Glu Tyr Val
    290                 295                 300
Val Leu Lys Asn Glu Met Ala Arg Ala Asn His Tyr Glu Asp Tyr Gly
305                 310                 315                 320
Asp Tyr Trp Arg Gly Asp Tyr Glu Val Asn Gly Val Asp Gly Tyr Asp
                325                 330                 335
Tyr Ser Arg Gly Gln Leu Ile Glu Asp Val Glu His Thr Phe Glu Glu
            340                 345                 350
Ile Lys Pro Leu Tyr Glu His Leu His Ala Tyr Val Arg Ala Lys Leu
    355                 360                 365
Met Asn Ala Tyr Pro Ser Tyr Ile Ser Pro Ile Gly Cys Leu Pro Ala
370                 375                 380
His Leu Leu Gly Asp Met Trp Gly Arg Phe Trp Thr Asn Leu Tyr Ser
385                 390                 395                 400
Leu Thr Val Pro Phe Gly Gln Lys Pro Asn Ile Asp Val Thr Asp Ala
                405                 410                 415
Met Val Asp Gln Ala Trp Asp Ala Gln Arg Ile Phe Lys Glu Ala Glu
            420                 425                 430
Lys Phe Phe Val Ser Val Gly Leu Pro Asn Met Thr Gln Gly Phe Trp
    435                 440                 445
Glu Asn Ser Met Leu Thr Asp Pro Gly Asn Val Gln Lys Ala Val Cys
    450                 455                 460
His Pro Thr Ala Trp Asp Leu Gly Lys Gly Asp Phe Arg Ile Leu Met
465                 470                 475                 480
Cys Thr Lys Val Thr Met Asp Asp Phe Leu Thr Ala His His Glu Met
                485                 490                 495
Gly His Ile Gln Tyr Asp Met Ala Tyr Ala Ala Gln Pro Phe Leu Leu
            500                 505                 510
Arg Asn Gly Ala Asn Glu Gly Phe His Glu Ala Val Gly Glu Ile Met
    515                 520                 525
Ser Leu Ser Ala Ala Thr Pro Lys His Leu Lys Ser Ile Gly Leu Leu
530                 535                 540
```

-continued

```
Ser Pro Asp Phe Gln Glu Asp Asn Glu Thr Glu Ile Asn Phe Leu Leu
545                 550                 555                 560

Lys Gln Ala Leu Thr Ile Val Gly Thr Leu Pro Phe Thr Tyr Met Leu
                565                 570                 575

Glu Lys Trp Arg Trp Met Val Phe Lys Gly Glu Ile Pro Lys Asp Gln
            580                 585                 590

Trp Met Lys Lys Trp Trp Glu Met Lys Arg Glu Ile Val Gly Val Val
        595                 600                 605

Glu Pro Val Pro His Asp Glu Thr Tyr Cys Asp Pro Ala Ser Leu Phe
    610                 615                 620

His Val Ser Asn Asp Tyr Ser Phe Ile Arg Tyr Tyr Thr Arg Thr Leu
625                 630                 635                 640

Tyr Gln Phe Gln Phe Gln Glu Ala Leu Cys Gln Ala Ala Lys His Glu
                645                 650                 655

Gly Pro Leu His Lys Cys Asp Ile Ser Asn Ser Thr Glu Ala Gly Gln
            660                 665                 670

Lys Leu Phe Asn Met Leu Arg Leu Gly Lys Ser Glu Pro Trp Thr Leu
        675                 680                 685

Ala Leu Glu Asn Val Val Gly Ala Lys Asn Met Asn Val Arg Pro Leu
    690                 695                 700

Leu Asn Tyr Phe Glu Pro Leu Phe Thr Trp Leu Lys Asp Gln Asn Lys
705                 710                 715                 720

Asn Ser Phe Val Gly Trp Ser Thr Asp Trp Ser Pro Tyr Ala Asp Gln
                725                 730                 735

Ser Ile Lys Val Arg Ile Ser Leu Lys Ser Ala Leu Gly Asp Lys Ala
            740                 745                 750

Tyr Glu Trp Asn Asp Asn Glu Met Tyr Leu Phe Arg Ser Ser Val Ala
        755                 760                 765

Tyr Ala Met Arg Gln Tyr Phe Leu Lys Val Lys Asn Gln Met Ile Leu
    770                 775                 780

Phe Gly Glu Glu Asp Val Arg Val Ala Asn Leu Lys Pro Arg Ile Ser
785                 790                 795                 800

Phe Asn Phe Phe Val Thr Ala Pro Lys Asn Val Ser Asp Ile Ile Pro
                805                 810                 815

Arg Thr Glu Val Glu Lys Ala Ile Arg Met Ser Arg Ser Arg Ile Asn
            820                 825                 830

Asp Ala Phe Arg Leu Asn Asp Asn Ser Leu Glu Phe Leu Glu Pro Lys
        835                 840                 845

Ser Ser Asp Lys Thr His Thr Cys Pro Pro Cys Pro Ala Pro Glu Leu
    850                 855                 860

Leu Gly Gly Pro Ser Val Phe Leu Phe Pro Pro Lys Pro Lys Asp Thr
865                 870                 875                 880

Leu Met Ile Ser Arg Thr Pro Glu Val Thr Cys Val Val Val Asp Val
                885                 890                 895

Ser His Glu Asp Pro Glu Val Lys Phe Asn Trp Tyr Val Asp Gly Val
            900                 905                 910

Glu Val His Asn Ala Lys Thr Lys Pro Arg Glu Glu Gln Tyr Asn Ser
        915                 920                 925

Thr Tyr Arg Val Val Ser Val Leu Thr Val Leu His Gln Asp Trp Leu
    930                 935                 940

Asn Gly Lys Glu Tyr Lys Cys Lys Val Ser Asn Lys Ala Leu Pro Ala
945                 950                 955                 960

Pro Ile Glu Lys Thr Ile Ser Lys Ala Lys Gly Gln Pro Arg Glu Pro
```

-continued

```
                965                 970                 975
Gln Val Tyr Thr Leu Pro Pro Ser Arg Glu Glu Met Thr Lys Asn Gln
            980                 985                 990

Val Ser Leu Thr Cys Leu Val Lys Gly Phe Tyr Pro Ser Asp Ile Ala
            995                1000                1005

Val Glu Trp Glu Ser Asn Gly Gln Pro Glu Asn Asn Tyr Lys Thr
       1010                1015                1020

Thr Pro Pro Val Leu Asp Ser Asp Gly Ser Phe Phe Leu Tyr Ser
       1025                1030                1035

Lys Leu Thr Val Asp Lys Ser Arg Trp Gln Gln Gly Asn Val Phe
       1040                1045                1050

Ser Cys Ser Val Met His Glu Ala Leu His Asn His Tyr Thr Gln
       1055                1060                1065

Lys Ser Leu Ser Leu Ser Pro Gly Lys
       1070                1075
```

<210> SEQ ID NO 123
<211> LENGTH: 1076
<212> TYPE: PRT
<213> ORGANISM: Artificial Sequence
<220> FEATURE:
<223> OTHER INFORMATION: pIgR-VHH2-Fc-MSCD342-ACE2-18-725 HC1 AA

<400> SEQUENCE: 123

```
Glu Val Gln Val Val Glu Ser Gly Gly Gly Leu Val Gln Ala Gly Gly
1               5                  10                  15

Ser Leu Lys Leu Ala Cys Ala Ala Pro Gly Leu Thr Phe Ser Ser Tyr
            20                  25                  30

Arg Met Gly Trp Phe Arg Gln Ala Pro Gly Gln Glu Arg Glu Phe Val
        35                  40                  45

Ala Ala Ile Asp Trp Asn Gly Arg Gly Thr Tyr Tyr Arg Tyr Tyr Ala
    50                  55                  60

Asp Ser Val Lys Gly Arg Ser Thr Ile Ser Arg Asp Asn Ala Lys Asn
65                  70                  75                  80

Thr Val Tyr Leu Gln Met Asn Ser Leu Lys Pro Glu Asp Thr Ala Val
                85                  90                  95

Tyr Tyr Cys Ala Ala Thr Thr Val Leu Thr Asp Pro Arg Val Leu Asn
            100                 105                 110

Glu Tyr Ala Thr Trp Gly Gln Gly Thr Gln Val Thr Val Ser Ser Glu
        115                 120                 125

Pro Lys Ser Ser Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
```

-continued

```
            245                 250                 255
Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
            275                 280                 285

Ile Ala Val Glu Trp Glu Ser Asn Gly Gln Pro Glu Asn Asn Tyr Lys
            290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
                340                 345                 350

Leu Ser Leu Ser Pro Gly Gly Gly Gly Ser Gly Gly Gly Gly Ser
                355                 360                 365

Gln Ser Thr Ile Glu Glu Gln Ala Lys Thr Phe Leu Asp Lys Phe Asn
        370                 375                 380

His Glu Ala Glu Asp Leu Phe Tyr Gln Ser Ser Leu Ala Ser Trp Asn
385                 390                 395                 400

Tyr Asn Thr Asn Ile Thr Glu Glu Asn Val Gln Asn Met Asn Asn Ala
                    405                 410                 415

Gly Asp Lys Trp Ser Ala Phe Leu Lys Glu Gln Ser Thr Leu Ala Gln
                420                 425                 430

Met Tyr Pro Leu Gln Glu Ile Gln Asn Leu Thr Val Lys Leu Gln Leu
                435                 440                 445

Gln Ala Leu Gln Gln Asn Gly Ser Ser Val Leu Ser Glu Asp Lys Ser
        450                 455                 460

Lys Arg Leu Asn Thr Ile Leu Asn Thr Met Ser Thr Ile Tyr Ser Thr
465                 470                 475                 480

Gly Lys Val Cys Asn Pro Asp Asn Pro Gln Glu Cys Leu Leu Leu Glu
                    485                 490                 495

Pro Gly Leu Asn Glu Ile Met Ala Asn Ser Leu Asp Tyr Asn Glu Arg
                500                 505                 510

Leu Trp Ala Trp Glu Ser Trp Arg Ser Glu Val Gly Lys Gln Leu Arg
                515                 520                 525

Pro Leu Tyr Glu Glu Tyr Val Val Leu Lys Asn Glu Met Ala Arg Ala
        530                 535                 540

Asn His Tyr Glu Asp Tyr Gly Asp Tyr Trp Arg Gly Asp Tyr Glu Val
545                 550                 555                 560

Asn Gly Val Asp Gly Tyr Asp Tyr Ser Arg Gly Gln Leu Ile Glu Asp
                565                 570                 575

Val Glu His Thr Phe Glu Glu Ile Lys Pro Leu Tyr Glu His Leu His
                580                 585                 590

Ala Tyr Val Arg Ala Lys Leu Met Asn Ala Tyr Pro Ser Tyr Ile Ser
                595                 600                 605

Pro Ile Gly Cys Leu Pro Ala His Leu Leu Gly Asp Met Trp Gly Arg
        610                 615                 620

Phe Trp Thr Asn Leu Tyr Ser Leu Thr Val Pro Phe Gly Gln Lys Pro
625                 630                 635                 640

Asn Ile Asp Val Thr Asp Ala Met Val Asp Gln Ala Trp Asp Ala Gln
                    645                 650                 655

Arg Ile Phe Lys Glu Ala Glu Lys Phe Phe Val Ser Val Gly Leu Pro
                660                 665                 670
```

-continued

Asn Met Thr Gln Gly Phe Trp Glu Asn Ser Met Leu Thr Asp Pro Gly
        675                 680                 685

Asn Val Gln Lys Ala Val Cys His Pro Thr Ala Trp Asp Leu Gly Lys
    690                 695                 700

Gly Asp Phe Arg Ile Leu Met Cys Thr Lys Val Thr Met Asp Asp Phe
705                 710                 715                 720

Leu Thr Ala His His Glu Met Gly His Ile Gln Tyr Asp Met Ala Tyr
                725                 730                 735

Ala Ala Gln Pro Phe Leu Leu Arg Asn Gly Ala Asn Glu Gly Phe His
            740                 745                 750

Glu Ala Val Gly Glu Ile Met Ser Leu Ser Ala Ala Thr Pro Lys His
                755                 760                 765

Leu Lys Ser Ile Gly Leu Leu Ser Pro Asp Phe Gln Glu Asp Asn Glu
    770                 775                 780

Thr Glu Ile Asn Phe Leu Leu Lys Gln Ala Leu Thr Ile Val Gly Thr
785                 790                 795                 800

Leu Pro Phe Thr Tyr Met Leu Glu Lys Trp Arg Trp Met Val Phe Lys
                805                 810                 815

Gly Glu Ile Pro Lys Asp Gln Trp Met Lys Lys Trp Trp Glu Met Lys
            820                 825                 830

Arg Glu Ile Val Gly Val Val Glu Pro Val Pro His Asp Glu Thr Tyr
                835                 840                 845

Cys Asp Pro Ala Ser Leu Phe His Val Ser Asn Asp Tyr Ser Phe Ile
850                 855                 860

Arg Tyr Tyr Thr Arg Thr Leu Tyr Gln Phe Gln Phe Gln Glu Ala Leu
865                 870                 875                 880

Cys Gln Ala Ala Lys His Glu Gly Pro Leu His Lys Cys Asp Ile Ser
                885                 890                 895

Asn Ser Thr Glu Ala Gly Gln Lys Leu Phe Asn Met Leu Arg Leu Gly
            900                 905                 910

Lys Ser Glu Pro Trp Thr Leu Ala Leu Glu Asn Val Val Gly Ala Lys
    915                 920                 925

Asn Met Asn Val Arg Pro Leu Leu Asn Tyr Phe Glu Pro Leu Phe Thr
930                 935                 940

Trp Leu Lys Asp Gln Asn Lys Asn Ser Phe Val Gly Trp Ser Thr Asp
945                 950                 955                 960

Trp Ser Pro Tyr Ala Asp Gln Ser Ile Lys Val Arg Ile Ser Leu Lys
                965                 970                 975

Ser Ala Leu Gly Asp Lys Ala Tyr Glu Trp Asn Asp Asn Glu Met Tyr
            980                 985                 990

Leu Phe Arg Ser Ser Val Ala Tyr Ala Met Arg Gln Tyr Phe Leu Lys
    995                 1000                1005

Val Lys Asn Gln Met Ile Leu Phe Gly Glu Glu Asp Val Arg Val
    1010                1015                1020

Ala Asn Leu Lys Pro Arg Ile Ser Phe Asn Phe Phe Val Thr Ala
    1025                1030                1035

Pro Lys Asn Val Ser Asp Ile Ile Pro Arg Thr Glu Val Glu Lys
    1040                1045                1050

Ala Ile Arg Met Ser Arg Ser Arg Ile Asn Asp Ala Phe Arg Leu
    1055                1060                1065

Asn Asp Asn Ser Leu Glu Phe Leu
    1070                1075

<210> SEQ ID NO 124
<211> LENGTH: 962
<212> TYPE: PRT
<213> ORGANISM: Artificial Sequence
<220> FEATURE:
<223> OTHER INFORMATION: pIgR-VHH2-Fc-MSCD342-ACE2-18-611 HC1 AA

<400> SEQUENCE: 124

| | | | | | | | | | | | | | | | |
|---|---|---|---|---|---|---|---|---|---|---|---|---|---|---|---|
| Glu | Val | Gln | Val | Val | Glu | Ser | Gly | Gly | Gly | Leu | Val | Gln | Ala | Gly | Gly |
| 1 | | | | 5 | | | | | 10 | | | | | 15 | |
| Ser | Leu | Lys | Leu | Ala | Cys | Ala | Ala | Pro | Gly | Leu | Thr | Phe | Ser | Ser | Tyr |
| | | | 20 | | | | | 25 | | | | | 30 | | |
| Arg | Met | Gly | Trp | Phe | Arg | Gln | Ala | Pro | Gly | Gln | Glu | Arg | Glu | Phe | Val |
| | | 35 | | | | | 40 | | | | | 45 | | | |
| Ala | Ala | Ile | Asp | Trp | Asn | Gly | Arg | Gly | Thr | Tyr | Tyr | Arg | Tyr | Tyr | Ala |
| | 50 | | | | | 55 | | | | | 60 | | | | |
| Asp | Ser | Val | Lys | Gly | Arg | Ser | Thr | Ile | Ser | Arg | Asp | Asn | Ala | Lys | Asn |
| 65 | | | | | 70 | | | | | 75 | | | | | 80 |
| Thr | Val | Tyr | Leu | Gln | Met | Asn | Ser | Leu | Lys | Pro | Glu | Asp | Thr | Ala | Val |
| | | | | 85 | | | | | 90 | | | | | 95 | |
| Tyr | Tyr | Cys | Ala | Ala | Thr | Thr | Val | Leu | Thr | Asp | Pro | Arg | Val | Leu | Asn |
| | | | 100 | | | | | 105 | | | | | 110 | | |
| Glu | Tyr | Ala | Thr | Trp | Gly | Gln | Gly | Thr | Gln | Val | Thr | Val | Ser | Ser | Glu |
| | | | 115 | | | | | 120 | | | | | 125 | | |
| Pro | Lys | Ser | Ser | Asp | Lys | Thr | His | Thr | Cys | Pro | Pro | Cys | Pro | Ala | Pro |
| | 130 | | | | | 135 | | | | | 140 | | | | |
| Glu | Leu | Leu | Gly | Gly | Pro | Ser | Val | Phe | Leu | Phe | Pro | Pro | Lys | Pro | Lys |
| 145 | | | | | 150 | | | | | 155 | | | | | 160 |
| Asp | Thr | Leu | Met | Ile | Ser | Arg | Thr | Pro | Glu | Val | Thr | Cys | Val | Val | Val |
| | | | | 165 | | | | | 170 | | | | | 175 | |
| Asp | Val | Ser | His | Glu | Asp | Pro | Glu | Val | Lys | Phe | Asn | Trp | Tyr | Val | Asp |
| | | | 180 | | | | | 185 | | | | | 190 | | |
| Gly | Val | Glu | Val | His | Asn | Ala | Lys | Thr | Lys | Pro | Arg | Glu | Glu | Gln | Tyr |
| | | | 195 | | | | | 200 | | | | | 205 | | |
| Asn | Ser | Thr | Tyr | Arg | Val | Val | Ser | Val | Leu | Thr | Val | Leu | His | Gln | Asp |
| | 210 | | | | | 215 | | | | | 220 | | | | |
| Trp | Leu | Asn | Gly | Lys | Glu | Tyr | Lys | Cys | Lys | Val | Ser | Asn | Lys | Ala | Leu |
| 225 | | | | | 230 | | | | | 235 | | | | | 240 |
| Pro | Ala | Pro | Ile | Glu | Lys | Thr | Ile | Ser | Lys | Ala | Lys | Gly | Gln | Pro | Arg |
| | | | | 245 | | | | | 250 | | | | | 255 | |
| Glu | Pro | Gln | Val | Tyr | Thr | Leu | Pro | Pro | Ser | Arg | Glu | Glu | Met | Thr | Lys |
| | | | 260 | | | | | 265 | | | | | 270 | | |
| Asn | Gln | Val | Ser | Leu | Thr | Cys | Leu | Val | Lys | Gly | Phe | Tyr | Pro | Ser | Asp |
| | | | 275 | | | | | 280 | | | | | 285 | | |
| Ile | Ala | Val | Glu | Trp | Glu | Ser | Asn | Gly | Gln | Pro | Glu | Asn | Asn | Tyr | Lys |
| | 290 | | | | | 295 | | | | | 300 | | | | |
| Thr | Thr | Pro | Pro | Val | Leu | Asp | Ser | Asp | Gly | Ser | Phe | Phe | Leu | Tyr | Ser |
| 305 | | | | | 310 | | | | | 315 | | | | | 320 |
| Lys | Leu | Thr | Val | Asp | Lys | Ser | Arg | Trp | Gln | Gln | Gly | Asn | Val | Phe | Ser |
| | | | | 325 | | | | | 330 | | | | | 335 | |
| Cys | Ser | Val | Met | His | Glu | Ala | Leu | His | Asn | His | Tyr | Thr | Gln | Lys | Ser |
| | | | 340 | | | | | 345 | | | | | 350 | | |
| Leu | Ser | Leu | Ser | Pro | Gly | Gly | Gly | Gly | Ser | Gly | Gly | Gly | Gly | Ser | |
| | | | 355 | | | | | 360 | | | | | 365 | | |

-continued

```
Gln Ser Thr Ile Glu Glu Gln Ala Lys Thr Phe Leu Asp Lys Phe Asn
    370                 375                 380

His Glu Ala Glu Asp Leu Phe Tyr Gln Ser Ser Leu Ala Ser Trp Asn
385                 390                 395                 400

Tyr Asn Thr Asn Ile Thr Glu Glu Asn Val Gln Asn Met Asn Asn Ala
                405                 410                 415

Gly Asp Lys Trp Ser Ala Phe Leu Lys Glu Gln Ser Thr Leu Ala Gln
            420                 425                 430

Met Tyr Pro Leu Gln Glu Ile Gln Asn Leu Thr Val Lys Leu Gln Leu
        435                 440                 445

Gln Ala Leu Gln Gln Asn Gly Ser Ser Val Leu Ser Glu Asp Lys Ser
450                 455                 460

Lys Arg Leu Asn Thr Ile Leu Asn Thr Met Ser Thr Ile Tyr Ser Thr
465                 470                 475                 480

Gly Lys Val Cys Asn Pro Asp Asn Pro Gln Glu Cys Leu Leu Leu Glu
                485                 490                 495

Pro Gly Leu Asn Glu Ile Met Ala Asn Ser Leu Asp Tyr Asn Glu Arg
            500                 505                 510

Leu Trp Ala Trp Glu Ser Trp Arg Ser Glu Val Gly Lys Gln Leu Arg
        515                 520                 525

Pro Leu Tyr Glu Glu Tyr Val Val Leu Lys Asn Glu Met Ala Arg Ala
530                 535                 540

Asn His Tyr Glu Asp Tyr Gly Asp Tyr Trp Arg Gly Asp Tyr Glu Val
545                 550                 555                 560

Asn Gly Val Asp Gly Tyr Asp Tyr Ser Arg Gly Gln Leu Ile Glu Asp
                565                 570                 575

Val Glu His Thr Phe Glu Glu Ile Lys Pro Leu Tyr Glu His Leu His
            580                 585                 590

Ala Tyr Val Arg Ala Lys Leu Met Asn Ala Tyr Pro Ser Tyr Ile Ser
        595                 600                 605

Pro Ile Gly Cys Leu Pro Ala His Leu Leu Gly Asp Met Trp Gly Arg
610                 615                 620

Phe Trp Thr Asn Leu Tyr Ser Leu Thr Val Pro Phe Gly Gln Lys Pro
625                 630                 635                 640

Asn Ile Asp Val Thr Asp Ala Met Val Asp Gln Ala Trp Asp Ala Gln
                645                 650                 655

Arg Ile Phe Lys Glu Ala Glu Lys Phe Phe Val Ser Val Gly Leu Pro
            660                 665                 670

Asn Met Thr Gln Gly Phe Trp Glu Asn Ser Met Leu Thr Asp Pro Gly
        675                 680                 685

Asn Val Gln Lys Ala Val Cys His Pro Thr Ala Trp Asp Leu Gly Lys
690                 695                 700

Gly Asp Phe Arg Ile Leu Met Cys Thr Lys Val Thr Met Asp Asp Phe
705                 710                 715                 720

Leu Thr Ala His His Glu Met Gly His Ile Gln Tyr Asp Met Ala Tyr
                725                 730                 735

Ala Ala Gln Pro Phe Leu Leu Arg Asn Gly Ala Asn Glu Gly Phe His
            740                 745                 750

Glu Ala Val Gly Glu Ile Met Ser Leu Ser Ala Ala Thr Pro Lys His
        755                 760                 765

Leu Lys Ser Ile Gly Leu Leu Ser Pro Asp Phe Gln Glu Asp Asn Glu
770                 775                 780

Thr Glu Ile Asn Phe Leu Leu Lys Gln Ala Leu Thr Ile Val Gly Thr
```

-continued

```
                785                 790                 795                 800
Leu Pro Phe Thr Tyr Met Leu Glu Lys Trp Arg Trp Met Val Phe Lys
                    805                 810                 815

Gly Glu Ile Pro Lys Asp Gln Trp Met Lys Lys Trp Trp Glu Met Lys
                    820                 825                 830

Arg Glu Ile Val Gly Val Val Glu Pro Val Pro His Asp Glu Thr Tyr
                    835                 840                 845

Cys Asp Pro Ala Ser Leu Phe His Val Ser Asn Asp Tyr Ser Phe Ile
850                 855                 860

Arg Tyr Tyr Thr Arg Thr Leu Tyr Gln Phe Gln Phe Gln Glu Ala Leu
865                 870                 875                 880

Cys Gln Ala Ala Lys His Glu Gly Pro Leu His Lys Cys Asp Ile Ser
                    885                 890                 895

Asn Ser Thr Glu Ala Gly Gln Lys Leu Phe Asn Met Leu Arg Leu Gly
                    900                 905                 910

Lys Ser Glu Pro Trp Thr Leu Ala Leu Glu Asn Val Val Gly Ala Lys
                    915                 920                 925

Asn Met Asn Val Arg Pro Leu Leu Asn Tyr Phe Glu Pro Leu Phe Thr
                    930                 935                 940

Trp Leu Lys Asp Gln Asn Lys Asn Ser Phe Val Gly Trp Ser Thr Asp
945                 950                 955                 960

Trp Ser

<210> SEQ ID NO 125
<211> LENGTH: 1063
<212> TYPE: PRT
<213> ORGANISM: Artificial Sequence
<220> FEATURE:
<223> OTHER INFORMATION: pIgR-VHH6-MSCD342-ACE2 18-725-Fc HC1 AA

<400> SEQUENCE: 125

Glu Val Gln Leu Val Glu Ser Gly Gly Gly Leu Val Gln Ala Gly Gly
1               5                   10                  15

Ser Leu Arg Leu Ser Cys Ala Val Ser Gly Ser Ser Val Ser Ser Asp
                20                  25                  30

Ala Met Gly Trp Tyr Arg Gln Ala Pro Gly Asn Gln Arg Ala Trp Val
            35                  40                  45

Ala Phe Ile Ser Gly Gly Thr Thr Thr Tyr Ala Asp Ser Val Lys
        50                  55                  60

Gly Arg Phe Thr Ile Ser Arg Asp Asn Thr Lys Asn Thr Val Tyr Leu
65                  70                  75                  80

His Met Asn Ser Leu Lys Pro Glu Asp Thr Ala Val Tyr Tyr Cys Asn
                85                  90                  95

His Pro Leu Thr Ser Arg Trp Gly Gln Gly Thr Gln Val Thr Val Ser
                100                 105                 110

Ser Gly Gly Gly Gly Ser Gly Gly Gly Gly Ser Gln Ser Thr Ile Glu
            115                 120                 125

Glu Gln Ala Lys Thr Phe Leu Asp Lys Phe Asn His Glu Ala Glu Asp
            130                 135                 140

Leu Phe Tyr Gln Ser Ser Leu Ala Ser Trp Asn Tyr Asn Thr Asn Ile
145                 150                 155                 160

Thr Glu Glu Asn Val Gln Asn Met Asn Asn Ala Gly Asp Lys Trp Ser
                165                 170                 175

Ala Phe Leu Lys Glu Gln Ser Thr Leu Ala Gln Met Tyr Pro Leu Gln
                180                 185                 190
```

```
Glu Ile Gln Asn Leu Thr Val Lys Leu Gln Leu Gln Ala Leu Gln Gln
            195                 200                 205

Asn Gly Ser Ser Val Leu Ser Glu Asp Lys Ser Lys Arg Leu Asn Thr
    210                 215                 220

Ile Leu Asn Thr Met Ser Thr Ile Tyr Ser Thr Gly Lys Val Cys Asn
225                 230                 235                 240

Pro Asp Asn Pro Gln Glu Cys Leu Leu Leu Glu Pro Gly Leu Asn Glu
                245                 250                 255

Ile Met Ala Asn Ser Leu Asp Tyr Asn Glu Arg Leu Trp Ala Trp Glu
            260                 265                 270

Ser Trp Arg Ser Glu Val Gly Lys Gln Leu Arg Pro Leu Tyr Glu Glu
            275                 280                 285

Tyr Val Val Leu Lys Asn Glu Met Ala Arg Ala Asn His Tyr Glu Asp
            290                 295                 300

Tyr Gly Asp Tyr Trp Arg Gly Asp Tyr Glu Val Asn Gly Val Asp Gly
305                 310                 315                 320

Tyr Asp Tyr Ser Arg Gly Gln Leu Ile Glu Asp Val Glu His Thr Phe
                325                 330                 335

Glu Glu Ile Lys Pro Leu Tyr Glu His Leu His Ala Tyr Val Arg Ala
            340                 345                 350

Lys Leu Met Asn Ala Tyr Pro Ser Tyr Ile Ser Pro Ile Gly Cys Leu
            355                 360                 365

Pro Ala His Leu Leu Gly Asp Met Trp Gly Arg Phe Trp Thr Asn Leu
            370                 375                 380

Tyr Ser Leu Thr Val Pro Phe Gly Gln Lys Pro Asn Ile Asp Val Thr
385                 390                 395                 400

Asp Ala Met Val Asp Gln Ala Trp Asp Ala Gln Arg Ile Phe Lys Glu
                405                 410                 415

Ala Glu Lys Phe Phe Val Ser Val Gly Leu Pro Asn Met Thr Gln Gly
            420                 425                 430

Phe Trp Glu Asn Ser Met Leu Thr Asp Pro Gly Asn Val Gln Lys Ala
            435                 440                 445

Val Cys His Pro Thr Ala Trp Asp Leu Gly Lys Gly Asp Phe Arg Ile
450                 455                 460

Leu Met Cys Thr Lys Val Thr Met Asp Asp Phe Leu Thr Ala His His
465                 470                 475                 480

Glu Met Gly His Ile Gln Tyr Asp Met Ala Tyr Ala Ala Gln Pro Phe
                485                 490                 495

Leu Leu Arg Asn Gly Ala Asn Glu Gly Phe His Glu Ala Val Gly Glu
            500                 505                 510

Ile Met Ser Leu Ser Ala Ala Thr Pro Lys His Leu Lys Ser Ile Gly
            515                 520                 525

Leu Leu Ser Pro Asp Phe Gln Glu Asp Asn Glu Thr Glu Ile Asn Phe
            530                 535                 540

Leu Leu Lys Gln Ala Leu Thr Ile Val Gly Thr Leu Pro Phe Thr Tyr
545                 550                 555                 560

Met Leu Glu Lys Trp Arg Trp Met Val Phe Lys Gly Glu Ile Pro Lys
                565                 570                 575

Asp Gln Trp Met Lys Lys Trp Trp Glu Met Lys Arg Glu Ile Val Gly
            580                 585                 590

Val Val Glu Pro Val Pro His Asp Glu Thr Tyr Cys Asp Pro Ala Ser
            595                 600                 605
```

-continued

```
Leu Phe His Val Ser Asn Asp Tyr Ser Phe Ile Arg Tyr Tyr Thr Arg
    610             615                 620

Thr Leu Tyr Gln Phe Gln Phe Gln Glu Ala Leu Cys Gln Ala Ala Lys
625             630                 635                 640

His Glu Gly Pro Leu His Lys Cys Asp Ile Ser Asn Ser Thr Glu Ala
                645                 650                 655

Gly Gln Lys Leu Phe Asn Met Leu Arg Leu Gly Lys Ser Glu Pro Trp
            660                 665                 670

Thr Leu Ala Leu Glu Asn Val Val Gly Ala Lys Asn Met Asn Val Arg
                675                 680             685

Pro Leu Leu Asn Tyr Phe Glu Pro Leu Phe Thr Trp Leu Lys Asp Gln
690                 695                 700

Asn Lys Asn Ser Phe Val Gly Trp Ser Thr Asp Trp Ser Pro Tyr Ala
705                 710                 715                 720

Asp Gln Ser Ile Lys Val Arg Ile Ser Leu Lys Ser Ala Leu Gly Asp
                725                 730                 735

Lys Ala Tyr Glu Trp Asn Asp Asn Glu Met Tyr Leu Phe Arg Ser Ser
                740                 745                 750

Val Ala Tyr Ala Met Arg Gln Tyr Phe Leu Lys Val Lys Asn Gln Met
            755                 760                 765

Ile Leu Phe Gly Glu Glu Asp Val Arg Val Ala Asn Leu Lys Pro Arg
            770                 775                 780

Ile Ser Phe Asn Phe Phe Val Thr Ala Pro Lys Asn Val Ser Asp Ile
785                 790                 795                 800

Ile Pro Arg Thr Glu Val Glu Lys Ala Ile Arg Met Ser Arg Ser Arg
                805                 810                 815

Ile Asn Asp Ala Phe Arg Leu Asn Asp Asn Ser Leu Glu Phe Leu Glu
                820                 825                 830

Pro Lys Ser Ser Asp Lys Thr His Thr Cys Pro Pro Cys Pro Ala Pro
    835                 840                 845

Glu Leu Leu Gly Gly Pro Ser Val Phe Leu Phe Pro Pro Lys Pro Lys
    850                 855                 860

Asp Thr Leu Met Ile Ser Arg Thr Pro Glu Val Thr Cys Val Val Val
865                 870                 875                 880

Asp Val Ser His Glu Asp Pro Glu Val Lys Phe Asn Trp Tyr Val Asp
                885                 890                 895

Gly Val Glu Val His Asn Ala Lys Thr Lys Pro Arg Glu Glu Gln Tyr
                900                 905                 910

Asn Ser Thr Tyr Arg Val Val Ser Val Leu Thr Val Leu His Gln Asp
                915                 920                 925

Trp Leu Asn Gly Lys Glu Tyr Lys Cys Lys Val Ser Asn Lys Ala Leu
930                 935                 940

Pro Ala Pro Ile Glu Lys Thr Ile Ser Lys Ala Lys Gly Gln Pro Arg
945                 950                 955                 960

Glu Pro Gln Val Tyr Thr Leu Pro Pro Ser Arg Glu Glu Met Thr Lys
                965                 970                 975

Asn Gln Val Ser Leu Thr Cys Leu Val Lys Gly Phe Tyr Pro Ser Asp
                980                 985                 990

Ile Ala Val Glu Trp Glu Ser Asn Gly Gln Pro Glu Asn Asn Tyr Lys
            995                 1000                1005

Thr Thr Pro Pro Val Leu Asp Ser Asp Gly Ser Phe Phe Leu Tyr
    1010                1015                1020

Ser Lys Leu Thr Val Asp Lys Ser Arg Trp Gln Gln Gly Asn Val
```

```
                    1025                1030                1035

Phe Ser Cys Ser Val Met His Glu Ala Leu His Asn His Tyr Thr
            1040                1045                1050

Gln Lys Ser Leu Ser Leu Ser Pro Gly Lys
        1055                1060

<210> SEQ ID NO 126
<211> LENGTH: 1062
<212> TYPE: PRT
<213> ORGANISM: Artificial Sequence
<220> FEATURE:
<223> OTHER INFORMATION: pIgR-VHH6-Fc-MSCD342-ACE2 18-725 HC1 AA

<400> SEQUENCE: 126

Glu Val Gln Leu Val Glu Ser Gly Gly Gly Leu Val Gln Ala Gly Gly
1               5                   10                  15

Ser Leu Arg Leu Ser Cys Ala Val Ser Gly Ser Ser Val Ser Ser Asp
            20                  25                  30

Ala Met Gly Trp Tyr Arg Gln Ala Pro Gly Asn Gln Arg Ala Trp Val
        35                  40                  45

Ala Phe Ile Ser Gly Gly Thr Thr Thr Tyr Ala Asp Ser Val Lys
    50                  55                  60

Gly

```
                325                 330                 335
Lys Ser Leu Ser Leu Ser Pro Gly Gly Gly Gly Ser Gly Gly Gly
            340                 345                 350
Gly Ser Gln Ser Thr Ile Glu Glu Gln Ala Lys Thr Phe Leu Asp Lys
            355                 360                 365
Phe Asn His Glu Ala Glu Asp Leu Phe Tyr Gln Ser Ser Leu Ala Ser
    370                 375                 380
Trp Asn Tyr Asn Thr Asn Ile Thr Glu Glu Asn Val Gln Asn Met Asn
385                 390                 395                 400
Asn Ala Gly Asp Lys Trp Ser Ala Phe Leu Lys Glu Gln Ser Thr Leu
                405                 410                 415
Ala Gln Met Tyr Pro Leu Gln Glu Ile Gln Asn Leu Thr Val Lys Leu
            420                 425                 430
Gln Leu Gln Ala Leu Gln Gln Asn Gly Ser Ser Val Leu Ser Glu Asp
            435                 440                 445
Lys Ser Lys Arg Leu Asn Thr Ile Leu Asn Thr Met Ser Thr Ile Tyr
    450                 455                 460
Ser Thr Gly Lys Val Cys Asn Pro Asp Asn Pro Gln Glu Cys Leu Leu
465                 470                 475                 480
Leu Glu Pro Gly Leu Asn Glu Ile Met Ala Asn Ser Leu Asp Tyr Asn
                485                 490                 495
Glu Arg Leu Trp Ala Trp Glu Ser Trp Arg Ser Glu Val Gly Lys Gln
            500                 505                 510
Leu Arg Pro Leu Tyr Glu Glu Tyr Val Val Leu Lys Asn Glu Met Ala
            515                 520                 525
Arg Ala Asn His Tyr Glu Asp Tyr Gly Asp Tyr Trp Arg Gly Asp Tyr
    530                 535                 540
Glu Val Asn Gly Val Asp Gly Tyr Asp Tyr Ser Arg Gly Gln Leu Ile
545                 550                 555                 560
Glu Asp Val Glu His Thr Phe Glu Glu Ile Lys Pro Leu Tyr Glu His
                565                 570                 575
Leu His Ala Tyr Val Arg Ala Lys Leu Met Asn Ala Tyr Pro Ser Tyr
            580                 585                 590
Ile Ser Pro Ile Gly Cys Leu Pro Ala His Leu Leu Gly Asp Met Trp
            595                 600                 605
Gly Arg Phe Trp Thr Asn Leu Tyr Ser Leu Thr Val Pro Phe Gly Gln
    610                 615                 620
Lys Pro Asn Ile Asp Val Thr Asp Ala Met Val Asp Gln Ala Trp Asp
625                 630                 635                 640
Ala Gln Arg Ile Phe Lys Glu Ala Glu Lys Phe Phe Val Ser Val Gly
                645                 650                 655
Leu Pro Asn Met Thr Gln Gly Phe Trp Glu Asn Ser Met Leu Thr Asp
            660                 665                 670
Pro Gly Asn Val Gln Lys Ala Val Cys His Pro Thr Ala Trp Asp Leu
            675                 680                 685
Gly Lys Gly Asp Phe Arg Ile Leu Met Cys Thr Lys Val Thr Met Asp
            690                 695                 700
Asp Phe Leu Thr Ala His His Glu Met Gly His Ile Gln Tyr Asp Met
705                 710                 715                 720
Ala Tyr Ala Ala Gln Pro Phe Leu Leu Arg Asn Gly Ala Asn Glu Gly
                725                 730                 735
Phe His Glu Ala Val Gly Glu Ile Met Ser Leu Ser Ala Ala Thr Pro
            740                 745                 750
```

Lys His Leu Lys Ser Ile Gly Leu Leu Ser Pro Asp Phe Gln Glu Asp
                755                 760                 765

Asn Glu Thr Glu Ile Asn Phe Leu Leu Lys Gln Ala Leu Thr Ile Val
        770                 775                 780

Gly Thr Leu Pro Phe Thr Tyr Met Leu Glu Lys Trp Arg Trp Met Val
785                 790                 795                 800

Phe Lys Gly Glu Ile Pro Lys Asp Gln Trp Met Lys Lys Trp Trp Glu
                805                 810                 815

Met Lys Arg Glu Ile Val Gly Val Val Glu Pro Val Pro His Asp Glu
            820                 825                 830

Thr Tyr Cys Asp Pro Ala Ser Leu Phe His Val Ser Asn Asp Tyr Ser
            835                 840                 845

Phe Ile Arg Tyr Tyr Thr Arg Thr Leu Tyr Gln Phe Gln Phe Gln Glu
        850                 855                 860

Ala Leu Cys Gln Ala Ala Lys His Glu Gly Pro Leu His Lys Cys Asp
865                 870                 875                 880

Ile Ser Asn Ser Thr Glu Ala Gly Gln Lys Leu Phe Asn Met Leu Arg
                885                 890                 895

Leu Gly Lys Ser Glu Pro Trp Thr Leu Ala Leu Glu Asn Val Val Gly
            900                 905                 910

Ala Lys Asn Met Asn Val Arg Pro Leu Leu Asn Tyr Phe Glu Pro Leu
        915                 920                 925

Phe Thr Trp Leu Lys Asp Gln Asn Lys Asn Ser Phe Val Gly Trp Ser
930                 935                 940

Thr Asp Trp Ser Pro Tyr Ala Asp Gln Ser Ile Lys Val Arg Ile Ser
945                 950                 955                 960

Leu Lys Ser Ala Leu Gly Asp Lys Ala Tyr Glu Trp Asn Asp Asn Glu
                965                 970                 975

Met Tyr Leu Phe Arg Ser Ser Val Ala Tyr Ala Met Arg Gln Tyr Phe
            980                 985                 990

Leu Lys Val Lys Asn Gln Met Ile Leu Phe Gly Glu Glu Asp Val Arg
        995                 1000                1005

Val Ala Asn Leu Lys Pro Arg Ile Ser Phe Asn Phe Phe Val Thr
    1010                1015                1020

Ala Pro Lys Asn Val Ser Asp Ile Ile Pro Arg Thr Glu Val Glu
    1025                1030                1035

Lys Ala Ile Arg Met Ser Arg Ser Arg Ile Asn Asp Ala Phe Arg
    1040                1045                1050

Leu Asn Asp Asn Ser Leu Glu Phe Leu
    1055                1060

<210> SEQ ID NO 127
<211> LENGTH: 3231
<212> TYPE: DNA
<213> ORGANISM: Artificial Sequence
<220> FEATURE:
<223> OTHER INFORMATION: pIgR-VHH2-MSCD342-ACE2-18-725-Fc HC1 DNA

<400> SEQUENCE: 127
gaagtgcaag tagtggagtc tggaggtggt ttggtacagg ccggggggtc attgaagctg      60
gcttgcgctg ccccaggctt gaccttttca tcttacagga tgggttggtt caggcaggca     120
ccaggacagg aacgtgaatt tgttgctgcc attgactgga atggacgcgg aacatattat     180
aggtactatg cagatagcgt caagggccga agtacaatta gccgggacaa tgccaagaac     240

| | |
|---|---|
| accgtgtatc tccaaatgaa tagtttgaag cctgaagaca ccgctgtata ctactgtgct | 300 |
| gccacaacag ttttgactga cccccgcgtc cttaacgagt atgctacctg gggacagggg | 360 |
| actcaagtca ctgtgtcttc tggaggcgga gggagtggcg ggggaggctc tcaatccacc | 420 |
| atcgaggaac aggctaagac ctttctggac aagttcaacc acgaggccga ggacctgttc | 480 |
| taccagagca gcctggcttc ctggaactac aacacaaaca tcaccgagga gaacgtgcag | 540 |
| aacatgaaca acgctggcga caagtggtcc gcctttctca agagcagtc taccctggcc | 600 |
| cagatgtatc ctctgcaaga gatccagaat ctcaccgtga aactgcagct gcaggccctg | 660 |
| cagcagaacg ctcctctgt gctgtccgag gataagtcca gcggctcaa caccatcctg | 720 |
| aacaccatgt ctacaatcta ctccaccggc aaggtgtgca ccccgacaa ccctcaggag | 780 |
| tgcctgctgc tggaacctgg cctgaatgaa atcatggcta attctctgga ctacaacgag | 840 |
| cgcctgtggg cttgggagtc ttggcggtct gaagtgggca agcagctgag accactgtac | 900 |
| gaagagtacg tggtgctgaa gaacgagatg gctagagcca atcactacga ggactacggc | 960 |
| gactactggc ggggcgatta cgaggtgaac ggcgtggacg gctacgatta ctctcgcggc | 1020 |
| caactgatcg aggacgtcga gcacaccttc gaggaaatca agcccctgta tgaacatctg | 1080 |
| cacgcctacg tgagagccaa gctgatgaac gcctacccct tcctacatctc tcctatcgga | 1140 |
| tgtctgcctg ctcatctgct gggagatatg tggggcagat tctggaccaa cctgtactcc | 1200 |
| ctgaccgtgc ccttcggcca gaagccaaac atcgacgtga ccgatgctat ggtggaccag | 1260 |
| gcctgggacg cccagagaat cttcaaagaa gctgagaagt tcttcgtgtc tgttggactg | 1320 |
| cccaacatga cccagggctt ctgggagaac tccatgctga ccgaccccgg caacgtgcag | 1380 |
| aaagctgtgt gccatcctac cgcctgggat ctgggcaagg gcgacttcag aatcctgatg | 1440 |
| tgcaccaagg tgaccatgga cgacttcctg accgctcacc acgagatggg ccacatccag | 1500 |
| tacgacatgg cctacgctgc tcagccttc ctactgcgga acggagcaaa cgagggcttc | 1560 |
| catgaggccg tgggcgagat catgtccctg tctgctgcta cccctaagca cctgaagtct | 1620 |
| atcggcctgc tgagccctga tttccaggaa gataacgaga cagagatcaa cttcctgctg | 1680 |
| aaacaggccc tgaccatcgt gggcacactg cctttcacct acatgctgga aaagtggaga | 1740 |
| tggatggtgt tcaagggcga gatccctaag gaccagtgga tgaagaagtg gtgggaaatg | 1800 |
| aagagagaga tcgtgggcgt ggtggagccc gtgcctcacg acgaaacata ctgtgatcct | 1860 |
| gcctctctgt tccacgtgtc caacgactac tcttttatca gatactacac caggaccctg | 1920 |
| tatcagtttc agttccaaga agcgctgtgc caagccgcca agcacgaagg ccctctgcac | 1980 |
| aagtgcgaca tctccaattc cactgaagcc ggccagaagc tgttcaacat gctgagactg | 2040 |
| ggcaaatccg agccttggac cctggccctg gaaaatgtcg tgggcgccaa gaacatgaac | 2100 |
| gtgcggcctc tgctgaacta cttcgagcct ttgttcacct ggctgaagga ccagaacaag | 2160 |
| aactccttcg tcggctggtc caccgactgg tctccttacg ccgatcagtc catcaaggtg | 2220 |
| cggatctctc tgaagtctgc tctggggac aaggcctacg agtggaacga caatgagatg | 2280 |
| tacctgttcc ggtcctccgt ggcttacgcc atgcggcagt acttcctgaa agtgaagaac | 2340 |
| cagatgatac tgtttggtga agaggacgtg agagtggcca acctgaagcc tagaatcagc | 2400 |
| ttcaacttct tcgtaacagc tcctaagaat gtgtccgaca tcatcccag aaccgaagtg | 2460 |
| gaaaaggcca tccggatgtc cagaagccgg atcaacgacg cctttagact gaacgacaac | 2520 |
| agcctggagt tcctggagcc caaatctagc gacaaaactc acacatgtcc accgtgccca | 2580 |
| gcacctgaac tcctggggggg accgtcagtc ttcctcttcc ccccaaaacc caaggacacc | 2640 |

| | |
|---|---:|
| ctcatgatct cccggacccc tgaggtcaca tgcgtggtgg tggacgtgag ccacgaagac | 2700 |
| cctgaggtca agttcaactg gtacgtggac ggcgtggagg tgcataatgc caagacaaag | 2760 |
| ccgcgggagg agcagtacaa cagcacgtac cgtgtggtca gcgtcctcac cgtcctgcac | 2820 |
| caggactggc tgaatggcaa ggagtacaag tgcaaggtct ccaacaaagc cctcccagcc | 2880 |
| cccatcgaga aaaccatctc caaagccaaa gggcagcccc gagaaccaca ggtgtacacc | 2940 |
| ctgcccccat cccgggagga gatgaccaag aaccaggtca gcctgacctg cctggtcaaa | 3000 |
| ggcttctatc ccagcgacat cgccgtggag tgggagagca atgggcagcc ggagaacaac | 3060 |
| tacaagacca cgcctcccgt gctggactcc gacggctcct tcttcctcta cagcaagctc | 3120 |
| accgtggaca gtctagatg gcagcagggg aacgtcttct catgctccgt gatgcatgag | 3180 |
| gctctgcaca accactacac gcagaagagc ctctccctgt ctccgggtaa a | 3231 |

<210> SEQ ID NO 128
<211> LENGTH: 3228
<212> TYPE: DNA
<213> ORGANISM: Artificial Sequence
<220> FEATURE:
<223> OTHER INFORMATION: pIgR-VHH2-Fc-MSCD342-ACE2-18-725 HC1 DNA

<400> SEQUENCE: 128

| | |
|---|---:|
| gaagtgcaag tagtggagtc tggaggtggt ttggtacagg ccgggggtc attgaagctg | 60 |
| gcttgcgctg ccccaggctt gacctttttca tcttacagga tgggttggtt caggcaggca | 120 |
| ccaggacagg aacgtgaatt tgttgctgcc attgactgga atggacgcgg aacatattat | 180 |
| aggtactatg cagatagcgt caagggccga agtacaatta gccgggacaa tgccaagaac | 240 |
| accgtgtatc tccaaatgaa tagttttgaag cctgaagaca ccgctgtata ctactgtgct | 300 |
| gccacaacag ttttgactga ccccccgcgtc cttaacgagt atgctacctg gggacagggg | 360 |
| actcaagtca ctgtgtcttc tgagcccaaa tctagcgaca aaactcacac atgtccaccg | 420 |
| tgcccagcac ctgaactcct ggggggaccg tcagtcttcc tcttcccccc aaaacccaag | 480 |
| gacaccctca tgatctcccg gacccctgag gtcacatgcg tggtggtgga cgtgagccac | 540 |
| gaagaccctg aggtcaagtt caactggtac gtggacggcg tggaggtgca taatgccaag | 600 |
| acaaagccgc gggaggagca gtacaacagc acgtaccgtg tggtcagcgt cctcaccgtc | 660 |
| ctgcaccagg actggctgaa tggcaaggag tacaagtgca aggtctccaa caaagccctc | 720 |
| ccagccccca tcgagaaaac catctccaaa gccaaagggc agccccgaga accacaggtg | 780 |
| tacaccctgc cccatcccg ggaggagatg accaagaacc aggtcagcct gacctgcctg | 840 |
| gtcaaaggct tctatcccag cgacatcgcc gtggagtggg agagcaatgg gcagccggag | 900 |
| aacaactaca agaccacgcc tcccgtgctg gactccgacg gctccttctt cctctacagc | 960 |
| aagctcaccg tggacaagtc tagatggcag caggggaacg tcttctcatg ctccgtgatg | 1020 |
| catgaggctc tgcacaacca ctacacgcag aagagcctct ccctgtctcc gggtggaggc | 1080 |
| ggagggagtg gcgggggagg ctctcaatcc accatcgagg aacaggctaa gacctttctg | 1140 |
| gacaagttca accacgaggc cgaggacctg ttctaccaga gcagcctggc ttcctggaac | 1200 |
| tacaacacaa acatcaccga ggagaacgtg cagaacatga acaacgctgg cgacaagtgg | 1260 |
| tccgcctttc tcaaagagca gtctaccctg gcccagatgt atcctctgca agagatccag | 1320 |
| aatctcaccg tgaaactgca gctgcaggcc ctgcagcaga acggctcctc tgtgctgtcc | 1380 |
| gaggataagt ccaagcggct caacaccatc ctgaacacca tgtctacaat ctactccacc | 1440 |

```
ggcaaggtgt gcaaccccga caaccctcag gagtgcctgc tgctggaacc tggcctgaat      1500
gaaatcatgg ctaattctct ggactacaac gagcgcctgt gggcttggga gtcttggcgg      1560
tctgaagtgg gcaagcagct gagaccactg tacgaagagt acgtggtgct gaagaacgag      1620
atggctagag ccaatcacta cgaggactac ggcgactact ggcggggcga ttacgaggtg      1680
aacggcgtgg acggctacga ttactctcgc ggccaactga tcgaggacgt cgagcacacc      1740
ttcgaggaaa tcaagcccct gtatgaacat ctgcacgcct acgtgagagc caagctgatg      1800
aacgcctacc cttcctacat ctctcctatc ggatgtctgc ctgctcatct gctgggagat      1860
atgtggggca gattctggac caacctgtac tccctgaccg tgcccttcgg ccagaagcca      1920
aacatcgacg tgaccgatgc tatggtggac caggcctggg acgcccagag aatcttcaaa      1980
gaagctgaga agttcttcgt gtctgttgga ctgcccaaca tgacccaggg cttctgggag      2040
aactccatgc tgaccgaccc cggcaacgtg cagaaagctg tgtgccatcc taccgcctgg      2100
gatctgggca agggcgactt cagaatcctg atgtgcacca aggtgaccat ggacgacttc      2160
ctgaccgctc accacgagat gggccacatc cagtacgaca tggcctacgc tgctcagcct      2220
ttcctactgc ggaacggagc aaacgagggc ttccatgagg ccgtgggcga gatcatgtcc      2280
ctgtctgctg ctaccccta a gcacctgaag tctatcggcc tgctgagccc tgatttccag      2340
gaagataacg agacagagat caacttcctg ctgaaacagg ccctgaccat cgtgggcaca      2400
ctgccttcta cctacatgct ggaaaagtgg agatggatgg tgttcaaggg cgagatccct      2460
aaggaccagt ggatgaagaa gtggtgggaa atgaagagag atcgtgggc gtggtggag       2520 cccgtgcctc acgacgaaac atactgtgat cctgcctctc tgttccacgt gtccaacgac      2580
tactctttta tcagatacta caccaggacc ctgtatcagt ttcagttcca agaagcgctg      2640
tgccaagccg ccaagcacga aggccctctg cacaagtgcg acatctccaa ttccactgaa      2700
gccggccaga agctgttcaa catgctgaga ctgggcaaat ccgagccttg gaccctggcc      2760
ctggaaaatg tcgtgggcgc caagaacatg aacgtcgcc tctgctgaa ctacttcgag       2820 cctttgttca cctggctgaa ggaccagaac aagaactcct tcgtcggctg gtccaccgac      2880
tggtctcctt acgccgatca gtccatcaag gtgcggatct ctctgaagtc tgctctgggg      2940
gacaaggcct acgagtggaa cgacaatgag atgtacctgt tccggtcctc cgtggcttac      3000
gccatgcggc agtacttcct gaaagtgaag aaccagatga tactgtttgg tgaagaggac      3060
gtgagagtgg ccaacctgaa gcctagaatc agcttcaact tcttcgtaac agctcctaag      3120
aatgtgtccg acatcatccc cagaaccgaa gtggaaaagg ccatccggat gtccagaagc      3180
cggatcaacg acgcctttag actgaacgac aacagcctgg agttcctg              3228
```

<210> SEQ ID NO 129
<211> LENGTH: 2886
<212> TYPE: DNA
<213> ORGANISM: Artificial Sequence
<220> FEATURE:
<223> OTHER INFORMATION: pIgR-VHH2-Fc-MSCD342-ACE2-18-611 HC1 DNA

<400> SEQUENCE: 129

```
gaagtgcaag tagtggagtc tggaggtggt ttggtacagg ccgggggtc attgaagctg        60 gcttgcgctg ccccaggctt gacctttca tcttacagga tgggttggtt caggcaggca       120
ccaggacagg aacgtgaatt tgttgctgcc attgactgga atggacgcgg aacatattat      180
aggtactatg cagatagcgt caagggccga agtacaatta gccgggacaa tgccaagaac      240
accgtgtatc tccaaatgaa tagtttgaag cctgaagaca ccgctgtata ctactgtgct      300
```

```
gccacaacag ttttgactga cccccgcgtc cttaacgagt atgctacctg gggacagggg    360
actcaagtca ctgtgtcttc tgagcccaaa tctagcgaca aaactcacac atgtccaccg    420
tgcccagcac ctgaactcct gggggaccg tcagtcttcc tcttccccc aaaacccaag      480 gacaccctca tgatctcccg acccctgag gtcacatgcg tggtggtgga cgtgagccac     540
gaagaccctg aggtcaagtt caactggtac gtggacggcg tggaggtgca taatgccaag    600
acaaagccgc gggaggagca gtacaacagc acgtaccgtg tggtcagcgt cctcaccgtc    660
ctgcaccagg actggctgaa tggcaaggag tacaagtgca aggtctccaa caaagccctc    720
ccagccccca tcgagaaaac catctccaaa gccaagggc agccccgaga ccacaggtg      780 tacaccctgc cccatcccg ggaggagatg accaagaacc aggtcagcct gacctgcctg     840
gtcaaaggct tctatcccag cgacatcgcc gtggagtggg agagcaatgg gcagccggag    900
aacaactaca agaccacgcc tcccgtgctg gactccgacg gctccttctt cctctacagc    960
aagctcaccg tggacaagtc tagatggcag caggggaacg tcttctcatg ctccgtgatg   1020
catgaggctc tgcacaacca ctacacgcag aagagcctct ccctgtctcc gggtggaggc   1080
ggagggagtg gcgggggagg ctctcagtct acaatcgaag agcaggccaa gacctttctg   1140
gacaagttca accatgaagc cgaggacctg ttctaccagt ccagcctggc ctcttggaac   1200
tacaacacca atatcaccga ggaaaacgtg cagaacatga acaacgccgg cgacaagtgg   1260
tctgccttcc tcaaagaaca gtctacactg gctcagatgt accccttgca agagatccag   1320
aacctgacag tgaagctgca actgcaggct ctgcagcaga acggctcttc cgtgctatct   1380
gaggataagt ccagcgggct gaacaccatc ctgaacacaa tgtccaccat ctacagcacc   1440
ggcaaagtgt gcaaccctga taatcctcaa gagtgtctgc ttctggaacc cggcctgaac   1500
gagatcatgg ccaactccct ggattataac gagaggctgt gggcttggga gtcctggcgc   1560
agcgaggtgg aaaagcagct cagacctctg tacgaagagt acgtcgtgct gaagaacgag   1620
atggccagag ccaaccacta cgaggactac ggcgactact ggagaggcga ctatgaagtc   1680
aatggcgtag acggctacga ctactccaga ggccagctga tcgaggatgt ggagcacacc   1740
ttcgaggaga tcaagcctct gtacgaacat ctgcacgcct acgtgcgggc caagctgatg   1800
aacgcctacc cttcctacat ctcccctatc ggctgcctgc ctgcccatct gctgggtgat   1860
atgtggggca gattctggac caacctgtat tctctcaccg tgcccttggg ccagaaaccc   1920
aatatcgacg tgaccgacgc catggtcgat caggcctggg atgcccagag aatcttcaaa   1980
gaggctgaga agttcttcgt gtccgtggga ctgcctaaca tgacccaggg cttttgggaa   2040
aactccatgc tgaccgatcc tggcaacgtg cagaaggccg tgtgtcaccc taccgcttgg   2100
gatctgggca agggcgattt ccggatcctg atgtgcacca aggtgaccat ggacgacttc   2160
ctaaccgctc accacgagat gggccacatc cagtacgaca tggcttacgc cgctcagcct   2220
tttctgctgc ggaacggagc taatgaaggc ttccatgaag ccgtgggcga aatcatgtct   2280
ctgtccgccg ccaccctaa gcacctgaag tctatcggcc tgctgtctcc tgacttccag   2340
gaggacaacg agacagagat caacttcctg ctgaagcagg ccctgacaat cgtgggcacc   2400
ctgcccttca cctacatgct ggaaaagtgg agatggatgg tgttcaaggg cgaaatcccc   2460
aaggaccagt ggatgaaaaa gtggtgggag atgaagagag agattgttgg cgtggtggaa   2520
cctgtgcctc acgacgagac ctactgcgac cccgctagcc tgttccacgt gtccaacgac   2580
tactctttca tccggtacta caccagaacc ctgtaccagt ccagttccca ggaagctctg   2640
```

| | |
|---|---|
| tgccaggctg ccaaacacga aggccctctg cacaagtgcg acatctctaa cagcaccgag | 2700 |
| gccggacaaa agctgttcaa catgctgaga ctgggcaagt ccgagccttg gaccctggct | 2760 |
| ctggagaacg tggtgggagc taagaacatg aatgtgcggc cactgctcaa ctacttcgag | 2820 |
| cctctgttta cctggctgaa ggaccagaac aagaactcct tcgtgggctg gtccaccgac | 2880 |
| tggtcc | 2886 |

<210> SEQ ID NO 130
<211> LENGTH: 3189
<212> TYPE: DNA
<213> ORGANISM: Artificial Sequence
<220> FEATURE:
<223> OTHER INFORMATION: pIgR-VHH6-MSCD342-ACE2 18-725-Fc HC1 DNA

<400> SEQUENCE: 130

| | |
|---|---|
| gaggtgcagt tggtggagtc tggtggaggt ctggtccagg ctggaggatc tctcagactt | 60 |
| agttgcgccg tttcaggcag ttccgtatct agcgatgcaa tggggtggta tcggcaggca | 120 |
| ccagggaatc agcgtgcctg ggttgccttt atcagtggtg gcggcactac cacttatgcc | 180 |
| gattcagtaa agggaaggtt taccatatct agggataaca caaagaatac agtgtatttg | 240 |
| cacatgaact cactgaaacc agaagacact gccgtgtact attgcaatca tcctcttaca | 300 |
| agccgctggg gtcaaggcac acaggtgacc gtgtcttctg gaggcggagg gagtggcggg | 360 |
| ggaggctctc aatccaccat cgaggaacag gctaagacct ttctggacaa gttcaaccac | 420 |
| gaggccgagg acctgttcta ccagagcagc ctggcttcct ggaactacaa cacaaacatc | 480 |
| accgaggaga acgtgcagaa catgaacaac gctggcgaca gtggtccgc ctttctcaaa | 540 |
| gagcagtcta ccctggccca gatgtatcct ctgcaagaga tccagaatct caccgtgaaa | 600 |
| ctgcagctgc aggccctgca gcagaacggc tcctctgtgc tgtccgagga taagtccaag | 660 |
| cggctcaaca ccatcctgaa caccatgtct acaatctact ccaccggcaa ggtgtgcaac | 720 |
| cccgacaacc ctcaggagtg cctgctgctg gaacctggcc tgaatgaaat catggctaat | 780 |
| tctctggact acaacgagcg cctgtgggct tgggagtctt ggcggtctga agtgggcaag | 840 |
| cagctgagac cactgtacga agagtacgtg gtgctgaaga acgagatggc tagagccaat | 900 |
| cactacgagg actacggcga ctactggcgg ggcgattacg aggtgaacgg cgtggacggc | 960 |
| tacgattact ctcgcggcca actgatcgag gacgtcgagc acaccttcga ggaaatcaag | 1020 |
| cccctgtatg aacatctgca cgcctacgtg agagccaagc tgatgaacgc ctacccttcc | 1080 |
| tacatctctc ctatcggatg tctgcctgct catctgctgg agatatgtg gggcagattc | 1140 |
| tggaccaacc tgtactccct gaccgtgccc ttcggccaga gccaaacat cgacgtgacc | 1200 |
| gatgctatgg tggaccaggc ctgggacgcc cagagaatct tcaaagaagc tgagaagttc | 1260 |
| ttcgtgtctg ttggactgcc caacatgacc cagggcttct gggagaactc catgctgacc | 1320 |
| gaccccggca cgtgcagaa agctgtgtgc catcctaccg cctgggatct gggcaagggc | 1380 |
| gacttcagaa tcctgatgtg caccaaggtg accatggacg acttcctgac cgctcaccac | 1440 |
| gagatgggcc acatccagta cgacatggcc tacgctgctc agccttcct actgcggaac | 1500 |
| ggagcaaacg agggcttcca tgaggccgtg ggcgagatca tgtccctgtc tgctgctacc | 1560 |
| cctaagcacc tgaagtctat cggcctgctg agccctgatt ccaggaaga taacgagaca | 1620 |
| gagatcaact tcctgctgaa acaggccctg accatcgtgg gcacactgcc tttcacctac | 1680 |
| atgctggaaa agtggagatg gatggtgttc aagggcgaga tccctaagga ccagtggatg | 1740 |
| aagaagtggt gggaaatgaa gagagagatc gtgggcgtgg tggagcccgt gcctcacgac | 1800 |

-continued

```
gaaacatact gtgatcctgc ctctctgttc cacgtgtcca acgactactc ttttatcaga    1860
tactacacca ggaccctgta tcagtttcag ttccaagaag cgctgtgcca agccgccaag    1920
cacgaaggcc ctctgcacaa gtgcgacatc tccaattcca ctgaagccgg ccagaagctg    1980
ttcaacatgc tgagactggg caaatccgag ccttggaccc tggccctgga aaatgtcgtg    2040
ggcgccaaga acatgaacgt gcggcctctg ctgaactact cgagccttt gttcacctgg    2100
ctgaaggacc agaacaagaa ctccttcgtc ggctggtcca ccgactggtc tccttacgcc    2160
gatcagtcca tcaaggtgcg gatctctctg aagtctgctc tgggggacaa ggcctacgag    2220
tggaacgaca atgagatgta cctgttccgg tcctccgtgg cttacgccat gcggcagtac    2280
ttcctgaaag tgaagaacca gatgatactg tttggtgaag aggacgtgag agtggccaac    2340
ctgaagccta gaatcagctt caacttcttc gtaacagctc ctaagaatgt gtccgacatc    2400
atccccagaa ccgaagtgga aaaggccatc cggatgtcca agccggat caacgacgcc     2460
tttagactga cgacaacag cctggagttc ctggagccca aatctagcga caaaactcac    2520
acatgtccac cgtgcccagc acctgaactc ctgggggac cgtcagtctt cctcttcccc    2580
ccaaaaccca aggacaccct catgatctcc cggacccctg aggtcacatg cgtggtggtg    2640
gacgtgagcc acgaagaccc tgaggtcaag ttcaactggt acgtggacgg cgtggaggtg    2700
cataatgcca agacaaagcc gcgggaggag cagtacaaca gcacgtaccg tgtggtcagc    2760
gtcctcaccg tcctgcacca ggactggctg aatggcaagg agtacaagtg caaggtctcc    2820
aacaaagccc tcccagcccc catcgagaaa accatctcca aagccaaagg cagccccga    2880
gaaccacagg tgtacaccct gccccatcc cgggaggaga tgaccaagaa ccaggtcagc    2940
ctgacctgcc tggtcaaagg cttctatccc agcgacatcg ccgtggagtg ggagagcaat    3000
gggcagccgg agaacaacta caagaccacg cctcccgtgc tggactccga cggctccttc    3060
ttcctctaca gcaagctcac cgtggacaag tctagatggc agcaggggaa cgtcttctca    3120
tgctccgtga tgcatgaggc tctgcacaac cactacacgc agaagagcct ctccctgtct    3180
ccgggtaaa                                                           3189
```

<210> SEQ ID NO 131
<211> LENGTH: 3186
<212> TYPE: DNA
<213> ORGANISM: Artificial Sequence
<220> FEATURE:
<223> OTHER INFORMATION: pIgR-VHH6-Fc-MSCD342-ACE2 18-725 HC1 DNA

<400> SEQUENCE: 131

```
gaggtgcagt tggtggagtc tggtggaggt ctggtccagg ctggaggatc tctcagactt      60
agttgcgccg tttcaggcag ttccgtatct agcgatgcaa tgggtggta tcggcaggca     120
ccagggaatc agcgtgcctg ggttgccttt atcagtggtg gcggcactac cacttatgcc     180
gattcagtaa agggaaggtt taccatatct agggataaca caagaatac agtgtatttg     240
cacatgaact cactgaaacc agaagacact gccgtgtact attgcaatca tcctcttaca     300
agccgctggg gtcaaggcac acaggtgacc gtgtcttctg agcccaaatc tagcgacaaa     360
actcacacat gtccaccgtg cccagcacct gaactcctgg gggaccgtc agtcttcctc     420
ttccccccaa aacccaagga caccctcatg atctcccgga cccctgaggt cacatgcgtg     480
gtggtggacg tgagccacga agaccctgag gtcaagttca actggtacgt ggacggcgtg     540
gaggtgcata atgccaagac aaagccgcgg gaggagcagt acaacagcac gtaccgtgtg     600
```

```
gtcagcgtcc tcaccgtcct gcaccaggac tggctgaatg gcaaggagta caagtgcaag    660
gtctccaaca aagccctccc agccccatc gagaaaacca tctccaaagc caagggcag      720 ccccgagaac cacaggtgta caccctgccc ccatcccggg aggagatgac caagaaccag    780
gtcagcctga cctgcctggt caaaggcttc tatcccagcg acatcgccgt ggagtgggag    840
agcaatgggc agccggagaa caactacaag accacgcctc ccgtgctgga ctccgacggc    900
tccttcttcc tctacagcaa gctcaccgtg gacaagtcta gatggcagca ggggaacgtc    960
ttctcatgct ccgtgatgca tgaggctctg cacaaccact acacgcagaa gagcctctcc    1020
ctgtctccgg gtggaggcgg agggagtggc gggggaggct ctcaatccac catcgaggaa    1080
caggctaaga cctttctgga caagttcaac cacgaggccg aggacctgtt ctaccagagc    1140
agcctggctt cctggaacta aacacaaac atcaccgagg agaacgtgca gaacatgaac     1200
aacgctggcg acaagtggtc cgcctttctc aaagagcagt ctaccctggc ccagatgtat    1260
cctctgcaag agatccagaa tctcaccgtg aaactgcagc tgcaggccct gcagcagaac    1320
ggctcctctg tgctgtccga ggataagtcc aagcggctca acaccatcct gaacaccatg    1380
tctacaatct actccaccgg caaggtgtgc aaccccgaca accctcagga gtgcctgctg    1440
ctggaacctg gcctgaatga aatcatggct aattctctgg actacaacga cgcctgtgg    1500 gcttgggagt cttggcggtc tgaagtgggc aagcagctga ccactgta cgaagagtac     1560 gtggtgctga gaacgagat ggctagagcc aatcactacg aggactacgg cgactactgg     1620
cggggcgatt acgaggtgaa cggcgtggac ggctacgatt actctcgcgg ccaactgatc    1680
gaggacgtcg agcacacctt cgaggaaatc aagcccctgt atgaacatct gcacgcctac    1740
gtgagagcca agctgatgaa cgcctaccct tcctacatct ctcctatcgg atgtctgcct    1800
gctcatctgc tgggagatat gtggggcaga ttctggacca acctgtactc cctgaccgtg    1860
cccttcggcc agaagccaaa catcgacgtg accgatgcta tggtggacca ggcctgggac    1920
gcccagagaa tcttcaaaga agctgagaag ttcttcgtgt ctgttggact gcccaacatg    1980
acccagggct tctgggagaa ctccatgctg accgaccccg gcaacgtgca gaaagctgtg    2040
tgccatccta ccgcctggga tctgggcaag ggcgacttca gaatcctgat gtgcaccaag    2100
gtgaccatgg acgacttcct gaccgctcac cacgagatgg ccacatcca gtacgacatg    2160 gcctacgctg ctcagccttt cctactgcgg aacggagcaa acgagggctt ccatgaggcc    2220
gtgggcgaga tcatgtccct gtctgctgct accccctaagc acctgaagtc tatcggcctg    2280
ctgagccctg atttccagga agataacgag acagagatca acttcctgct gaaacaggcc    2340
ctgaccatcg tgggcacact gcctttcacc tacatgctgg aaaagtggag atggatggtg    2400
ttcaagggcg agatccctaa ggaccagtgg atgaagaagt ggtgggaaat gaagagagag    2460
atcgtgggcg tggtggagcc cgtgcctcac gacgaaacat actgtgatcc tgcctctctg    2520
ttccacgtgt ccaacgacta ctctttatc agatactaca ccaggaccct gtatcagttt    2580
cagttccaag aagcgctgtg ccaagccgcc aagcacgaag ccctctgca caagtgcgac    2640 atctccaatt ccactgaagc cggccagaag ctgttcaaca tgctgagact gggcaaatcc    2700
gagccttgga ccctggccct ggaaaatgtc gtgggcgcca gaacatgaa cgtgcggcct    2760 ctgctgaact acttcgagcc tttgttcacc tggctgaagg accagaacaa gaactccttc    2820
gtcggctggt ccaccgactg gtctccttac gccgatcagt ccatcaaggt gcggatctct    2880
ctgaagtctg ctctggggga caaggcctac gagtggaacg acaatgagat gtacctgttc    2940
cggtcctccg tggcttacgc catgcggcag tacttcctga aagtgaagaa ccagatgata    3000
```

```
ctgtttggtg aagaggacgt gagagtggcc aacctgaagc ctagaatcag cttcaacttc    3060
ttcgtaacag ctcctaagaa tgtgtccgac atcatcccca gaaccgaagt ggaaaaggcc    3120
atccggatgt ccagaagccg atcaacgac gcctttagac tgaacgacaa cagcctggag     3180
ttcctg                                                                3186
```

<210> SEQ ID NO 132
<211> LENGTH: 195
<212> TYPE: PRT
<213> ORGANISM: Artificial Sequence
<220> FEATURE:
<223> OTHER INFORMATION: SARS-CoV-2 RBD

<400> SEQUENCE: 132

```
Thr Asn Leu Cys Pro Phe Gly Glu Val Phe Asn Ala Thr Arg Phe Ala
1               5                   10                  15

Ser Val Tyr Ala Trp Asn Arg Lys Arg Ile Ser Asn Cys Val Ala Asp
            20                  25                  30

Tyr Ser Val Leu Tyr Asn Ser Ala Ser Phe Ser Thr Phe Lys Cys Tyr
        35                  40                  45

Gly Val Ser Pro Thr Lys Leu Asn Asp Leu Cys Phe Thr Asn Val Tyr
    50                  55                  60

Ala Asp Ser Phe Val Ile Arg Gly Asp Glu Val Arg Gln Ile Ala Pro
65                  70                  75                  80

Gly Gln Thr Gly Lys Ile Ala Asp Tyr Asn Tyr Lys Leu Pro Asp Asp
                85                  90                  95

Phe Thr Gly Cys Val Ile Ala Trp Asn Ser Asn Asn Leu Asp Ser Lys
            100                 105                 110

Val Gly Gly Asn Tyr Asn Tyr Leu Tyr Arg Leu Phe Arg Lys Ser Asn
        115                 120                 125

Leu Lys Pro Phe Glu Arg Asp Ile Ser Thr Glu Ile Tyr Gln Ala Gly
    130                 135                 140

Ser Thr Pro Cys Asn Gly Val Glu Gly Phe Asn Cys Tyr Phe Pro Leu
145                 150                 155                 160

Gln Ser Tyr Gly Phe Gln Pro Thr Asn Gly Val Gly Tyr Gln Pro Tyr
                165                 170                 175

Arg Val Val Val Leu Ser Phe Glu Leu Leu His Ala Pro Ala Thr Val
            180                 185                 190

Cys Gly Pro
        195
```

<210> SEQ ID NO 133
<211> LENGTH: 194
<212> TYPE: PRT
<213> ORGANISM: Artificial Sequence
<220> FEATURE:
<223> OTHER INFORMATION: SARS-CoV RBD

<400> SEQUENCE: 133

```
Thr Asn Leu Cys Pro Phe Gly Glu Val Phe Asn Ala Thr Lys Phe Pro
1               5                   10                  15

Ser Val Tyr Ala Trp Glu Arg Lys Lys Ile Ser Asn Cys Val Ala Asp
            20                  25                  30

Tyr Ser Val Leu Tyr Asn Ser Thr Phe Phe Ser Thr Phe Lys Cys Tyr
        35                  40                  45

Gly Val Ser Ala Thr Lys Leu Asn Asp Leu Cys Phe Ser Asn Val Tyr
    50                  55                  60
```

```
Ala Asp Ser Phe Val Val Lys Gly Asp Asp Val Arg Gln Ile Ala Pro
 65                  70                  75                  80

Gly Gln Thr Gly Val Ile Ala Asp Tyr Asn Tyr Lys Leu Pro Asp Asp
                 85                  90                  95

Phe Met Gly Cys Val Leu Ala Trp Asn Thr Arg Asn Ile Asp Ala Thr
            100                 105                 110

Ser Thr Gly Asn Tyr Asn Tyr Lys Tyr Arg Tyr Leu Arg His Gly Lys
        115                 120                 125

Leu Arg Pro Phe Glu Arg Asp Ile Ser Asn Val Pro Phe Ser Pro Asp
130                 135                 140

Gly Lys Pro Cys Thr Pro Pro Ala Leu Asn Cys Tyr Trp Pro Leu Asn
145                 150                 155                 160

Asp Tyr Gly Phe Tyr Thr Thr Thr Gly Ile Gly Tyr Gln Pro Tyr Arg
                165                 170                 175

Val Val Val Leu Ser Phe Glu Leu Leu Asn Ala Pro Ala Thr Val Cys
            180                 185                 190

Gly Pro

<210> SEQ ID NO 134
<211> LENGTH: 723
<212> TYPE: PRT
<213> ORGANISM: Homo sapiens
<220> FEATURE:
<223> OTHER INFORMATION: Human ACE2 Extra cellular Domain

<400> SEQUENCE: 134

Gln Ser Thr Ile Glu Glu Gln Ala Lys Thr Phe Leu Asp Lys Phe Asn
  1               5                  10                  15

His Glu Ala Glu Asp Leu Phe Tyr Gln Ser Ser Leu Ala Ser Trp Asn
             20                  25                  30

Tyr Asn Thr Asn Ile Thr Glu Glu Asn Val Gln Asn Met Asn Asn Ala
         35                  40                  45

Gly Asp Lys Trp Ser Ala Phe Leu Lys Glu Gln Ser Thr Leu Ala Gln
 50                  55                  60

Met Tyr Pro Leu Gln Glu Ile Gln Asn Leu Thr Val Lys Leu Gln Leu
 65                  70                  75                  80

Gln Ala Leu Gln Gln Asn Gly Ser Ser Val Leu Ser Glu Asp Lys Ser
                 85                  90                  95

Lys Arg Leu Asn Thr Ile Leu Asn Thr Met Ser Thr Ile Tyr Ser Thr
            100                 105                 110

Gly Lys Val Cys Asn Pro Asp Asn Pro Gln Glu Cys Leu Leu Leu Glu
        115                 120                 125

Pro Gly Leu Asn Glu Ile Met Ala Asn Ser Leu Asp Tyr Asn Glu Arg
130                 135                 140

Leu Trp Ala Trp Glu Ser Trp Arg Ser Glu Val Gly Lys Gln Leu Arg
145                 150                 155                 160

Pro Leu Tyr Glu Glu Tyr Val Val Leu Lys Asn Glu Met Ala Arg Ala
                165                 170                 175

Asn His Tyr Glu Asp Tyr Gly Asp Tyr Trp Arg Gly Asp Tyr Glu Val
            180                 185                 190

Asn Gly Val Asp Gly Tyr Asp Tyr Ser Arg Gly Gln Leu Ile Glu Asp
        195                 200                 205

Val Glu His Thr Phe Glu Glu Ile Lys Pro Leu Tyr Glu His Leu His
    210                 215                 220
```

```
Ala Tyr Val Arg Ala Lys Leu Met Asn Ala Tyr Pro Ser Tyr Ile Ser
225                 230                 235                 240

Pro Ile Gly Cys Leu Pro Ala His Leu Leu Gly Asp Met Trp Gly Arg
            245                 250                 255

Phe Trp Thr Asn Leu Tyr Ser Leu Thr Val Pro Phe Gly Gln Lys Pro
        260                 265                 270

Asn Ile Asp Val Thr Asp Ala Met Val Asp Gln Ala Trp Asp Ala Gln
    275                 280                 285

Arg Ile Phe Lys Glu Ala Glu Lys Phe Val Ser Val Gly Leu Pro
290                 295                 300

Asn Met Thr Gln Gly Phe Trp Glu Asn Ser Met Leu Thr Asp Pro Gly
305                 310                 315                 320

Asn Val Gln Lys Ala Val Cys His Pro Thr Ala Trp Asp Leu Gly Lys
            325                 330                 335

Gly Asp Phe Arg Ile Leu Met Cys Thr Lys Val Thr Met Asp Asp Phe
        340                 345                 350

Leu Thr Ala His His Glu Met Gly His Ile Gln Tyr Asp Met Ala Tyr
    355                 360                 365

Ala Ala Gln Pro Phe Leu Leu Arg Asn Gly Ala Asn Glu Gly Phe His
370                 375                 380

Glu Ala Val Gly Glu Ile Met Ser Leu Ser Ala Ala Thr Pro Lys His
385                 390                 395                 400

Leu Lys Ser Ile Gly Leu Leu Ser Pro Asp Phe Gln Glu Asp Asn Glu
            405                 410                 415

Thr Glu Ile Asn Phe Leu Leu Lys Gln Ala Leu Thr Ile Val Gly Thr
        420                 425                 430

Leu Pro Phe Thr Tyr Met Leu Glu Lys Trp Arg Trp Met Val Phe Lys
    435                 440                 445

Gly Glu Ile Pro Lys Asp Gln Trp Met Lys Lys Trp Trp Glu Met Lys
450                 455                 460

Arg Glu Ile Val Gly Val Val Glu Pro Val Pro His Asp Glu Thr Tyr
465                 470                 475                 480

Cys Asp Pro Ala Ser Leu Phe His Val Ser Asn Asp Tyr Ser Phe Ile
            485                 490                 495

Arg Tyr Tyr Thr Arg Thr Leu Tyr Gln Phe Gln Phe Gln Glu Ala Leu
        500                 505                 510

Cys Gln Ala Ala Lys His Glu Gly Pro Leu His Lys Cys Asp Ile Ser
    515                 520                 525

Asn Ser Thr Glu Ala Gly Gln Lys Leu Phe Asn Met Leu Arg Leu Gly
530                 535                 540

Lys Ser Glu Pro Trp Thr Leu Ala Leu Glu Asn Val Val Gly Ala Lys
545                 550                 555                 560

Asn Met Asn Val Arg Pro Leu Leu Asn Tyr Phe Glu Pro Leu Phe Thr
            565                 570                 575

Trp Leu Lys Asp Gln Asn Lys Asn Ser Phe Val Gly Ser Thr Asp
        580                 585                 590

Trp Ser Pro Tyr Ala Asp Gln Ser Ile Lys Val Arg Ile Ser Leu Lys
    595                 600                 605

Ser Ala Leu Gly Asp Lys Ala Tyr Glu Trp Asn Asp Asn Glu Met Tyr
610                 615                 620

Leu Phe Arg Ser Ser Val Ala Tyr Ala Met Arg Gln Tyr Phe Leu Lys
625                 630                 635                 640

Val Lys Asn Gln Met Ile Leu Phe Gly Glu Glu Asp Val Arg Val Ala
```

```
                    645                 650                 655
Asn Leu Lys Pro Arg Ile Ser Phe Asn Phe Val Thr Ala Pro Lys
            660                 665                 670

Asn Val Ser Asp Ile Ile Pro Arg Thr Glu Val Glu Lys Ala Ile Arg
        675                 680                 685

Met Ser Arg Ser Arg Ile Asn Asp Ala Phe Arg Leu Asn Asp Asn Ser
    690                 695                 700

Leu Glu Phe Leu Gly Ile Gln Pro Thr Leu Gly Pro Pro Asn Gln Pro
705                 710                 715                 720

Pro Val Ser

<210> SEQ ID NO 135
<211> LENGTH: 10
<212> TYPE: PRT
<213> ORGANISM: Artificial Sequence
<220> FEATURE:
<223> OTHER INFORMATION: SAD-S35H CDR1 (AbM)

<400> SEQUENCE: 135

Gly Ile Thr Val Ser Ser Asn Tyr Met Ser
1               5                   10

<210> SEQ ID NO 136
<211> LENGTH: 9
<212> TYPE: PRT
<213> ORGANISM: Artificial Sequence
<220> FEATURE:
<223> OTHER INFORMATION: SAD-S35H CDR2 (AbM)

<400> SEQUENCE: 136

Val Ile Tyr Ser Gly Gly Ser Thr Tyr
1               5

<210> SEQ ID NO 137
<211> LENGTH: 10
<212> TYPE: PRT
<213> ORGANISM: Artificial Sequence
<220> FEATURE:
<223> OTHER INFORMATION: SAD-S35H CDR3 (AbM)

<400> SEQUENCE: 137

Asp Leu Gln Glu Arg Gly Gly Met Asp Val
1               5                   10

<210> SEQ ID NO 138
<211> LENGTH: 5
<212> TYPE: PRT
<213> ORGANISM: Artificial Sequence
<220> FEATURE:
<223> OTHER INFORMATION: SAD-S35H CDR1 (Kabat)

<400> SEQUENCE: 138

Ser Asn Tyr Met Ser
1               5

<210> SEQ ID NO 139
<211> LENGTH: 16
<212> TYPE: PRT
<213> ORGANISM: Artificial Sequence
<220> FEATURE:
<223> OTHER INFORMATION: SAD-S35H CDR2 (Kabat)

<400> SEQUENCE: 139

Val Ile Tyr Ser Gly Gly Ser Thr Tyr Tyr Ala Asp Ser Val Lys Gly
```

```
<210> SEQ ID NO 140
<211> LENGTH: 10
<212> TYPE: PRT
<213> ORGANISM: Artificial Sequence
<220> FEATURE:
<223> OTHER INFORMATION: SAD-S35H CDR3 (Kabat)

<400> SEQUENCE: 140

Asp Leu Gln Glu Arg Gly Gly Met Asp Val
1               5                   10

<210> SEQ ID NO 141
<211> LENGTH: 7
<212> TYPE: PRT
<213> ORGANISM: Artificial Sequence
<220> FEATURE:
<223> OTHER INFORMATION: SAD-S35H CDR1 (Chothia)

<400> SEQUENCE: 141

Gly Ile Thr Val Ser Ser Asn
1               5

<210> SEQ ID NO 142
<211> LENGTH: 5
<212> TYPE: PRT
<213> ORGANISM: Artificial Sequence
<220> FEATURE:
<223> OTHER INFORMATION: SAD-S35H CDR2 (Chothia)

<400> SEQUENCE: 142

Tyr Ser Gly Gly Ser
1               5

<210> SEQ ID NO 143
<211> LENGTH: 9
<212> TYPE: PRT
<213> ORGANISM: Artificial Sequence
<220> FEATURE:
<223> OTHER INFORMATION: SAD-S35H CDR3 (Chothia)

<400> SEQUENCE: 143

Asp Leu Gln Glu Arg Gly Gly Met Asp
1               5

<210> SEQ ID NO 144
<211> LENGTH: 8
<212> TYPE: PRT
<213> ORGANISM: Artificial Sequence
<220> FEATURE:
<223> OTHER INFORMATION: SAD-S35H CDR1 (IMGT)

<400> SEQUENCE: 144

Gly Ile Thr Val Ser Ser Asn Tyr
1               5

<210> SEQ ID NO 145
<211> LENGTH: 7
<212> TYPE: PRT
<213> ORGANISM: Artificial Sequence
<220> FEATURE:
<223> OTHER INFORMATION: SAD-S35H CDR2 (IMGT)

<400> SEQUENCE: 145

Ile Tyr Ser Gly Gly Ser Thr
1               5
```

<210> SEQ ID NO 146
<211> LENGTH: 12
<212> TYPE: PRT
<213> ORGANISM: Artificial Sequence
<220> FEATURE:
<223> OTHER INFORMATION: SAD-S35H CDR3 (IMGT)

<400> SEQUENCE: 146

Ala Arg Asp Leu Gln Glu Arg Gly Gly Met Asp Val
1               5                   10

<210> SEQ ID NO 147
<211> LENGTH: 6
<212> TYPE: PRT
<213> ORGANISM: Artificial Sequence
<220> FEATURE:
<223> OTHER INFORMATION: SAD-S35H CDR1 (Contact)

<400> SEQUENCE: 147

Ser Ser Asn Tyr Met Ser
1               5

<210> SEQ ID NO 148
<211> LENGTH: 12
<212> TYPE: PRT
<213> ORGANISM: Artificial Sequence
<220> FEATURE:
<223> OTHER INFORMATION: SAD-S35H CDR2 (Contact)

<400> SEQUENCE: 148

Trp Val Ser Val Ile Tyr Ser Gly Gly Ser Thr Tyr
1               5                   10

<210> SEQ ID NO 149
<211> LENGTH: 11
<212> TYPE: PRT
<213> ORGANISM: Artificial Sequence
<220> FEATURE:
<223> OTHER INFORMATION: SAD-S35H CDR3 (Contact)

<400> SEQUENCE: 149

Ala Arg Asp Leu Gln Glu Arg Gly Gly Met Asp
1               5                   10

<210> SEQ ID NO 150
<211> LENGTH: 12
<212> TYPE: PRT
<213> ORGANISM: Artificial Sequence
<220> FEATURE:
<223> OTHER INFORMATION: SAD-S35L CDR1 (AbM)

<400> SEQUENCE: 150

Gly Ala Ser Gln Ser Val Ser Ser Ser Tyr Leu Ala
1               5                   10

<210> SEQ ID NO 151
<211> LENGTH: 7
<212> TYPE: PRT
<213> ORGANISM: Artificial Sequence
<220> FEATURE:
<223> OTHER INFORMATION: SAD-S35L CDR2 (AbM)

<400> SEQUENCE: 151

Asp Ala Ser Ser Arg Ala Thr
1               5

```
<210> SEQ ID NO 152
<211> LENGTH: 9
<212> TYPE: PRT
<213> ORGANISM: Artificial Sequence
<220> FEATURE:
<223> OTHER INFORMATION: SAD-S35L CDR3 (AbM)

<400> SEQUENCE: 152

Gln Gln Tyr Gly Ser Ser Pro Leu Thr
1               5

<210> SEQ ID NO 153
<211> LENGTH: 12
<212> TYPE: PRT
<213> ORGANISM: Artificial Sequence
<220> FEATURE:
<223> OTHER INFORMATION: SAD-S35L CDR1 (Kabat)

<400> SEQUENCE: 153

Gly Ala Ser Gln Ser Val Ser Ser Ser Tyr Leu Ala
1               5                   10

<210> SEQ ID NO 154
<211> LENGTH: 7
<212> TYPE: PRT
<213> ORGANISM: Artificial Sequence
<220> FEATURE:
<223> OTHER INFORMATION: SAD-S35L CDR2 (Kabat)

<400> SEQUENCE: 154

Asp Ala Ser Ser Arg Ala Thr
1               5

<210> SEQ ID NO 155
<211> LENGTH: 9
<212> TYPE: PRT
<213> ORGANISM: Artificial Sequence
<220> FEATURE:
<223> OTHER INFORMATION: SAD-S35L CDR3 (Kabat)

<400> SEQUENCE: 155

Gln Gln Tyr Gly Ser Ser Pro Leu Thr
1               5

<210> SEQ ID NO 156
<211> LENGTH: 8
<212> TYPE: PRT
<213> ORGANISM: Artificial Sequence
<220> FEATURE:
<223> OTHER INFORMATION: SAD-S35L CDR1 (Chothia)

<400> SEQUENCE: 156

Ser Gln Ser Val Ser Ser Ser Tyr
1               5

<210> SEQ ID NO 157
<211> LENGTH: 3
<212> TYPE: PRT
<213> ORGANISM: Artificial Sequence
<220> FEATURE:
<223> OTHER INFORMATION: SAD-S35L CDR2 (Chothia)

<400> SEQUENCE: 157

Asp Ala Ser
1
```

```
<210> SEQ ID NO 158
<211> LENGTH: 6
<212> TYPE: PRT
<213> ORGANISM: Artificial Sequence
<220> FEATURE:
<223> OTHER INFORMATION: SAD-S35L CDR3 (Chothia)

<400> SEQUENCE: 158

Tyr Gly Ser Ser Pro Leu
1               5

<210> SEQ ID NO 159
<211> LENGTH: 7
<212> TYPE: PRT
<213> ORGANISM: Artificial Sequence
<220> FEATURE:
<223> OTHER INFORMATION: SAD-S35L CDR1 (IMGT)

<400> SEQUENCE: 159

Gln Ser Val Ser Ser Ser Tyr
1               5

<210> SEQ ID NO 160
<211> LENGTH: 3
<212> TYPE: PRT
<213> ORGANISM: Artificial Sequence
<220> FEATURE:
<223> OTHER INFORMATION: SAD-S35L CDR2 (IMGT)

<400> SEQUENCE: 160

Asp Ala Ser
1

<210> SEQ ID NO 161
<211> LENGTH: 9
<212> TYPE: PRT
<213> ORGANISM: Artificial Sequence
<220> FEATURE:
<223> OTHER INFORMATION: SAD-S35L CDR3 (IMGT)

<400> SEQUENCE: 161

Gln Gln Tyr Gly Ser Ser Pro Leu Thr
1               5

<210> SEQ ID NO 162
<211> LENGTH: 8
<212> TYPE: PRT
<213> ORGANISM: Artificial Sequence
<220> FEATURE:
<223> OTHER INFORMATION: SAD-S35L CDR1 (Contact)

<400> SEQUENCE: 162

Ser Ser Ser Tyr Leu Ala Trp Tyr
1               5

<210> SEQ ID NO 163
<211> LENGTH: 10
<212> TYPE: PRT
<213> ORGANISM: Artificial Sequence
<220> FEATURE:
<223> OTHER INFORMATION: SAD-S35L CDR2 (Contact)

<400> SEQUENCE: 163

Leu Leu Ile Tyr Asp Ala Ser Ser Arg Ala
1               5                   10

<210> SEQ ID NO 164
```

```
<211> LENGTH: 8
<212> TYPE: PRT
<213> ORGANISM: Artificial Sequence
<220> FEATURE:
<223> OTHER INFORMATION: SAD-S35L CDR3 (Contact)

<400> SEQUENCE: 164

Gln Gln Tyr Gly Ser Ser Pro Leu
1               5

<210> SEQ ID NO 165
<211> LENGTH: 963
<212> TYPE: PRT
<213> ORGANISM: Artificial Sequence
<220> FEATURE:
<223> OTHER INFORMATION: pIgR-VHH2-MSCD342-ACE2-18-611-Fc HC1 AA

<400> SEQUENCE: 165

Glu Val Gln Val Val Glu Ser Gly Gly Gly Leu Val Gln Ala Gly Gly
1               5                   10                  15

Ser Leu Lys Leu Ala Cys Ala Ala Pro Gly Leu Thr Phe Ser Ser Tyr
            20                  25                  30

Arg Met Gly Trp Phe Arg Gln Ala Pro Gly Gln Glu Arg Glu Phe Val
        35                  40                  45

Ala Ala Ile Asp Trp Asn Gly Arg Gly Thr Tyr Tyr Arg Tyr Tyr Ala
    50                  55                  60

Asp Ser Val Lys Gly Arg Ser Thr Ile Ser Arg Asp Asn Ala Lys Asn
65                  70                  75                  80

Thr Val Tyr Leu Gln Met Asn Ser Leu Lys Pro Glu Asp Thr Ala Val
                85                  90                  95

Tyr Tyr Cys Ala Ala Thr Thr Val Leu Thr Asp Pro Arg Val Leu Asn
            100                 105                 110

Glu Tyr Ala Thr Trp Gly Gln Gly Thr Gln Val Thr Val Ser Ser Gly
        115                 120                 125

Gly Gly Gly Ser Gly Gly Gly Ser Gln Ser Thr Ile Glu Glu Gln
    130                 135                 140

Ala Lys Thr Phe Leu Asp Lys Phe Asn His Glu Ala Glu Asp Leu Phe
145                 150                 155                 160

Tyr Gln Ser Ser Leu Ala Ser Trp Asn Tyr Asn Thr Asn Ile Thr Glu
                165                 170                 175

Glu Asn Val Gln Asn Met Asn Asn Ala Gly Asp Lys Trp Ser Ala Phe
            180                 185                 190

Leu Lys Glu Gln Ser Thr Leu Ala Gln Met Tyr Pro Leu Gln Glu Ile
        195                 200                 205

Gln Asn Leu Thr Val Lys Leu Gln Leu Gln Ala Leu Gln Gln Asn Gly
    210                 215                 220

Ser Ser Val Leu Ser Glu Asp Lys Ser Lys Arg Leu Asn Thr Ile Leu
225                 230                 235                 240

Asn Thr Met Ser Thr Ile Tyr Ser Thr Gly Lys Val Cys Asn Pro Asp
                245                 250                 255

Asn Pro Gln Glu Cys Leu Leu Leu Glu Pro Gly Leu Asn Glu Ile Met
            260                 265                 270

Ala Asn Ser Leu Asp Tyr Asn Glu Arg Leu Trp Ala Trp Glu Ser Trp
        275                 280                 285

Arg Ser Glu Val Gly Lys Gln Leu Arg Pro Leu Tyr Glu Glu Tyr Val
    290                 295                 300

Val Leu Lys Asn Glu Met Ala Arg Ala Asn His Tyr Glu Asp Tyr Gly
```

```
                305                 310                 315                 320
Asp Tyr Trp Arg Gly Asp Tyr Glu Val Asn Gly Val Asp Gly Tyr Asp
                    325                 330                 335
Tyr Ser Arg Gly Gln Leu Ile Glu Asp Val Glu His Thr Phe Glu Glu
                    340                 345                 350
Ile Lys Pro Leu Tyr Glu His Leu His Ala Tyr Val Arg Ala Lys Leu
                    355                 360                 365
Met Asn Ala Tyr Pro Ser Tyr Ile Ser Pro Ile Gly Cys Leu Pro Ala
            370                 375                 380
His Leu Leu Gly Asp Met Trp Gly Arg Phe Trp Thr Asn Leu Tyr Ser
385                 390                 395                 400
Leu Thr Val Pro Phe Gly Gln Lys Pro Asn Ile Asp Val Thr Asp Ala
                405                 410                 415
Met Val Asp Gln Ala Trp Asp Ala Gln Arg Ile Phe Lys Glu Ala Glu
                420                 425                 430
Lys Phe Phe Val Ser Val Gly Leu Pro Asn Met Thr Gln Gly Phe Trp
                435                 440                 445
Glu Asn Ser Met Leu Thr Asp Pro Gly Asn Val Gln Lys Ala Val Cys
            450                 455                 460
His Pro Thr Ala Trp Asp Leu Gly Lys Gly Asp Phe Arg Ile Leu Met
465                 470                 475                 480
Cys Thr Lys Val Thr Met Asp Asp Phe Leu Thr Ala His His Glu Met
                485                 490                 495
Gly His Ile Gln Tyr Asp Met Ala Tyr Ala Ala Gln Pro Phe Leu Leu
                500                 505                 510
Arg Asn Gly Ala Asn Glu Gly Phe His Glu Ala Val Gly Glu Ile Met
            515                 520                 525
Ser Leu Ser Ala Ala Thr Pro Lys His Leu Lys Ser Ile Gly Leu Leu
    530                 535                 540
Ser Pro Asp Phe Gln Glu Asp Asn Glu Thr Glu Ile Asn Phe Leu Leu
545                 550                 555                 560
Lys Gln Ala Leu Thr Ile Val Gly Thr Leu Pro Phe Thr Tyr Met Leu
                565                 570                 575
Glu Lys Trp Arg Trp Met Val Phe Lys Gly Glu Ile Pro Lys Asp Gln
                580                 585                 590
Trp Met Lys Lys Trp Trp Glu Met Lys Arg Glu Ile Val Gly Val Val
            595                 600                 605
Glu Pro Val Pro His Asp Glu Thr Tyr Cys Asp Pro Ala Ser Leu Phe
    610                 615                 620
His Val Ser Asn Asp Tyr Ser Phe Ile Arg Tyr Tyr Thr Arg Thr Leu
625                 630                 635                 640
Tyr Gln Phe Gln Phe Gln Glu Ala Leu Cys Gln Ala Ala Lys His Glu
                645                 650                 655
Gly Pro Leu His Lys Cys Asp Ile Ser Asn Ser Thr Glu Ala Gly Gln
                660                 665                 670
Lys Leu Phe Asn Met Leu Arg Leu Gly Lys Ser Glu Pro Trp Thr Leu
            675                 680                 685
Ala Leu Glu Asn Val Val Gly Ala Lys Asn Met Asn Val Arg Pro Leu
            690                 695                 700
Leu Asn Tyr Phe Glu Pro Leu Phe Thr Trp Leu Lys Asp Gln Asn Lys
705                 710                 715                 720
Asn Ser Phe Val Gly Trp Ser Thr Asp Trp Ser Glu Pro Lys Ser Ser
                725                 730                 735
```

Asp Lys Thr His Thr Cys Pro Pro Cys Pro Ala Pro Glu Leu Leu Gly
                740                 745                 750

Gly Pro Ser Val Phe Leu Phe Pro Pro Lys Pro Lys Asp Thr Leu Met
            755                 760                 765

Ile Ser Arg Thr Pro Glu Val Thr Cys Val Val Val Asp Val Ser His
770                 775                 780

Glu Asp Pro Glu Val Lys Phe Asn Trp Tyr Val Asp Gly Val Glu Val
785                 790                 795                 800

His Asn Ala Lys Thr Lys Pro Arg Glu Glu Gln Tyr Asn Ser Thr Tyr
                805                 810                 815

Arg Val Val Ser Val Leu Thr Val Leu His Gln Asp Trp Leu Asn Gly
                820                 825                 830

Lys Glu Tyr Lys Cys Lys Val Ser Asn Lys Ala Leu Pro Ala Pro Ile
                835                 840                 845

Glu Lys Thr Ile Ser Lys Ala Lys Gly Gln Pro Arg Glu Pro Gln Val
850                 855                 860

Tyr Thr Leu Pro Pro Ser Arg Glu Glu Met Thr Lys Asn Gln Val Ser
865                 870                 875                 880

Leu Thr Cys Leu Val Lys Gly Phe Tyr Pro Ser Asp Ile Ala Val Glu
                885                 890                 895

Trp Glu Ser Asn Gly Gln Pro Glu Asn Asn Tyr Lys Thr Thr Pro Pro
                900                 905                 910

Val Leu Asp Ser Asp Gly Ser Phe Phe Leu Tyr Ser Lys Leu Thr Val
                915                 920                 925

Asp Lys Ser Arg Trp Gln Gln Gly Asn Val Phe Ser Cys Ser Val Met
                930                 935                 940

His Glu Ala Leu His Asn His Tyr Thr Gln Lys Ser Leu Ser Leu Ser
945                 950                 955                 960

Pro Gly Lys

<210> SEQ ID NO 166
<211> LENGTH: 2889
<212> TYPE: DNA
<213> ORGANISM: Artificial Sequence
<220> FEATURE:
<223> OTHER INFORMATION: pIgR-VHH2-MSCD342-ACE2-18-611-Fc HC1 DNA

<400> SEQUENCE: 166

```
gaagtgcaag tagtggagtc tggaggtggt ttggtacagg ccgggggtc attgaagctg      60
gcttgcgctg ccccaggctt gacctttca tcttacagga tgggttggtt caggcaggca     120
ccaggacagg aacgtgaatt tgttgctgcc attgactgga atggacgcgg aacatattat     180
aggtactatg cagatagcgt caagggccga agtacaatta gccgggacaa tgccaagaac     240
accgtgtatc tccaaatgaa tagtttgaag cctgaagaca ccgctgtata ctactgtgct     300
gccacaacag ttttgactga cccccgcgtc cttaacgagt atgctacctg gggacagggg     360
actcaagtca ctgtgtcttc tggaggcgga gggagtggcg ggggaggctc tcagtctaca     420
atcgaagagc aggccaagac ctttctggac aagttcaacc atgaagccga ggacctgttc     480
taccagtcca gcctggcctc ttggaactac aacaccaata tcaccgagga aaacgtgcag     540
aacatgaaca acgccggcga caagtggtct gccttcctca agaacagtc tacactggct     600
cagatgtacc ccttgcaaga gatccagaac ctgacagtga agctgcaact gcaggctctg     660
cagcagaacg gctcttccgt gctatctgag gataagtcca gcggctgaa caccatcctg     720
```

```
aacacaatgt ccaccatcta cagcaccggc aaagtgtgca accctgataa tcctcaagag    780
tgtctgcttc tggaacccgg cctgaacgag atcatggcca actccctgga ttataacgag    840
aggctgtggg cttgggagtc ctggcgcagc gaggtgggaa agcagctcag acctctgtac    900
gaagagtacg tcgtgctgaa gaacgagatg gccagagcca accactacga ggactacggc    960
gactactgga gaggcgacta tgaagtcaat ggcgtagacg gctacgacta ctccagaggc   1020
cagctgatcg aggatgtgga gcacaccttc gaggagatca agcctctgta cgaacatctg   1080
cacgcctacg tgcgggccaa gctgatgaac gcctacccct cctacatctc ccctatcggc   1140
tgcctgcctg cccatctgct gggtgatatg tggggcagat tctggaccaa cctgtattct   1200
ctcaccgtgc cctttggcca gaaacccaat atcgacgtga ccgacgccat ggtcgatcag   1260
gcctgggatg cccagagaat cttcaaagag gctgagaagt tcttcgtgtc cgtgggactg   1320
cctaacatga cccagggctt tgggaaaaac tccatgctga ccgatcctgg caacgtgcag   1380
aaggccgtgt gtcaccctac cgcttgggat ctgggcaagg gcgatttccg gatcctgatg   1440
tgcaccaagg tgaccatgga cgacttccta accgctcacc acgagatggg ccacatccag   1500
tacgacatgg cttacgccgc tcagccttttt ctgctgcgga acggagctaa tgaaggcttc   1560
catgaagccg tgggcgaaat catgtctctg tccgccgcca cccctaagca cctgaagtct   1620
atcggcctgc tgtctcctga cttccaggag acaacgaga cagagatcaa cttcctgctg   1680
aagcaggccc tgacaatcgt gggcaccctg cccttcacct acatgctgga aaagtggaga   1740
tggatggtgt tcaagggcga atccccaag gaccagtgga tgaaaaagtg gtgggagatg   1800
aagagagaga ttgttggcgt ggtggaacct gtgcctcacg acgagaccta ctgcgacccc   1860
gctagcctgt ccacgtgtc caacgactac tctttcatcc ggtactacac cagaaccctg   1920
taccagttcc agttccagga agctctgtgc caggctgcca acacgaagg ccctctgcac   1980
aagtgcgaca tctctaacag caccgaggcc ggacaaaagc tgttcaacat gctgagactg   2040
ggcaagtccg agccttggac cctggctctg gagaacgtgg tgggagctaa gaacatgaat   2100
gtgcggccac tgctcaacta cttcgagcct ctgtttacct ggctgaagga ccagaacaag   2160
aactccttcg tgggctggtc caccgactgg tccgagccca atctagcga caaaactcac   2220
acatgtccac cgtgcccagc acctgaactc ctggggggac cgtcagtctt cctcttcccc   2280
ccaaaaccca aggacaccct catgatctcc cggacccctg aggtcacatg cgtggtggtg   2340
gacgtgagcc acgaagaccc tgaggtcaag ttcaactggt acgtggacgg cgtggaggtg   2400
cataatgcca agacaaagcc gcgggaggag cagtacaaca gcacgtaccg tgtggtcagc   2460
gtcctcaccg tcctgcacca ggactggctg aatggcaagg agtacaagtg caaggtctcc   2520
aacaaagccc tcccagcccc catcgagaaa accatctcca aagccaaagg cagccccga   2580
gaaccacagg tgtacaccct gcccccatcc cgggaggaga tgaccaagaa ccaggtcagc   2640
ctgacctgcc tggtcaaagg cttctatccc agcgacatcg ccgtggagtg ggagagcaat   2700
gggcagccgg agaacaacta caagaccacg cctcccgtgc tggactccga cggctccttc   2760
ttcctctaca gcaagctcac cgtggacaag tctagatggc agcagggaa cgtcttctca   2820
tgctccgtga tgcatgaggc tctgcacaac cactacacgc agaagagcct ctccctgtct   2880
ccgggtaaa                                                           2889
```

<210> SEQ ID NO 167
<211> LENGTH: 949
<212> TYPE: PRT
<213> ORGANISM: Artificial Sequence
<220> FEATURE:
<223> OTHER INFORMATION: pIgR-VHH6-MSCD342-ACE2-18-611-Fc HC1 AA

<400> SEQUENCE: 167

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Ala | Gly | Gly |
| 1 | | | | 5 | | | | | 10 | | | | | 15 | |
| Ser | Leu | Arg | Leu | Ser | Cys | Ala | Val | Ser | Gly | Ser | Ser | Val | Ser | Ser | Asp |
| | | | 20 | | | | | 25 | | | | | 30 | | |
| Ala | Met | Gly | Trp | Tyr | Arg | Gln | Ala | Pro | Gly | Asn | Gln | Arg | Ala | Trp | Val |
| | | 35 | | | | | 40 | | | | | 45 | | | |
| Ala | Phe | Ile | Ser | Gly | Gly | Thr | Thr | Thr | Tyr | Ala | Asp | Ser | Val | Lys | |
| | 50 | | | | | 55 | | | | | 60 | | | | |
| Gly | Arg | Phe | Thr | Ile | Ser | Arg | Asp | Asn | Thr | Lys | Asn | Thr | Val | Tyr | Leu |
| 65 | | | | | 70 | | | | | 75 | | | | | 80 |
| His | Met | Asn | Ser | Leu | Lys | Pro | Glu | Asp | Thr | Ala | Val | Tyr | Tyr | Cys | Asn |
| | | | | 85 | | | | | 90 | | | | | 95 | |
| His | Pro | Leu | Thr | Ser | Arg | Trp | Gly | Gln | Gly | Thr | Gln | Val | Thr | Val | Ser |
| | | | 100 | | | | | 105 | | | | | 110 | | |
| Ser | Gly | Gly | Gly | Gly | Ser | Gly | Gly | Gly | Ser | Gln | Ser | Thr | Ile | Glu | |
| | | 115 | | | | | 120 | | | | | 125 | | | |
| Glu | Gln | Ala | Lys | Thr | Phe | Leu | Asp | Lys | Phe | Asn | His | Glu | Ala | Glu | Asp |
| | 130 | | | | | 135 | | | | | 140 | | | | |
| Leu | Phe | Tyr | Gln | Ser | Ser | Leu | Ala | Ser | Trp | Asn | Tyr | Asn | Thr | Asn | Ile |
| 145 | | | | | 150 | | | | | 155 | | | | | 160 |
| Thr | Glu | Glu | Asn | Val | Gln | Asn | Met | Asn | Asn | Ala | Gly | Asp | Lys | Trp | Ser |
| | | | | 165 | | | | | 170 | | | | | 175 | |
| Ala | Phe | Leu | Lys | Glu | Gln | Ser | Thr | Leu | Ala | Gln | Met | Tyr | Pro | Leu | Gln |
| | | | 180 | | | | | 185 | | | | | 190 | | |
| Glu | Ile | Gln | Asn | Leu | Thr | Val | Lys | Leu | Gln | Leu | Gln | Ala | Leu | Gln | Gln |
| | | 195 | | | | | 200 | | | | | 205 | | | |
| Asn | Gly | Ser | Ser | Val | Leu | Ser | Glu | Asp | Lys | Ser | Lys | Arg | Leu | Asn | Thr |
| | 210 | | | | | 215 | | | | | 220 | | | | |
| Ile | Leu | Asn | Thr | Met | Ser | Thr | Ile | Tyr | Ser | Thr | Gly | Lys | Val | Cys | Asn |
| 225 | | | | | 230 | | | | | 235 | | | | | 240 |
| Pro | Asp | Asn | Pro | Gln | Glu | Cys | Leu | Leu | Leu | Glu | Pro | Gly | Leu | Asn | Glu |
| | | | | 245 | | | | | 250 | | | | | 255 | |
| Ile | Met | Ala | Asn | Ser | Leu | Asp | Tyr | Asn | Glu | Arg | Leu | Trp | Ala | Trp | Glu |
| | | | 260 | | | | | 265 | | | | | 270 | | |
| Ser | Trp | Arg | Ser | Glu | Val | Gly | Lys | Gln | Leu | Arg | Pro | Leu | Tyr | Glu | Glu |
| | | 275 | | | | | 280 | | | | | 285 | | | |
| Tyr | Val | Val | Leu | Lys | Asn | Glu | Met | Ala | Arg | Ala | Asn | His | Tyr | Glu | Asp |
| | 290 | | | | | 295 | | | | | 300 | | | | |
| Tyr | Gly | Asp | Tyr | Trp | Arg | Gly | Asp | Tyr | Glu | Val | Asn | Gly | Val | Asp | Gly |
| 305 | | | | | 310 | | | | | 315 | | | | | 320 |
| Tyr | Asp | Tyr | Ser | Arg | Gly | Gln | Leu | Ile | Glu | Asp | Val | Glu | His | Thr | Phe |
| | | | | 325 | | | | | 330 | | | | | 335 | |
| Glu | Glu | Ile | Lys | Pro | Leu | Tyr | Glu | His | Leu | His | Ala | Tyr | Val | Arg | Ala |
| | | | 340 | | | | | 345 | | | | | 350 | | |
| Lys | Leu | Met | Asn | Ala | Tyr | Pro | Ser | Tyr | Ile | Ser | Pro | Ile | Gly | Cys | Leu |
| | | 355 | | | | | 360 | | | | | 365 | | | |
| Pro | Ala | His | Leu | Leu | Gly | Asp | Met | Trp | Gly | Arg | Phe | Trp | Thr | Asn | Leu |
| | 370 | | | | | 375 | | | | | 380 | | | | |
| Tyr | Ser | Leu | Thr | Val | Pro | Phe | Gly | Gln | Lys | Pro | Asn | Ile | Asp | Val | Thr |
| 385 | | | | | 390 | | | | | 395 | | | | | 400 |

```
Asp Ala Met Val Asp Gln Ala Trp Asp Ala Gln Arg Ile Phe Lys Glu
            405                 410                 415

Ala Glu Lys Phe Phe Val Ser Val Gly Leu Pro Asn Met Thr Gln Gly
            420                 425                 430

Phe Trp Glu Asn Ser Met Leu Thr Asp Pro Gly Asn Val Gln Lys Ala
            435                 440                 445

Val Cys His Pro Thr Ala Trp Asp Leu Gly Lys Gly Asp Phe Arg Ile
            450                 455                 460

Leu Met Cys Thr Lys Val Thr Met Asp Asp Phe Leu Thr Ala His His
465                 470                 475                 480

Glu Met Gly His Ile Gln Tyr Asp Met Ala Tyr Ala Ala Gln Pro Phe
            485                 490                 495

Leu Leu Arg Asn Gly Ala Asn Glu Gly Phe His Glu Ala Val Gly Glu
            500                 505                 510

Ile Met Ser Leu Ser Ala Ala Thr Pro Lys His Leu Lys Ser Ile Gly
            515                 520                 525

Leu Leu Ser Pro Asp Phe Gln Glu Asp Asn Glu Thr Glu Ile Asn Phe
            530                 535                 540

Leu Leu Lys Gln Ala Leu Thr Ile Val Gly Thr Leu Pro Phe Thr Tyr
545                 550                 555                 560

Met Leu Glu Lys Trp Arg Trp Met Val Phe Lys Gly Glu Ile Pro Lys
            565                 570                 575

Asp Gln Trp Met Lys Lys Trp Trp Glu Met Lys Arg Glu Ile Val Gly
            580                 585                 590

Val Val Glu Pro Val Pro His Asp Glu Thr Tyr Cys Asp Pro Ala Ser
            595                 600                 605

Leu Phe His Val Ser Asn Asp Tyr Ser Phe Ile Arg Tyr Tyr Thr Arg
            610                 615                 620

Thr Leu Tyr Gln Phe Gln Phe Gln Glu Ala Leu Cys Gln Ala Ala Lys
625                 630                 635                 640

His Glu Gly Pro Leu His Lys Cys Asp Ile Ser Asn Ser Thr Glu Ala
            645                 650                 655

Gly Gln Lys Leu Phe Asn Met Leu Arg Leu Gly Lys Ser Glu Pro Trp
            660                 665                 670

Thr Leu Ala Leu Glu Asn Val Val Gly Ala Lys Asn Met Asn Val Arg
            675                 680                 685

Pro Leu Leu Asn Tyr Phe Glu Pro Leu Phe Thr Trp Leu Lys Asp Gln
            690                 695                 700

Asn Lys Asn Ser Phe Val Gly Trp Ser Thr Asp Trp Ser Glu Pro Lys
705                 710                 715                 720

Ser Ser Asp Lys Thr His Thr Cys Pro Pro Cys Pro Ala Pro Glu Leu
            725                 730                 735

Leu Gly Gly Pro Ser Val Phe Leu Phe Pro Pro Lys Pro Lys Asp Thr
            740                 745                 750

Leu Met Ile Ser Arg Thr Pro Glu Val Thr Cys Val Val Val Asp Val
            755                 760                 765

Ser His Glu Asp Pro Glu Val Lys Phe Asn Trp Tyr Val Asp Gly Val
            770                 775                 780

Glu Val His Asn Ala Lys Thr Lys Pro Arg Glu Glu Gln Tyr Asn Ser
785                 790                 795                 800

Thr Tyr Arg Val Val Ser Val Leu Thr Val Leu His Gln Asp Trp Leu
            805                 810                 815
```

Asn Gly Lys Glu Tyr Lys Cys Lys Val Ser Asn Lys Ala Leu Pro Ala
            820                 825                 830

Pro Ile Glu Lys Thr Ile Ser Lys Ala Lys Gly Gln Pro Arg Glu Pro
        835                 840                 845

Gln Val Tyr Thr Leu Pro Pro Ser Arg Glu Glu Met Thr Lys Asn Gln
    850                 855                 860

Val Ser Leu Thr Cys Leu Val Lys Gly Phe Tyr Pro Ser Asp Ile Ala
865                 870                 875                 880

Val Glu Trp Glu Ser Asn Gly Gln Pro Glu Asn Asn Tyr Lys Thr Thr
                885                 890                 895

Pro Pro Val Leu Asp Ser Asp Gly Ser Phe Phe Leu Tyr Ser Lys Leu
            900                 905                 910

Thr Val Asp Lys Ser Arg Trp Gln Gln Gly Asn Val Phe Ser Cys Ser
        915                 920                 925

Val Met His Glu Ala Leu His Asn His Tyr Thr Gln Lys Ser Leu Ser
    930                 935                 940

Leu Ser Pro Gly Lys
945

<210> SEQ ID NO 168
<211> LENGTH: 2847
<212> TYPE: DNA
<213> ORGANISM: Artificial Sequence
<220> FEATURE:
<223> OTHER INFORMATION: pIgR-VHH6-MSCD342-ACE2-18-611-Fc HC1 DNA

<400> SEQUENCE: 168

```
gaggtgcagt tggtggagtc tggtggaggt ctggtccagg ctggaggatc tctcagactt      60
agttgcgccg tttcaggcag ttccgtatct agcgatgcaa tggggtggta tcggcaggca     120
ccagggaatc agcgtgcctg ggttgccttt atcagtggtg gcggcactac cacttatgcc     180
gattcagtaa agggaaggtt taccatatct agggataaca caaagaatac agtgtatttg     240
cacatgaact cactgaaacc agaagacact gccgtgtact attgcaatca tcctcttaca     300
agccgctggg gtcaaggcac acaggtgacc gtgtcttctg gaggcggagg gagtggcggg     360
ggaggctctc agtctacaat cgaagagcag gccaagacct ttctggacaa gttcaaccat     420
gaagccgagg acctgttcta ccagtccagc ctggcctctt ggaactacaa caccaatatc     480
accgaggaaa acgtgcagaa catgaacaac gccggcgaca gtggtctgc cttcctcaaa     540 gaacagtcta cactggctca gatgtacccc ttgcaagaga tccagaacct gacagtgaag     600
ctgcaactgc aggctctgca gcagaacggc tcttccgtgc tatctgagga taagtccaag     660
cggctgaaca ccatcctgaa cacaatgtcc accatctaca gcaccggcaa agtgtgcaac     720
cctgataatc ctcaagagtg tctgcttctg gaacccggcc tgaacgagat catggccaac     780
tccctggatt ataacgagag gctgtgggct tgggagtcct ggcgcagcga ggtgggaaag     840
cagctcagac tctgtacga agagtacgtc gtgctgaaga cgagatggc cagagccaac     900 cactacgagg actacggcga ctactggaga ggcgactatg aagtcaatgg cgtagacggc     960
tacgactact ccagaggcca gctgatcgag gatgtggagc acaccttcga ggagatcaag    1020
cctctgtacg aacatctgca cgcctacgtg cgggccaagt gatgaacgc ctacccttcc    1080 tacatctccc ctatcggctg cctgcctgcc catctgctgg gtgatatgtg gggcagattc    1140
tggaccaacc tgtattctct caccgtgccc tttggccaga aacccaatat cgacgtgacc    1200
gacgccatgg tcgatcaggc ctgggatgcc cagagaatct tcaaagaggc tgagaagttc    1260
```

```
ttcgtgtccg tgggactgcc taacatgacc cagggctttt gggaaaactc catgctgacc      1320
gatcctggca acgtgcagaa ggccgtgtgt caccctaccg cttgggatct gggcaagggc      1380
gatttccgga tcctgatgtg caccaaggtg accatggacg acttcctaac cgctcaccac      1440
gagatgggcc acatccagta cgacatggct tacgccgctc agccttttct gctgcggaac      1500
ggagctaatg aaggcttcca tgaagccgtg ggcgaaatca tgtctctgtc cgccgccacc      1560
cctaagcacc tgaagtctat cggcctgctg tctcctgact ccaggagga caacgagaca      1620
gagatcaact tcctgctgaa gcaggccctg acaatcgtgg gcaccctgcc cttcacctac      1680
atgctggaaa gtggagatgg atggtgttc aagggcgaaa tccccaagga ccagtggatg       1740
aaaaagtggt gggagatgaa gagagagatt gttggcgtgg tggaacctgt gcctcacgac      1800
gagacctact gcgaccccgc tagcctgttc acgtgtcca acgactactc tttcatccgg       1860
tactacacca gaaccctgta ccagttccag ttccaggaag ctctgtgcca ggctgccaaa      1920
cacgaaggcc ctctgcacaa gtgcgacatc tctaacagca ccgaggccgg acaaaagctg      1980
ttcaacatgc tgagactggg caagtccgag ccttggaccc tggctctgga aacgtggtg      2040
ggagctaaga acatgaatgt gcggccactg ctcaactact tcgagcctct gtttacctgg      2100
ctgaaggacc agaacaagaa ctccttcgtg ggctggtcca ccgactggtc cgagcccaaa      2160
tctagcgaca aaactcacac atgtccaccg tgcccagcac ctgaactcct ggggggaccg      2220
tcagtcttcc tcttcccccc aaaacccaag gacaccctca tgatctcccg gacccctgag      2280
gtcacatgcg tggtggtgga cgtgagccac gaagaccctg aggtcaagtt caactggtac      2340
gtggacggcg tggaggtgca taatgccaag acaaagccgc gggaggagca gtacaacagc      2400
acgtaccgtg tggtcagcgt cctcaccgtc ctgcaccagg actggctgaa tggcaaggag      2460
tacaagtgca aggtctccaa caaagccctc ccagccccca tcgagaaaac catctccaaa      2520
gccaaagggc agccccgaga accacaggtg tacaccctgc ccccatcccg ggaggagatg      2580
accaagaacc aggtcagcct gacctgcctg gtcaaaggct tctatcccag cgacatcgcc      2640
gtggagtggg agagcaatgg gcagccggag aacaactaca agaccacgcc tcccgtgctg      2700
gactccgacg gctccttctt cctctacagc aagctcaccg tggacaagtc tagatggcag      2760
caggggaacg tcttctcatg ctccgtgatg catgaggctc tgcacaacca ctacacgcag      2820
aagagcctct ccctgtctcc gggtaaa                                          2847
```

```
<210> SEQ ID NO 169
<211> LENGTH: 948
<212> TYPE: PRT
<213> ORGANISM: Artificial Sequence
<220> FEATURE:
<223> OTHER INFORMATION: pIgR-VHH6-Fc-MSCD342-ACE2-18-611 HC1 AA

<400> SEQUENCE: 169

Glu Val Gln Leu Val Glu Ser Gly Gly Gly Leu Val Gln Ala Gly Gly
1               5                   10                  15

Ser Leu Arg Leu Ser Cys Ala Val Ser Gly Ser Ser Val Ser Ser Asp
            20                  25                  30

Ala Met Gly Trp Tyr Arg Gln Ala Pro Gly Asn Gln Arg Ala Trp Val
        35                  40                  45

Ala Phe Ile Ser Gly Gly Gly Thr Thr Thr Tyr Ala Asp Ser Val Lys
    50                  55                  60

Gly Arg Phe Thr Ile Ser Arg Asp Asn Thr Lys Asn Thr Val Tyr Leu
65                  70                  75                  80
```

```
His Met Asn Ser Leu Lys Pro Glu Asp Thr Ala Val Tyr Tyr Cys Asn
            85                  90                  95
His Pro Leu Thr Ser Arg Trp Gly Gln Gly Thr Gln Val Thr Val Ser
        100                 105                 110
Ser Glu Pro Lys Ser Ser Asp Lys Thr His Thr Cys Pro Pro Cys Pro
        115                 120                 125
Ala Pro Glu Leu Leu Gly Gly Pro Ser Val Phe Leu Phe Pro Pro Lys
        130                 135                 140
Pro Lys Asp Thr Leu Met Ile Ser Arg Thr Pro Glu Val Thr Cys Val
145                 150                 155                 160
Val Val Asp Val Ser His Glu Asp Pro Glu Val Lys Phe Asn Trp Tyr
                165                 170                 175
Val Asp Gly Val Glu Val His Asn Ala Lys Thr Lys Pro Arg Glu Glu
            180                 185                 190
Gln Tyr Asn Ser Thr Tyr Arg Val Val Ser Val Leu Thr Val Leu His
        195                 200                 205
Gln Asp Trp Leu Asn Gly Lys Glu Tyr Lys Cys Lys Val Ser Asn Lys
        210                 215                 220
Ala Leu Pro Ala Pro Ile Glu Lys Thr Ile Ser Lys Ala Lys Gly Gln
225                 230                 235                 240
Pro Arg Glu Pro Gln Val Tyr Thr Leu Pro Pro Ser Arg Glu Glu Met
                245                 250                 255
Thr Lys Asn Gln Val Ser Leu Thr Cys Leu Val Lys Gly Phe Tyr Pro
            260                 265                 270
Ser Asp Ile Ala Val Glu Trp Glu Ser Asn Gly Gln Pro Glu Asn Asn
        275                 280                 285
Tyr Lys Thr Thr Pro Pro Val Leu Asp Ser Asp Gly Ser Phe Phe Leu
        290                 295                 300
Tyr Ser Lys Leu Thr Val Asp Lys Ser Arg Trp Gln Gln Gly Asn Val
305                 310                 315                 320
Phe Ser Cys Ser Val Met His Glu Ala Leu His Asn His Tyr Thr Gln
                325                 330                 335
Lys Ser Leu Ser Leu Ser Pro Gly Gly Gly Gly Ser Gly Gly Gly
            340                 345                 350
Gly Ser Gln Ser Thr Ile Glu Glu Gln Ala Lys Thr Phe Leu Asp Lys
        355                 360                 365
Phe Asn His Glu Ala Glu Asp Leu Phe Tyr Gln Ser Ser Leu Ala Ser
        370                 375                 380
Trp Asn Tyr Asn Thr Asn Ile Thr Glu Glu Asn Val Gln Asn Met Asn
385                 390                 395                 400
Asn Ala Gly Asp Lys Trp Ser Ala Phe Leu Lys Glu Gln Ser Thr Leu
                405                 410                 415
Ala Gln Met Tyr Pro Leu Gln Glu Ile Gln Asn Leu Thr Val Lys Leu
            420                 425                 430
Gln Leu Gln Ala Leu Gln Gln Asn Gly Ser Ser Val Leu Ser Glu Asp
        435                 440                 445
Lys Ser Lys Arg Leu Asn Thr Ile Leu Asn Thr Met Ser Thr Ile Tyr
        450                 455                 460
Ser Thr Gly Lys Val Cys Asn Pro Asp Asn Pro Gln Glu Cys Leu Leu
465                 470                 475                 480
Leu Glu Pro Gly Leu Asn Glu Ile Met Ala Asn Ser Leu Asp Tyr Asn
                485                 490                 495
Glu Arg Leu Trp Ala Trp Glu Ser Trp Arg Ser Glu Val Gly Lys Gln
```

```
                500             505             510
Leu Arg Pro Leu Tyr Glu Glu Tyr Val Val Leu Lys Asn Glu Met Ala
            515             520             525

Arg Ala Asn His Tyr Glu Asp Tyr Gly Asp Tyr Trp Arg Gly Asp Tyr
            530             535             540

Glu Val Asn Gly Val Asp Gly Tyr Asp Tyr Ser Arg Gly Gln Leu Ile
545             550             555             560

Glu Asp Val Glu His Thr Phe Glu Glu Ile Lys Pro Leu Tyr Glu His
                565             570             575

Leu His Ala Tyr Val Arg Ala Lys Leu Met Asn Ala Tyr Pro Ser Tyr
            580             585             590

Ile Ser Pro Ile Gly Cys Leu Pro Ala His Leu Leu Gly Asp Met Trp
            595             600             605

Gly Arg Phe Trp Thr Asn Leu Tyr Ser Leu Thr Val Pro Phe Gly Gln
            610             615             620

Lys Pro Asn Ile Asp Val Thr Asp Ala Met Val Asp Gln Ala Trp Asp
625             630             635             640

Ala Gln Arg Ile Phe Lys Glu Ala Glu Lys Phe Phe Val Ser Val Gly
            645             650             655

Leu Pro Asn Met Thr Gln Gly Phe Trp Glu Asn Ser Met Leu Thr Asp
            660             665             670

Pro Gly Asn Val Gln Lys Ala Val Cys His Pro Thr Ala Trp Asp Leu
            675             680             685

Gly Lys Gly Asp Phe Arg Ile Leu Met Cys Thr Lys Val Thr Met Asp
            690             695             700

Asp Phe Leu Thr Ala His His Glu Met Gly His Ile Gln Tyr Asp Met
705             710             715             720

Ala Tyr Ala Ala Gln Pro Phe Leu Leu Arg Asn Gly Ala Asn Glu Gly
            725             730             735

Phe His Glu Ala Val Gly Glu Ile Met Ser Leu Ser Ala Ala Thr Pro
            740             745             750

Lys His Leu Lys Ser Ile Gly Leu Leu Ser Pro Asp Phe Gln Glu Asp
            755             760             765

Asn Glu Thr Glu Ile Asn Phe Leu Leu Lys Gln Ala Leu Thr Ile Val
            770             775             780

Gly Thr Leu Pro Phe Thr Tyr Met Leu Glu Lys Trp Arg Trp Met Val
785             790             795             800

Phe Lys Gly Glu Ile Pro Lys Asp Gln Trp Met Lys Lys Trp Trp Glu
            805             810             815

Met Lys Arg Glu Ile Val Gly Val Val Glu Pro Val Pro His Asp Glu
            820             825             830

Thr Tyr Cys Asp Pro Ala Ser Leu Phe His Val Ser Asn Asp Tyr Ser
            835             840             845

Phe Ile Arg Tyr Tyr Thr Arg Thr Leu Tyr Gln Phe Gln Phe Gln Glu
            850             855             860

Ala Leu Cys Gln Ala Ala Lys His Glu Gly Pro Leu His Lys Cys Asp
865             870             875             880

Ile Ser Asn Ser Thr Glu Ala Gly Gln Lys Leu Phe Asn Met Leu Arg
            885             890             895

Leu Gly Lys Ser Glu Pro Trp Thr Leu Ala Leu Glu Asn Val Val Gly
            900             905             910

Ala Lys Asn Met Asn Val Arg Pro Leu Leu Asn Tyr Phe Glu Pro Leu
            915             920             925
```

Phe Thr Trp Leu Lys Asp Gln Asn Lys Asn Ser Phe Val Gly Trp Ser
    930                 935                 940

Thr Asp Trp Ser
945

<210> SEQ ID NO 170
<211> LENGTH: 2844
<212> TYPE: DNA
<213> ORGANISM: Artificial Sequence
<220> FEATURE:
<223> OTHER INFORMATION: pIgR-VHH6-Fc-MSCD342-ACE2-18-611 HC1 DNA

<400> SEQUENCE: 170

| | | | | |
|---|---|---|---|---|
| gaggtgcagt | tggtggagtc | tggtggaggt | ctggtccagg | ctggaggatc | tctcagactt | 60 |
| agttgcgccg | tttcaggcag | ttccgtatct | agcgatgcaa | tggggtggta | tcggcaggca | 120 |
| ccagggaatc | agcgtgcctg | ggttgccttt | atcagtggtg | gcggcactac | cacttatgcc | 180 |
| gattcagtaa | agggaaggtt | taccatatct | agggataaca | caaagaatac | agtgtatttg | 240 |
| cacatgaact | cactgaaacc | agaagacact | gccgtgtact | attgcaatca | tcctcttaca | 300 |
| agccgctggg | gtcaaggcac | acaggtgacc | gtgtcttctg | agcccaaatc | tagcgacaaa | 360 |
| actcacacat | gtccaccgtg | cccagcacct | gaactcctgg | ggggaccgtc | agtcttcctc | 420 |
| ttccccccaa | aacccaagga | caccctcatg | atctcccgga | cccctgaggt | cacatgcgtg | 480 |
| gtggtggacg | tgagccacga | agaccctgag | gtcaagttca | actggtacgt | ggacggcgtg | 540 |
| gaggtgcata | atgccaagac | aaagccgcgg | gaggagcagt | acaacagcac | gtaccgtgtg | 600 |
| gtcagcgtcc | tcaccgtcct | gcaccaggac | tggctgaatg | gcaaggagta | caagtgcaag | 660 |
| gtctccaaca | aagccctccc | agcccccatc | gagaaaacca | tctccaaagc | caaagggcag | 720 |
| ccccgagaac | cacaggtgta | caccctgccc | ccatcccggg | aggagatgac | caagaaccag | 780 |
| gtcagcctga | cctgcctggt | caaaggcttc | tatcccagcg | acatcgccgt | ggagtgggag | 840 |
| agcaatgggc | agccggagaa | caactacaag | accacgcctc | ccgtgctgga | ctccgacggc | 900 |
| tccttcttcc | tctacagcaa | gctcaccgtg | gacaagtcta | gatggcagca | ggggaacgtc | 960 |
| ttctcatgct | ccgtgatgca | tgaggctctg | cacaaccact | acacgcagaa | gagcctctcc | 1020 |
| ctgtctccgg | gtggaggcgg | agggagtggc | gggggaggct | ctcagtctac | aatcgaagag | 1080 |
| caggccaaga | cctttctgga | caagttcaac | catgaagccg | aggacctgtt | ctaccagtcc | 1140 |
| agcctggcct | cttggaacta | caacaccaat | atcaccgagg | aaaacgtgca | gaacatgaac | 1200 |
| aacgccggcg | acaagtggtc | tgccttcctc | aaagaacagt | ctacactggc | tcagatgtac | 1260 |
| cccttgcaag | agatccagaa | cctgacagtg | aagctgcaac | tgcaggctct | gcagcagaac | 1320 |
| ggctcttccg | tgctatctga | ggataagtcc | aagcggctga | acaccatcct | gaacacaatg | 1380 |
| tccaccatct | acagcaccgg | caaagtgtgc | aaccctgata | atcctcaaga | gtgtctgctt | 1440 |
| ctggaacccg | gcctgaacga | gatcatggcc | aactccctgg | attataacga | gaggctgtgg | 1500 |
| gcttgggagt | cctggcgcag | cgaggtggga | aagcagctca | gacctctgta | cgaagagtac | 1560 |
| gtcgtgctga | gaacgagat | ggccagagcc | aaccactacg | aggactacgg | cgactactgg | 1620 |
| agaggcgact | atgaagtcaa | tggcgtagac | ggctacgact | actccagagg | ccagctgatc | 1680 |
| gaggatgtgg | agcacacctt | cgaggagatc | aagcctctgt | acgaacatct | gcacgcctac | 1740 |
| gtgcgggcca | gctgatgaa | cgcctaccct | tcctacatct | cccctatcgg | ctgcctgcct | 1800 |
| gcccatctgc | tgggtgatat | gtggggcaga | ttctggacca | acctgtattc | tctcaccgtg | 1860 |

```
cccttttggcc agaaacccaa tatcgacgtg accgacgcca tggtcgatca ggcctgggat    1920
gcccagagaa tcttcaaaga ggctgagaag ttcttcgtgt ccgtgggact gcctaacatg    1980
acccagggct tttgggaaaa ctccatgctg accgatcctg caacgtgca gaaggccgtg     2040 tgtcaccta ccgcttggga tctgggcaag ggcgatttcc ggatcctgat gtgcaccaag     2100
gtgaccatgg acgacttcct aaccgctcac cacgagatgg ccacatcca gtacgacatg     2160 gcttacgccg ctcagccttt tctgctgcgg aacggagcta atgaaggctt ccatgaagcc    2220
gtgggcgaaa tcatgtctct gtccgccgcc acccctaagc acctgaagtc tatcggcctg    2280
ctgtctcctg acttccagga ggacaacgag acagagatca acttcctgct gaagcaggcc    2340
ctgacaatcg tgggcaccct gcccttcacc tacatgctgg aaaagtggag atggatggtg    2400
ttcaagggcg aaatcccca ggaccagtgg atgaaaaagt ggtgggagat gaagagagag     2460
attgttggcg tggtggaacc tgtgcctcac gacgagacct actgcgaccc cgctagcctg    2520
ttccacgtgt ccaacgacta ctctttcatc cggtactaca ccagaacccct gtaccagttc   2580 cagttccagg aagctctgtg ccaggctgcc aaacacgaag ccctctgca caagtgcgac     2640 atctctaaca gcaccgaggc cggacaaaag ctgttcaaca tgctgagact gggcaagtcc    2700
gagccttgga ccctggctct ggagaacgtg gtgggagcta agaacatgaa tgtgcggcca    2760
ctgctcaact acttcgagcc tctgtttacc tggctgaagg accagaacaa gaactccttc    2820
gtgggctggt ccaccgactg gtcc                                            2844
```

<210> SEQ ID NO 171
<211> LENGTH: 449
<212> TYPE: PRT
<213> ORGANISM: Artificial Sequence
<220> FEATURE:
<223> OTHER INFORMATION: CR3022-Fab HC1 AA

<400> SEQUENCE: 171

```
Gln Met Gln Leu Val Gln Ser Gly Thr Glu Val Lys Lys Pro Gly Glu
1               5                   10                  15

Ser Leu Lys Ile Ser Cys Lys Gly Ser Gly Tyr Gly Phe Ile Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Glu Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Ile Tyr Tyr Cys
                85                  90                  95

Ala Gly Gly Ser Gly Ile Ser Thr Pro Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
    435                 440                 445

Lys

<210> SEQ ID NO 172
<211> LENGTH: 1347
<212> TYPE: DNA
<213> ORGANISM: Artificial Sequence
<220> FEATURE:
<223> OTHER INFORMATION: CR3022-Fab HC1 DNA

<400> SEQUENCE: 172
cagatgcaac tggtgcagtc tggaaccgag gtgaagaagc ccggcgagtc tctgaaaatc        60
tcctgcaagg gctccggcta cggcttcatc acctactgga tcggctgggt gcggcagatg       120
cctggaaaag gcctggaatg gatgggcatt atctatcctg cgactccga dacaagatac        180 tccccttcct tccagggcca ggtgaccatc tctgccgaca gtccatcaa caccgcttac        240 ctgcagtggt cctccctgaa ggcctctgat accgccatct actactgtgc tggcggatct       300
ggcatctcca cccctatgga cgtgtggggc caaggcacca cagtcaccgt gtcctccgcc       360
tccaccaagg gcccatcggt cttccccctg gcaccctcct ccaagagcac ctctgggggc       420
acagcggccc tgggctgcct ggtcaaggac tacttccccg aaccggtgac ggtgtcgtgg       480
aactcaggcg ccctgaccag cggcgtgcac accttcccgg ctgtcctaca gtcctcagga       540

```
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgtccaccg tgcccagcac ctgaactcct ggggggaccg    720
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggaggagatg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagtc tagatggcag   1260
caggggaacg tcttctcatg ctccgtgatg catgaggctc tgcacaacca ctacacgcag   1320
aagagcctct ccctgtctcc gggtaaa                                       1347
```

<210> SEQ ID NO 173
<211> LENGTH: 220
<212> TYPE: PRT
<213> ORGANISM: Artificial Sequence
<220> FEATURE:
<223> OTHER INFORMATION: CR3022-Fab LC1 AA

<400> SEQUENCE: 173

Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Ile Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 174
<211> LENGTH: 660
<212> TYPE: DNA
<213> ORGANISM: Artificial Sequence
<220> FEATURE:
<223> OTHER INFORMATION: CR3022-Fab LC1 DNA

<400> SEQUENCE: 174

```
gacatccaac tgacccagtc tccagattct ctcgctgtct ccctgggcga gagagccaca      60
atcaactgca agtcctctca gtccgtgctg tactcctcca tcaacaagaa ctacctggcc     120
tggtaccagc agaaacctgg ccagcctcct aagctgctga tctactgggc ttctacaaga     180
gagtctggcg tgcccgaccg gttttccggc tctggctccg gaaccgactt caccctgacc     240
atctccagcc tgcaggccga ggacgtggcc gtgtactatt gtcaacagta ctactccacc     300
ccttacacct tcggccaggg caccaaggtg gaaatcaagc gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga acacaaagt ctacgcctgc      600
gaagtcaccc atcagggcct gagctcgccc gtcacaaaga gcttcaacag gggagagtgt     660
```

<210> SEQ ID NO 175
<211> LENGTH: 448
<212> TYPE: PRT
<213> ORGANISM: Artificial Sequence
<220> FEATURE:
<223> OTHER INFORMATION: SAD-S35-Fab HC1 AA

<400> SEQUENCE: 175

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Ser Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Leu Gln Glu Arg Gly Gly Met Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

Ser Leu Gly Thr Gln Thr Tyr Ile Cys Asn Val Asn His Lys Pro Ser
           195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
               245                 250                 255

Thr Pro Glu Val Thr Cys Val Val Asp Val Ser His Glu Asp Pro
           260                 265                 270

Glu Val Lys Phe Asn Trp Tyr Val Asp Gly Val Glu Val His Asn Ala
               275                 280                 285

Lys Thr Lys Pro Arg Glu Glu Gln Tyr Asn Ser Thr Tyr Arg Val Val
           290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
               325                 330                 335

Ile Ser Lys Ala Lys Gly Gln Pro Arg Glu Pro Gln Val Tyr Thr Leu
           340                 345                 350

Pro Pro Ser Arg Glu Glu Met Thr Lys Asn Gln Val Ser Leu Thr Cys
           355                 360                 365

Leu Val Lys Gly Phe Tyr Pro Ser Asp Ile Ala Val Glu Trp Glu Ser
           370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
               405                 410                 415

Arg Trp Gln Gln Gly Asn Val Phe Ser Cys Ser Val Met His Glu Ala
           420                 425                 430

Leu His Asn His Tyr Thr Gln Lys Ser Leu Ser Leu Ser Pro Gly Lys
           435                 440                 445

<210> SEQ ID NO 176
<211> LENGTH: 1344
<212> TYPE: DNA
<213> ORGANISM: Artificial Sequence
<220> FEATURE:
<223> OTHER INFORMATION: SAD-S35-Fab HC1 DNA

<400> SEQUENCE: 176
caagtgcagt tggtggaatc aggcggggc ctggttcagc caggaggctc attgcggctg     60
agttgtgccg ccagtggtat aactgtaagt tctaattata tgtcttgggt ccgtcaagca    120
cctggaaagg gtctggaatg ggtaagtgtt atctattcag gaggatctac ctattatgcc    180
gattcagtga aggtcgctt tagcatttct cgtgataatt ccaaaaacac actctacctg    240
caaatgaaca gcctcagggc tgaagatacc gccgtctact actgcgctcg ggaccttcag    300
gaacgcggcg ggatggacgt atggggacaa ggaactactg taacagttag ttcagcctcc    360
accaagggcc catcggtctt ccccctggca ccctcctcca agagcacctc tggggggcaca    420 gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct tgggcaccca gacctacatc    600
tgcaacgtga atcacaagcc cagcaacacc aaggtggaca gaaagttga gcccaaatct    660

```
tgtgacaaaa ctcacacatg tccaccgtgc ccagcacctg aactcctggg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctccca gcccccatcg agaaaaccat ctccaaagcc   1020
aaagggcagc cccgagaacc acaggtgtac accctgcccc catcccggga ggagatgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctacagcaag ctcaccgtgg acaagtctag atggcagcag   1260
gggaacgtct tctcatgctc cgtgatgcat gaggctctgc acaaccacta cacgcagaag   1320
agcctctccc tgtctccggg taaa                                           1344
```

<210> SEQ ID NO 177
<211> LENGTH: 215
<212> TYPE: PRT
<213> ORGANISM: Artificial Sequence
<220> FEATURE:
<223> OTHER INFORMATION: SAD-S35-Fab LC1 AA

<400> SEQUENCE: 177

```
Glu Ile Val Leu Thr Gln Ser Pro Ala Thr Leu Ser Leu Ser Pro Gly
  1               5                  10                  15
Glu Arg Ala Thr Leu Ser Cys Gly Ala Ser Gln Ser Val Ser Ser Ser
             20                  25                  30
Tyr Leu Ala Trp Tyr Gln Gln Lys Pro Gly Leu Ala Pro Arg Leu Leu
         35                  40                  45
Ile Tyr Asp Ala Ser Ser Arg Ala Thr Gly Ile Pro Asp Arg Phe Ser
     50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Ser Pro
                 85                  90                  95
Leu Thr Phe Gly Gly Gly Thr Lys Val Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
    130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
    210                 215
```

<210> SEQ ID NO 178

<211> LENGTH: 645
<212> TYPE: DNA
<213> ORGANISM: Artificial Sequence
<220> FEATURE:
<223> OTHER INFORMATION: SAD-S35-Fab LC1 DNA

<400> SEQUENCE: 178

```
gaaatagtgc tgacacagtc acccgcaact ctttctctct cacccggaga gagggctact    60
ctctcttgtg gagcttcaca gtctgtgtct tctagctacc tggcctggta tcagcagaag   120
ccaggacttg ccccccgact gttgatatat gatgcaagca gccgcgccac tggtattcct   180
gaccgattta gcgggagcgg gtccgggacc gacttcaccc tgactatatc cgactcgaa    240
ccagaagact tcgccgtcta ttattgtcaa cagtacggga gcagcccct cacatttggg    300
ggcggtacta aagtcgaaat taagcgtacg gtggctgcac catctgtctt catcttcccg   360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgt                   645
```

<210> SEQ ID NO 179
<211> LENGTH: 450
<212> TYPE: PRT
<213> ORGANISM: Artificial Sequence
<220> FEATURE:
<223> OTHER INFORMATION: D001-Fab HC1 AA

<400> SEQUENCE: 179

Gln Val Gln Leu Gln Gln Ser Gly Pro Glu Leu Met Lys Pro Gly Ala
1               5                   10                  15

Ser Val Lys Ile Ser Cys Lys Ala Ser Gly Tyr Ser Phe Thr Asn Tyr
            20                  25                  30

Tyr Ile His Trp Val Lys Gln Ser His Gly Lys Ser Leu Glu Trp Ile
        35                  40                  45

Gly Tyr Ile Asp Pro Phe Asn Gly Gly Thr Ser Asp Asn Leu Lys Phe
    50                  55                  60

Lys Gly Ala Ala Thr Leu Thr Val Asp Lys Ser Ser Ser Thr Ala Tyr
65                  70                  75                  80

Met His Leu Ser Ser Leu Thr Ser Glu Asp Ser Ala Val Tyr Tyr Cys
                85                  90                  95

Ala Arg Ser Glu Tyr Asp Pro Tyr Tyr Val Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

```
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 180
<211> LENGTH: 1350
<212> TYPE: DNA
<213> ORGANISM: Artificial Sequence
<220> FEATURE:
<223> OTHER INFORMATION: D001-Fab HC1 DNA

<400> SEQUENCE: 180
caagtacagt tgcaacagtc tggacccgag ttgatgaagc caggcgctag cgttaaaata      60
agttgcaagg cttcaggcta cagcttcacc aactactaca tcattgggt caagcagtca     120 catggaaaga gtttggagtg gataggctac atagatcctt caacggggg aactagtgat     180 aacttgaaat ttaagggcgc agcaactctg accgtggaca atctagctc tactgcttat     240 atgcacctct ctagcttgac ttctgaagac agtgctgtat attattgcgc cagaagtgag     300
tacgatccct attatgttat ggattactgg ggacaaggca cctctgtaac cgtatccagc     360
gcctccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
```

```
aaatcttgtg acaaaactca cacatgtcca ccgtgcccag cacctgaact cctgggggga      720
ccgtcagtct tcctcttccc cccaaaaccc aaggacaccc tcatgatctc ccggacccct      780
gaggtcacat gcgtggtggt ggacgtgagc cacgaagacc ctgaggtcaa gttcaactgg      840
tacgtggacg gcgtggaggt gcataatgcc aagacaaagc cgcgggagga gcagtacaac      900
agcacgtacc gtgtggtcag cgtcctcacc gtcctgcacc aggactggct gaatggcaag      960
gagtacaagt gcaaggtctc caacaaagcc ctcccagccc ccatcgagaa aaccatctcc     1020
aaagccaaag ggcagccccg agaaccacag gtgtacaccc tgcccccatc ccgggaggag     1080
atgaccaaga accaggtcag cctgacctgc ctggtcaaag gcttctatcc cagcgacatc     1140
gccgtggagt gggagagcaa tgggcagccg gagaacaact acaagaccac gcctcccgtg     1200
ctggactccg acggctcctt cttcctctac agcaagctca ccgtggacaa gtctagatgg     1260
cagcagggga acgtcttctc atgctccgtg atgcatgagg ctctgcacaa ccactacacg     1320
cagaagagcc tctccctgtc tccgggtaaa                                     1350
```

```
<210> SEQ ID NO 181
<211> LENGTH: 214
<212> TYPE: PRT
<213> ORGANISM: Artificial Sequence
<220> FEATURE:
<223> OTHER INFORMATION: D001-Fab LC1 AA

<400> SEQUENCE: 181

Glu Ile Val Leu Thr Gln Ser Pro Asp Thr Leu Ser Val Thr Pro Gly
1               5                   10                  15

Asp Ser Val Ser Leu Ser Cys Arg Ala Ser Gln Ser Ile Ser Ser Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Ile Tyr Phe Cys Gln Gln Thr Asn Phe Trp Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 182
```

<211> LENGTH: 642
<212> TYPE: DNA
<213> ORGANISM: Artificial Sequence
<220> FEATURE:
<223> OTHER INFORMATION: D001-Fab LC1 DNA

<400> SEQUENCE: 182

```
gaaattgttc ttacccaatc acctgataca ctgagtgtaa cacccggtga ctcagtttcc     60
ttgtcatgcc gagcctccca gagcatatcc agtaatttgc actggtatca gcagaaatcc    120
cacgagagcc cacggttgtt gattaaatac gctagccagt ccattagtgg gataccatca    180
cgtttcagtg gtcagggtc tgggactgac tttactctgt ccatcaacag cgtgaaaca     240
gaagattttg gaatatactt ctgccaacag acaaactttt ggccttatac atttggcggg    300
ggaactaagt tggaaattaa gcgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg ataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 183
<211> LENGTH: 1074
<212> TYPE: PRT
<213> ORGANISM: Artificial Sequence
<220> FEATURE:
<223> OTHER INFORMATION: EGFR-VHH-MSCD342-ACE2-18-725-Fc HC1 AA

<400> SEQUENCE: 183

```
Gln Val Lys Leu Glu Glu Ser Gly Gly Gly Ser Val Gln Thr Gly Gly
1               5                   10                  15

Ser Leu Arg Leu Thr Cys Ala Ala Ser Gly Phe Thr Phe Ser Ser Tyr
            20                  25                  30

Ala Met Gly Trp Phe Arg Gln Ala Pro Gly Lys Glu Arg Glu Phe Val
        35                  40                  45

Ser Gly Ile Ser Gly Ser Gly Gly Ser Thr Gly Tyr Ala Asp Ser Val
    50                  55                  60

Lys Gly Arg Phe Thr Ile Ser Arg Asp Asn Ala Lys Asn Thr Val Asp
65                  70                  75                  80

Leu Gln Met Asn Ser Leu Lys Pro Glu Asp Thr Ala Ile Tyr Tyr Cys
                85                  90                  95

Ala Ala Ala Ala Gly Ser Gly Gly Ser Gly Gly Ser Gly Ser Phe Asp
            100                 105                 110

Tyr Trp Gly Gln Gly Thr Gln Val Thr Val Ser Ser Gly Gly Gly Gly
        115                 120                 125

Ser Gly Gly Gly Gly Ser Gln Ser Thr Ile Glu Glu Gln Ala Lys Thr
    130                 135                 140

Phe Leu Asp Lys Phe Asn His Glu Ala Glu Asp Leu Phe Tyr Gln Ser
145                 150                 155                 160

Ser Leu Ala Ser Trp Asn Tyr Asn Thr Asn Ile Thr Glu Glu Asn Val
                165                 170                 175

Gln Asn Met Asn Asn Ala Gly Asp Lys Trp Ser Ala Phe Leu Lys Glu
            180                 185                 190

Gln Ser Thr Leu Ala Gln Met Tyr Pro Leu Gln Glu Ile Gln Asn Leu
        195                 200                 205
```

```
Thr Val Lys Leu Gln Leu Gln Ala Leu Gln Gln Asn Gly Ser Ser Val
    210                 215                 220

Leu Ser Glu Asp Lys Ser Lys Arg Leu Asn Thr Ile Leu Asn Thr Met
225                 230                 235                 240

Ser Thr Ile Tyr Ser Thr Gly Lys Val Cys Asn Pro Asp Asn Pro Gln
                245                 250                 255

Glu Cys Leu Leu Leu Glu Pro Gly Leu Asn Glu Ile Met Ala Asn Ser
            260                 265                 270

Leu Asp Tyr Asn Glu Arg Leu Trp Ala Trp Ser Trp Arg Ser Glu
                275                 280                 285

Val Gly Lys Gln Leu Arg Pro Leu Tyr Glu Glu Tyr Val Val Leu Lys
    290                 295                 300

Asn Glu Met Ala Arg Ala Asn His Tyr Glu Asp Tyr Gly Asp Tyr Trp
305                 310                 315                 320

Arg Gly Asp Tyr Glu Val Asn Gly Val Asp Gly Tyr Asp Tyr Ser Arg
                325                 330                 335

Gly Gln Leu Ile Glu Asp Val Glu His Thr Phe Glu Glu Ile Lys Pro
            340                 345                 350

Leu Tyr Glu His Leu His Ala Tyr Val Arg Ala Lys Leu Met Asn Ala
                355                 360                 365

Tyr Pro Ser Tyr Ile Ser Pro Ile Gly Cys Leu Pro Ala His Leu Leu
    370                 375                 380

Gly Asp Met Trp Gly Arg Phe Trp Thr Asn Leu Tyr Ser Leu Thr Val
385                 390                 395                 400

Pro Phe Gly Gln Lys Pro Asn Ile Asp Val Thr Asp Ala Met Val Asp
                405                 410                 415

Gln Ala Trp Asp Ala Gln Arg Ile Phe Lys Glu Ala Glu Lys Phe Phe
            420                 425                 430

Val Ser Val Gly Leu Pro Asn Met Thr Gln Gly Phe Trp Glu Asn Ser
                435                 440                 445

Met Leu Thr Asp Pro Gly Asn Val Gln Lys Ala Val Cys His Pro Thr
    450                 455                 460

Ala Trp Asp Leu Gly Lys Gly Asp Phe Arg Ile Leu Met Cys Thr Lys
465                 470                 475                 480

Val Thr Met Asp Asp Phe Leu Thr Ala His His Glu Met Gly His Ile
                485                 490                 495

Gln Tyr Asp Met Ala Tyr Ala Ala Gln Pro Phe Leu Leu Arg Asn Gly
            500                 505                 510

Ala Asn Glu Gly Phe His Glu Ala Val Gly Glu Ile Met Ser Leu Ser
                515                 520                 525

Ala Ala Thr Pro Lys His Leu Lys Ser Ile Gly Leu Leu Ser Pro Asp
    530                 535                 540

Phe Gln Glu Asp Asn Glu Thr Glu Ile Asn Phe Leu Leu Lys Gln Ala
545                 550                 555                 560

Leu Thr Ile Val Gly Thr Leu Pro Phe Thr Tyr Met Leu Glu Lys Trp
                565                 570                 575

Arg Trp Met Val Phe Lys Gly Glu Ile Pro Lys Asp Gln Trp Met Lys
            580                 585                 590

Lys Trp Trp Glu Met Lys Arg Glu Ile Val Gly Val Val Glu Pro Val
                595                 600                 605

Pro His Asp Glu Thr Tyr Cys Asp Pro Ala Ser Leu Phe His Val Ser
    610                 615                 620

Asn Asp Tyr Ser Phe Ile Arg Tyr Tyr Thr Arg Thr Leu Tyr Gln Phe
```

```
             625                 630                 635                 640
        Gln Phe Gln Glu Ala Leu Cys Gln Ala Ala Lys His Glu Gly Pro Leu
                        645                 650                 655

His Lys Cys Asp Ile Ser Asn Ser Thr Glu Ala Gly Gln Lys Leu Phe
                        660                 665                 670

Asn Met Leu Arg Leu Gly Lys Ser Glu Pro Trp Thr Leu Ala Leu Glu
                        675                 680                 685

Asn Val Val Gly Ala Lys Asn Met Asn Val Arg Pro Leu Leu Asn Tyr
                        690                 695                 700

Phe Glu Pro Leu Phe Thr Trp Leu Lys Asp Gln Asn Lys Asn Ser Phe
        705                 710                 715                 720

Val Gly Trp Ser Thr Asp Trp Ser Pro Tyr Ala Asp Gln Ser Ile Lys
                        725                 730                 735

Val Arg Ile Ser Leu Lys Ser Ala Leu Gly Asp Lys Ala Tyr Glu Trp
                        740                 745                 750

Asn Asp Asn Glu Met Tyr Leu Phe Arg Ser Ser Val Ala Tyr Ala Met
                        755                 760                 765

Arg Gln Tyr Phe Leu Lys Val Lys Asn Gln Met Ile Leu Phe Gly Glu
                        770                 775                 780

Glu Asp Val Arg Val Ala Asn Leu Lys Pro Arg Ile Ser Phe Asn Phe
        785                 790                 795                 800

Phe Val Thr Ala Pro Lys Asn Val Ser Asp Ile Ile Pro Arg Thr Glu
                        805                 810                 815

Val Glu Lys Ala Ile Arg Met Ser Arg Ser Arg Ile Asn Asp Ala Phe
                        820                 825                 830

Arg Leu Asn Asp Asn Ser Leu Glu Phe Leu Glu Pro Lys Ser Ser Asp
                        835                 840                 845

Lys Thr His Thr Cys Pro Pro Cys Pro Ala Pro Glu Leu Leu Gly Gly
                        850                 855                 860

Pro Ser Val Phe Leu Phe Pro Pro Lys Pro Lys Asp Thr Leu Met Ile
        865                 870                 875                 880

Ser Arg Thr Pro Glu Val Thr Cys Val Val Val Asp Val Ser His Glu
                        885                 890                 895

Asp Pro Glu Val Lys Phe Asn Trp Tyr Val Asp Gly Val Glu Val His
                        900                 905                 910

Asn Ala Lys Thr Lys Pro Arg Glu Glu Gln Tyr Asn Ser Thr Tyr Arg
                        915                 920                 925

Val Val Ser Val Leu Thr Val Leu His Gln Asp Trp Leu Asn Gly Lys
                        930                 935                 940

Glu Tyr Lys Cys Lys Val Ser Asn Lys Ala Leu Pro Ala Pro Ile Glu
        945                 950                 955                 960

Lys Thr Ile Ser Lys Ala Lys Gly Gln Pro Arg Glu Pro Gln Val Tyr
                        965                 970                 975

Thr Leu Pro Pro Ser Arg Glu Glu Met Thr Lys Asn Gln Val Ser Leu
                        980                 985                 990

Thr Cys Leu Val Lys Gly Phe Tyr Pro Ser Asp Ile Ala Val Glu Trp
                        995                 1000                1005

Glu Ser Asn Gly Gln Pro Glu Asn Asn Tyr Lys Thr Thr Pro Pro
                        1010                1015                1020

Val Leu Asp Ser Asp Gly Ser Phe Phe Leu Tyr Ser Lys Leu Thr
                        1025                1030                1035

Val Asp Lys Ser Arg Trp Gln Gln Gly Asn Val Phe Ser Cys Ser
                        1040                1045                1050
```

```
Val Met His Glu Ala Leu His Asn His Tyr Thr Gln Lys Ser Leu
    1055                1060                1065
Ser Leu Ser Pro Gly Lys
    1070

<210> SEQ ID NO 184
<211> LENGTH: 3222
<212> TYPE: DNA
<213> ORGANISM: Artificial Sequence
<220> FEATURE:
<223> OTHER INFORMATION: EGFR-VHH-MSCD342-ACE2-18-725-Fc HC1 DNA

<400> SEQUENCE: 184
caggtgaaac tggaagagag tgggggaggg tctgttcaaa ctggtggaag tctcaggctc    60
acatgcgctg cctctgggtt cactttctcc agctacgcaa tggggtggtt tagacaagcg   120
cccggtaaag agagggaatt tgtttccggc atatcaggtt ctggaggctc aacgggtac    180
gcggacagcg taaagggaag atttaccatc tcacgcgata cgctaaaaaa tacggttgat   240
cttcaaatga actctttgaa gcccgaagac acggcgattt actattgtgc agcagcggcc   300
gggagcggag gctctggcgg ttctggctca ttcgattact gggggcaggg tacgcaggta   360
accgtatctt caggaggcgg agggagtggc gggggaggct ctcaatccac catcgaggaa   420
caggctaaga cctttctgga caagttcaac cacgaggccg aggacctgtt ctaccagagc   480
agcctggctt cctggaacta caacacaaac atcaccgagg agaacgtgca gaacatgaac   540
aacgctggcg acaagtggtc cgcctttctc aaagagcagt ctaccctggc ccagatgtat   600
cctctgcaag agatccagaa tctcaccgtg aaactgcagc tgcaggccct gcagcagaac   660
ggctcctctg tgctgtccga ggataagtcc aagcggctca acaccatcct gaacaccatg   720
tctacaatct actccaccgg caaggtgtgc aaccccgaca ccctcagga gtgcctgctg   780
ctggaacctg gcctgaatga aatcatggct aattctctgg actacaacga gcgcctgtgg   840
gcttgggagt cttggcggtc tgaagtgggc aagcagctga ccactgta cgaagagtac   900
gtggtgctga gaacgagat ggctagagcc aatcactacg aggactacgg cgactactgg   960
cggggcgatt acgaggtgaa cggcgtggac ggctacgatt actctcgcgg ccaactgatc  1020
gaggacgtcg agcacacctt cgaggaaatc aagcccctgt atgaacatct gcacgcctac  1080
gtgagagcca agctgatgaa cgcctaccct cctacatct ctcctatcgg atgtctgcct  1140
gctcatctgc tgggagatat gtggggcaga ttctggacca acctgtactc cctgaccgtg  1200
cccttcggcc agaagccaaa catcgacgtg accgatgcta tggtggacca ggcctgggac  1260
gcccagagaa tcttcaaaga agctgagaag ttcttcgtgt ctgttggact gcccaacatg  1320
acccagggct ctgggagaa ctccatgctg accgacccg caacgtgca gaaagctgtg  1380
tgccatccta ccgcctggga tctgggcaag ggcgacttca gaatcctgat gtgcaccaag  1440
gtgaccatgg acgacttcct gaccgctcac cacgagatgg ccacatcca gtacgacatg  1500
gcctacgctg ctcagccttt cctactgcgg aacggagcaa acgagggctt ccatgaggcc  1560
gtgggcgaga tcatgtccct gtctgctgct ccccctaagc acctgaagtc tatcggcctg  1620
ctgagccctg atttccagga agataacgag acagagatca acttcctgct gaaacaggcc  1680
ctgaccatcg tgggcacact gccttccacc tacatgctgg aaaagtggag atggatggtg  1740
ttcaagggcg agatccctaa ggaccagtgg atgaagaagt ggtgggaaat gaagagagag  1800
atcgtgggcg tggtggagcc cgtgcctcac gacgaaacat actgtgatcc tgcctctctg  1860
```

| | |
|---|---|
| ttccacgtgt ccaacgacta ctcttttatc agatactaca ccaggaccct gtatcagttt | 1920 |
| cagttccaag aagcgctgtg ccaagccgcc aagcacgaag ccctctgca caagtgcgac | 1980 |
| atctccaatt ccactgaagc cggccagaag ctgttcaaca tgctgagact gggcaaatcc | 2040 |
| gagccttgga ccctggccct ggaaaatgtc gtgggcgcca gaacatgaa cgtgcggcct | 2100 |
| ctgctgaact acttcgagcc tttgttcacc tggctgaagg accagaacaa gaactccttc | 2160 |
| gtcggctggt ccaccgactg gtctccttac gccgatcagt ccatcaaggt gcggatctct | 2220 |
| ctgaagtctg ctctggggga caaggcctac gagtggaacg acaatgagat gtacctgttc | 2280 |
| cggtcctccg tggcttacgc catgcggcag tacttcctga agtgaagaa ccagatgata | 2340 |
| ctgtttggtg aagaggacgt gagagtggcc aacctgaagc ctagaatcag cttcaacttc | 2400 |
| ttcgtaacag ctcctaagaa tgtgtccgac atcatcccca gaaccgaagt ggaaaaggcc | 2460 |
| atccggatgt ccagaagccg gatcaacgac gcctttagac tgaacgacaa cagcctggag | 2520 |
| ttcctggagc ccaaatctag cgacaaaact cacacatgtc caccgtgccc agcacctgaa | 2580 |
| ctcctggggg gaccgtcagt cttcctcttc cccccaaaac ccaaggacac cctcatgatc | 2640 |
| tcccggaccc ctgaggtcac atgcgtggtg gtggacgtga gccacgaaga ccctgaggtc | 2700 |
| aagttcaact ggtacgtgga cggcgtggag gtgcataatg ccaagacaaa gccgcgggag | 2760 |
| gagcagtaca acagcacgta ccgtgtggtc agcgtcctca ccgtcctgca ccaggactgg | 2820 |
| ctgaatggca aggagtacaa gtgcaaggtc tccaacaaag ccctcccagc ccccatcgag | 2880 |
| aaaaccatct ccaaagccaa agggcagccc cgagaaccac aggtgtacac cctgccccca | 2940 |
| tcccgggagg agatgaccaa gaaccaggtc agcctgacct gcctggtcaa aggcttctat | 3000 |
| cccagcgaca tcgccgtgga gtgggagagc aatgggcagc cggagaacaa ctacaagacc | 3060 |
| acgcctcccg tgctggactc cgacggctcc ttcttcctct acagcaagct caccgtggac | 3120 |
| aagtctagat ggcagcaggg gaacgtcttc tcatgctccg tgatgcatga ggctctgcac | 3180 |
| aaccactaca cgcagaagag cctctccctg tctccgggta aa | 3222 |

```
<210> SEQ ID NO 185
<211> LENGTH: 960
<212> TYPE: PRT
<213> ORGANISM: Artificial Sequence
<220> FEATURE:
<223> OTHER INFORMATION: EGFR-VHH-MSCD342-ACE2-18-611-Fc HC1 AA

<400> SEQUENCE: 185

Gln Val Lys Leu Glu Glu Ser Gly Gly Gly Ser Val Gln Thr Gly Gly
1               5                   10                  15

Ser Leu Arg Leu Thr Cys Ala Ala Ser Gly Phe Thr Phe Ser Ser Tyr
            20                  25                  30

Ala Met Gly Trp Phe Arg Gln Ala Pro Gly Lys Glu Arg Glu Phe Val
        35                  40                  45

Ser Gly Ile Ser Gly Ser Gly Gly Ser Thr Gly Tyr Ala Asp Ser Val
    50                  55                  60

Lys Gly Arg Phe Thr Ile Ser Arg Asp Asn Ala Lys Asn Thr Val Asp
65                  70                  75                  80

Leu Gln Met Asn Ser Leu Lys Pro Glu Asp Thr Ala Ile Tyr Tyr Cys
                85                  90                  95

Ala Ala Ala Ala Gly Ser Gly Gly Ser Gly Gly Ser Gly Ser Phe Asp
            100                 105                 110

Tyr Trp Gly Gln Gly Thr Gln Val Thr Val Ser Ser Gly Gly Gly Gly
        115                 120                 125
```

```
Ser Gly Gly Gly Gly Ser Gln Ser Thr Ile Glu Glu Gln Ala Lys Thr
    130             135             140
Phe Leu Asp Lys Phe Asn His Glu Ala Glu Asp Leu Phe Tyr Gln Ser
145             150             155             160
Ser Leu Ala Ser Trp Asn Tyr Asn Thr Asn Ile Thr Glu Glu Asn Val
            165             170             175
Gln Asn Met Asn Asn Ala Gly Asp Lys Trp Ser Ala Phe Leu Lys Glu
        180             185             190
Gln Ser Thr Leu Ala Gln Met Tyr Pro Leu Gln Glu Ile Gln Asn Leu
    195             200             205
Thr Val Lys Leu Gln Leu Gln Ala Leu Gln Gln Asn Gly Ser Ser Val
    210             215             220
Leu Ser Glu Asp Lys Ser Lys Arg Leu Asn Thr Ile Leu Asn Thr Met
225             230             235             240
Ser Thr Ile Tyr Ser Thr Gly Lys Val Cys Asn Pro Asp Asn Pro Gln
            245             250             255
Glu Cys Leu Leu Leu Glu Pro Gly Leu Asn Glu Ile Met Ala Asn Ser
        260             265             270
Leu Asp Tyr Asn Glu Arg Leu Trp Ala Trp Glu Ser Trp Arg Ser Glu
    275             280             285
Val Gly Lys Gln Leu Arg Pro Leu Tyr Glu Glu Tyr Val Val Leu Lys
    290             295             300
Asn Glu Met Ala Arg Ala Asn His Tyr Glu Asp Tyr Gly Asp Tyr Trp
305             310             315             320
Arg Gly Asp Tyr Glu Val Asn Gly Val Asp Gly Tyr Asp Tyr Ser Arg
            325             330             335
Gly Gln Leu Ile Glu Asp Val Glu His Thr Phe Glu Glu Ile Lys Pro
        340             345             350
Leu Tyr Glu His Leu His Ala Tyr Val Arg Ala Lys Leu Met Asn Ala
    355             360             365
Tyr Pro Ser Tyr Ile Ser Pro Ile Gly Cys Leu Pro Ala His Leu Leu
    370             375             380
Gly Asp Met Trp Gly Arg Phe Trp Thr Asn Leu Tyr Ser Leu Thr Val
385             390             395             400
Pro Phe Gly Gln Lys Pro Asn Ile Asp Val Thr Asp Ala Met Val Asp
            405             410             415
Gln Ala Trp Asp Ala Gln Arg Ile Phe Lys Glu Ala Glu Lys Phe Phe
        420             425             430
Val Ser Val Gly Leu Pro Asn Met Thr Gln Gly Phe Trp Glu Asn Ser
    435             440             445
Met Leu Thr Asp Pro Gly Asn Val Gln Lys Ala Val Cys His Pro Thr
    450             455             460
Ala Trp Asp Leu Gly Lys Gly Asp Phe Arg Ile Leu Met Cys Thr Lys
465             470             475             480
Val Thr Met Asp Asp Phe Leu Thr Ala His His Glu Met Gly His Ile
            485             490             495
Gln Tyr Asp Met Ala Tyr Ala Ala Gln Pro Phe Leu Leu Arg Asn Gly
        500             505             510
Ala Asn Glu Gly Phe His Glu Ala Val Gly Glu Ile Met Ser Leu Ser
    515             520             525
Ala Ala Thr Pro Lys His Leu Lys Ser Ile Gly Leu Leu Ser Pro Asp
    530             535             540
```

```
Phe Gln Glu Asp Asn Glu Thr Glu Ile Asn Phe Leu Leu Lys Gln Ala
545                 550                 555                 560

Leu Thr Ile Val Gly Thr Leu Pro Phe Thr Tyr Met Leu Glu Lys Trp
            565                 570                 575

Arg Trp Met Val Phe Lys Gly Glu Ile Pro Lys Asp Gln Trp Met Lys
            580                 585                 590

Lys Trp Trp Glu Met Lys Arg Glu Ile Val Gly Val Val Glu Pro Val
        595                 600                 605

Pro His Asp Glu Thr Tyr Cys Asp Pro Ala Ser Leu Phe His Val Ser
        610                 615                 620

Asn Asp Tyr Ser Phe Ile Arg Tyr Tyr Thr Arg Thr Leu Tyr Gln Phe
625                 630                 635                 640

Gln Phe Gln Glu Ala Leu Cys Gln Ala Ala Lys His Glu Gly Pro Leu
                645                 650                 655

His Lys Cys Asp Ile Ser Asn Ser Thr Glu Ala Gly Gln Lys Leu Phe
            660                 665                 670

Asn Met Leu Arg Leu Gly Lys Ser Glu Pro Trp Thr Leu Ala Leu Glu
            675                 680                 685

Asn Val Val Gly Ala Lys Asn Met Asn Val Arg Pro Leu Leu Asn Tyr
690                 695                 700

Phe Glu Pro Leu Phe Thr Trp Leu Lys Asp Gln Asn Lys Asn Ser Phe
705                 710                 715                 720

Val Gly Trp Ser Thr Asp Trp Ser Glu Pro Lys Ser Ser Asp Lys Thr
                725                 730                 735

His Thr Cys Pro Pro Cys Pro Ala Pro Glu Leu Leu Gly Gly Pro Ser
                740                 745                 750

Val Phe Leu Phe Pro Pro Lys Pro Lys Asp Thr Leu Met Ile Ser Arg
        755                 760                 765

Thr Pro Glu Val Thr Cys Val Val Val Asp Val Ser His Glu Asp Pro
770                 775                 780

Glu Val Lys Phe Asn Trp Tyr Val Asp Gly Val Glu Val His Asn Ala
785                 790                 795                 800

Lys Thr Lys Pro Arg Glu Glu Gln Tyr Asn Ser Thr Tyr Arg Val Val
                805                 810                 815

Ser Val Leu Thr Val Leu His Gln Asp Trp Leu Asn Gly Lys Glu Tyr
            820                 825                 830

Lys Cys Lys Val Ser Asn Lys Ala Leu Pro Ala Pro Ile Glu Lys Thr
        835                 840                 845

Ile Ser Lys Ala Lys Gly Gln Pro Arg Glu Pro Gln Val Tyr Thr Leu
850                 855                 860

Pro Pro Ser Arg Glu Glu Met Thr Lys Asn Gln Val Ser Leu Thr Cys
865                 870                 875                 880

Leu Val Lys Gly Phe Tyr Pro Ser Asp Ile Ala Val Glu Trp Glu Ser
                885                 890                 895

Asn Gly Gln Pro Glu Asn Asn Tyr Lys Thr Thr Pro Pro Val Leu Asp
            900                 905                 910

Ser Asp Gly Ser Phe Phe Leu Tyr Ser Lys Leu Thr Val Asp Lys Ser
        915                 920                 925

Arg Trp Gln Gln Gly Asn Val Phe Ser Cys Ser Val Met His Glu Ala
        930                 935                 940

Leu His Asn His Tyr Thr Gln Lys Ser Leu Ser Leu Ser Pro Gly Lys
945                 950                 955                 960
```

<210> SEQ ID NO 186
<211> LENGTH: 2880
<212> TYPE: DNA
<213> ORGANISM: Artificial Sequence
<220> FEATURE:
<223> OTHER INFORMATION: EGFR-VHH-MSCD342-ACE2-18-611-Fc HC1 DNA

<400> SEQUENCE: 186

```
caggtgaaac tggaagagag tgggggaggg tctgttcaaa ctggtggaag tctcaggctc      60
acatgcgctg cctctgggtt cactttctcc agctacgcaa tggggtggtt tagacaagcg     120
cccggtaaag agagggaatt tgtttccggc atatcaggtt ctggaggctc aacgggtac      180
gcggacagcg taaagggaag atttaccatc tcacgcgata cgctaaaaa tacggttgat      240
cttcaaatga actctttgaa gcccgaagac acggcgattt actattgtgc agcagcggcc     300
gggagcggag gctctggcgg ttctggctca ttcgattact gggggcaggg tacgcaggta     360
accgtatctt caggaggcgg agggagtggc gggggaggct ctcagtctac aatcgaagag     420
caggccaaga ccttttctgga caagttcaac catgaagccg aggacctgtt ctaccagtcc     480
agcctggcct cttggaacta aacaccaat atcaccgagg aaaacgtgca gaacatgaac     540
aacgccggcg acaagtggtc tgccttcctc aaagaacagt ctacactggc tcagatgtac     600
cccttgcaag agatccagaa cctgacagtg aagctgcaac tgcaggctct gcagcagaac     660
ggctcttccg tgctatctga ggataagtcc aagcggctga acaccatcct gaacacaatg     720
tccaccatct acagcaccgg caaagtgtgc aaccctgata atcctcaaga gtgtctgctt     780
ctggaacccg gcctgaacga gatcatggcc aactccctgg attataacga gaggctgtgg     840
gcttgggagt cctggcgcag cgaggtggga aagcagctca gacctctgta cgaagagtac     900
gtcgtgctga gaacgagat ggccagagcc aaccactacg aggactacgg cgactactgg     960
agaggcgact atgaagtcaa tggcgtagac ggctacgact actccagagg ccagctgatc    1020
gaggatgtgg agcacacctt cgaggagatc aagcctctgt acgaacatct gcacgcctac    1080
gtgcgggcca agctgatgaa cgcctaccct tcctacatct ccctatcgg ctgcctgcct    1140
gcccatctgc tggtgatat gtggggcaga ttctggacca acctgtattc tctcaccgtg    1200
cccttttggcc agaaacccaa tatcgacgtg accgacgcca tggtcgatca ggcctgggat    1260
gcccagagaa tcttcaaaga ggctgagaag ttcttcgtgt ccgtgggact gcctaacatg    1320
acccagggct tttgggaaaa ctccatgctg accgatcctg caacgtgca gaaggccgtg    1380
tgtcacccta ccgcttggga tctgggcaag ggcgattcc ggatcctgat gtgcaccaag    1440
gtgaccatgg acgacttcct aaccgctcac cacgagatgg ccacatcca gtacgacatg    1500
gcttacgccg ctcagccttt tctgctgcgg aacggagcta atgaaggct ccatgaagcc    1560
gtgggcgaaa tcatgtctct gtccgccgcc accctaagc acctgaagtc tatcggcctg    1620
ctgtctcctg acttccagga ggacaacgag acagagatca cttcctgct gaagcaggcc    1680
ctgacaatcg tgggcacct gcccttcacc tacatgctgg aaaagtggag atggatggtg    1740
ttcaagggcg aaatccccaa ggaccagtgg atgaaaaagt ggtgggagat gaagagagag    1800
attgttggcg tggtggaacc tgtgcctcac gacgagacct actgcgaccc cgctagcctg    1860
ttccacgtgt ccaacgacta ctctttcatc cggtactaca cagaaccct gtaccagttc    1920
cagttccagg aagctctgtg ccaggctgcc aaacacgaag ccctctgca agtgcgac    1980
atctctaaca gcaccgaggc cggacaaaag ctgttcaaca tgctgagact gggcaagtcc    2040
gagccttgga ccctggctct ggagaacgtg gtgggagcta agaacatgaa tgtgcggcca    2100
```

```
ctgctcaact acttcgagcc tctgtttacc tggctgaagg accagaacaa gaactccttc    2160
gtgggctggt ccaccgactg gtccgagccc aaatctagcg acaaaactca cacatgtcca    2220
ccgtgcccag cacctgaact cctgggggga ccgtcagtct tcctcttccc cccaaaaccc    2280
aaggacaccc tcatgatctc ccggacccct gaggtcacat gcgtggtggt ggacgtgagc    2340
cacgaagacc ctgaggtcaa gttcaactgg tacgtggacg gcgtggaggt gcataatgcc    2400
aagacaaagc cgcgggagga gcagtacaac agcacgtacc gtgtggtcag cgtcctcacc    2460
gtcctgcacc aggactggct gaatggcaag gagtacaagt gcaaggtctc caacaaagcc    2520
ctcccagccc ccatcgagaa aaccatctcc aaagccaaag gcagccccg  agaaccacag    2580 gtgtacaccc tgcccccatc ccgggaggag atgaccaaga accaggtcag cctgacctgc    2640
ctggtcaaag  gcttctatcc cagcgacatc gccgtggagt gggagagcaa tgggcagccg    2700
gagaacaact acaagaccac gcctcccgtg ctggactccg acggctcctt cttcctctac    2760
agcaagctca ccgtggacaa gtctagatgg cagcagggga acgtcttctc atgctccgtg    2820
atgcatgagg ctctgcacaa ccactacacg cagaagagcc tctccctgtc tccgggtaaa    2880
```

<210> SEQ ID NO 187
<211> LENGTH: 1073
<212> TYPE: PRT
<213> ORGANISM: Artificial Sequence
<220> FEATURE:
<223> OTHER INFORMATION: EGFR-VHH-Fc-MSCD342-ACE2-18-725 HC1 AA

<400> SEQUENCE: 187

```
Gln Val Lys Leu Glu Glu Ser Gly Gly Gly Ser Val Gln Thr Gly Gly
1               5                   10                  15

Ser Leu Arg Leu Thr Cys Ala Ala Ser Gly Phe Thr Phe Ser Ser Tyr
            20                  25                  30

Ala Met Gly Trp Phe Arg Gln Ala Pro Gly Lys Glu Arg Glu Phe Val
        35                  40                  45

Ser Gly Ile Ser Gly Ser Gly Gly Ser Thr Gly Tyr Ala Asp Ser Val
    50                  55                  60

Lys Gly Arg Phe Thr Ile Ser Arg Asp Asn Ala Lys Asn Thr Val Asp
65                  70                  75                  80

Leu Gln Met Asn Ser Leu Lys Pro Glu Asp Thr Ala Ile Tyr Tyr Cys
                85                  90                  95

Ala Ala Ala Ala Gly Ser Gly Gly Ser Gly Gly Ser Gly Ser Phe Asp
            100                 105                 110

Tyr Trp Gly Gln Gly Thr Gln Val Thr Val Ser Ser Glu Pro Lys Ser
        115                 120                 125

Ser Asp Lys Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
```

```
        225                 230                 235                 240
Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
                260                 265                 270

Ser Leu Thr Cys Leu Val Lys Gly Phe Tyr Pro Ser Asp Ile Ala Val
                275                 280                 285

Glu Trp Glu Ser Asn Gly Gln Pro Glu Asn Asn Tyr Lys Thr Thr Pro
                290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
                340                 345                 350

Ser Pro Gly Gly Gly Gly Ser Gly Gly Gly Ser Gln Ser Thr
                355                 360                 365

Ile Glu Glu Gln Ala Lys Thr Phe Leu Asp Lys Phe Asn His Glu Ala
                370                 375                 380

Glu Asp Leu Phe Tyr Gln Ser Ser Leu Ala Ser Trp Asn Tyr Asn Thr
385                 390                 395                 400

Asn Ile Thr Glu Glu Asn Val Gln Asn Met Asn Asn Ala Gly Asp Lys
                405                 410                 415

Trp Ser Ala Phe Leu Lys Glu Gln Ser Thr Leu Ala Gln Met Tyr Pro
                420                 425                 430

Leu Gln Glu Ile Gln Asn Leu Thr Val Lys Leu Gln Leu Gln Ala Leu
                435                 440                 445

Gln Gln Asn Gly Ser Ser Val Leu Ser Glu Asp Lys Ser Lys Arg Leu
                450                 455                 460

Asn Thr Ile Leu Asn Thr Met Ser Thr Ile Tyr Ser Thr Gly Lys Val
465                 470                 475                 480

Cys Asn Pro Asp Asn Pro Gln Glu Cys Leu Leu Leu Glu Pro Gly Leu
                485                 490                 495

Asn Glu Ile Met Ala Asn Ser Leu Asp Tyr Asn Glu Arg Leu Trp Ala
                500                 505                 510

Trp Glu Ser Trp Arg Ser Glu Val Gly Lys Gln Leu Arg Pro Leu Tyr
                515                 520                 525

Glu Glu Tyr Val Val Leu Lys Asn Glu Met Ala Arg Ala Asn His Tyr
                530                 535                 540

Glu Asp Tyr Gly Asp Tyr Trp Arg Gly Asp Tyr Glu Val Asn Gly Val
545                 550                 555                 560

Asp Gly Tyr Asp Tyr Ser Arg Gly Gln Leu Ile Glu Asp Val Glu His
                565                 570                 575

Thr Phe Glu Glu Ile Lys Pro Leu Tyr Glu His Leu His Ala Tyr Val
                580                 585                 590

Arg Ala Lys Leu Met Asn Ala Tyr Pro Ser Tyr Ile Ser Pro Ile Gly
                595                 600                 605

Cys Leu Pro Ala His Leu Leu Gly Asp Met Trp Gly Arg Phe Trp Thr
                610                 615                 620

Asn Leu Tyr Ser Leu Thr Val Pro Phe Gly Gln Lys Pro Asn Ile Asp
625                 630                 635                 640

Val Thr Asp Ala Met Val Asp Gln Ala Trp Asp Ala Gln Arg Ile Phe
                645                 650                 655
```

```
Lys Glu Ala Glu Lys Phe Phe Val Ser Val Gly Leu Pro Asn Met Thr
                660                 665                 670

Gln Gly Phe Trp Glu Asn Ser Met Leu Thr Asp Pro Gly Asn Val Gln
            675                 680                 685

Lys Ala Val Cys His Pro Thr Ala Trp Asp Leu Gly Lys Gly Asp Phe
690                 695                 700

Arg Ile Leu Met Cys Thr Lys Val Thr Met Asp Asp Phe Leu Thr Ala
705                 710                 715                 720

His His Glu Met Gly His Ile Gln Tyr Asp Met Ala Tyr Ala Ala Gln
                725                 730                 735

Pro Phe Leu Leu Arg Asn Gly Ala Asn Glu Gly Phe His Glu Ala Val
            740                 745                 750

Gly Glu Ile Met Ser Leu Ser Ala Ala Thr Pro Lys His Leu Lys Ser
        755                 760                 765

Ile Gly Leu Leu Ser Pro Asp Phe Gln Glu Asp Asn Glu Thr Glu Ile
770                 775                 780

Asn Phe Leu Leu Lys Gln Ala Leu Thr Ile Val Gly Thr Leu Pro Phe
785                 790                 795                 800

Thr Tyr Met Leu Glu Lys Trp Arg Trp Met Val Phe Lys Gly Glu Ile
                805                 810                 815

Pro Lys Asp Gln Trp Met Lys Lys Trp Trp Glu Met Lys Arg Glu Ile
            820                 825                 830

Val Gly Val Val Glu Pro Val Pro His Asp Glu Thr Tyr Cys Asp Pro
        835                 840                 845

Ala Ser Leu Phe His Val Ser Asn Asp Tyr Ser Phe Ile Arg Tyr Tyr
850                 855                 860

Thr Arg Thr Leu Tyr Gln Phe Gln Phe Gln Glu Ala Leu Cys Gln Ala
865                 870                 875                 880

Ala Lys His Glu Gly Pro Leu His Lys Cys Asp Ile Ser Asn Ser Thr
                885                 890                 895

Glu Ala Gly Gln Lys Leu Phe Asn Met Leu Arg Leu Gly Lys Ser Glu
            900                 905                 910

Pro Trp Thr Leu Ala Leu Glu Asn Val Val Gly Ala Lys Asn Met Asn
        915                 920                 925

Val Arg Pro Leu Leu Asn Tyr Phe Glu Pro Leu Phe Thr Trp Leu Lys
930                 935                 940

Asp Gln Asn Lys Asn Ser Phe Val Gly Trp Ser Thr Asp Trp Ser Pro
945                 950                 955                 960

Tyr Ala Asp Gln Ser Ile Lys Val Arg Ile Ser Leu Lys Ser Ala Leu
                965                 970                 975

Gly Asp Lys Ala Tyr Glu Trp Asn Asp Asn Glu Met Tyr Leu Phe Arg
            980                 985                 990

Ser Ser Val Ala Tyr Ala Met Arg Gln Tyr Phe Leu Lys Val Lys Asn
        995                 1000                1005

Gln Met Ile Leu Phe Gly Glu Glu Asp Val Arg Val Ala Asn Leu
        1010                1015                1020

Lys Pro Arg Ile Ser Phe Asn Phe Phe Val Thr Ala Pro Lys Asn
        1025                1030                1035

Val Ser Asp Ile Ile Pro Arg Thr Glu Val Glu Lys Ala Ile Arg
        1040                1045                1050

Met Ser Arg Ser Arg Ile Asn Asp Ala Phe Arg Leu Asn Asp Asn
        1055                1060                1065
```

Ser Leu Glu Phe Leu
     1070

<210> SEQ ID NO 188
<211> LENGTH: 3219
<212> TYPE: DNA
<213> ORGANISM: Artificial Sequence
<220> FEATURE:
<223> OTHER INFORMATION: EGFR-VHH-Fc-MSCD342-ACE2-18-725 HC1 DNA

<400> SEQUENCE: 188

```
caggtgaaac tggaagagag tgggggaggg tctgttcaaa ctggtggaag tctcaggctc      60
acatgcgctg cctctgggtt cactttctcc agctacgcaa tggggtggtt tagacaagcg     120
cccggtaaag agagggaatt tgtttccggc atatcaggtt ctggaggctc aacggggtac     180
gcggacagcg taaagggaag atttaccatc tcacgcgata cgctaaaaaa tacgttgat     240
cttcaaatga actctttgaa gcccgaagac acggcgattt actattgtgc agcagcggcc     300
gggagcggag gctctggcgg ttctggctca ttcgattact gggggcaggg tacgcaggta     360
accgtatctt cagagcccaa atctagcgac aaaactcaca catgtccacc gtgcccagca     420
cctgaactcc tggggggacc gtcagtcttc ctcttccccc caaaacccaa ggacaccctc     480
atgatctccc ggacccctga ggtcacatgc gtggtggtgg acgtgagcca cgaagaccct     540
gaggtcaagt tcaactggta cgtggacggc gtggaggtgc ataatgccaa gacaaagccg     600
cgggaggagc agtacaacag cacgtaccgt gtggtcagcg tcctcaccgt cctgcaccag     660
gactggctga atggcaagga gtacaagtgc aaggtctcca acaaagccct cccagccccc     720
atcgagaaaa ccatctccaa agccaaaggg cagccccgag aaccacaggt gtacaccctg     780
cccccatccc gggaggagat gaccaagaac caggtcagcc tgacctgcct ggtcaaaggc     840
ttctatccca gcgacatcgc cgtggagtgg gagagcaatg ggcagccgga gaacaactac     900
aagaccacgc ctcccgtgct ggactccgac ggctccttct tcctctacag caagctcacc     960
gtggacaagt ctagatggca gcaggggaac gtcttctcat gctccgtgat gcatgaggct    1020
ctgcacaacc actacacgca gaagagcctc tccctgtctc cgggtggagg cggagggagt    1080
ggcggggag gctctcaatc caccatcgag gaacaggcta gacctttct ggacaagttc    1140
aaccacgagg ccgaggacct gttctaccag agcagcctgg cttcctggaa ctacaacaca    1200
aacatcaccg aggagaacgt gcagaacatg aacaacgctg cgacaagtg gtccgccttt    1260
ctcaaagagc agtctaccct ggcccagatg tatcctctgc aagagatcca gaatctcacc    1320
gtgaaactgc agctgcaggc cctgcagcag aacggctcct ctgtgctgtc cgaggataag    1380
tccaagcggc tcaacaccat cctgaacacc atgtctacaa tctactccac cggcaaggtg    1440
tgcaaccccg acaaccctca ggagtgcctg ctgctggaac tggcctgaa tgaaatcatg    1500
gctaattctc tggactacaa cgagcgcctg tgggcttggg agtcttggcg gtctgaagtg    1560
ggcaagcagc tgagaccact gtacgaagag tacgtggtgc tgaagaacga gatggctaga    1620
gccaatcact acgaggacta cggcgactac tggcggggcg attacgaggt gaacggcgtg    1680
gacggctacg attactctcg cggccaactg atcgaggacg tcgagcacac cttcgaggaa    1740
atcaagcccc tgtatgaaca tctgcacgcc tacgtgagac ccagctgat gaacgcctac    1800
ccttcctaca tctctccgat cggatgtctg cctgctcatc tgctgggaga tatgtgggc    1860
agattctgga ccaacctgta ctccctgacc gtgccttcg ccagaagcc aaacatcgac    1920
gtgaccgatg ctatggtgga ccaggcctgg gacgcccaga gaatcttcaa agaagctgag    1980
```

```
aagttcttcg tgtctgttgg actgcccaac atgacccagg gcttctggga gaactccatg    2040
ctgaccgacc ccggcaacgt gcagaaagct gtgtgccatc ctaccgcctg ggatctgggc    2100
aagggcgact tcagaatcct gatgtgcacc aaggtgacca tggacgactt cctgaccgct    2160
caccacgaga tgggccacat ccagtacgac atggcctacg ctgctcagcc tttcctactg    2220
cggaacggag caaacgaggg cttccatgag gccgtgggcg agatcatgtc cctgtctgct    2280
gctaccccta agcacctgaa gtctatcggc ctgctgagcc ctgatttcca ggaagataac    2340
gagacagaga tcaacttcct gctgaaacag gccctgacca tcgtgggcac actgcctttc    2400
acctacatgc tggaaaagtg gagatggatg gtgttcaagg gcgagatccc taaggaccag    2460
tggatgaaga agtggtggga atgaagagag agatcgtgg gcgtggtgga gcccgtgcct    2520
cacgacgaaa catactgtga tcctgcctct ctgttccacg tgtccaacga ctactctttt    2580
atcagatact acaccaggac cctgtatcag tttcagttcc agaagcgct gtgccaagcc    2640 gccaagcacg aaggccctct gcacaagtgc gacatctcca attccactga gccggccag    2700 aagctgttca acatgctgag actgggcaaa tccgagcctt ggaccctggc cctggaaaat    2760
gtcgtgggcg ccaagaacat gaacgtgcgg cctctgctga actacttcga gcctttgttc    2820
acctggctga aggaccagaa caagaactcc ttcgtcggct ggtccaccga ctggtctcct    2880
tacgccgatc agtccatcaa ggtgcggatc tctctgaagt ctgctctggg ggacaaggcc    2940
tacgagtgga cgacaatga tgtacctg ttccggtcct ccgtggctta cgccatgcgg    3000
cagtacttcc tgaaagtgaa gaaccagatg atactgtttg gtgaagagga cgtgagagtg    3060
gccaacctga gcctagaat cagcttcaac ttcttcgtaa cagctcctaa gaatgtgtcc    3120
gacatcatcc ccagaaccga agtggaaaag gccatccgga tgtccagaag ccggatcaac    3180
gacgccttta gactgaacga caacagcctg gagttcctg                           3219
```

<210> SEQ ID NO 189
<211> LENGTH: 959
<212> TYPE: PRT
<213> ORGANISM: Artificial Sequence
<220> FEATURE:
<223> OTHER INFORMATION: EGFR-VHH-Fc-MSCD342-ACE2-18-611 HC1 AA

<400> SEQUENCE: 189

```
Gln Val Lys Leu Glu Glu Ser Gly Gly Gly Ser Val Gln Thr Gly Gly
1               5                   10                  15

Ser Leu Arg Leu Thr Cys Ala Ala Ser Gly Phe Thr Phe Ser Ser Tyr
            20                  25                  30

Ala Met Gly Trp Phe Arg Gln Ala Pro Gly Lys Glu Arg Glu Phe Val
        35                  40                  45

Ser Gly Ile Ser Gly Ser Gly Gly Ser Thr Gly Tyr Ala Asp Ser Val
    50                  55                  60

Lys Gly Arg Phe Thr Ile Ser Arg Asp Asn Ala Lys Asn Thr Val Asp
65                  70                  75                  80

Leu Gln Met Asn Ser Leu Lys Pro Glu Asp Thr Ala Ile Tyr Tyr Cys
                85                  90                  95

Ala Ala Ala Ala Gly Ser Gly Gly Ser Gly Gly Ser Gly Ser Phe Asp
            100                 105                 110

Tyr Trp Gly Gln Gly Thr Gln Val Thr Val Ser Ser Glu Pro Lys Ser
        115                 120                 125

Ser Asp Lys Thr His Thr Cys Pro Pro Cys Pro Ala Pro Glu Leu Leu
    130                 135                 140
```

```
Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Gly Gly Gly Ser Gly Gly Gly Ser Gln Ser Thr
        355                 360                 365

Ile Glu Glu Gln Ala Lys Thr Phe Leu Asp Lys Phe Asn His Glu Ala
    370                 375                 380

Glu Asp Leu Phe Tyr Gln Ser Ser Leu Ala Ser Trp Asn Tyr Asn Thr
385                 390                 395                 400

Asn Ile Thr Glu Glu Asn Val Gln Asn Met Asn Asn Ala Gly Asp Lys
                405                 410                 415

Trp Ser Ala Phe Leu Lys Glu Gln Ser Thr Leu Ala Gln Met Tyr Pro
            420                 425                 430

Leu Gln Glu Ile Gln Asn Leu Thr Val Lys Leu Gln Leu Gln Ala Leu
        435                 440                 445

Gln Gln Asn Gly Ser Ser Val Leu Ser Glu Asp Lys Ser Lys Arg Leu
    450                 455                 460

Asn Thr Ile Leu Asn Thr Met Ser Thr Ile Tyr Ser Thr Gly Lys Val
465                 470                 475                 480

Cys Asn Pro Asp Asn Pro Gln Glu Cys Leu Leu Leu Glu Pro Gly Leu
                485                 490                 495

Asn Glu Ile Met Ala Asn Ser Leu Asp Tyr Asn Glu Arg Leu Trp Ala
            500                 505                 510

Trp Glu Ser Trp Arg Ser Glu Val Gly Lys Gln Leu Arg Pro Leu Tyr
        515                 520                 525

Glu Glu Tyr Val Val Leu Lys Asn Glu Met Ala Arg Ala Asn His Tyr
    530                 535                 540

Glu Asp Tyr Gly Asp Tyr Trp Arg Gly Asp Tyr Glu Val Asn Gly Val
545                 550                 555                 560

Asp Gly Tyr Asp Tyr Ser Arg Gly Gln Leu Ile Glu Asp Val Glu His
```

```
                565                 570                 575
Thr Phe Glu Glu Ile Lys Pro Leu Tyr Glu His Leu His Ala Tyr Val
            580                 585                 590

Arg Ala Lys Leu Met Asn Ala Tyr Pro Ser Tyr Ile Ser Pro Ile Gly
            595                 600                 605

Cys Leu Pro Ala His Leu Leu Gly Asp Met Trp Gly Arg Phe Trp Thr
            610                 615                 620

Asn Leu Tyr Ser Leu Thr Val Pro Phe Gly Gln Lys Pro Asn Ile Asp
625                 630                 635                 640

Val Thr Asp Ala Met Val Asp Gln Ala Trp Asp Ala Gln Arg Ile Phe
            645                 650                 655

Lys Glu Ala Glu Lys Phe Phe Val Ser Val Gly Leu Pro Asn Met Thr
            660                 665                 670

Gln Gly Phe Trp Glu Asn Ser Met Leu Thr Asp Pro Gly Asn Val Gln
            675                 680                 685

Lys Ala Val Cys His Pro Thr Ala Trp Asp Leu Gly Lys Gly Asp Phe
            690                 695                 700

Arg Ile Leu Met Cys Thr Lys Val Thr Met Asp Asp Phe Leu Thr Ala
705                 710                 715                 720

His His Glu Met Gly His Ile Gln Tyr Asp Met Ala Tyr Ala Ala Gln
            725                 730                 735

Pro Phe Leu Leu Arg Asn Gly Ala Asn Glu Gly Phe His Glu Ala Val
            740                 745                 750

Gly Glu Ile Met Ser Leu Ser Ala Ala Thr Pro Lys His Leu Lys Ser
            755                 760                 765

Ile Gly Leu Leu Ser Pro Asp Phe Gln Glu Asp Asn Glu Thr Glu Ile
            770                 775                 780

Asn Phe Leu Leu Lys Gln Ala Leu Thr Ile Val Gly Thr Leu Pro Phe
785                 790                 795                 800

Thr Tyr Met Leu Glu Lys Trp Arg Trp Met Val Phe Lys Gly Glu Ile
            805                 810                 815

Pro Lys Asp Gln Trp Met Lys Lys Trp Trp Glu Met Lys Arg Glu Ile
            820                 825                 830

Val Gly Val Val Glu Pro Val Pro His Asp Glu Thr Tyr Cys Asp Pro
            835                 840                 845

Ala Ser Leu Phe His Val Ser Asn Asp Tyr Ser Phe Ile Arg Tyr Tyr
            850                 855                 860

Thr Arg Thr Leu Tyr Gln Phe Gln Phe Gln Glu Ala Leu Cys Gln Ala
865                 870                 875                 880

Ala Lys His Glu Gly Pro Leu His Lys Cys Asp Ile Ser Asn Ser Thr
            885                 890                 895

Glu Ala Gly Gln Lys Leu Phe Asn Met Leu Arg Leu Gly Lys Ser Glu
            900                 905                 910

Pro Trp Thr Leu Ala Leu Glu Asn Val Val Gly Ala Lys Asn Met Asn
            915                 920                 925

Val Arg Pro Leu Leu Asn Tyr Phe Glu Pro Leu Phe Thr Trp Leu Lys
            930                 935                 940

Asp Gln Asn Lys Asn Ser Phe Val Gly Trp Ser Thr Asp Trp Ser
945                 950                 955

<210> SEQ ID NO 190
<211> LENGTH: 2877
<212> TYPE: DNA
<213> ORGANISM: Artificial Sequence
```

<220> FEATURE:
<223> OTHER INFORMATION: EGFR-VHH-Fc-MSCD342-ACE2-18-611 HC1 DNA

<400> SEQUENCE: 190

```
caggtgaaac tggaagagag tgggggaggg tctgttcaaa ctggtggaag tctcaggctc      60
acatgcgctg cctctgggtt cactttctcc agctacgcaa tggggtggtt tagacaagcg     120
cccggtaaag agagggaatt tgtttccggc atatcaggtt ctggaggctc aacggggtac     180
gcggacagcg taaagggaag atttaccatc tcacgcgata acgctaaaaa tacgttgat      240
cttcaaatga actctttgaa gcccgaagac acggcgattt actattgtgc agcagcggcc     300
gggagcggag gctctggcgg ttctggctca ttcgattact gggggcaggg tacgcaggta     360
accgtatctt cagagcccaa atctagcgac aaaactcaca catgtccacc gtgcccagca     420
cctgaactcc tggggggacc gtcagtcttc ctcttccccc caaaacccaa ggacaccctc     480
atgatctccc ggacccctga ggtcacatgc gtggtggtgg acgtgagcca cgaagaccct     540
gaggtcaagt tcaactggta cgtggacggc gtggaggtgc ataatgccaa gacaaagccg     600
cgggaggagc agtacaacag cacgtaccgt gtggtcagcg tcctcaccgt cctgcaccag     660
gactggctga atggcaagga gtacaagtgc aaggtctcca acaaagccct cccagccccc     720
atcgagaaaa ccatctccaa agccaaaggg cagccccgag aaccacaggt gtacaccctg     780
cccccatccc gggaggagat gaccaagaac caggtcagcc tgacctgcct ggtcaaaggc     840
ttctatccca gcgacatcgc cgtggagtgg gagagcaatg ggcagccgga gaacaactac     900
aagaccacgc ctcccgtgct ggactccgac ggctccttct cctctacag caagctcacc     960
gtggacaagt ctagatggca gcaggggaac gtcttctcat gctccgtgat gcatgaggct    1020
ctgcacaacc actacacgca gaagagcctc tccctgtctc cgggtggagg cggagggagt    1080
ggcggggag gctctcagtc tacaatcgaa gagcaggcca agacctttct ggacaagttc    1140
aaccatgaag ccgaggacct gttctaccag tccagcctgg cctcttggaa ctacaacacc    1200
aatatcaccg aggaaaacgt gcagaacatg aacaacgccg cgacaagtg gtctgccttc    1260
ctcaaagaac agtctacact ggctcagatg taccccttgc aagagatcca gaacctgaca    1320
gtgaagctgc aactgcaggc tctgcagcag aacggctctt ccgtgctatc tgaggataag    1380
tccaagcggc tgaacaccat cctgaacaca atgtccacca tctacagcac cggcaaagtg    1440
tgcaaccctg ataatcctca agagtgtctg cttctggaac ccggcctgaa cgagatcatg    1500
gccaactccc tggattataa cgagaggctg tgggcttggg agtcctggcg cagcgaggtg    1560
ggaaagcagc tcagacctct gtacgaagag tacgtcgtgc tgaagaacga gatggccaga    1620
gccaaccact acgaggacta cggcgactac tggagaggcg actatgaagt caatggcgta    1680
gacggctacg actactccag aggccagctg atcgaggatg tggagcacac cttcgaggag    1740
atcaagcctc tgtacgaaca tctgcacgcc tacgtgcggg ccaagctgat gaacgcctac    1800
ccttcctaca tctcccctat cggctgcctg cctgcccatc tgctgggtga tatgtggggc    1860
agattctgga ccaacctgta ttctctcacc gtgcccttg ccagaaacc caatatcgac    1920
gtgaccgacg ccatggtcga tcaggcctgg gatgcccaga gaatcttcaa agaggctgag    1980
aagttcttcg tgtccgtggg actgcctaac atgacccagg cttttggga aaactccatg    2040
ctgaccgatc ctggcaacgt gcagaaggcc gtgtgtcacc ctaccgcttg ggatctgggc    2100
aagggcgatt tccggatcct gatgtgcacc aaggtgacca tggacgactt cctaaccgct    2160
caccacgaga tgggccacat ccagtacgac atggcttacg ccgctcagcc ttttctgctg    2220
```

```
cggaacggag ctaatgaagg cttccatgaa gccgtgggcg aaatcatgtc tctgtccgcc    2280
gccaccccta agcacctgaa gtctatcggc ctgctgtctc ctgacttcca ggaggacaac    2340
gagacagaga tcaacttcct gctgaagcag gccctgacaa tcgtgggcac cctgcccttc    2400
acctacatgc tggaaaagtg gagatggatg gtgttcaagg gcgaaatccc caaggaccag    2460
tggatgaaaa agtggtggga gatgaagaga gagattgttg gcgtggtgga acctgtgcct    2520
cacgacgaga cctactgcga ccccgctagc ctgttccacg tgtccaacga ctactctttc    2580
atccggtact acaccagaac cctgtaccag ttccagttcc aggaagctct gtgccaggct    2640
gccaaacacg aaggccctct gcacaagtgc gacatctcta acagcaccga ggccggacaa    2700
aagctgttca acatgctgag actgggcaag tccgagcctt ggaccctggc tctggagaac    2760
gtggtgggag ctaagaacat gaatgtgcgg ccactgctca actacttcga gcctctgttt    2820
acctggctga aggaccagaa caagaactcc ttcgtgggct ggtccaccga ctggtcc       2877
```

<210> SEQ ID NO 191
<211> LENGTH: 13
<212> TYPE: PRT
<213> ORGANISM: Artificial Sequence
<220> FEATURE:
<223> OTHER INFORMATION: VHH2 CDR3 (Chothia) - alternative

<400> SEQUENCE: 191

Thr Val Leu Thr Asp Pro Arg Val Leu Asn Glu Tyr Ala
1               5                   10

<210> SEQ ID NO 192
<211> LENGTH: 3
<212> TYPE: PRT
<213> ORGANISM: Artificial Sequence
<220> FEATURE:
<223> OTHER INFORMATION: VHH6 CDR2 (Chothia) - alternative

<400> SEQUENCE: 192

Gly Gly Gly
1

<210> SEQ ID NO 193
<211> LENGTH: 3
<212> TYPE: PRT
<213> ORGANISM: Artificial Sequence
<220> FEATURE:
<223> OTHER INFORMATION: VHH6 CDR3 (Chothia) - alternative

<400> SEQUENCE: 193

Leu Thr Ser
1

<210> SEQ ID NO 194
<211> LENGTH: 805
<212> TYPE: PRT
<213> ORGANISM: Homo sapiens
<220> FEATURE:
<223> OTHER INFORMATION: Human ACE2 (Uniprot ID Q9BYF1) - full length

<400> SEQUENCE: 194

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

```
Asn Tyr Asn Thr Asn Ile Thr Glu Glu Asn Val Gln Asn Met Asn Asn
 50                  55                  60

Ala Gly Asp Lys Trp Ser Ala Phe Leu Lys Glu Gln Ser Thr Leu Ala
 65                  70                  75                  80

Gln Met Tyr Pro Leu Gln Glu Ile Gln Asn Leu Thr Val Lys Leu Gln
                 85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460
```

Lys Gly Glu Ile Pro Lys Asp Gln Trp Met Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
                500                 505                 510

Ile Arg Tyr Tyr Thr Arg Thr Leu Tyr Gln Phe Gln Phe Gln Glu Ala
                515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
                580                 585                 590

Thr Trp Leu Lys Asp Gln Asn Lys Asn Ser Phe Val Gly Trp Ser Thr
                595                 600                 605

Asp Trp Ser Pro Tyr Ala Asp Gln Ser Ile Lys Val Arg Ile Ser Leu
                610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
                660                 665                 670

Ala Asn Leu Lys Pro Arg Ile Ser Phe Asn Phe Phe Val Thr Ala Pro
                675                 680                 685

Lys Asn Val Ser Asp Ile Ile Pro Arg Thr Glu Val Glu Lys Ala Ile
                690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ile Trp Leu Ile Val Phe Gly Val Val Met Gly Val
                740                 745                 750

Ile Val Val Gly Ile Val Ile Leu Ile Phe Thr Gly Ile Arg Asp Arg
                755                 760                 765

Lys Lys Lys Asn Lys Ala Arg Ser Gly Glu Asn Pro Tyr Ala Ser Ile
770                 775                 780

Asp Ile Ser Lys Gly Glu Asn Asn Pro Gly Phe Gln Asn Thr Asp Asp
785                 790                 795                 800

Val Gln Thr Ser Phe
                805

<210> SEQ ID NO 195
<211> LENGTH: 27
<212> TYPE: PRT
<213> ORGANISM: Artificial Sequence
<220> FEATURE:
<223> OTHER INFORMATION: flexible linker

<400> SEQUENCE: 195

Glu Pro Lys Thr Pro Lys Pro Gln Pro Gln Pro Gln Leu Gln Pro Gln
1               5                   10                  15

```
Pro Asn Pro Thr Thr Glu Ser Lys Ser Pro Lys
            20                  25
```

<210> SEQ ID NO 196
<211> LENGTH: 5
<212> TYPE: PRT
<213> ORGANISM: Artificial Sequence
<220> FEATURE:
<223> OTHER INFORMATION: flexible linker
<220> FEATURE:
<221> NAME/KEY: MISC_FEATURE
<222> LOCATION: (1)..(5)
<223> OTHER INFORMATION: can be repeated n times, where n is an integer
      from 1 to 20

<400> SEQUENCE: 196

```
Glu Ala Ala Ala Lys
1               5
```

<210> SEQ ID NO 197
<211> LENGTH: 5
<212> TYPE: PRT
<213> ORGANISM: Artificial Sequence
<220> FEATURE:
<223> OTHER INFORMATION: flexible linker
<220> FEATURE:
<221> NAME/KEY: MISC_FEATURE
<222> LOCATION: (1)..(5)
<223> OTHER INFORMATION: can be repeated n times, where n is an integer
      from 1 to 20

<400> SEQUENCE: 197

```
Gly Gly Gly Gly Ser
1               5
```

<210> SEQ ID NO 198
<211> LENGTH: 4
<212> TYPE: PRT
<213> ORGANISM: Artificial Sequence
<220> FEATURE:
<223> OTHER INFORMATION: flexible linker
<220> FEATURE:
<221> NAME/KEY: MISC_FEATURE
<222> LOCATION: (1)..(4)
<223> OTHER INFORMATION: can be repeated n times, where n is an integer
      from 1 to 20

<400> SEQUENCE: 198

```
Gly Gly Gly Ser
1
```

<210> SEQ ID NO 199
<211> LENGTH: 12
<212> TYPE: PRT
<213> ORGANISM: Artificial Sequence
<220> FEATURE:
<223> OTHER INFORMATION: hinge region

<400> SEQUENCE: 199

```
Glu Arg Lys Cys Cys Val Glu Cys Pro Pro Cys Pro
1               5                   10
```

<210> SEQ ID NO 200
<211> LENGTH: 62
<212> TYPE: PRT
<213> ORGANISM: Artificial Sequence
<220> FEATURE:
<223> OTHER INFORMATION: hinge region

<400> SEQUENCE: 200

```
Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
                20                  25                  30

Glu Pro Lys Ser Cys Asp Thr Pro Pro Pro Cys Pro Arg Cys Pro Glu
            35                  40                  45

Pro Lys Ser Cys Asp Thr Pro Pro Pro Cys Pro Arg Cys Pro
    50                  55                  60

<210> SEQ ID NO 201
<211> LENGTH: 12
<212> TYPE: PRT
<213> ORGANISM: Artificial Sequence
<220> FEATURE:
<223> OTHER INFORMATION: hinge region

<400> SEQUENCE: 201

Glu Ser Lys Tyr Gly Pro Pro Cys Pro Ser Cys Pro
1               5                   10
```